United States Patent [19]
Tucker et al.

[11] Patent Number: 6,093,732
[45] Date of Patent: Jul. 25, 2000

[54] 4-HYDROXYQUINOLINE-3-CARBOXAMIDES AND HYDRAZIDES AS ANTIVIRAL AGENTS

[75] Inventors: John Alan Tucker; Valerie A. Vaillancourt, both of Kalamazoo; Joseph Walter Strohbach, Mendon; Karen Rene Romines, Paw Paw; Mark E. Schnute, Kalamazoo; Michele M. Cudahy, Kalamazoo; Suvit Thaisrivongs, Kalamazoo; Steven Ronald Turner, Kalamazoo, all of Mich.

[73] Assignee: Pharmacia & Upjohn Company, Kalamazoo, Mich.

[21] Appl. No.: 09/203,259

[22] Filed: Dec. 1, 1998

Related U.S. Application Data

[60] Provisional application No. 60/068,460, Dec. 22, 1997, and provisional application No. 60/076,717, Mar. 4, 1998.

[51] Int. Cl.[7] .................... C07D 215/00; A61K 31/47
[52] U.S. Cl. .................................. 514/312; 546/156
[58] Field of Search .................... 546/156; 514/312

[56] References Cited

U.S. PATENT DOCUMENTS

| | | | |
|---|---|---|---|
| 3,496,184 | 2/1970 | Mizzoni et al. | 546/135 |
| 3,864,329 | 2/1975 | Tobiki et al. | 546/153 |
| 3,951,955 | 4/1976 | Tobiki et al. | 546/153 |
| 3,960,868 | 6/1976 | Ferrini et al. | 546/153 |
| 4,397,856 | 8/1983 | Allais et al. | 546/153 |
| 4,450,167 | 5/1984 | Martret et al. | 546/153 |
| 4,777,252 | 10/1988 | Slusarchyk et al. | 540/363 |
| 4,786,644 | 11/1988 | Glamkowski et al. | 514/312 |
| 4,870,182 | 9/1989 | Schriewer et al. | 546/156 |
| 4,959,363 | 9/1990 | Wentland | 546/156 |
| 4,965,266 | 10/1990 | Uno et al. | 514/253 |
| 5,019,570 | 5/1991 | Arnould et al. | 514/202 |
| 5,175,151 | 12/1992 | Afonso et al. | 514/63 |
| 5,318,963 | 6/1994 | Ermann et al. | 514/210 |
| 5,491,139 | 2/1996 | Demuth, Jr. et al. | 514/192 |
| 5,563,141 | 10/1996 | Wayne et al. | 514/252 |
| 5,610,192 | 3/1997 | Cohen et al. | 514/614 |

FOREIGN PATENT DOCUMENTS

| | | |
|---|---|---|
| 2024282 | 3/1991 | Canada . |
| 736531 | 10/1996 | European Pat. Off. . |
| 1 908 548 | 11/1970 | Germany . |
| 3808118 | 9/1989 | Germany . |
| 279887 | 6/1990 | Germany . |
| 19642290 | 5/1998 | Germany . |
| 2-152966 | 12/1988 | Japan . |
| 2-264724 | 4/1989 | Japan . |
| 8-151368 | 11/1994 | Japan . |
| 8-301849 | 11/1996 | Japan . |
| WO92/04328 | 3/1992 | WIPO . |
| WO95/11592 | 5/1995 | WIPO . |
| WO96/16046 | 5/1996 | WIPO . |
| WO96/32015 | 12/1996 | WIPO . |
| WO97/04779 | 2/1997 | WIPO . |
| WO97/15557 | 5/1997 | WIPO . |
| WO97/48694 | 3/1998 | WIPO . |
| WO98/12180 | 5/1998 | WIPO . |

OTHER PUBLICATIONS

J. Med. Chem. 36, 1580–1596 (1993).
Book of Abstracts, 211th National ACS Meeting, New Orleans, LA (1996).
Indian J. Chem. 7, 1010–1016 (1969).
Indian J. Chem. 24B, 737–746 (1985).
J. Indian Chem. Soc. 68, 138–141 (1991).
J. Sci. Ind. Res. 14C, 228–230 (1955).
J. Sci. Ind. Res. 14B, 261–263 (1955).
Indian J. Chem. 165, 231–234 (1978).

*Primary Examiner*—Zinna Northington Davis
*Attorney, Agent, or Firm*—Lucy X. Yang

[57] ABSTRACT

The present invention provides 4-hydroxyquinoline-3-carboxamide and hydrazide compounds of formula I

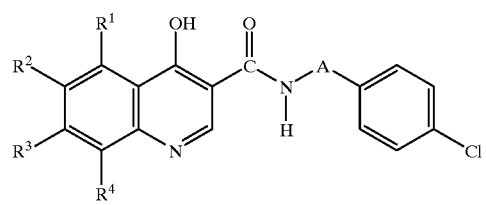

These compounds are useful to treat or prevent the herpesviral infections, particularly, human cytomegaloviral infection.

17 Claims, No Drawings

4-HYDROXYQUINOLINE-3-CARBOXAMIDES AND HYDRAZIDES AS ANTIVIRAL AGENTS

CROSS-REFERENCE TO RELATED APPLICATIONS

This application claims the benefit of the following provisional applications: U.S. Ser. No. 60/068,460, filed Dec. 22, 1997, and Ser. No. 60/076,717, filed Mar. 4, 1998.

FIELD OF THE INVENTION

The present invention provides 4-hydroxyquinoline-3-carboxamide derivatives, more specifically, provides N-[(4-chlorophenyl)methyl]-4-hydroxy-3-quinolinecarboxamide of formula I. These compounds are useful as antiviral agents, in particular, as agents against viruses of the herpes family.

BACKGROUND OF THE INVENTION

The herpesviruses comprise a large family of double stranded DNA viruses. They are the source of the most common viral illnesses in man. Eight of the herpesviruses, herpes simplex virus types 1 and 2 (HSV-1 and HSV-2), varicella zoster virus (VZV), human cytomegalovirus (HCMV), Epstein-Barr virus (EBV), and human herpes viruses 6, 7, and 8 (HHV-6, HHV-7, and HHV-8), have been shown to infect humans.

HSV-1 and HSV-2 cause herpetic lesions on the lips and genitals, respectively. They also occasionally cause infections of the eye and encephalitis. HCMV causes birth defects in infants and a variety of diseases in immunocompromised patients such as retinitis, pneumonia, and gastrointestinal disease. VZV is the causitive agent of chicken pox and shingles. EBV causes infectious mononucleosis. It can also cause lymphomas in immunocompromised patients and has been associated with Burkitt's lymphoma, nasopharyngeal carcinoma, and Hodgkins disease. HHV-6 is the causitive agent of roseola and may be associated with multiple sclerosis and chronic fatigue syndrome. HHV-7 disease association is unclear, but it may be involved in some cases of roseola. HHV-8 has been associated with Kaposi's sarcoma, body cavity based lymphomas, and multiple myeloma.

Compounds of the present invention are distinct from all other hydroxyquinoline pharmaceutical agents in that the unique position of chloro substitutent on the N-phenylmethyl of formula I is critical for having useful antiviral activities. These compounds are useful to treat or prevent the above referenced herpesviral infections, particularly, human cytomegaloviral infection.

INFORMATION DISCLOSURE

U.S. Pat. No. 4,959,363 discloses quinolones of structure 3 useful as anti-herpes virus agents:

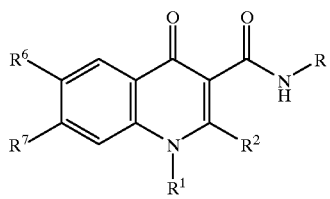

wherein R is hydrogen, hydroxy, amino or lower alkyl; $R^1$ is lower alkyl, lower alkenyl, cycloalkyl, pyridinyl, phenyl, or substituted phenyl; $R^2$ is hydrogen, amino, or hydroxy; $R^6$ is H or F; and $R^7$ is phenyl, pyridyl, or selected other heterocycles. It does not disclose compounds wherein R is alkylaryl (substituted) and $R^1$ is hydrogen.

Related compounds in which the NHR group of structure 3 is replaced by groups, such as $N(CH_3)_2$, $NHOCH_3$, or $N(CH_3)OH$, are described in the Journal of Medicinal Chemistry 36, 1580–1596 (1993); and Book of Abstracts, 211th National ACS meeting, New Orleans, La. (1996).

German patent application 1,908,548 discloses antiviral agents of structure 4:

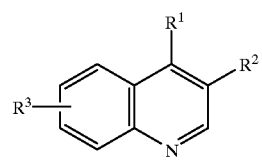

wherein $R^1$ is H, —OH, halogen, —SH, or lower alkyl sulfides; $R^2$ is H, —COOH, —CN, —CHO, lower alkyl carboxylic, —CONHR$^4$, or —CON(R$^4$)$_2$; $R^3$ is a wide variety of substituent groups; and $R^4$ is lower alkyl, aryl, arylalkyl, or lower alkylamine. However, this application does not disclose the preparation or testing of any specific carboxamide-quinoline compounds.

U.S. Pat. No. 5,175,151 discloses compounds of structures 5 and 6 having antiviral and antihypotensive properties. A large number of quinoline compounds are disclosed generically, including structures 5 and 6. The preferred compounds of this patent are disclosed as being carboxylic esters:

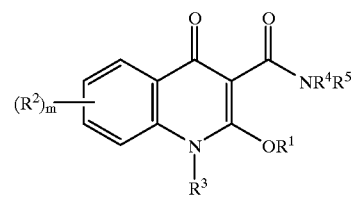

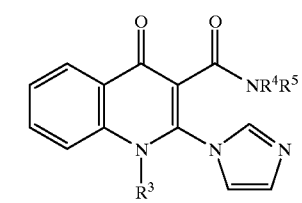

Among the groups disclosed for these compounds are the following: $R^1$ is alkyl, alkenyl, acyl and other groups; $R^2$ is alkyl, alkoxy, aryloxy, araalkyloxy, halogen and a wide variety of polar and/or acidic functional groups; $R^3$ is H, alkyl, aryl araalkyl and other groups; $R^4$ and $R^5$ are H, alkyl, aryl, alkaryl, alkenyl, heteroalkyl, heteroaryl, and other groups, and are the same or different. All of these compounds have an oxygen substituent or an imidazolyl group in the 2-position of the quinoline ring.

Japanese patent JP 08151368 discloses compounds of structure 7 having activity against herpes viruses:

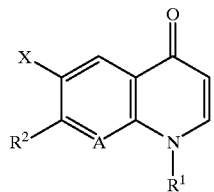

wherein $R^1$ is alkenyl, cycloalkyl, aryl or heterocycle; $R^2$ is optionally substituted aryl or heterocycle; and X is H or halogen; and A is N or CH.

Japanese patent 02264724 discloses antiviral agents having structure 8:

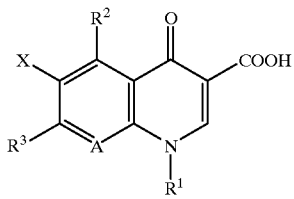

wherein $R^1$ is alkyl, alkenyl, cycloalkyl, aryl or heterocycle; $R^2$ is H, halogen, alkoxy, OH, protected OH, or mono or dialkylamino; $R^3$ is optionally substituted cycloalkyl or vinyl; A is N or C($R_4$); and $R^4$ is H or halo.

Japanese patent 02152966 discloses compounds of structure 9 useful as anti-asthma and anti-allergy agents:

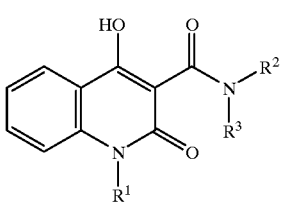

wherein $R^1$ is H, lower alkyl, phenyl, or phenyl-lower alkyl; $R^2$ is hydrogen or lower alkyl; and $R^3$ is alkyl (optionally substituted by lower alkoxy or heterocyclic group), phenyl lower alkyl (optionally substituted by lower alkyl, halogen, lower alkoxy or sulphamoyl on the phenyl ring) or naphthyl-lower alkyl. The combination of $R^2$ and $R^3$ into a heterocycle encompassing the amide nitrogen is also disclosed.

Phenethyl compounds, such as structures 10–14, have been described as synthetic intermediates in the synthesis of antimalarial compounds (Indian J. of Chemistry, 1010 (1969); Indian J. of Chemistry, vol. 24B, 737 (1985)).

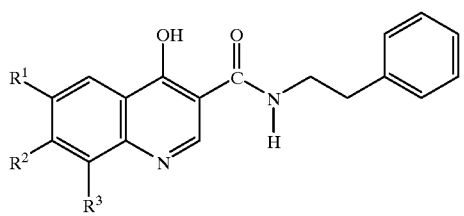

| Compound-# | R1 | R2 | R3 |
|---|---|---|---|
| 10 | H | H | H |
| 11 | H | Cl | H |
| 12 | OMe | H | H |
| 13 | H | OMe | H |
| 14 | H | H | OMe |

U.S. Pat. No. 4,450,167 discloses compounds of structure 15 useful as anxiolytics.

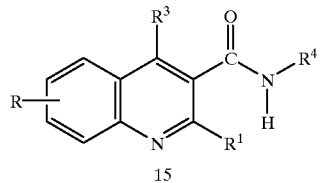

$R^1$ = H, alkyl, phenyl, $PhCH_2$
$R^4$ = alkyl, aryl, heteroaryl
$R^3$ = H, OH
R = 6- or 7-H, halogen, alkyl, cycloalkyl, etc.

These compounds are derivatives of arylamines or alkylamines, unlike the compounds of the present invention which are derivatives of benzylamine (an arylalkylamine).

U.S. Pat. No. 4,786,644 discloses quinoline carboxamides of structure 16 useful as analgesics:

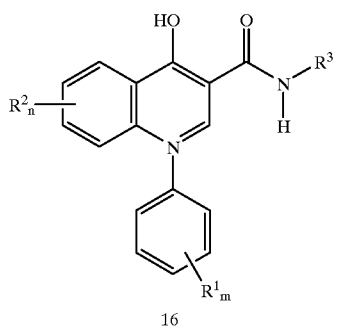

$R^1$, $R^2$ = halogen, lower alkyl, lower alkoxy, same or different
$R^3$ = phenyl or heteroaryl, optionally substituted.
m, n = 0 or 1

U.S. Pat. No. 4,397,856 discloses structural variations of 4-hydroxyquinolines, such as structure 17, which have analgesic activity.

X = H, halogen, lower alkyl, lower alkoxy, $OCF_3$, $SCF_3$, or $CF_3$
$R^1$ = H, lower alkyl -continued R² = H or a ring which is optionally unsaturated, optionally heterocyclic, optionally substituted.
R³ = H, lower alkyl, halogen
R⁴ = H or halogen
R⁵ = halogen DE 3808118 discloses synthetic intermediates of general structure 18.

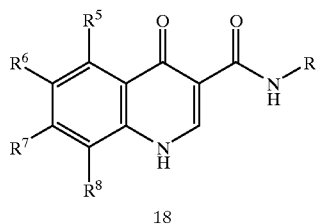

18

R = lower alkyl, phenyl, or substituted phenyl
R⁵, R⁶ = H, NO₂, or halogen, same or different
R⁷ = H, lower alkyl, halogen, amino, or subst. amino
R⁸ = H, lower alkyl, alkoxy (1–3 carbons), alkylmercapto (1–3 carbons), halogen, nitro, alkoxycarbonyl, or cyano.

These compounds are derivatives of arylamines or alkylamines, unlike the compounds of the present invention, which are derivatives of benzylamine (an arylalkylamine).

The use of quinolines, such as general structure 19, as synthetic intermediates in the synthesis of antibiotics, such as general structure 20, are described in several sources, for example, in U.S. Pat. No. 3,864,329; U.S. Pat. No. 3,951,955; EP 736531 (which discloses alpha-substituted pyridazino quinoline compounds); and DD 279887. In some of these references, the structures below, which are phenylglycine derivatives, are drawn as quinolone tautomers.

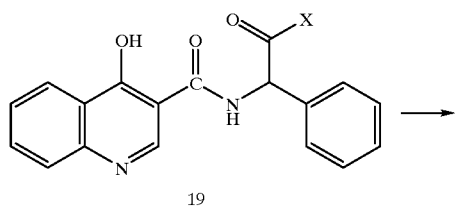

19

X = OH, OCH₂CH₃

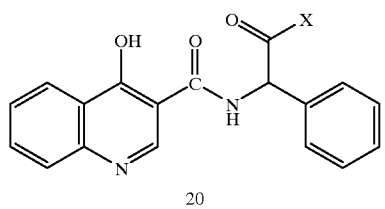

20

X = A beta lactam antibiotic fragment

-continued

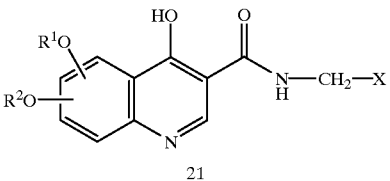

21

X = a beta lactam antibiotic R1, R2 = H, or acyl

Hydroxyquinoline-beta lactam conjugates, such as structure 21, have also been described in, for example, U.S. Pat. No. 5,019,570 (and its equivalent EP 304158) and U.S. Pat. No. 5,491,139.

U.S. Pat. No. 3,496,184 (and its equivalents, GB 1270412 and DE 1929165) discloses carboxylic esters of general structure 22 as livestock growth-promoters. The corresponding carboxylic acids, amides, nitrites, and hydrazides are generically claimed. The amides and hydrazides are described as optionally substituted on nitrogen with one or more alkyl or araalkyl groups. One amide, 23, and one hydrazide, 24, are described in the examples.

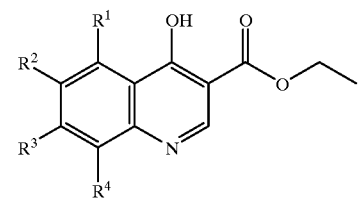

22

At least one of R¹, R², R³, or R⁴ is (cycloalkyl-A—X—)
where X = S or O and A =
—(CH₂)ₙ— or a single bond between
the alkyl of cycloalkyl group and A.

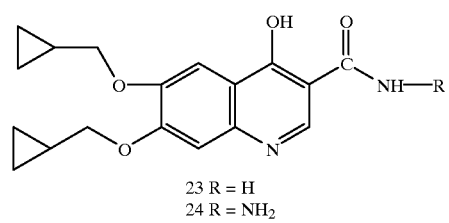

23 R = H
24 R = NH₂

U.S. Pat. No. 3,960,868 discloses acid, esters, and amides of structure 25 having antiinflammatory, analgesic, antimicrobial, and histimine liberation inhibiting activities.

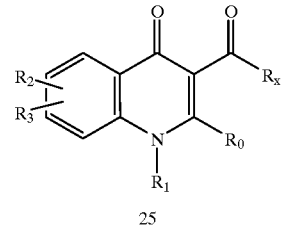

25

-continued $R_x$ = OH, lower alkoxy, —$NH_2$,
lower alkylamino, lower dialkylamino
cyclic amines, phenylamines (anilines) and arylalkylamines such as
benzyl, optionally substituted.
$R_0$ = H, alkyl, OH, or lower alkoxy.
$R_1$ = alkyl or cycloalkyl, optionally substituted.
$R_2$ = cycloalkyl, cycloalkenyl or 1-adamentyl.
$R_3$ = alkyl, halogen or hydrogen.

U.S. Pat. No. 5,563,141 discloses compounds of structure 26 containing an acidic and a basic functional group separated by an appropriate linker as antagonists of adhesion molecules.

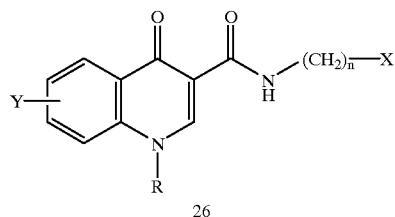

26

R = H, alkyl, or phenyl-$(CH_2)_n$—
X = an amino-substituted aromatic heterocycle
Y = an acidic functional group These compounds contain an amino-substituted heterocycle attached through a suitable linker to the carboxamide nitrogen.

Published PCT application, WO 96/16046, discloses pyrimidine derivatives, including structures 27 and 28 as antibacterial agents.

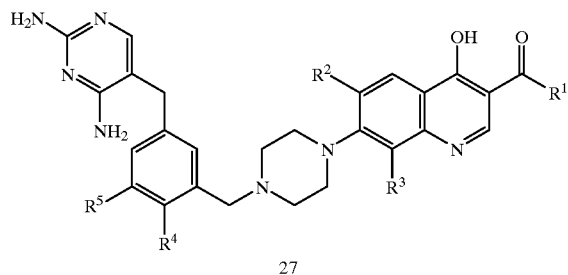

27

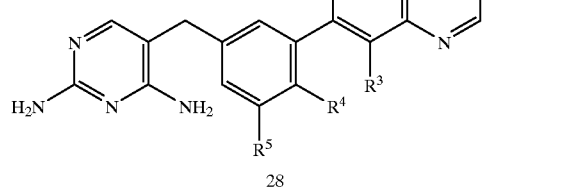

28

$R^1$ = OH, alkoxy, amino, or (hydroxyalkyl)amino
$R^2$ and $R^3$ = H, F, OH or OMe, same or different -continued $R^4$ = Br or lower alkoxy
$R^5$ = lower alkoxy The compounds described by structures 27 and 28 all contain a diaminopyrimidine group attached to the quinoline ring by a piperazine or phenyl ring spacer.

Published PCT application, WO 95/11592, discloses substituted quinolines 29 as marine anti-fouling agents. WO 96/32015 claims an equally broad group of quinolines as antifungal agents.

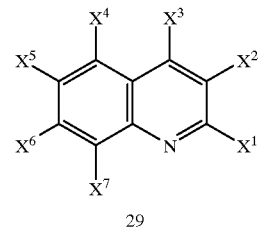

29

$X_1$, $X_2$, $X_4$, $X_5$, $X_6$, and $X_7$ are independently any of an extemely wide range of substituents including OH,
(C=O) NHR where R is $C_1$–$C_{12}$ alkyl.

Published PCT application, WO 97/15557 discloses a method for preparing combinatorial libraries of substituted quinolines of structure 29. According to the broad definitions of $X^1$–$X^6$, any of the quinoline ring substituents may independently be OH or (C=O)$NHR^7$, where $R^7$ is an arylalkyl group. "Nuc" is defined as a chemical moiety having a reactive pair of electrons, including but not limited to, amines, enolates, Gringard reagents, alkoxides, and cyanide.

Several sources describe the synthesis of hydrazides their conversion to acylhydrazones 30, such as the following: J. Indian Chem. Soc., vol. 68, 138–141 (1991); J. Sci Ind. Res., vol. 14c, 228–230 (1955); and J. Sci Ind. Res., vol. 14b, 261–263 (1955).

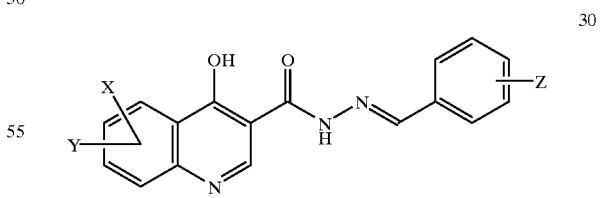

30

Compounds of structure 30 are substituted on the outer hydrazide nitrogen via a carbon-nitrogen double bond.

The acylthiosemicarbazides 31 in chemical synthesis have been described in Indian J. Chem., vol. 16B, 231–234 (1978). Structures 32 are listed in the CAS registry file, but do not appear to have corresponding literature references.

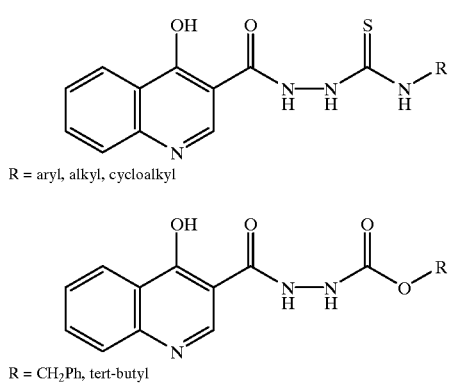

31

R = aryl, alkyl, cycloalkyl

32

R = CH₂Ph, tert-butyl

The compounds described by these two structures have a carbonyl (C=O) or thiocarbonyl (C=S) group attached to the outer hydrazine nitrogen atom.

U.S. Pat. No. 5,318,96; U.S. Pat. No. 4,777,252; and Canadian patent application 2,024,282 disclose compounds of structures 33 and 34.

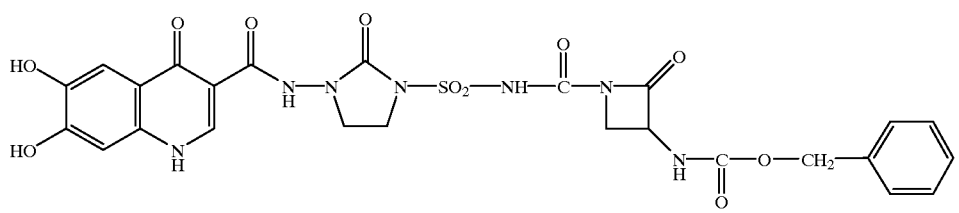

33

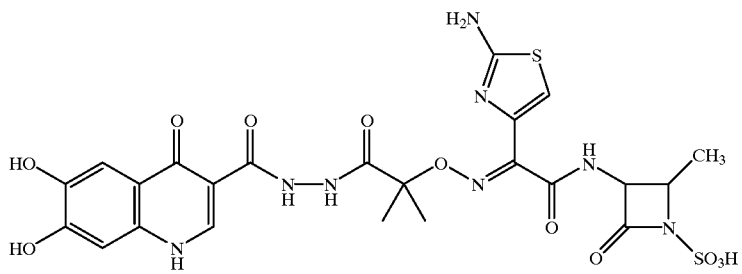

34

U.S. Pat. No. 5,610,192 discloses compounds of structure 35 useful as metazoan protease inhibitors wherein X is a planar linker group including amide, urea, fumarate bisamides, and N-acyl hydrazones.

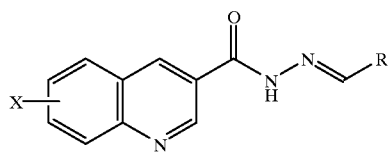

35

R = aryl or heteroaryl
Quinoline ring optionally substituted with OH or a variety of other groups in either or both rings.

The compounds of structure 35 have a substituent attached to the outer hydrazine nitrogen by a carbon-nitrogen double bond.

Japanese patent application JP8301849-A discloses a heterocyclic compound of structure 36 as tachykinin receptor antagonists:

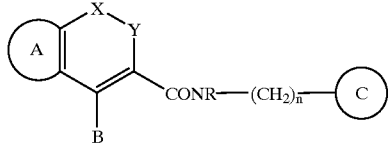

36 wherein ring A is an optionally substituted homocyclic or heterocyclic ring; B is an optionally substituted amino group or optionally substituted hydroxyl group; ring C is an optionally substituted homocyclic or heterocyclic ring; —X—Y— is an entity in which (1) one element is —NR₁— (R₁ is H, or an optionally substituted hydrocarbon group) or —O—, and the second element is —CO— or CS—, or (2) one element is —N= and the other element is =CR₂— (R₂ is H, halogen, optionally substituted hydrocarbon group, optionally substituted amino group, or optionally substituted hydroxyl group); R is H or optionally substituted hydrocarbon group; and n is 1–3.

Published PCT application, WO 98/12180, discloses compounds of structrue 37 for controlling undersirable plants:

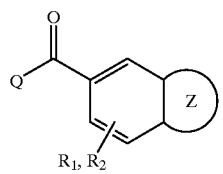

37 wherein R₁, R₂ are hydrogen, nitro, halogen, nitrile, SCN, hydroxyl, thiol, optionally substituted alkyl(C1–6), alkoxy (1–6), alkylthio (C1–6), alkylsulfinyl (C1–6), alkylsulfonly (C1–6), alkoxysulfonly (C1–6), or optionally substituted phenyl, phenylthio, phenoxy, phenylsufinyl or phenylsulfonyl; Z is an optionally substituted, 4-membered, unsaturated, partially or completely saturated chain with three carbon atoms and one nitrogen atom; Q is an optionally substituted cyclohexane-1,3-dione linked at position 2.

WO 97/48694 discloses compounds of structure 38 useful for treating bone growth:

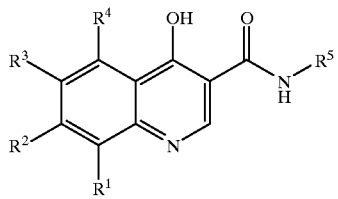

wherein $R^1$-4 are a variety of substituents including alkyl optionally substituted by halogen and alkenyl. $R^5$ is an optionally substituted carbocyclic or heterocyclic ring.

DE 19642290 discloses compounds of structure 39 useful for treating Alzheimer's disease:

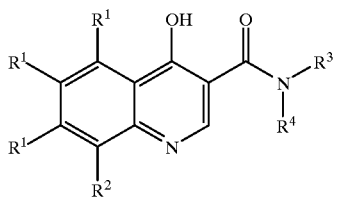

wherein $R^1$ is hydrogen, halogen, alkyl(1–4), or alkoxy (1–4). $R^2$ is hydrogen, halogen, alkyl(1–4) opt. substituted by fluorine, alkylthio(1–4) opt. substituted by fluorine, alkoxy(1–4) opt. substituted by fluorine, $O(CH_2)_{0-3}$(aryl) amino. $R^3$ and $R^4$ are hydrogen, alkyl(1–4), $(CH_2)_0$ $N(alkyl)_{1-2}$, alkylamino linked amides, $-C_5H_N(CH_2)_{0-9}Ph$ (OS).

U.S. Pat. No. 4870182 discloses compounds of structure 40 useful as antiallergics:

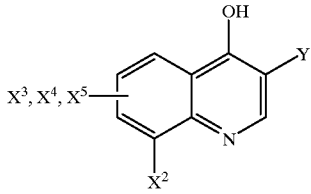

wherein Y is CONR'R", R' and R" are hydrogen or alkyl (1–4), R" may also be phenyl; $X^2$ may be nitro, amino, cyano, alkyl(1–3), alkoxy(1–3), alkylmercapto(1–3), alkylsulfonyl(1–3), or phenylsulfonyl; $X^3$, $X^4$ and $X^5$ are hydrogen, halogen, nitro, cyano, alkyl(1–3), alkoxy(1–3), alkylmercapto(1–3), alkylsulfonyl(1–3), or a phenylsulfonyl group which is optionally substituted in the aryl radical.

U.S. Pat. No. 4965266 discloses compounds of structure 41 useful as antiallergics:

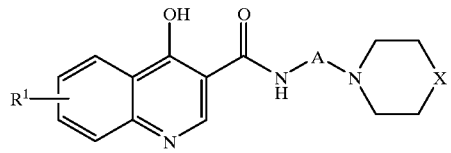

wherein A is an alkylene group; X is $NCHPh_2$ or $C=CPh_2$; $R^1$ is hydrogen, halogen, hydroxy, alkyl(1–6), alkoxy(1–6), nitro, or cyano.

Published PCT application, WO 97/04779 discloses compounds of structure 42 useful as inhibitors of Phosphodiesterase IV esterase and/or Tumour Necrosis Factor activity.

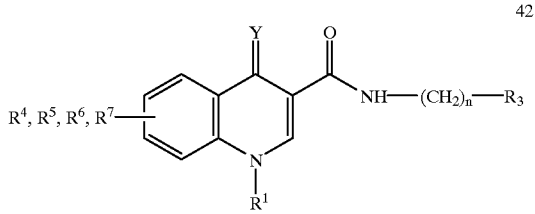

In structure 42, wherein $R^1$ is optionally substituted alkyl (1–6), alkylcycloalkyl(1–6), alkylaryl (1–6), alkylheterocyclo(1–6), or alkylheteroaryl (1–6), unlike the compounds of the present invention wherein $R^1$ is hydrogen.

SUMMARY OF THE INVENTION

The present invention provides a compound of formula I

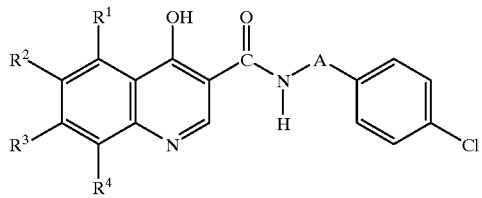

or pharmaceutically acceptable salts thereof wherein
A is:
a) $-CH_2-$, or
b) $-NH-$;
$R^1$, $R^2$, $R^3$ and $R^4$ are independently
a) $-H$,
b) halo,
c) $-CN$,
d) $-NO_2$,
e) aryl,
f) het,
g) $-OR^5$,
h) $C_{1-2}$ alkyl,
i) $C_{1-12}$ alkyl substituted with one to three $-CN$, halo, $-NO_2$, $OR^5$, $-C(=O)R^5$, $-COOR^5$, het, aryl, $-SR^5$, $-OR^6$, $-NR^7R^8$, $-OP(=O)(R^9)_2$, $-OPH(=O)R^9$, $-OC(=O)R^{10}$, $-O$-glycyl, $-O$-valyl, or $-O$-lysyl,
j) $-C\equiv CR^{11}$,
k) $-CH=CH-R^{12}$, l) —(CH$_2$)$_m$—C(=O)R$^{13}$,
m) —SR$^{14}$,
n) —C(=S)R$^{15}$,
o) —(CH$_2$)$_m$—SO$_i$R$^{13}$,
p) —NR$^7$R$^8$,
q) —NHSO$_i$R$^{13}$,
r) R$^1$ and R$^2$ taken together are het or C$_{4-6}$ cycloalkyl, or
s) R$^2$ and R$^3$ taken together are het or C$_{4-6}$ cycloalkyl;
R$^5$ is
  a) H,
  b) C$_{1-8}$ alkyl, optionally substituted with one to three —OH, CN, C$_{1-4}$ alkoxy, halo, —NO$_2$, het or aryl,
  c) aryl, or
  d) het;
R$^6$ is
  a) —SO$_2$C$_{1-6}$ alkyl,
  b) —SO$_2$—(CH$_2$)$_m$-aryl, or
  c) —SO$_2$—(CH$_2$)$_m$-het;
R$^7$ and R$^8$ are independently
  a) H,
  b) C$_{1-8}$ alkyl, optionally substituted with one to three —NO$_2$, halo, —CN, OR$^5$, aryl, het, C$_{3-6}$ cycloalkyl, C$_{1-6}$ alkynyl, C$_{1-6}$ alkenyl, —SR$^{14}$, or —NR$^{16}$R$^{17}$,
  c) aryl,
  d) het,
  e) —(CH$_2$)$_m$—C(=O)OR$^5$,
  f) —(CH$_2$)$_m$—C(=O)R$^5$, or
  g) R$^7$ and R$^8$ taken together to form het;
R$^9$ is
  a) —OH, or
  b) —OC$_{1-8}$ alkyl;
R$^{10}$ is
  a) H,
  b) C$_{1-8}$ alkyl,
  c) —NR$^7$R$^8$,
  c) C$_{1-8}$ alkyl substituted with one to two halo, het, —NR$^7$R$^8$, —COOH —O(CH$_2$)$_m$COOH or —C(=O)N(C$_{1-4}$ alkyl)(CH$_2$)$_n$S(=O)$_2$O$^-$M$^+$;
R$^{11}$ is
  a) C$_{1-8}$ alkyl,
  b) C$_{1-8}$ alkyl substituted with one to three —CN, halo, —NO$_2$, —COOR$^5$, —C(=O)R$^5$, —SR$^5$, aryl, —OR$^5$, —NR$^7$R$^8$, —OP(=O)(R$^9$)$_2$, —OPH(=O)R$^9$ —OC(=O)R$^{10}$, —O-glycyl, —O-valyl, —O-lysyl or —O-seluptamatyl, or
  c) —(CH$_2$)$_m$-het;
R$^{12}$ is
  a) H,
  b) —CN,
  c) C$_{1-8}$ alkyl,
  d) C$_{1-8}$ alkyl substituted with one to three —CN, halo, —NO$_2$, —C(=O)R$^5$, —COOR$^5$, aryl, het, —SR$^5$, —OR$^5$, —NR$^7$R$^8$, —OP(=O)(R$^9$)$_2$ or —OPH(=O)R$^9$,
  e) —C(=O)R$^5$, or
  f) —COOR$^5$;
R$^{13}$ is
  a) C$_{1-8}$ alkyl,
  b) C$_{1-8}$ alkyl substituted one to three —CN, halo, —NO$_2$, —C(=O)R$^5$, het, aryl, —COOR$^5$, —SR$^5$, —OR$^5$ or —NR$^7$R$^8$,
  c) het,
  d) aryl,
  e) —NR$^7$R$^8$,
  f) OR$^5$, or
  h) halo;
R$^{14}$ is
  a) C$_{1-8}$ alkyl, or
  b) C$_{1-8}$ alkyl substituted with one to three —CN, halo, —NO$_2$, —C(=O)R$^5$, —COOR$^5$, het, aryl, —OR$^5$, or —NR$^7$R$^8$;
R$^{15}$ is
  a) —NH$_2$, or
  b) —NHNH$_2$;
R$^{16}$ and R$^{17}$ is independently
  a) H,
  b) C$_{1-4}$ alkyl,
  b) —C(=O)C$_{1-4}$ alkyl, or
  c) —C(=O)—(CH)$_m$-aryl;
aryl is phenyl or naphthyl, optionally substituted with R$^{18}$;
het is a 5-, 6- or 7-membered saturated or unsaturated heterocyclic ring having 1–3 heteroatoms selected from the group consisting of nitrogen, oxygen and sulfur, wherein the heteroclyclic ring is optionally fused to a benzene ring, wherein aryl, het and benzene ring are optionally substituted with R$^{18}$;
R$^{18}$ is
  a) halo,
  b) —NO$_2$,
  c) phenyl, optionally substituted with one to five —OH, —CN, halo, —NO$_2$, C$_{1-6}$ alkyl, het, or OC$_{1-4}$ alkyl,
  d) C$_{1-8}$ alkyl, optionally substituted with one to three halo, —CN, —NO$_2$, aryl, —SR$^5$, —OR$^5$ or —NR$^7$R$^8$,
  e) OR$^5$, or
  f) —SO$_2$NH$_2$;
M is sodium, potassium or lithium atom;
i is 1 or 2;
m is 0, 1, 2, or 4;
n is 1, 2, 3 or 4;
and with the following provisos:
(a) where R$^2$, R$^3$ and R$^4$ are each hydrogen, then R$^1$ is other than methoxy,
(b) where R$^4$ is Cl, and R$^2$ and R$^3$ are each hydrogen, then R$^1$ is other than methyl,
(c) where R$^1$ is hydrogen, R$^2$ and R$^4$ are each fluoro, R$^3$ is het, then het is other than substituted piperazinyl,
(d) where R$^1$ and R$^3$ are each hydrogen, R$^2$ is fluoro, then R$^4$ is other than fluoro,
(e) where R$^2$ and R$^4$ are each hydrogen, R$^1$ is fluoro, then R$^3$ is other than fluoro,
(f) where R$^1$ and R$^3$ are each hydrogen, R$^2$ is chloro, then R$^4$ is other than chloro,
(g) where R$^1$, R$^2$ and R$^3$ are each hydrogen, then R$^4$ is not bromo,
(h) where R$^1$, R$^3$ and R$^4$ are each hydrogen, then R$^2$ is not trifluoromethoxy,
(i) where R$^1$, R$^2$ and R$^4$ are each hydrogen, then R$^3$ is not trifluoromethoxy, and
(j) where R$^1$, R$^2$ and R$^3$ are each hydrogen, then R$^4$ is not morpholinyl.

In another aspect, the present invention also provides:
an antiviral pharmaceutical composition which comprises a pharmaceutically acceptable excipient and an effective amount of a compound of formula I,
a method of treating and preventing herpesviral infections in a mammal, including human, and a use of a compound of formula I to prepare a medicament for treating and preventing herpesviral infections in a mammal, including human.

DETAILED DESCRIPTION OF THE INVENTION

For the purpose of the present invention, the carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $(C_{1-3})$alkyl refers to alkyl of one to three carbon atoms, inclusive, or methyl, ethyl, propyl and isopropyl, straight and branched forms thereof.

The compounds of the present invention are named according to the IUPAC or CAS nomenclature system.

The term "$C_{1-8}$", "$C_{1-6}$" and "$C_{1-4}$" alkyl refer to an alkyl group having one to eight, one to six and one to four carbon atoms respectively such as, for example, methyl, ethyl, propyl, butyl, pentyl, hexyl, heptyl, octyl and their isomeric forms thereof.

The term "$C_{1-6}$ alkynyl" refers to at least one triple bond alkynyl group having two to six carbon atoms.

The term "$C_{1-6}$" alkenyl refers to at least one double bond alkenyl group having two to six carbon atoms.

The term "$C_{3-6}$ cycloalkyl" refers to a saturated or unsaturated ring having three to six atoms such as, for example, cyclopropyl, cyclobutyl, cyclopentyl, cyclohexyl and their isomeric forms thereof.

The term "$C_{1-4}$ alkoxy" refers to an alkyl group having one to four carbon atoms attached to an oxygen atom of a hydroxyl group such as, for example, methoxy, ethoxy, propyloxy, butyloxy and their isomeric forms thereof.

The term "aryl" refers to phenyl or naphthyl, which is optionally substituted with one to five appropriate substitutents.

The term "het" refers to a 5- or 6-membered saturated or unsaturated heterocyclic ring having 1–3 heteroatoms selected from the group consisting of nitrogen, oxygen and sulfur. The nitrogen atom may be in the protected form. The "het" is optionally substituted with one to three appropriate substitutents. Examples of "het" are thiadiazolyl, thiazolyl, benzothiazolyl, pyridinyl, morpholinyl, imidazolyl, indolyl, pyrrolyl, morpholinyl, thiophenyl and 2-oxo-oxazolyl,.

The term "halo" refers to fluoro, chloro, bromo or iodo.

Throughout this application, abbreviations which are well known to one of ordinary skill in the art may be used such as, for example, "Ph" for phenyl, "Me" for methyl, "Et" for ethyl, "h" for hour or hours and "rt" for room temperature.

Compounds of the present invention may be in a form of pharmaceutically acceptable salts.

"Pharmaceutically acceptable salts" refers to those salts which possess the biological effectiveness and properties of the parent compound and which are not biologically or otherwise undesirable.

"N-oxide" refers to the oxidized form of the nitrogen in the ring of the 4-hydroxy-quinoline compounds of the present invention. The preparation of such compounds is well known to one of ordinary skill in organic chemistry, including methods such as oxidation with metachloroperoxy-benzoic acid.

"Electron-withdrawing group" means any substituent on the ring which tends to draw electron density from the ring.

Examples of such groups include halogen, nitro, cyano, carboxylic acids, carboxylic esters, sulfoxides, sulfones, sulfonamides, ketones and aldehydes.

The compounds of the present invention may be alternatively designated by the tautomeric structure of formula II in which the variables are the same as defined in formula I.

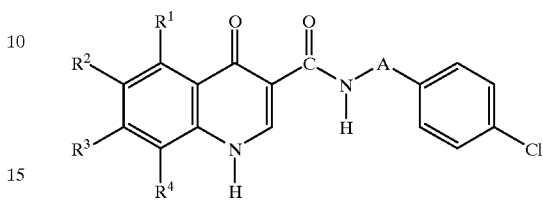

The following Charts A–V describe the preparation of the compounds of the present invention. All of the starting materials are prepared by procedures described in these charts or by procedures analogous thereto, which would be well known to one of ordinary skill in organic chemistry. All of the final compounds of the present invention are prepared by procedures described in these charts or by procedures analogous thereto, which would be well known to one of ordinary skill in organic chemistry. All of the variables used in the charts are as defined below or as in the claims.

In CHART A, the compounds of this invention can be prepared by one of several methods starting from appropriate 4-hydroxyquinoline-3-carboxylic esters a-1. In the first method A-1 the ester a-1 is suspended in 5–10 parts of an amine and the mixture is heated to 190–200° C. for a period of 30 min to 4 hours. The product a-2 is isolated by diluting the cooled reaction mixture with hexanes or toluene and collecting the solid precipitate by filtration. In some cases it is necessary to further purify this initial product by chromatography or by recrystallization from a suitable solvent mixture, typically acetic acid/water.

In a second method A-2, the ester a-1 is treated with two or more equivalents of the dimethylaluminum salt of an appropriate amine to produce the desired amide. The product a-2 is separated from aluminum salts which are present in the reaction mixture by treatment with hydrochloric acid, and it is further purified by recrystallization or chromatography. This latter method has the advantage that less heating of the reactants is required than in the first method, and it is consequently successful in some cases in which the first method is not applicable.

In the third method A-3, the ester a-1 is hydrolyzed to the corresponding carboxylic acid a-3 by the action of sodium or lithium hydroxide followed by neutralization. Carboxylic acid a-3 is then converted to the imidazolide a-4 by the action of 1,1'-carbonyldiimidazole. The imidazolide, which may be either isolated or used in situ, is converted to the desired amide a-2 by treatment with the requisite amine. The product is typically isolated from the reaction mixture by evaporation of the solvent followed by chromatography or recrystallization, or by precipitation of the product from the reaction mixture by dilution with several volumes of water.

In the fourth method A-4, the carboxylic acid a-3 is converted to the acid chloride a-5 by the action of thionyl chloride, and it is then converted to the desired amide a-2 in a manner similar to that described for the imidazolide a-4. The starting materials a-1 used in this chart are prepared by a well-known procedure, the reaction of an appropriately substituted aniline with diethyl ethoxymethylene malonate followed by pyrolysis of the resulting adduct (J. Amer. Chem. Soc., 68, 1264 (1946) and other references cited below).

Compounds of the present invention may also be prepared by following the procedures described in Chart B. This procedure is further detailed the Examples 38–47.

Compounds of the present invention may also be prepared by following the procedures described in Chart C. This procedure is futher detailed the Examples 48–49.

Compounds of the present invention may also be prepared by following the procedures described in Chart D. This procedure is futher detailed the Examples 54–55.

Compounds of the present invention may also be prepared by following the procedures described in Chart E. Condensation of the aniline of structure e-1 with diethylethoxyethylene malonate (neat, 140° C., 1.5 hours) gives an enamine intermediate. Addition of diphenyl ether to the reaction mixture containing this intermediate followed by heating to 250° C. for a 2 h affords the quinoline intermediate e-2. This ester is converted to the desired amide of formula e-3 by heating neat in p-chlorobenzyl amine at 190° C. for 1.5 hours.

Compounds of the present invention may also be prepared by following the procedures described in Chart F. Commercially available 2-fluoroaniline (f-1) is converted to the ethyl 8-fluoro-4-hydroxy-3-quinolinecarboxylate (f-2) by treatment with diethyl ethoxymethylenemalonate and heating at 135° C. for 1 hour, followed by dilution with diphenyl ether and heating at 260° C. for an additional 3 hour. The resulting ester is saponified with aqueous lithium hydroxide to afford acid f-3, which is then activated with 1,1'-carbonyldiimidazole to yield imidazolide f-4. Reaction with various amines affords the desired amides of formula f-5. The amides are prepared either as discrete analogues or as part of a parallel synthesis effort.

Compounds of the present invention may also be prepared by following the procedures described in Chart G. In CHART G, a solution of the compound g-1 and a primary amine are heated to 90° C. overnight to yield the compound g-2.

Compounds of the present invention may also be prepared by following the procedures described in Chart H. In CHART H, acetylenes h-2 are coupled to the iodoquinolines h-1 via palladium catalysis. The resulting quinolinyl-acetylenes h-3 are partially reduced by hydrogen over a poisoned palladium catalyst to give the cis-alkenes h-4. Alternatively, the quinolinyl-acetylenes h-3 are fully reduced by hydrogen and an active palladium catalyst to give the corresponding alkanes h-5.

Compounds of the present invention may also be prepared by following the procedures described in Chart I. In CHART I, heterocyclic substituted quinolines h-2 are prepared by a palladium catalyzed coupling of the corresponding tributylstannyl-heterocycle to the iodoquinoline h-1.

Compounds of the present invention may also be prepared by following the procedures described in Chart J. In CHART J, cyano-substituted quinolines j-2 are prepared from the iodoquinolines j-1 via a palladium catalyzed coupling of potassium cyanide. The cyanoquinolines j-2 are then treated with hydrogen sulfide to generate the corresponding thioamides j-3. The thioamides j-3 are versatile intermediates for the synthesis of various heterocycles. For example, treatment of the thioamide j-3 with bromoacetaldehyde diethyl acetal leads to the thiazole j-4. Alternatively, the thioamide j-3 is treated with methyl triflate, followed by hydrogen sulfide and hydrazine to yield the thiocarbonylhydrazide j-5. This also is a versatile intermediate for heterocycle synthesis. For example, treatment with acetyl chloride produces the methylthiadiazole j-6.

Compounds of the present invention may also be prepared by following the procedures described in Chart K. In CHART K, thiocyanates k-1 are prepared by electrophilic aromatic substitution reactions on anilines, using ammonium thiocyanate and bromine. Conversion of the thiocyanate to a benzyl sulfide is accomplished by alkaline hydrolysis followed by alkylation of the intermediate thiol with benzyl chloride, giving compounds k-2. Elaboration of the aniline to the 4-hydroxyquinoline ring system, represented by k-3, is accomplished by heating with diethyl ethoxymethylenemalonate, first at 130–150° C., then in refluxing diphenyl ether. Treatment of esters of k-3 with 4-chlorobenzylamine at elevated temperature effects aminolysis, leading to compounds of Formula k-4. Oxidation of the sulfide to sulfonyl choride is effected by treatment with chlorine in aqueous acetic acid. The resulting sulfonyl chlorides of Formula k-5 are transformed to sulfonamides k-6 by treatment with amines in pyridine solution.

Compounds of the present invention may also be prepared by following the procedures described in ChartL. In CHART L, compounds of l-1 are phosphitylated with di-tert-butyl diethyl phosphoramidite to give an intermediate phosphite, which is oxidized in situ with m-chloroperbenzoic acid to provide di-tert-butyl phosphates of l-2. Treatment of the phosphates with trifluoroacetic acid cleaves the tert-butyl groups, providing phosphoric acids of l-3. If the m-chloroperbenzoic acid oxidation step is omitted from the phosphitylation reaction, mono-tert-butyl phosphites of l-4 may be isolated. Treatment of these with trifluoroacetic acid provides phosphites of l-5.

Compounds of the present invention may also be prepared by following the procedures described in Chart M. In CHART M, alcohols of m-1 are coupled with suleptanic acid triethylammonium salt (triethylammonium 2-[(7-carboxyheptanoyl)-(methyl)amino]-1-ethanesulfonate), using diisopropylcarbodiimide and 4-dimethylaminopyridine, to provide the corresponding esters. Exchange of the triethylammonium salt with sodium ion affords sodium salts m-2.

Compounds of the present invention may also be prepared by following the procedures described in Chart N. In CHART N, alkylation of 3-mercaptoaniline with benzyl chloride and sodium hydride affords benzyl sulfide of n-1. Elaboration of the aniline to the 4-hydroxyquinoline ring system of n-2 is accomplished by heating with diethyl ethoxymethylenemalonate, first at 135° C., then in refluxing diphenyl ether. Treatment of ester n-2 with 4-chlorobenzylamine at elevated temperature effects aminolysis, leading to amide n-3. Oxidation of the sulfide to sulfonyl choride is effected by treatment with chlorine in aqueous acetic acid. The resulting sulfonyl chloride of Formula n-4 is transformed to sulfonamides n-5 by treatment with amines in pyridine solution.

Compounds of the present invention may also be prepared by following the procedures described in Chart O. In CHART O, intermediate o-2 is prepared by treating the phenol o-1 with chloroethanol and sodium hydroxide. Hydrogenation of o-2 in the presence of a palladium catalyst provides o-3, which upon stirring neat with diethyl ethoxymethylenemalonate provides the intermediate o-4. Selective acetylation of the hydroxyl group of o-4 with a mixture of acetic acid and acetic anhydride gives the intermediate o-5, which is cyclized in refluxing diphenyl ether to give the hydroxyquinoline o-6. Treating this compound with a benzylamine derivative at 190° C. gives the desired product o-7.

Compounds of the present invention may also be prepared by following the procedures described in Chart P. In CHART P, treating 4-cyanobenzyl bromide p-1 with sodium azide in dimethylformamide gives the benzylic azide p-2. This intermediate is reduced by the action of triphenylphosphine in wet tetrahydrofuran to give the desired amine p-3. The amine p-3 is used as the amine component in amide bond forming reactions such as those shown in Charts A, B, C, D, and F.

Compounds of the present invention may also be prepared by following the procedures described in Chart Q. In CHART Q, the aniline q-1 is treated with diethyl ethoxymethylenemalonate at 135° C. and the resulting adduct is heated in refluxing diphenyl ether to give the quinlone q-2. Treating q-2 with dithiothreitol gives the thiol q-3, which is alkylated with an appropriate alkyl halide to give q-4. Treating q-4 with 4-chlorobenzylamine at 190° C. gives the amide q-5. Treating this amide with a single equivalent of meta-chloroperbenzoic acid gives the sulfoxide q-7, whereas the use of two or more exquivalents gives the sulfone q-6.

Compounds of the present invention may also be prepared by following the procedures described in Chart R. In CHART R, N-[(4-Chlorophenyl)methyl]-8-fluoro-4-hydroxy-6-iodo-3-quinolinecarboxamide of r-1 is converted to the 6-carboxamide r-2 by treatment with palladium (II) acetate, 1,3-bis(diphenylphosphino)propane and various amines under a carbon monoxide atmosphere with heating.

Compounds of the present invention may also be prepared by following the procedures described in Chart S. In CHART S, N-[(4-Chlorophenyl)methyl]-8-fluoro-4-hydroxy-6-iodo-3-quinolinecarboxamide of s-1 is converted to the 6-carboxylic acid s-2 by treatment with palladium (II) acetate, 1,3-bis(diphenylphosphino)propane and water under a carbon monoxide atmosphere with heating. The acid s-2 is treated thionyl chloride to afford the acid chloride, then converted to the 6-carboxamide s-3 by treatment with p-chlorobenzylamine in pyridine.

Compounds of the present invention may also be prepared by following the procedures described in Chart T. In CHART T, 3-{[(4-Chlorobenzyl)amino]-carbonyl}-8-fluoro-4-hydroxy-6-quinolinecarboxylic acid of example t-1 is converted to the 6-tert-butyl carbamate t-2 by treatment with diphenylphosphoryl azide in tert-butanol with heating. The carbamate is removed with trifluoroacetic acid to afford the 6-aminoquinoline t-3. The amine is sulfonylated with 4-methoxyphenylsulfonyl chloride in pyridine to yield the 6-sulfonamide t-4.

Compounds of the present invention may also be prepared by following the procedures described in Chart U. In CHART U, 1-Fluoro-4-nitrobenzene u-1 is converted to 2-(4-nitroanilino)-1-ethanol u-2 (R=H) by heating with the ethanolamine in ethanol. 2-(4-nitroanilino)-1-ethanol u-2 is converted to 2-(4-nitroanilino)ethyl acetate u-3 by treatment with acetyl chloride. The nitro group is reduced to the free amine with palladium on carbon and hydrogen gas. The resulting aniline is treated with diethyl ethoxymethylenemalonate to give u-4. The enamine is cyclized by heating in diphenyl ether to give the quinoline u-5. Treatment with excess p-chlorobenzylamine affords the 3-carboxamide u-6.

Compounds of the present invention may also be prepared by following the procedures described in Chart V. In CHART V, 2-(4-nitroanilino)-1-ethanol v-1(R=H) is reduced with palladium on carbon and hydrogen gas. The resulting aniline is treated with diethyl ethoxymethylenemalonate to give v-2. Treatment with 1,1'-carbonyldiimidazole cyclizes v-2 to give v-3. The enamine is then cyclized by heating in diphenyl ether to give the quinoline v-4. Treatment with excess p-chlorobenzyl-amine affords the 3-carboxamide v-5.

It will be apparent to those skilled in the art that the described synthetic procedures are merely representative in nature and that alternative synthetic processes are known to one of ordinary skill in organic chemistry.

The examples of the present invention are:

(1) N-[(4-chlorophenyl)methyl]-4-hydroxy-7-(trifluoromethyl)-3-quinoline-carboxamide;

(2) 7-amino-N-[(4-chlorophenyl)methyl]-4-hydroxy-3-quinolinecarboxamide;

(3) N-[(4-chlorophenyl)methyl]-8-fluoro-4,6-dihydroxy-3-quinoline-carboxamide;

(4) 6-bromo-N-[(4-chlorophenyl)methyl]-8-fluoro-3-quinolinecarboxamide;

(5) N-[(4-chlorophenyl)methyl]-8-fluoro-4-hydroxy-6-iodo-3-quinolinecarboxamide;

(6) N-[(4-chlorophenyl)methyl]-4-hydroxy-3-quinolinecarboxamide;

(7) N-[(4-chlorophenyl)methyl]-4-hydroxy-7-methoxy-3-quinolinecarboxamide;

(8) N-[(4-chlorophenyl)methyl]-4-hydroxy-5,7-bis (trifluoromethyl)-3-quinoline-carboxamide;

(9) N-[(4-chlorophenyl)methyl]-7-fluoro-4-hydroxy-3-quinolinecarboxamide;

(10) N-[(4-chlorophenyl)methyl]-6-fluoro-4-hydroxy-3-quinolinecarboxamide;

(11) N-[(4-chlorophenyl)methyl]-4-hydroxy-7-methyl-3-quinolinecarboxamide;

(12) N-[(4-chlorophenyl)methyl]-8-fluoro-4-hydroxy-3-quinolinecarboxamide;

(13) N-[(4-chlorophenyl)methyl]-4-hydroxy-6-nitro-3-quinolinecarboxamide;

(14) N-[(4-chlorophenyl)methyl]-5,6,7,8-tetrafluoro-4-hydroxy-3-quinoline-carboxamide;

(15) N-[(4-chlorophenyl)methyl]-6,7,8-trifluoro-4-hydroxy-3-quinolinecarboxamide;

(16) 6,7,8-trifluoro-4-hydroxy-3-quinolinecarboxylic acid 2-(4-chloro-phenyl)hydrazide;

(17) N-[(4-chlorophenyl)methyl]-5,8-difluoro-4-hydroxy-3-quinolinecarboxamide;

(18) N-[(4-chlorophenyl)methyl]-7,8-difluoro-4-hydroxy-3-quinolinecarboxamide;

(19) 6-benzoyl-N-(4-chlorobenzyl)-4-hydroxy-3-quinolinecarboxamide;

(20) N-[(4-chlorophenyl)methyl]-4-hydroxy-8-methoxy-3-quinoline-carboxamide;

(21) 6-chloro-N-[(4-chlorophenyl)methyl]-4-hydroxy-3-quinolinecarboxamide;

(22) N-[(4-chlorophenyl)methyl]-4-hydroxy-6-methyl-3-quinolinecarboxamide;

(23) N-[(4-chlorophenyl)methyl]-4-hydroxy-6-methoxy-3-quinoline-carboxamide;

(24) N-[(4-chlorophenyl)methyl]-6-cyano-4-hydroxy-3-quinolinecarboxamide;

(25) 7-(acetylamino)-N-[(4-chlorophenyl)methyl]-4-hydroxy-3-quinoline-carboxamide;

(26) N-[(4-chlorophenyl)methyl]-4-hydroxy-7-[(methylsulfonyl)amino]-3-quinolinecarboxamide;

(27) N-[(4-chlorophenyl)methyl]-7-(dimethylamino)-4-hydroxy-3-quinoline-carboxamide;

(28) 6-amino-N-[(4-chlorophenyl)methyl]-4-hydroxy-3-quinolinecarboxamide;

(29) N-[(4-chlorophenyl)methyl]-4-hydroxy-6-[(methylsulfonyl)amino]-3-quinolinecarboxamide;

(30) N-[(4-chlorophenyl)methyl]-6-(dimethylamino)-4-hydroxy-3-quinoline-carboxamide;

(31) 6-(acetylamino)-N-[(4-chlorophenyl)methyl]-4-hydroxy-3-quinoline-carboxamide;

(32) N-[(4-chlorophenyl)methyl]-4-hydroxy-7-(1-pyrrolyl)-3-quinolinecarboxamide;

(33) N-[(4-chlorophenyl)methyl]-4-hydroxy-7-[(phenylsulfonyl)amino]-3-quinolinecarboxamide;

(34) N-[(4-chlorophenyl)methyl]-4-hydroxy-7-[[(phenylmethyl)sulfonyl]amino]-3-quinolinecarboxamide;

(35) N-[(4-chlorophenyl)methyl]-7-[[(4-chlorophenyl)sulfonyl]amino]-4-hydroxy-3-quinolinecarboxamide;

(36) 8-fluoro-4-hydroxy-3-quinolinecarboxylic acid 2-(4-chlorophenyl)hydrazide;

(37) N-[(4-chlorophenyl)methyl]-8-fluoro-4-hydroxy-6-methyl-3-quinoline-carboxamide;

(38) (278) N-(4-chlorobenzyl)-8-hydroxy[1,3]dioxolo[4,5-g]quinoline-7-carboxamide;

(39) N-[(4-chlorophenyl)methyl]-4-hydroxy-6-iodo-3-quinolinecarboxamide;

(40) N-[(4-chlorophenyl)methyl]-6-(cyanomethyl)-4-hydroxy-3-quinoline-carboxamide;

(41) N-[(4-chlorophenyl)methyl]-4,5-dihydroxy-3-quinolinecarboxamide;

(42) 7,8-dichloro-N-[(4-chlorophenyl)methyl]-4-hydroxy-3-quinolinecarboxamide;

(43) N-[(4-chlorophenyl)methyl]-4,6-dihydroxy-3-quinolinecarboxamide;

(44) N-[(4-chlorophenyl)methyl]-4,8-dihydroxy-3-quinolinecarboxamide;

(45) 8-chloro-N-[(4-chlorophenyl)methyl]-4-hydroxy-3-quinolinecarboxamide;

(46) N-[(4-chlorophenyl)methyl]-4-hydroxy-6-[[(1-phenyl-1H-pyrazol-5-yl)amino]sulfonyl]-3-quinolinecarboxamide;

(47) N-[(4-chlorophenyl)methyl]-8-cyano-4-hydroxy-3-quinolinecarboxamide;

(48) N-[(4-chlorophenyl)methyl]-4-hydroxy-8-nitro-3-quinolinecarboxamide;

(49) 7-amino-N-[(4-chlorophenyl)methyl]-4-hydroxy-8-methyl-3-quinoline-carboxamide;

(50) N-[(4-chlorophenyl)methyl]-6-cyano-8-fluoro-4-hydroxy-3-quinoline-carboxamide;

(51) 6-(aminothioxomethyl)-N-[(4-chlorophenyl)methyl]-8-fluoro-4-hydroxy-3-quinolinecarboxamide;

(52) N-[(4-chlorophenyl)methyl]-8-fluoro-4-hydroxy-6-(3-hydroxy-1-propynyl)-3-quinolinecarboxamide;

(53) 8-fluoro-4-hydroxy-6-iodo-3-quinolinecarboxylic acid 2-(4-chlorophenyl)-hydrazide;

(54) 8-fluoro-4-hydroxy-6-methyl-3-quinolinecarboxylic acid 2-(4-chlorophenyl)hydrazide;

(55) N-((4-chlorophenyl)methyl)-7-chloro-4-hydroxy-3-quinolinecarboxamide;

(56) N-((4-chlorophenyl)methyl)-6-bromo-4-hydroxy-3-quinolinecarboxamide;

(57) N-((4-chlorophenyl)methyl)-4-hydroxy-6-phenyl-3-quinolinecarboxamide;

(58) N-((4-chlorophenyl)methyl)-8-chloro-4-hydroxy-5-trifluoromethyl-3-quinolinecarboxamide;

(59) N-((4-chlorophenyl)methyl)-6,8-dimethoxy-4-hydroxy-3-quinoline-carboxamide;

(60) N-((4-chlorophenyl)methyl)-6,7-dimethoxy-4-hydroxy-3-quinoline-carboxamide;

(61) N-((4-chlorophenyl)methyl)-4-hydroxy-5-methyl-3-quinolinecarboxamide;

(62) N-[(4-chlorophenyl)methyl]-6-(1,1-dimethylethyl)-4-hydroxy-3-quinoline-carboxamide;

(63) N-[(4-chlorophenyl)methyl]-7,8-dihydro-4-hydroxy-6H-cyclopenta[g]quinoline-3-carboxamide;

(64) N-[(4-chlorophenyl)methyl]-1,4-dihydro-8-(methylthio)-4-oxo-3-quinoline-carboxamide;

(65) N-[(4-chlorophenyl)methyl]-9-hydroxythiazolo[5,4-fl quinoline-8 -carboxamide;

(66) sodium 2-[(8-{1[3-(3-{[(4-chlorobenzyl)amino]carbonyl}-4-hydroxy-6-quinolinyl)-2-propynyl]oxy}-8-oxooctanoyl)(methyl)amino]-1-ethanesulfonate;

(67) sodium 2-[(8-{[3-(3-{[(4-chlorobenzyl)amino]carbonyl}-8-fluoro-4-hydroxy-6-quinolinyl)-2-propynyl]oxy}-8-oxooctanoyl)(methyl)amino]-1-ethanesulfonate;

(68) sodium 2-[{8-[3-(3-{[(4-chlorobenzyl)amino]carbonyl]-4-hydroxy-6-quinolinyl)propoxy]-8-oxooctanoyl}(methyl)amino]-1-ethanesulfonate;

(69) N-(4-chlorobenzyl)-4-hydroxy-7-{[(1-naphthylmethyl)amino]sulfonyl}-3-quinolinecarboxamide;

(70) N-(4-chlorobenzyl)-4-hydroxy-7-(methylsulfanyl)-3-quinolinecarboxamide;

(71) N-[(4-chlorophenyl)methyl]-4-hydroxy-6-[(phenylmethyl)thio]-7-(trifluoro-methyl)-3-quinolinecarboxamide;

(72) 3-(3-{[(4-chlorobenzyl)amino]carbonyl}-4-hydroxy-6-quinolinyl)propyl hydrogen phosphonate;

(73) N-[(4-chlorophenyl)methyl]-8-fluoro-4-hydroxy-6-(2-thiazolyl)-3-quinoline-carboxamide;

(74) N-[(4-chlorophenyl)methyl]-8-fluoro-4-hydroxy-6-(2-thiophenyl)-3-quinolinecarboxamide;

(75) N-((4-chlorophenyl)methyl)-4-hydroxy-5-trifluoromethyl-3-quinoline-carboxamide;

(76) N-((4-chlorophenyl)methyl)-8-fluoro-4-hydroxy-6-(2-methylphenyl)-3-quinolinecarboxamide;

(77) N-((4-chlorophenyl)methyl)-6,7-difluoro-4-hydroxy-8-(tetrahydro-2H-pyran-4-oxy)-3-quinolinecarboxamide;

(78) N-((4-chlorophenyl)methyl)-6,7-difluoro-4-hydroxy-8-methoxy-3-quinolinecarboxamide;

(79) N-((4-chlorophenyl)methyl)-7,8-dimethoxy-6-fluoro-4-hydroxy-3-quinolinecarboxamide;

(80) N-((4-chlorophenyl)methyl)-6,8-difluoro-4-hydroxy-7-(4-(hydroxymethyl)-phenoxy)-3-quinolinecarboxamide;

(81) N-((4-chlorophenyl)methyl)-6,8-difluoro-4-hydroxy-7-methoxy-3-quinolinecarboxamide;

(82) N-((4-chlorophenyl)methyl)-6,8-difluoro-4-hydroxy-7-(2-(methoxy)ethoxy)-3-quinolinecarboxamide;

(83) N-((4-chlorophenyl)methyl)-6,7-difluoro-4-hydroxy-8-(2-(methoxy)ethoxy)-3-quinolinecarboxamide;

(84) N-((4-chlorophenyl)methyl)-7,8-di(2-(methoxy) ethoxy)-6-fluoro-4-hydroxy-3-quinolinecarboxamide;

(85) N-((4-chlorophenyl)methyl)-6,8-difluoro-4-hydroxy-7-(1-methylethoxy)-3-quinolinecarboxamide;

(86) N-(4-chlorobenzyl)-8-fluoro-4-hydroxy-6-(1,3-thiazol-2-yl)-3-quinoline-carboxamide;

(87) N-(4-chlorobenzyl)-6,8-difluoro-4-hydroxy-7-[(2-methoxyethyl)amino]-3-quinolinecarboxamide;

(88) N-(4-chlorobenzyl)-6-(5-cyano-1-pentynyl)-8-fluoro-4-hydroxy-3-quinoline-carboxamide;

(89) N-(4-chlorobenzyl)-8-fluoro-4-hydroxy-6-(2-pyridinyl)-3-quinolinecarboxamide;

(90) N'-(4-chlorophenyl)-4-hydroxy-6-iodo-3-quinolinecarbohydrazide;

(91) N-(4-chlorobenzyl)-8-fluoro-4-hydroxy-6-[2-(2-pyridinyl)ethynyl]-3-quinolinecarboxamide;

(92) N-(4-chlorobenzyl)-6,8-difluoro-4-hydroxy-7-[(2-hydroxyethyl)amino]-3-quinolinecarboxamide;

(93) N-(4-chlorobenzyl)-8-fluoro-4-hydroxy-6-(4-hydroxy-1-butynyl)-3-quinolinecarboxamide;

(94) N-(4-chlorobenzyl)-8-fluoro-4-hydroxy-6-(3-methoxy-1-propynyl)-3-quinolinecarboxamide;

(95) N-(4-chlorobenzyl)-8-fluoro-4-hydroxy-6-(3-hydroxy-1-butynyl)-3-quinolinecarboxamide;

(96) 6-(4-bromo-2-thienyl)-N-(4-chlorobenzyl)-8-fluoro-4-hydroxy-3-quinoline-carboxamide;

(97) N-(4-chlorobenzyl)-8-fluoro-6-(hydrazinocarbothioyl)-4-hydroxy-3-quinolinecarboxamide;

(98) N-(4-chlorobenzyl)-8-fluoro-4-hydroxy-6-(4-hydroxybutyl)-3-quinoline-carboxamide;

(99) N-(4-chlorobenzyl)-8-fluoro-4-hydroxy-6-(5-methyl-1,3,4-thiadiazol-2-yl)-3-quinolinecarboxamide;

(100) N-(4-chlorobenzyl)-4-hydroxy-7-(3-hydroxy-1-propynyl)-3-quinoline-carboxamide;

(101) 7-(aminocarbothioyl)-N-(4-chlorobenzyl)-4-hydroxy-3-quinolinecarboxamide;

(102) N-(4-chlorobenzyl)-8-fluoro-4-hydroxy-6-(3-methoxypropyl)-3-quinoline-carboxamide;

(103) N-(4-chlorobenzyl)-8-fluoro-4-hydroxy-6-[(Z)-4-hydroxy-1-butenyl]-3-quinolinecarboxamide;

(104) N-(4-chlorobenzyl)-6-(5-cyanopentyl)-8-fluoro-4-hydroxy-3-quinoline-carboxamide;

(105) N-(4-chlorobenzyl)-8-fluoro-4-hydroxy-6-(3-hydroxy-3-methylbutyl)-3-quinolinecarboxamide;

(106) N-(4-chlorobenzyl)-8-fluoro-4-hydroxy-6-(5-hydroxy-1-pentynyl)-3-quinolinecarboxamide;

(107) 6-{3-[benzyl(methyl)amino]propyl}-N-(4-chlorobenzyl)-8-fluoro-4-hydroxy-3-quinolinecarboxamide;

(108) methyl 3-{[(4-chlorobenzyl)amino]carbonyl}-8-fluoro-4-hydroxy-6-quinolinecarboxylate;

(109) N-(4-chlorobenzyl)-8-fluoro-4-hydroxy-6-(3-hydroxypropyl)-3-quinoline-carboxamide;

(110) N-(4-chlorobenzyl)-4-hydroxy-7-(3-hydroxypropyl)-3-quinoline-carboxamide;

(111) ethyl (E)-3-(3-{[(4-chlorobenzyl)amino]carbonyl}-8-fluoro-4-hydroxy-6-quinolinyl)-2-propenoate;

(112) sodium 2-[{(8-[3-(3-{[(4-chlorobenzyl)amino] carbonyl}-8-fluoro-4-hydroxy-6-quinolinyl)propoxy]-8-oxooctanoy}(methyl)amino]-1-ethanesulfonate;

(113) 3-(3-{[(4-chlorobenzyl)amino]carbonyl}-8-fluoro-4-hydroxy-6-quinolinyl)-propanoic acid;

(114) 5-(3-{[(4-chlorobenzyl)amino]carbonyl}-8-fluoro-4-hydroxy-6-quinolinyl)-4-pentynoic acid;

(115) N-[(4-chlorophenyl)methyl]-9]hydroxy-3H-pyrazolo[4,3-f]quinoline-8-carboxamide;

(116) N-(4-chlorobenzyl)-4-hydroxy-6-iodo-8-methoxy-3-quinolinecarboxamide;

(117) N-(4-chlorobenzyl)-4-hydroxy-6-(3-hydroxy-1-propynyl)-8-methoxy-3-quinolinecarboxamide;

(118) N-(4-chlorobenzyl)-4-hydroxy-8-methoxy-6-(3-methoxy-1-propynyl)-3-quinolinecarboxamide;

(119) N-(4-chlorobenzyl)-4-hydroxy-6-(3-hydroxypropyl)-8-methoxy-3-quinolinecarboxamide;

(120) N-(4-chlorobenzyl)-4-hydroxy-6-(3-hydroxy-1-propynyl)-8-(trifluoromethyl)-3-quinolinecarboxamide;

(121) N-(4-chlorobenzyl)-4-hydroxy-6-(3-hydroxy-1-propynyl)-8-(trifluoromethoxy)-3-quinolinecarboxamide;

(122) N-(4-chlorobenzyl)-4-hydroxy-6-(3-hydroxypropyl)-8-(trifluoromethyl)-3-quinolinecarboxamide;

(123) N-(4-chlorobenzyl)-4-hydroxy-8-(2-hydroxyethoxy)-6-(3-hydroxypropyl)-3-quinolinecarboxamide;

(124) N-(4-chlorobenzyl)-4-hydroxy-6-(3-hydroxy-1,1-dimethylpropyl)-3-quinolinecarboxamide;

(125) N-(4-chlorobenzyl)-8-fluoro-4-hydroxy-6-[3-(methylsulfanyl)-1-propynyl]-3-quinolinecarboxamide;

(126) N-(4-chlorobenzyl)-6-[3-(ethylsulfanyl)-1-propynyl]-8-fluoro-4-hydroxy-3-quinolinecarboxamide;

(127) N-(4-chlorobenzyl)-8-fluoro-4-hydroxy-6-[(Z)-3-(methylsulfanyl)-1-propenyl]-3-quinolinecarboxamide;

(128) N-(4-chlorobenzyl)-6-[(Z)-3-(ethylsulfanyl)-1-propenyl]-8-fluoro-4-hydroxy-3-quinolinecarboxamide;

(129) N-(4-chlorobenzyl)-8-fluoro-4-hydroxy-6-[3-(methylsulfanyl)propyl]-3-quinolinecarboxamide;

(130) 3-(3-{[(4-chlorobenzyl)amino]carbonyl}-8-fluoro-4-hydroxy-6-quinolinyl)-2-propynyl formate;

(131) N-(4-chlorobenzyl)-8-fluoro-4-hydroxy-6-(3-hydroxybutyl)-3-quinolinecarboxamide;

(132) N-(4-chlorobenzyl)-6-[(E)-2-cyanoethenyl]-8-fluoro-4-hydroxy-3-quinolinecarboxamide;

(133) N-(4-chlorobenzyl)-4-hydroxy-6-(3-hydroxy-1-propynyl)-3-quinolinecarboxamide;

(134) N-(4-chlorobenzyl)-6-[(Z)-3-hydroxy-1-propenyl]-4-oxo-1,4-dihydro-3-quinolinecarboxamide;

(135) N-(4-chlorobenzyl)-6-[(E)-3-hydroxy-1-propenyl]-4-oxo-1,4-dihydro-3-quinolinecarboxamide;

(136) N-(4-chlorobenzyl)-8-fluoro-4-hydroxy-6-[(Z)-3-hydroxy-1-propenyl]-3-quinolinecarboxamide;

(137) N-(4-chlorobenzyl)-6-(2-cyanoethyl)-8-fluoro-4-hydroxy-3-quinolinecarboxamide;

(138) N-(4-chlorobenzyl)-8-fluoro-4-hydroxy-6-(3-oxopropyl)-3 -quinolinecarboxamide;

(139) N-(4-chlorobenzyl)-4-hydroxy-7-(4-hydroxybutyl)-3-quinolinecarboxamide;

(140) N-(4-chlorobenzyl)-8-fluoro-4-hydroxy-6-(hydroxymethyl)-3-quinolinecarboxamide;

(141) 3-(3-{[(4-chlorobenzyl)amino]carbonyl}-8-fluoro-4-hydroxy-6-quinolinyl)propyl methanesulfonate;

(142) N-(4-chlorobenzyl)-8-fluoro-6-(3-fluoro-1-propynyl)-4-hydroxy-3-quinolinecarboxamide;

(143) N-(4-chlorobenzyl)-4-hydroxy-6-(3-hydroxypropyl)-3-quinolinecarboxamide;

(144) 3-(3-{[(4-chlorobenzyl)amino]carbonyl}-8-fluoro-4-hydroxy-6-quinolinyl)propyl 2-bromoacetate;

(145) 3-(3-{[(4-chlorobenzyl)amino]carbonyl}-8-fluoro-4-hydroxy-6-quinolinyl)propyl 2-[(tert-butoxycarbonyl)amino]-3-methylbutanoate;

(146) 3-(3-{[(4-chlorobenzyl)amino]carbonyl}-8-fluoro-4-hydroxy-6-quinolinyl)propyl 2-(4-morpholinyl)acetate;

(147) 3-(3-{[(4-chlorobenzyl)amino]carbonyl}-8-fluoro-4-hydroxy-6-quinolinyl)propyl 2-(dimethylamino)acetate;

(148) 3-(3-{[(4-chlorobenzyl)amino]carbonyl}-8-fluoro-4-hydroxy-6-quinolinyl)propyl 2-amino-3-methylbutanoate;

(149) 3-(3-{[(4-chlorobenzyl)amino]carbonyl-8-fluoro-4-hydroxy-6-quinolinyl)-2-propynyl phenylcarbamate;

(150) N-(4-chlorobenzyl)-4-hydroxy-6-propyl-3-quinolinecarboxamide;

(151) N-(4-chlorobenzyl)-4-hydroxy-6-(3-hydroxy-1-butynyl)-3-quinolinecarboxamide;

(152) N-(4-chlorobenzyl)-8-fluoro-4-hydroxy-6-[(E)-3-oxo-1-butenyl]-3-quinolinecarboxamide;

(153) N-(4-chlorobenzyl)-8-fluoro-4-hydroxy-6-(5-hydroxypentyl)-3-quinolinecarboxamide;

(154) 3-(3-{[(4-chlorobenzyl)amino]carbonyl}-8-fluoro-4-hydroxy-6-quinolinyl)propyl 2,6-bis[(tert-butoxycarbonyl)amino]hexanoate;

(155) 3-(3-{[(4-chlorobenzyl)amino]carbonyl}-8-fluoro-4-hydroxy-6-quinolinyl)propyl 2,6-diaminohexanoate, trifluoroacetic acid salt;

(156) N-(4-chlorobenzyl)-4-hydroxy-6-(3-hydroxybutyl)-3-quinolinecarboxamide;

(157) N-(4-chlorobenzyl)-8-fluoro-4-hydroxy-6-(4-morpholinylmethyl)-3-quinolinecarboxamide;

(158) 3-(3-{[(4-chlorobenzyl)amino]carbonyl}-8-fluoro-4-hydroxy-6-quinolinyl)propyl phenylcarbamate;

(159) N-(4-chlorobenzyl)-8-fluoro-4-hydroxy-6-(3-oxobutyl)-3-quinolinecarboxamide;

(160) 3-(3-{[(4-chlorobenzyl)amino]carbonyl}-4-hydroxy-6-quinolinyl)-2-propynyl 2,6-bis[(tert-butoxycarbonyl)amino]hexanoate;

(161) 3-(3-[(4-chlorobenzyl)amino]carbonyl)-4-hydroxy-6-quinolinyl)-2-propynyl 2,6-diaminohexanoate, trifluoroacetic acid salt;

(162) N-(4-chlorobenzyl)-4-hydroxy-6-[(2-hydroxyethoxy)methyl]-3-quinolinecarboxamide;

(163) N-(4-chlorobenzyl)-4-hydroxy-6-{[2-hydroxy-1-(hydroxymethyl)ethoxy]methyl}-3-quinolinecarboxamide;

(164) Methyl 3-{[(4-chlorobenzyl)amino]carbonyl}-4-hydroxy-6-quinolinecarboxylate;

(165) N-(4-chlorobenzyl)-4-hydroxy-6-(hydroxymethyl)-3-quinolinecarboxamide;

(166) 6-chloro-N-(4-chlorobenzyl)-4-hydroxy-8-methyl-3-quinolinecarboxamide;

(167) N-(4-chlorobenzyl)-5,6,8-trifluoro-4-hydroxy-3-quinolinecarboxamide;

(168) N-(4-chlorobenzyl)-6,7-difluoro-4-hydroxy-3-quinolinecarboxamide;

(169) N-(4-chlorobenzyl)-8-fluoro-4-hydroxy-6-(methylsulfanyl)-3-quinolinecarboxamide;

(170) N-(4-chlorobenzyl)-8-fluoro-4-hydroxy-6-[(2-hydroxyethyl)sulfanyl]-3-quinolinecarboxamide;

(171) 6-[(2-aminoethyl)sulfanyl]-N-(4-chlorobenzyl)-8-fluoro-4-hydroxy-3-quinolinecarboxamide hydrobromide;

(172) N-(4-chlorobenzyl)-8-fluoro-4-hydroxy-6-{[(2-methoxyethoxy)methyl]sulfanyl}-3-quinolinecarboxamide;

(173) N-(4-chlorobenzyl)-8-fluoro-4-hydroxy-6-{[2-(4-morpholinyl)ethyl]sulfanyl}-3-quinolinecarboxamide;

(174) N-(4-chlorobenzyl)-8-fluoro-4-hydroxy-6-(methylsulfinyl)-3-quinolinecarboxamide;

(175) N-(4-chlorobenzyl)-8-fluoro-4-hydroxy-6-(methylsulfonyl)-3-quinolinecarboxamide;

(176) N-(4-chlorobenzyl)-8-fluoro-4-hydroxy-6-[(2-hydroxyethyl)sulfinyl]-3-quinolinecarboxamide;

(177) N-(4-chlorobenzyl)-4-hydroxy-6-(2-thienyl)-3-quinolinecarboxamide;

(178) N-(4-chlorobenzyl)-4-hydroxy-6-(2-hydroxyethoxy)-3-quinolinecarboxamide;

(179) N-(4-chlorobenzyl)-8-fluoro-4-hydroxy-6-(4-morpholinylcarbonyl)-3-quinolinecarboxamide;

(180) $N^3$-(4-chlorobenzyl)-8-fluoro-4-hydroxy-$N^6$-(2-hydroxyethyl)-3,6-quinolinedicarboxamide;

(181) $N^3$-(4-chlorobenzyl)-8-fluoro-4-hydroxy-$N^6$,N~6~-dimethyl-3,6-quinolinedicarboxamide;

(182) $N^3$-(4-chlorobenzyl)-8-fluoro-4-hydroxy-$N^6$-(4-hydroxyphenethyl)-3,6-quinolinedicarboxamide;

(183) $N^3$-(4-chlorobenzyl)-8-fluoro-4-hydroxy-3,6-quinolinedicarboxamide;

(184) $N^3$,$N^6$-bis(4-chlorobenzyl)-8-fluoro-4-hydroxy-3,6-quinolinedicarboxamide;

(185) 6-amino-N-(4-chlorobenzyl)-8-fluoro-4-hydroxy-3-quinolinecarboxamide;

(186) N-(4-chlorobenzyl)-8-fluoro-4-hydroxy-6-{[(4-methoxyphenyl)sulfonyl]amino}-3-quinolinecarboxamide;

(187) N-(4-chlorobenzyl)-4-hydroxy-6-[(2-hydroxyethyl)amino]-3-quinolinecarboxamide;

(188) N-(4-chlorobenzyl)-6-[ethyl(2-hydroxyethyl)amino]-4-hydroxy-3-quinolinecarboxamide;

(189) N-(4-chlorobenzyl)-4-hydroxy-6-(2-oxo-1,3-oxazolidin-3-yl)-3-quinolinecarboxamide;

(190) N-(4-chlorobenzyl)-4-hydroxy-6-(4-morpholinylmethyl)-3-quinolinecarboxamide;

(191) N-(4-chlorobenzyl)-8-fluoro-4-hydroxy-6-{[(1-naphthylmethyl)amino]sulfonyl}-3-quinolinecarboxamide;

(192) N-(4-chlorobenzyl)-8-fluoro-4-hydroxy-6-({[2-(1H-indol-3-yl)ethyl]amino}sulfonyl)-3-quinolinecarboxamide;

(193) N-(4-chlorobenzyl)-8-fluoro-6-{[(2-furylmethyl)amino]sulfonyl}-4-hydroxy-3-quinolinecarboxamide;

(194) 6-{[bis(2-hydroxyethyl)amino]sulfonyl}-N-(4-chlorobenzyl)-8-fluoro-4-hydroxy-3-quinolinecarboxamide;

(195) ethyl 2-{[(3-{[(4-chlorobenzyl)amino]carbonyl}-8-fluoro-4-hydroxy-6-quinolinyl)sulfonyl]amino}acetate;

(196) N-(4-chlorobenzyl)-8-fluoro-4-hydroxy-6-{[(2-hydroxyethyl)amino]sulfonyl}-3-quinolinecarboxamide;

(197) N-(4-chlorobenzyl)-8-fluoro-4-hydroxy-6-(4-morpholinylsulfonyl)-3-quinolinecarboxamide;

(198) N-(4-chlorobenzyl)-8-fluoro-4-hydroxy-6-{[(2-pyridinylmethyl)amino]sulfonyl)-3-quinolinecarboxamide;

(199) N-(4-chlorobenzyl)-8-fluoro-4-hydroxy-6-[(2-pyridinylamino)sulfonyl]-3-quinolinecarboxamide;

(200) N-(4-chlorobenzyl)-6-{[(cyclohexylmethyl)amino]sulfonyl}-8-fluoro-4-hydroxy-3-quinolinecarboxamide;

(201) N-(4-chlorobenzyl)-8-fluoro-4-hydroxy-6-({[2-(1-methyl-2-pyrrolidinyl)ethyl]amino)sulfonyl)-3-quinolinecarboxamide;

(202) N-(4-chlorobenzyl)-8-fluoro-4-hydroxy-6-({[2-(1-pyrrolidinyl)ethyl]amino}sulfonyl)-3-quinolinecarboxamide;

(203) N-(4-chlorobenzyl)-8-fluoro-6-{[(2-furylmethyl)amino]sulfonyl}-4-hydroxy-3-quinolinecarboxamide;

(204) N-(4-chlorobenzyl)-6-({[3-(cyclohexylamino)propylrlamino}sulfonyl)-8-fluoro-4-hydroxy-3-quinolinecarboxamide;

(205) N-(4-chlorobenzyl)-8-fluoro-4-hydroxy-6-([(1-naphthylmethyl)amino]sulfonyl}-3-quinolinecarboxamide;

(206) N-(4-chlorobenzyl)-8-fluoro-4-hydroxy-6-({[2-(1H-imidazol-4-yl)ethyl]amino}-sulfonyl)-3-quinolinecarboxamide;

(207) N-(4-chlorobenzyl)-8-fluoro-4-hydroxy-6-{[(tetrahydro-2-furanylmethyl)amino]-sulfonyl}-3-quinolinecarboxamide;

(208) N-(4-chlorobenzyl)-8-fluoro-4-hydroxy-6-{[(2-thienylmethyl)amino]sulfonyl}-3-quinolinecarboxamide;

(209) N-(4-chlorobenzyl)-8-fluoro-4-hydroxy-6-({[2-(1H-indol-3-yl)ethyl]amino)sulfonyl)-3-quinolinecarboxamide;

(210) N-(4-chlorobenzyl)-8-fluoro-4-hydroxy-6-({[2-(5-methoxy-1H-indol-3-yl)ethyl]amino}sulfonyl)-3-quinolinecarboxamide;

(211) 6-{[(1,3-benzodioxol-5-ylmethyl)amino]sulfonyl}-N-(4-chlorobenzyl)-8-fluoro-4-hydroxy-3-quinolinecarboxamide;

(212) N-(4-chlorobenzyl)-8-fluoro-4-hydroxy-6-({[2-(4-morpholinyl)ethyl]amino}-sulfonyl)-3-quinolinecarboxamide;

(213) N-(4-chlorobenzyl)-8-fluoro-4-hydroxy-6-({[3-(4-morpholinyl)propyl]amino}-sulfonyl)-3-quinolinecarboxamide;

(214) N-(4-chlorobenzyl)-8-fluoro-4-hydroxy-6-[({2-[(5-nitro-2-pyridinyl)amino]ethyl}-amino)sulfonyl]-3-quinolinecarboxamide;

(215) N-(4-chlorobenzyl)-8-fluoro-4-hydroxy-6-{[(2-pyridinylmethyl)amino]sulfonyl}-3-quinolinecarboxamide;

(216) N-(4-chlorobenzyl)-8-fluoro-4-hydroxy-6-({[2-(2-pyridinyl)ethyl]amino)sulfonyl)-3-quinolinecarboxamide;

(217) N-(4-chlorobenzyl)-8-fluoro-4-hydroxy-6-{[(3-pyridinylmethyl)amino]sulfonyl}-3-quinolinecarboxamide;

(218) N-(4-chlorobenzyl)-8-fluoro-4-hydroxy-6-{[(4-pyridinylmethyl)amino]sulfonyl}-3-quinolinecarboxamide;

(219) N-(4-chlorobenzyl)-6-{[(4-chlorobenzyl)amino]sulfonyl}-8-fluoro-4-hydroxy-3-quinolinecarboxamide;

(220) N-(4-chlorobenzyl)-8-fluoro-4-hydroxy-6-{[(4-methoxybenzyl)amino]sulfonyl}-3-quinolinecarboxamide;

(221) N-(4-chlorobenzyl)-8-fluoro-4-hydroxy-6-[(neopentylamino)sulfonyl]-3-quinolinecarboxamide;

(222) N-(4-chlorobenzyl)-8-fluoro-4-hydroxy-6-{[(2-hydroxypropyl)amino]sulfonyl}-3-quinolinecarboxamide;

(223) N-(4-chlorobenzyl)-6-{[(2,3-dihydroxypropyl)amino]sulfonyl}-8-fluoro-4-hydroxy-3-quinolinecarboxamide;

(224) N-(4-chlorobenzyl)-6-{[(2,2-diphenylethyl)amino]sulfonyl}-8-fluoro-4-hydroxy-3-quinolinecarboxamide;

(225) 11-{[(3-{[(4-chlorobenzyl)amino]carbonyl}-8-fluoro-4-hydroxy-6-quinolinyl)sulfonyl]amino}undecanoic acid;

(226) 6-({[2-(acetylamino)ethyl]amino}sulfonyl)-N-(4-chlorobenzyl)-8-fluoro-4-hydroxy-3-quinolinecarboxamide;

(227) N-(4-chlorobenzyl)-8-fluoro-4-hydroxy-6-({[2-(2-hydroxyethoxy)ethyl]amino}-sulfonyl)-3-quinolinecarboxamide;

(228) N-(4-chlorobenzyl)-8-fluoro-4-hydroxy-6-{[(2-hydroxyethyl)amino]sulfonyl}-3-quinolinecarboxamide;

(229) N-(4-chlorobenzyl)-8-fluoro-4-hydroxy-6-[(phenethylamino)sulfonyl]-3-quinolinecarboxamide;

(230) N-(4-chlorobenzyl)-6-{[(4-chlorophenethyl)amino]sulfonyl}-8-fluoro-4-hydroxy-3-quinolinecarboxamide;

(231) N-(4-chlorobenzyl)-8-fluoro-4-hydroxy-6-[(2-propynylamino)sulfonyl]-3-quinolinecarboxamide;

(232) N-(4-chlorobenzyl)-8-fluoro-4-hydroxy-6-[(isopentylamino)sulfonyl]-3-quinolinecarboxamide;

(233) N-(4-chlorobenzyl)-8-fluoro-4-hydroxy-6-{[(3-phenylpropyl)amino]sulfonyl}-3-quinolinecarboxamide;

(234) N-(4-chlorobenzyl)-8-fluoro-4-hydroxy-6-[(pentylamino)sulfonyl]-3-quinolinecarboxamide;

(235) 6-({[3,5-bis(trifluoromethyl)benzyl]amino}sulfonyl)-N-(4-chlorobenzyl)-8-fluoro-4-hydroxy-3-quinolinecarboxamide;

(236) N-(4-chlorobenzyl)-6-({[2-(1-cyclohexen-1-yl)ethyl]amino}sulfonyl)-8-fluoro-4-hydroxy-3-quinolinecarboxamide;

(237) N-(4-chlorobenzyl)-8-fluoro-4-hydroxy-6-({[2-(1-naphthylamino)ethyl]amino}-sulfonyl)-3-quinolinecarboxamide;

(238) N-(4-chlorobenzyl)-8-fluoro-4-hydroxy-6-[(methylamino)sulfonyl]-3-quinolinecarboxamide;

(239) N-(4-chlorobenzyl)-6-{[(cyanomethyl)amino]sulfonyl}-8-fluoro-4-hydroxy-3-quinolinecarboxamide;

(240) N-(4-chlorobenzyl)-6-{[(2,4-dimethoxybenzyl) amino]sulfonyl}-8-fluoro-4-hydroxy-3-quinolinecarboxamide;

(241) N-(4-chlorobenzyl)-8-fluoro-4-hydroxy-6-{[(3-iodobenzyl)amino]sulfonyl}-3-quinolinecarboxamide;

(242) N-(4-chlorobenzyl)-8-fluoro-4-hydroxy-6-{[(2,2,2-trifluoroethyl)amino]sulfonyl}-3-quinolinecarboxamide;

(243) 6-{[(2-bromoethyl)amino]sulfonyl}-N-(4-chlorobenzyl)-8-fluoro-4-hydroxy-3-quinolinecarboxamide;

(244) N-(4-chlorobenzyl)-6-{[(2-chloroethyl)amino]sulfonyl}-8-fluoro-4-hydroxy-3-quinolinecarboxamide;

(245) N-(4-chlorobenzyl)-6-{[(3,4-dihydroxyphenethyl)amino]sulfonyl}-8-fluoro-4-hydroxy-3-quinolinecarboxamide;

(246) N-(4-chlorobenzyl)-6-({[2-(ethylsulfanyl)ethyl]amino)sulfonyl)-8-fluoro-4-hydroxy-3-quinolinecarboxamide;

(247) 6-{[(3-bromopropyl)amino]sulfonyl}-N-(4-chlorobenzyl)-8-fluoro-4-hydroxy-3-quinolinecarboxamide;

(248) 6-({[4-(aminosulfonyl)benzyl]amino}sulfonyl)-N-(4-chlorobenzyl)-8-fluoro-4-hydroxy-3-quinolinecarboxamide;

(249) 6-[({2-[bis(2-hydroxyethyl)amino]ethyl}amino) sulfonyl]-N-(4 -chlorobenzyl)-8-fluoro-4-hydroxy-3-quinolinecarboxamide;

(250) N-(4-chlorobenzyl)-6-({[2-(ethylsulfanyl)ethyl]amino}sulfonyl)-8-fluoro-4-hydroxy-3-quinolinecarboxamide;

(251) N-(4-chlorobenzyl)-6-{[(3,4-dimethylbenzyl)amino]sulfonyl}-8-fluoro-4-hydroxy-3-quinolinecarboxamide;

(252) N-(4-chlorobenzyl)-6-{[(cyclopropylmethyl)amino]sulfonyl}-8-fluoro-4-hydroxy-3-quinolinecarboxamide;

(253) 6-{[(4-bromobenzyl)amino]sulfonyl}-N-(4-chlorobenzyl)-8-fluoro-4-hydroxy-3-quinolinecarboxamide;

(254) N-(4-chlorobenzyl)-8-fluoro-4-hydroxy-6-({[2-(2-thienyl)ethyl]amino}sulfonyl)-3-quinolinecarboxamide;

(255) N-(4-chlorobenzyl)-8-fluoro-4-hydroxy-6-{[(2-phenoxyethyl)amino]sulfonyl}-3-quinolinecarboxamide;

(256) tert-butyl 2-{[(3-{[(4-chlorobenzyl)amino]carbonyl}-8-fluoro-4-hydroxy-6-quinolinyl)sulfonyl]amino}acetate;

(257) tert-butyl 3-{[(3-{[(4-chlorobenzyl)amino]carbonyl}-8-fluoro-4-hydroxy-6-quinolinyl)sulfonyl]amino}propanoate;

(258) N-(4-chlorobenzyl)-8-fluoro-4-hydroxy-6-({[3-(trifluoromethoxy)benzyl]amino}-sulfonyl)-3-quinolinecarboxamide;

(259) N-(4-chlorobenzyl)-8-fluoro-4-hydroxy-6-{[(2-{[2-(hydroxymethyl)phenyl]sulfanyl}-benzyl)amino] sulfonyl}-3-quinolinecarboxamide;

(260) N-(4-chlorobenzyl)-8-fluoro-4-hydroxy-6-({[4-(1,2,3-thiadiazol-4-yl)benzyl]amino}sulfonyl)-3-quinolinecarboxamide;

(261) N-(4-chlorobenzyl)-6-{[(4-chloro-2-fluorobenzyl) amino]sulfonyl}-8-fluoro-4-hydroxy-3-quinolinecarboxamide;

(262) N-(4-chlorobenzyl)-8-fluoro-4-hydroxy-6-[({2-[(2-hydroxyethyl)sulfanyl]ethyl }-amino)sulfonyl]-3-quinolinecarboxamide (263) 6-{[(2-amino-2-methylpropyl)amino]sulfonyl}-N-(4-chlorobenzyl)-8-fluoro-4-hydroxy-3-quinolinecarboxamide;

(264) 6-{[(2-amino-2-oxoethyl)amino]sulfonyl}-N-(4-chlorobenzyl)-8-fluoro-4-hydroxy-3-quinolinecarboxamide;

(265) 6-{[(4-aminobenzyl)amino]sulfonyl}-N-(4-chlorobenzyl)-8-fluoro-4-hydroxy-3-quinolinecarboxamide;

(266) di(tert-butyl) 3-(3-{[(4-chlorobenzyl)amino]carbonyl}-8-fluoro-4-hydroxy-6-quinolinyl)propyl phosphate;

(267) 3-(3-{[(4-chlorobenzyl)amino]carbonyl}-8-fluoro-4-hydroxy-6 -quinolinyl)propyl dihydrogen phosphate;

(268) 3-(3-{[(4-chlorobenzyl)amino]carbonyl}-4-hydroxy-6-quinolinyl)propyl dihydrogen phosphate;

(269) tert-butyl 3-(3-{[(4-chlorobenzyl)amino]carbonyl}-4-hydroxy-6-quinolinyl)propyl phosphonate;

(270) tert-butyl 3-(3-{[(4-chlorobenzyl)amino]carbonyl}-8-fluoro-4-hydroxy-6-quinolinyl)propyl phosphonate;

(271) (E)-3-(3-{[(4-chlorobenzyl)amino]carbonyl}-8-fluoro-4-hydroxy-6-quinolinyl)-2-propenoic acid; or (272) N-[(4-chlorophenyl)methyl]-4-hydroxy-7-iodo-3-quinolinecarboamide.

The preferred compounds of the present invention are:

(1) 7-amino-N-(4-chlorobenzyl)-4-hydroxy-3-quinolinecarboxamide;

(2) N-(4-chlorobenzyl)-4-hydroxy-7-methoxy-3-quinolinecarboxamide;

(3) N-(4-chlorobenzyl)-7-fluoro-4-hydroxy-3-quinolinecarboxamide;

(4) N-(4-chlorobenzyl)-8-fluoro-4-hydroxy-3-quinolinecarboxamide;

(5) 6-chloro-N-(4-chlorobenzyl)-4-hydroxy-3-quinolinecarboxamide;

(6) N-(4-chlorobenzyl)-4-hydroxy-6-methyl-3-quinolinecarboxamide;

(7) N-(4-chlorobenzyl)-4-hydroxy-6-methoxy-3-quinolinecarboxamide;

(8) N-(4-chlorobenzyl)-8-fluoro-4-hydroxy-6-methyl-3-quinolinecarboxamide;

(9) N-(4-chlorobenzyl)-4-hydroxy-6-iodo-3-quinolinecarboxamide;

(10) N-(4-chlorobenzyl)-4-hydroxy-6-phenyl-3-quinolinecarboxamide;

(11) N-(4-chlorobenzyl)-4-hydroxy-6,8-dimethoxy-3-quinolinecarboxamide;

(12) 6-(tert-butyl)-N-(4-chlorobenzyl)-4-hydroxy-3-quinolinecarboxamide;

(13) N-(4-chlorobenzyl)-6-(cyanomethyl)-4-hydroxy-3-quinolinecarboxamide;

(14) N-(4-chlorobenzyl)-9-hydroxy [1,3]thiazolo[5,4-f] quinoline-8-carboxamide;

(15) N-(4-chlorobenzyl)-8-fluoro-4-hydroxy-6-(3-hydroxy-1-propynyl)-3-quinolinecarboxamide;

(16) N-(4-chlorobenzyl)-8-fluoro-4-hydroxy-6-(1,3-thiazol-2-yl)-3-quinolinecarboxamide;

(17) N-(4-chlorobenzyl)-8-fluoro-4-hydroxy-6-(2-thienyl)-3-quinolinecarboxamide;

(18) N-(4-chlorobenzyl)-8-fluoro-4-hydroxy-6-(3-methoxy-1-propynyl)-3-quinolinecarboxamide;

(19) 6-(4-bromo-2-thienyl)-N-(4-chlorobenzyl)-8-fluoro-4-hydroxy-3-quinolinecarboxamide;

(20) N-(4-chlorobenzyl)-8-fluoro-4-hydroxy-6-(4-hydroxybutyl)-3-quinolinecarboxamide;

(21) N-(4-chlorobenzyl)-8-fluoro-4-hydroxy-6-[(Z)-4-hydroxy-1-butenyl]-3-quinolinecarboxamide;

(22) N-((4-chlorobenzyl)-6,8-difluoro-4-hydroxy-7-[4-(hydroxymethyl)phenoxy]-3-quinolinecarboxamide;

(23) N-((4-chlorobenzyl)-6,8-difluoro-4-hydroxy-7-methoxy-3-quinolinecarboxamide;

(24) N-(4-chlorobenzyl)-8-fluoro-4-hydroxy-6-(5-hydroxy-1-pentynyl)-3-quinolinecarboxamide;

(25) 3-(3-{[(4-chlorobenzyl)amino]carbonyl}-8-fluoro-4-hydroxy-6-quinolinyl)-2-propynyl formate;

(26) N-(4-chlorobenzyl)-8-fluoro-4-hydroxy-6-(3-hydroxypropyl)-3-quinolinecarboxamide;

(27) N-(4-chlorobenzyl)-4-hydroxy-7-(3-hydroxypropyl)-3-quinolinecarboxamide;

(28) N-((4-chlorobenzyl)-8-fluoro-4-hydroxy-6-(3-hydroxybutyl)-3-quinolinecarboxamide;

(29) N-((4-chlorobenzyl)-6-[(E)-2-cyanoethenyl]-8-fluoro-4-hydroxy-3-quinolinecarboxamide;

(30) N-((4-chlorobenzyl)-4-hydroxy-6-(3-hydroxy-1-propynyl)-8-methoxy-3-quinolinecarboxamide;

(31) N-(4-chlorobenzyl)-4-hydroxy-6-(3-hydroxy-1-propynyl)-3-quinolinecarboxamide;

(32) N-(4-chlorobenzyl)-4-hydroxy-8-methoxy-6-(3-methoxy-1-propynyl)-3-quinolinecarboxamide;

(33) N-(4-chlorobenzyl)-8-fluoro-4-hydroxy-6-[(Z)-3-hydroxy-1-propenyl]-3-quinolinecarboxamide;

(34) N-(4-chlorobenzyl)-8-fluoro-4-hydroxy-6-(3-oxopropyl)-3-quinolinecarboxamide;

(35) N-(4-chlorobenzyl)-4-hydroxy-7-(4-hydroxybutyl)-3-quinolinecarboxamide;

(36) N-(4-chlorobenzyl)-4-hydroxy-6-iodo-8-methoxy-3-quinolinecarboxamide;

(37) N-(4-chlorobenzyl)-8-fluoro-6-(3-fluoro-1-propynyl)-4-hydroxy-3-quinolinecarboxamide;

(38) N-(4-chlorobenzyl)-4-hydroxy-6-(3-hydroxypropyl)-3-quinolinecarboxamide;

(39) 3-(3-{[(4-chlorobenzyl)amino]carbonyl}-8-fluoro-4-hydroxy-6-quinolinyl)propyl 2-bromoacetate;

(40) 3-(3-{[(4-chlorobenzyl)amino]carbonyl}-8-fluoro-4-hydroxy-6-quinolinyl)propyl 2-[(tert-butoxycarbonyl)amino]-3-methylbutanoate;

(41) 3-(3-{[(4-chlorobenzyl)amino]carbonyl}-8-fluoro-4-hydroxy-6-quinolinyl)propyl 2-amino-3-methylbutanoate;

(42) 3-(3-{[(4-chlorobenzyl)amino]carbonyl}-8-fluoro-4-hydroxy-6-quinolinyl)-2-propynyl phenylcarbamate;

(43) N-((4-chlorobenzyl)-4-hydroxy-6-propyl-3-quinolinecarboxamide

(44) N-((4-chlorobenzyl)-4-hydroxy-6-(3-hydroxypropyl)-8-methoxy-3-quinolinecarboxamide;

(45) N-(4-chlorobenzyl)-8-fluoro-4-hydroxy-6-(methylsulfanyl)-3-quinolinecarboxamide;

(46) N-(4-chlorobenzyl)-4-hydroxy-7-{[(1-naphthylmethyl)amino]sulfonyl}-3-quinolinecarboxamide;

(47) N-(4-chlorobenzyl)-8-fluoro-4-hydroxy-6-[(E)-3-oxo-1-butenyl]-3-quinolinecarboxamide;

(48) N-(4-chlorobenzyl)-4-hydroxy-6-(3-hydroxy-1-propynyl)-8-(trifluoromethoxy)-3-quinolinecarboxamide;

(49) sodium 2-[{8-[3-(3-{[(4-chlorobenzyl)amino]carbonyl}-8-fluoro-4-hydroxy-6-quinolinyl)propoxy]-8-oxooctanoyl}(methyl)amino]-1-ethanesulfonate;

(50) 3-(3-{[(4-chlorobenzyl)amino]carbonyl}-8-fluoro-4-hydroxy-6-quinolinyl)propyl dihydrogen phosphate;

(51) 3-(3-{[(4-chlorobenzyl)amino]carbonyl}-8-fluoro-4-hydroxy-6-quinolinyl)propyl 2,6-bis [(tert-butoxycarbonyl)amino]hexanoate;

(52) tert-butyl 3-(3-{[(4-chlorobenzyl)amino]carbonyl}-8-fluoro-4-hydroxy-6-quinolinyl)propyl phosphonate;

(53) sodium 2-[(8-{[3-(3-{[(4-chlorobenzyl)amino]carbonyl}-8-fluoro-4-hydroxy-6-quinolinyl)-2-propynyl]oxy}-8-oxooctanoyl)(methyl)amino]-1-ethanesulfonate;

(54) N-(4-chlorobenzyl)-4-hydroxy-6-(2-hydroxyethoxy)-3-quinolinecarboxamide;

(55) 3-(3-{[(4-chlorobenzyl)amino]carbonyl}-8-fluoro-4-hydroxy-6-quinolinyl)propyl 2,6-diaminohexanoate trifluoroacetic acid salt;

(56) N-(4-chlorobenzyl)-4-hydroxy-6-[(2-hydroxyethyl)amino]-3-quinolinecarboxamide;

(57) N-(4-chlorobenzyl)-4-hydroxy-6-(3-hydroxybutyl)-3-quinolinecarboxamide;

(58) sodium 2-[(8-{[3-(3-{[(4-chlorobenzyl)amino]carbonyl}-4-hydroxy-6-quinolinyl)-2-propynyl]oxy}-8-oxooctanoyl)(methyl)amino]-1-ethanesulfonate;

(59) sodium 2-[{8-[3-(3-{[(4-chlorobenzyl)amino]carbonyl}-4-hydroxy-6-quinolinyl)propoxy]-8-oxooctanoyl}(methyl)amino]-1-ethanesulfonate;

(60) tert-butyl 3-(3-{[(4-chlorobenzyl)amino]carbonyl}-4-hydroxy-6-quinolinyl)propyl phosphonate;

(61) 3-(3-{[(4-chlorobenzyl)amino]carbonyl}-4-hydroxy-6-quinolinyl)propyl dihydrogen phosphate;

(62) N-(4-chlorobenzyl)-4-hydroxy-8-(2-hydroxyethoxy)-6-(3-hydroxypropyl)-3-quinolinecarboxamide;

(63) N-(4-chlorobenzyl)-8-fluoro-4-hydroxy-6-(4-morpholinylmethyl)-3-quinolinecarboxamide;

(64) N-(4-chlorobenzyl)-8-fluoro-4-hydroxy-6-(3-oxobutyl)-3-quinolinecarboxamide;

(65) N-(4-chlorobenzyl)-4-hydroxy-6-(2-oxo-1,3-oxazolidin-3-yl)-3-quinolinecarboxamide;

(66) 3-(3-{[(4-chlorobenzyl)amino]carbonyl}-4-hydroxy-6-quinolinyl)-2-propynyl 2,6-bis [(tert-butoxycarbonyl)amino]hexanoate;

(67) N-(4-chlorobenzyl)-6-[(Z)-3-hydroxy-1-propenyl]-4-oxo-1,4-dihydro-3-quinolinecarboxamide;

(68) N-(4-chlorobenzyl)-6-[(E)-3-hydroxy-1-propenyl]-4-oxo-1,4-dihydro-3-quinolinecarboxamide;

(69) 3-(3-{[(4-chlorobenzyl)amino]carbonyl}-4-hydroxy-6-quinolinyl)-2-propynyl 2,6-diaminohexanoate trifluoroacetic acid salt;

(70) 3-(3-{[(4-chlorobenzyl)amino]carbonyl}-4-hydroxy-6-quinolinyl)propyl hydrogen phosphonate;

(71) N-(4-chlorobenzyl)-4-hydroxy-6-(2-thienyl)-3-quinolinecarboxamide;

(72) N-((4-chlorobenzyl)-4-hydroxy-6-[(2-hydroxyethoxy)methyl]-3-quinolinecarboxamide;

(73) N-(4-chlorobenzyl)-4-hydroxy-6-(3-hydroxy-1,1-dimethylpropyl)-3-quinolinecarboxamide;

(74) N-(4-chlorobenzyl)-4-hydroxy-6-{[2-hydroxy-1-(hydroxymethyl)ethoxy]methyl}-3-quinolinecarboxamide;
(75) N-((4-chlorobenzyl)-4-hydroxy-6-(hydroxymethyl)-3-quinolinecarboxamide;
(76) Methyl 3-{[(4-chlorobenzyl)amino]carbonyl}-4-hydroxy-6-quinolinecarboxylate; or
(77) N-(4-chlorobenzyl)-4-hydroxy-6-(4-morpholinylmethyl)-3-quinolinecarboxamide.

The more preferred compounds of the present invention are:

(1) N-(4-chlorobenzyl)-4-hydroxy-7-methoxy-3-quinolinecarboxamide;
(2) N-(4-chlorobenzyl)-7-fluoro-4-hydroxy-3-quinolinecarboxamide;
(3) N-(4-chlorobenzyl)-8-fluoro-4-hydroxy-3-quinolinecarboxamide;
(4) N-(4-chlorobenzyl)-4-hydroxy-6-methoxy-3-quinolinecarboxamide
(5) N-(4-chlorobenzyl)-8-fluoro-4-hydroxy-6-(2-thienyl)-3-quinolinecarboxamide;
(6) N-(4-chlorobenzyl)-8-fluoro-4-hydroxy-6-(4-hydroxybutyl)-3-quinolinecarboxamide;
(7) N-(4-chlorobenzyl)-8-fluoro-4-hydroxy-6-[(Z)-4-hydroxy-1-butenyl]-3-quinolinecarboxamide;
(8) N-(4-chlorobenzyl)-8-fluoro-4-hydroxy-6-(3-hydroxypropyl)-3-quinolinecarboxamide;
(9) N-(4-chlorobenzyl)-4-hydroxy-7-(3-hydroxypropyl)-3-quinolinecarboxamide;
(10) N-(4-chlorobenzyl)-4-hydroxy-6-(3-hydroxy-1-propynyl)-8-methoxy-3-quinolinecarboxamide;
(11) N-(4-chlorobenzyl)-4-hydroxy-6-(3-hydroxy-1-propynyl)-3-quinolinecarboxamide;
(12) N-(4-chlorobenzyl)-4-hydroxy-8-methoxy-6-(3-methoxy-1-propynyl)-3-quinolinecarboxamide;
(13) N-(4-chlorobenzyl)-4-hydroxy-7-(4-hydroxybutyl)-3-quinolinecarboxamide;
(14) N-(4-chlorobenzyl)-4-hydroxy-6-(3-hydroxypropyl)-3-quinolinecarboxamide;
(15) 3-(3-{[(4-chlorobenzyl)amino]carbonyl}-8-fluoro-4-hydroxy-6-quinolinyl)propyl 2-bromoacetate;
(16) 3-(3-{[(4-chlorobenzyl)amino]carbonyl}-8-fluoro-4-hydroxy-6-quinolinyl)propyl 2-amino-3-methylbutanoate;
(17) N-(4-chlorobenzyl)-4-hydroxy-6-(3-hydroxypropyl)-8-methoxy-3-quinolinecarboxamide;
(18) sodium 2-[{8-[3-(3-{[(4-chlorobenzyl)amino]carbonyl}-8-fluoro-4-hydroxy-6-quinolinyl)propoxy]-8-oxooctanoyl}(methyl)amino]-1-ethanesulfonate;
(19) 3-(3-{[(4-chlorobenzyl)amino]carbonyl}-8-fluoro-4-hydroxy-6-quinolinyl)propyl dihydrogen phosphate;
(20) 3-(3-{[(4-chlorobenzyl)amino]carbonyl}-8-fluoro-4-hydroxy-6 -quinolinyl)propyl 2,6-bis[(tert-butoxycarbonyl)amino]hexanoate;
(21) tert-butyl 3-(3-{[(4-chlorobenzyl)amino]carbonyl}-8-fluoro-4-hydroxy-6-quinolinyl)propyl phosphonate;
(22) 3-(3-{[(4-chlorobenzyl)amino]carbonyl}-8-fluoro-4-hydroxy-6-quinolinyl)propyl 2,6-diaminohexanoate trifluoroacetic acid salt;
(23) N-(4-chlorobenzyl)-4-hydroxy-6-[(2-hydroxyethyl)amino]-3-quinolinecarboxamide;
(24) N-(4-chlorobenzyl)-4-hydroxy-6-(3-hydroxybutyl)-3-quinolinecarboxamide;
(25) sodium 2-[(8-{[3-(3-{[(4-chlorobenzyl)amino]carbonyl}-4-hydroxy-6-quinolinyl)-2-propynyl]oxy)-8-oxooctanoyl)(methyl)amino]-1-ethanesulfonate;
(26) sodium 2-[{8-[3-(3-{[(4-chlorobenzyl)amino]carbonyl}-4-hydroxy-6-quinolinyl)propoxy]-8-oxooctanoyl)(methyl)amino]-1-ethanesulfonate;
(27) tert-butyl 3-(3-{[(4-chlorobenzyl)amino]carbonyl}-4-hydroxy-6-quinolinyl)propyl phosphonate;
(28) 3-(3-{[(4-chlorobenzyl)amino]carbonyl}-4-hydroxy-6-quinolinyl)propyl dihydrogen phosphate;
(29) N-(4-chlorobenzyl)-4-hydroxy-8-(2-hydroxyethoxy)-6-(3-hydroxypropyl)-3-quinolinecarboxamide;
(30) N-(4-chlorobenzyl)-8-fluoro-4-hydroxy-6-(4-morpholinylmethyl)-3-quinolinecarboxamide;
(31) 3-(3-{[(4-chlorobenzyl)amino]carbonyl}-4-hydroxy-6-quinolinyl)-2-propynyl 2,6-bis [(tert-butoxycarbonyl)amino]hexanoate;
(32) N-(4-chlorobenzyl)-6-[(Z)-3-hydroxy-1-propenyl]-4-oxo-1,4-dihydro-3-quinolinecarboxamide;
(33) N-(4-chlorobenzyl)-6-[(E)-3-hydroxy-1-propenyl]-4-oxo-1,4-dihydro-3-quinolinecarboxamide;
(34) 3-(3-{[(4-chlorobenzyl)amino]carbonyl}-4-hydroxy-6-quinolinyl)-2-propynyl 2,6-diaminohexanoate trifluoroacetic acid salt;
(35) 3-(3-{[(4-chlorobenzyl)amino]carbonyl}-4-hydroxy-6-quinolinyl)propyl hydrogen phosphonate;
(36) N-(4-chlorobenzyl)-4-hydroxy-6-(2-thienyl)-3-quinolinecarboxamide
(37) N-(4-chlorobenzyl)-4-hydroxy-6-[(2-hydroxyethoxy)methyl]-3-quinolinecarboxamide;
(38) N-(4-chlorobenzyl)-4-hydroxy-6-(3-hydroxy-1,1-dimethylpropyl)-3-quinolinecarboxamide;
(39) methyl 3-{[(4-chlorobenzyl)amino]carbonyl}-4-hydroxy-6 -quinolinecarboxylate; or
(40) N-(4-chlorobenzyl)-4-hydroxy-6-(4-morpholinylmethyl)-3-quinolinecarboxamide.

The most preferred compounds of the present invention are:

(1) N-(4-chlorobenzyl)-8-fluoro-4-hydroxy-6-(3-hydroxypropyl)-3-quinolinecarboxamide;
(2) N-(4-chlorobenzyl)-4-hydroxy-6-(3-hydroxy-1-propynyl)-8-methoxy-3-quinolinecarboxamide;
(3) N-(4-chlorobenzyl)-4-hydroxy-8-methoxy-6-(3-methoxy-1-propynyl)-3-quinolinecarboxamide;
(4) N-(4-chlorobenzyl)-4-hydroxy-6-(3-hydroxypropyl)-3-quinolinecarboxamide;
(5) N-(4-chlorobenzyl)-4-hydroxy-6-(3-hydroxypropyl)-8-methoxy-3-quinolinecarboxamide;
(6) sodium 2-[(8-{[3-(3-{[(4-chlorobenzyl)amino]carbonyl}-4-hydroxy-6-quinolinyl)-2-propynyl]oxy}-8-oxooctanoyl)(methyl)amino]-1-ethanesulfonate;
(7) sodium 2-[{8-[3-(3-{[(4-chlorobenzyl)amino]carbonyl}-4-hydroxy-6-quinolinyl)propoxy]-8-oxooctanoyl}(methyl)amino]-1-ethanesulfonate;
(8) 3-(3-{[(4-chlorobenzyl)amino]carbonyl}-4-hydroxy-6-quinolinyl)propyl dihydrogen phosphate;
(9) N-(4-chlorobenzyl)-6-[(Z)-3-hydroxy-1-propenyl]-4-oxo-1,4-dihydro-3-quinolinecarboxamide;
(10) N-(4-chlorobenzyl)-6-[(E)-3-hydroxy-1-propenyl]-4-oxo-1,4-dihydro-3-quinolinecarboxamide;
(11) 3-(3-{[(4-chlorobenzyl)amino]carbonyl}-4-hydroxy-6-quinolinyl)-2-propynyl 2,6-diaminohexanoate trifluoroacetic acid salt;

(12) 3-(3-{[(4-chlorobenzyl)amino]carbonyl}-4-hydroxy-6-quinolinyl)propyl hydrogen phosphonate;

(13) N-(4-chlorobenzyl)-4-hydroxy-6-(2-thienyl)-3-quinolinecarboxamide;

(14) N-((4-chlorobenzyl)-4-hydroxy-6-[(2-hydroxyethoxy)methyl]-3-quinolinecarboxamide; or

(15) N-(4-chlorobenzyl)-4-hydroxy-6-(4-morpholinylmethyl)-3-quinolinecarboxamide.

The compounds of the present invention and pharmaceutically acceptable salts thereof are useful as antiviral agents. Thus, these compounds are useful to combat viral infections in animals, including man. Specifically, these compounds have anti-viral activity against the herpes virus, cytomegalovirus (CMV). These compounds are also active against other herpes viruses, such as the varicella zoster virus, the Epstein-Barr virus, the herpes simplex virus, and the human herpes virus type 8 (HHV-8).

Also, while many of the compounds of the present invention have shown activity against the CMV polymerase, these compounds may be active against the cytomegalovirus by this or other mechanisms of action. Thus, the description below of these compounds' activity against the CMV polymerase is not meant to limit the present invention to a specific mechanism of action.

The compounds of the present invention have shown activity in one or more of the assays described below. All of these assays are indicative of a compound's activity and thus of its use as an anti-viral agent.

The HCMV polymerase assay is performed using a scintillation proximity assay (SPA) as described in several references, such as N. D. Cook, et al., Pharmaceutical Manufacturing International, pages 49–53 (1992); K. Takeuchi, Laboratory Practice, September issue (1992); U.S. Pat. No. 4,568,649 (1986); which are incorporated by reference herein. Reactions are performed in 96-well plates. The assay is conducted in 100 µl volume with 5.4 mM HEPES (pH 7.5), 11.7 mM KCl, 4.5 mM MgCl$_2$, 0.36 mg/ml BSA, and 90 nM $^3$H-dTTP. Assays are run with and without CHAPS, (3-[(3-Cholamidopropyl)-dimethylammonio]-1-propane-sulfonate) at a final concentration of 2 mM. HCMV polymerase is diluted in enzyme dilution buffer containing 50% glycerol, 250 mM NaCl, 10 mM HEPES (pH 7.5), 100 µg/ml BSA, and 0.01% sodium azide. The HCMV polymerase, which is expressed in recombinant baculovirus-infected SF-9 cells and purified according to literature procedures, is added at 10% (or 10 µl) of the final reaction volume, i.e., 100 µl. Compounds are diluted in 50% DMSO and 10 µl are added to each well. Control wells contain an equivalent concentration of DMSO. Unless noted otherwise, reactions are initiated via the addition of 6 nM biotinylated poly(dA)-oligo(dT) template/primer to reaction mixtures containing the enzyme, substrate, and compounds of interest. Plates are incubated in a 25° C. or 37° C. H$_2$O bath and terminated via the addition of 40 µl/reaction of 0.5 M EDTA (pH 8) per well. Reactions are terminated within the timeframe during which substrate incorporation is linear and varied depending upon the enzyme and conditions used, i.e., 30 min. for HCMV polymerase. Ten µl of streptavidin-SPA beads (20 mg/ml in PBS/10% glycerol) are added following termination of the reaction. Plates are incubated 10 min. at 37° C., then equilibrated to room temperature, and counted on a Packard Topcount. Linear regressions are performed and IC$_{50}$'s are calculated using computer software.

A modified version of the above HCMV polymerase assay is performed as described above, but with the following changes: Compounds are diluted in 100% DMSO until final dilution into assay buffer. In the previous assay, compounds are diluted in 50% DMSO. 4.5 mM dithiotherotol (DTT) is added to the polymerase buffer. Also, a different lot of CMV polymerase is used, which appears to be more active resulting in a more rapid polymerase reaction. Results of the testing of compounds of the present invention in this assay are shown in Tables 1 below. Other viral polymerase assays are performed using procedures similar to those described above.

These compounds of the present invention are administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 15th Ed., 1975), which is hereby incorporated by reference herein.

The compounds of the present invention are administered parenterally (for example, by intravenous, intraperitoneal or intramuscular injection), topically, orally, or rectally, depending on whether the preparation is used to treat internal or external viral infections.

For internal infections, the compositions are administered orally or parenterally at dose levels, calculated as the free base, of about 0.1 to 300 mg/kg, preferably 1.0 to 30 mg/kg of mammal body weight, and are used in man in a unit dosage form, administered one to four times daily in the amount of 1 to 1000 mg per unit dose.

For parenteral administration or for administration as drops, as for eye infections, the compounds are presented in aqueous solution in a concentration of from about 0.1 to 10%, more preferably about 0.1 to 7%. The solution may contain other ingredients, such as emulsifiers, antioxidants or buffers.

The exact regimen for administration of the compounds and compositions disclosed herein will necessarily be dependent upon the needs of the individual subject being treated, the type of treatment and, of course, the judgment of the attending practitioner.

TABLE 1

| Example No. | Antiviral Selective Polymerase IC50 Values | |
|---|---|---|
| | Polymerase | IC50 (uM) |
| 1 | CMV | 38.2 |
| | HSV | 35.5 |
| | VZV | 13.3 |
| 2 | CMV | 5.2 |
| | HSV | 3.5 |
| | VZV | 0.6 |
| 3 | CMV | 24.0 |
| 4 | CMV | 3.4 |
| 5 | CMV | 5.8 |
| 6 | CMV | 7.6 |
| | HSV | 2.3 |
| | VZV | 0.7 |
| 7 | CMV | 4.9 |
| | HSV | 5.5 |
| | VZV | 0.7 |
| 8 | CMV | 55.3 |
| 9 | CMV | <2.3 |
| | HSV | <2.3 |
| | VZV | 2.5 |
| 10 | CMV | 9.7 |
| | HSV | 14.0 |
| | VZV | 3.9 |

TABLE 1-continued

| Example No. | Polymerase | IC50 (uM) |
|---|---|---|
| 11 | CMV | 21.2 |
| 12 | CMV | 1.4 |
|  | HSV | 3.4 |
|  | VZV | <3.1 |
| 13 | CMV | <2.3 |
|  | HSV | 3.0 |
|  | VZV | <2.3 |
| 14 | CMV | 11.5 |
|  | HSV | 7.9 |
|  | VZV | 3.6 |
| 15 | CMV | 20.8 |
|  | HSV | 22.0 |
|  | VZV | 13.1 |
| 16 | CMV | 2.7 |
|  | HSV | 2.8 |
|  | VZV | 1.3 |
| 17 | CMV | 3.3 |
| 18 | CMV | <3.1 |
| 20 | CMV | 6.5 |
| 21 | CMV | 4.4 |
| 22 | CMV | 4.0 |
| 23 | CMV | 3.4 |
| 24 | CMV | 4.9 |
| 25 | CMV | 13.5 |
|  | HSV | 18.5 |
|  | VZV | 8.4 |
| 26 | CMV | 17.0 |
|  | HSV | 25.0 |
|  | VZV | 14.0 |
| 27 | CMV | 16.0 |
| 28 | CMV | 18.0 |
|  | HSV | 19.7 |
|  | VZV | 8.3 |
| 29 | CMV | 34.1 |
|  | HSV | 70.6 |
|  | VZV | 25.2 |
| 30 | CMV | 10.6 |
|  | HSV | 14.3 |
|  | VZV | 7.5 |
| 31 | CMV | 26.2 |
|  | HXV | 81.5 |
|  | VZV | 26.0 |
| 32 | CMV | 22.0 |
|  | HSV | >100.0 |
|  | VZV | 53.8 |
| 33 | CMV | 24.3 |
| 34 | CMV | 17.9 |
| 35 | CMV | 9.2 |
| 36 | CMV | 7.8 |
| 38 | CMV | 3.2 |
| 39 | CMV | <3.1 |
| 40 | CMV | 3.5 |
| 41 | CMV | 12.1 |
| 42 | CMV | 19.2 |
| 43 | CMV | 1.3 |
| 44 | CMV | 28.7 |
| 45 | CMV | 4.6 |
| 46 | CMV | 2.8 |
| 47 | CMV | 39.7 |
| 48 | CMV | 6.5 |
| 49 | CMV | 3.7 |
| 50 | CMV | 6.9 |
| 51 | CMV | 12.2 |
| 52 | CMV | 11.0 |
| 53 | CMV | <0.78 |
|  | HSV | 0.64 |
|  | VZV | 0.39 |
| 54 | CMV | 8.6 |
| 55 | CMV | 5.0 |
| 56 | CMV | 3.1 |
| 57 | CMV | 5.2 |
| 58 | CMV | 1 |
| 59 | CMV | 33.1 |
| 60 | CMV | 4.0 |
| 61 | CMV | 3.1 |
| 62 | CMV | 4.6 |
| 63 | CMV | 7.0 |
| 64 | CMV | 8.5 |
| 65 | CMV | 3.3 |
| 66 | CMV | 0.29 |
| 72 | CMV | 9.4 |
| 75 | CMV | 0.17 |
|  | HSV | 0.43 |
|  | VZV | 0.16 |
| 76 | CMV | 5.2 |
| 77 | CMV | 4.0 |
| 78 | CMV | 0.71 |
| 79 | CMV | 0.96 |
| 80 | CMV | 2.4 |
| 81 | CMV | 7.8 |
| 82 | CMV | 2.5 |
| 83 | CMV | 4.3 |
| 84 | CMV | 0.79 |
| 85 | CMV | 18.1 |
| 86 | CMV | 10.7 |
| 87 | CMV | 7.9 |
| 88 | CMV | 30.3 |
| 89 | CMV | 7.2 |
| 90 | CMV | 2.9 |
| 91 | CMV | 3.8 |
| 92 | CMV | 20.6 |
| 94 | CMV | 5.3 |
| 95 | CMV | 1.9 |
| 96 | CMV | 4.5 |
| 97 | CMV | 18.6 |
| 98 | CMV | 1.3 |
| 99 | CMV | 0.14 |
|  | HSV | 0.20 |
|  | VZV | 0.09 |
| 100 | CMV | 6.7 |
| 101 | CMV | 25.8 |
| 102 | CMV | 4.6 |
| 103 | CMV | 2.5 |
| 104 | CMV | <0.78 |
| 105 | CMV | 10.4 |
| 106 | CMV | 10.3 |
|  | HSV | 16.4 |
|  | VZV | 9.6 |
| 107 | CMV | 5.4 |
| 108 | CMV | 6.5 |
| 109 | CMV | 11 |
| 110 | CMV | 0.28 |
| 111 | CMV | 2.6 |
| 112 | CMV | 14.0 |
| 113 | CMV | 10.4 |
| 114 | CMV | 2.2 |
| 115 | CMV | 6.1 |
| 116 | CMV | 16.5 |
| 117 | CMV | 8.7 |
| 118 | CMV | 0.67 |
|  | VZV | 0.2 |
|  | HSV | 0.66 |
| 119 | CMV | 1.5 |
|  | VZV | 0.57 |
|  | HSV | 0.73 |
| 120 | CMV | 0.27 |
|  | VZV | 0.08 |
|  | HSV | 0.25 |
| 121 | CMV | 15.0 |
| 122 | CMV | 1.8 |
| 123 | CMV | 2.2 |
| 124 | CMV | 0.25 |
|  | HSV | 0.6 |
|  | VZV | 0.39 |
| 125 | CMV | 0.87 |
|  | HSV | 2.5 |
|  | VZV | 1.7 |
| 126 | CMV | 19.7 |

TABLE 1-continued

| Example No. | Polymerase | IC50 (uM) |
|---|---|---|
| 127 | CMV | 23.5 |
| 128 | CMV | 0.46 |
| 129 | CMV | 1.0 |
| 130 | CMV | 1.1 |
| 131 | CMV | 1.8 |
| 132 | CMV | 0.64 |
| 133 | CMV | 4.0 |
|  | VZV | 2.2 |
|  | HSV | 3.2 |
| 134 | CMV | 0.90 |
|  | VZV | 0.19 |
|  | HSV | 0.72 |
| 135 | CMV | 0.78 |
| 136 | CMV | 0.68 |
|  | HSV | 0.7 |
|  | VZV | 0.39 |
| 137 | CMV | 0.60 |
| 138 | CMV | 4.7 |
|  | VZV | 2.0 |
|  | HSV | 3.5 |
| 139 | CMV | 1.9 |
| 140 | CMV | 1.4 |
|  | VZV | 1.0 |
|  | HSV | 1.7 |
| 141 | CMV | 10.1 |
| 142 | CMV | 3.8 |
|  | VZV | 2.1 |
|  | HSV | 2.9 |
| 143 | CMV | 3.0 |
| 144 | CMV | 0.28 |
|  | VZV | 0.07 |
|  | HSV | 0.28 |
| 145 | CMV | 2.9 |
|  | VZV | 2.5 |
|  | HSV | 3.5 |
| 146 | CMV | 38.7 |
| 147 | CMV | 7.0 |
| 148 | CMV | 2.4 |
|  | VZV | 1.0 |
|  | HSV | 1.4 |
| 149 | CMV | 6.3 |
| 150 | CMV | 4.8 |
| 151 | CMV | 0.91 |
| 152 | CMV | 5.4 |
| 153 | CMV | 8.3 |
| 154 | CMV | 3.4 |
| 155 | CMV | ≧50 |
| 156 | CMV | 15.9 |
| 157 | CMV | 0.92 |
|  | HSV | 1.8 |
|  | VZV | 0.89 |
| 158 | CMV | <0.78 |
| 159 | CMV | 5.0 |
| 160 | CMV | 1.2 |
| 163 | CMV | 0.59 |
| 164 | CMV | 2.3 |
| 165 | CMV | 6.7 |
| 166 | CMV | 7 |
| 167 | CMV | 5 |
| 168 | CMV | 10 |
|  | HSV | 8.4 |
|  | VZV | 4.1 |
| 169 | CMV | 3.7 |
| 170 | CMV | 4.4 |
| 171 | CMV | 1.9 |
| 172 | CMV | 35.1 |
| 173 | CMV | 12.8 |
| 174 | CMV | 28.9 |
| 175 | CMV | 7.2 |
| 176 | CMV | 11.4 |
| 177 | CMV | 7.2 |
| 178 | CMV | 0.15 |
|  | HSV | 0.8 |
|  | VZV | 0.64 |
| 179 | CMV | 1.8 |
|  | VZV | 0.66 |
|  | HSV | 1.4 |
| 180 | CMV | 28.2 |
| 181 | CMV | 39.2 |
| 182 | CMV | 5.0 |
| 183 | CMV | 32.0 |
| 184 | CMV | 30.4 |
| 185 | CMV | 32.8 |
| 186 | CMV | 13.8 |
| 187 | CMV | 17.7 |
| 188 | CMV | 2.1 |
| 189 | CMV | 19.4 |
| 190 | CMV | 2.7 |
| 191 | CMV | 0.5 |
|  | HSV | 0.63 |
|  | VZV | 0.64 |
| 192 | CMV | 1.6 |
| 193 | CMV | 2.7 |
| 194 | CMV | 15.3 |
| 195 | CMV | 18.3 |
| 196 | CMV | 19.4 |
| 197 | CMV | 19.6 |
| 198 | CMV | 21.0 |
| 199 | CMV | 26.4 |
| 200 | CMV | 38.8 |
| 201 | CMV | 6.0 |
| 202 | CMV | ≧50 |
| 203 | CMV | 38.8 |
| 204 | CMV | 13.8 |
| 205 | CMV | ≧50 |
| 206 | CMV | 2.4 |
| 207 | CMV | 14.4 |
| 208 | CMV | 41.6 |
| 209 | CMV | 8.6 |
| 210 | CMV | 4.8 |
| 211 | CMV | 5.1 |
| 212 | CMV | 14.5 |
| 213 | CMV | 18.9 |
| 214 | CMV | 29.7 |
| 215 | CMV | 8.6 |
| 216 | CMV | 18.7 |
| 217 | CMV | 15.2 |
| 218 | CMV | 17.6 |
| 219 | CMV | 11.0 |
| 220 | CMV | 10.7 |
| 221 | CMV | 12.5 |
| 222 | CMV | 11.5 |
| 223 | CMV | 14.5 |
| 224 | CMV | 21.6 |
| 225 | CMV | 8.5 |
| 226 | CMV | 18.5 |
| 227 | CMV | 26.7 |
| 228 | CMV | 44.3 |
| 229 | CMV | 10.7 |
| 230 | CMV | 9.6 |
| 231 | CMV | 8.3 |
| 232 | CMV | 23.4 |
| 233 | CMV | 11.2 |
| 234 | CMV | 8.9 |
| 235 | CMV | 11.8 |
| 236 | CMV | 6.6 |
| 237 | CMV | 6.9 |
| 238 | CMV | 1.6 |
| 239 | CMV | 13.1 |
| 240 | CMV | 11.4 |
| 241 | CMV | 16.0 |
| 242 | CMV | 8.4 |
| 243 | CMV | 15.5 |
| 244 | CMV | 19.0 |
| 245 | CMV | 13.3 |
| 246 | CMV | 8.6 |
| 247 | CMV | 10.2 |
| 248 | CMV | 11.6 |

TABLE 1-continued

| | Antiviral Selective Polymerase IC50 Values | |
|---|---|---|
| Example No. | Polymerase | IC50 (uM) |
| 249 | CMV | 7.6 |
| 250 | CMV | 45.2 |
| 251 | CMV | 18.7 |
| 252 | CMV | 18.9 |
| 253 | CMV | 20.6 |
| 254 | CMV | 14.7 |
| 255 | CMV | 12.1 |
| 256 | CMV | 9.3 |
| 257 | CMV | 16.3 |
| 258 | CMV | 15.2 |
| 259 | CMV | 6.1 |
| 260 | CMV | 5.7 |
| 261 | CMV | 15.1 |
| 262 | CMV | 9.9 |
| 263 | CMV | 23.1 |
| 264 | CMV | 90.2 |
| 265 | CMV | 11.4 |
| 266 | CMV | 10.1 |
| 267 | CMV | 52.2 |
| 268 | CMV | 9.5 |
| 269 | CMV | 9.8 |
| 270 | CMV | 2.8 |
| 271 | CMV | 20.4 |
| 272 | CMV | 8.6 |
| 273 | CMV | 11.5 |
| 274 | CMV | 16.5 |
| 275 | CMV | 28.4 |
| 277 | CMV | 0.77 |
| 278 | CMV | 2.1 |
| 279 | CMV | 4.9 |
| 280 | CMV | 57.8 |

EXAMPLE 1

N-[(4-Chlorophenyl)methyl]-4-hydroxy-7-(trifluoromethyl)-3-quinoline-carboxamide

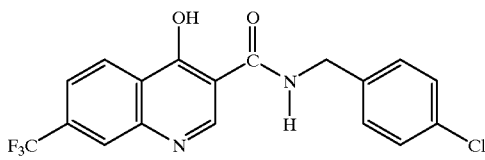

To a solution of 0.892 g 1,1'-carbonyldiimidazole in 30 mL of tetrahydrofuran is added 1.29 g 4-hydroxy-7-trifluoromethyl-3-quinolinecarboxylic acid. The reaction is stirred at room temperature for 1 h. A solution of 0.91 mL of 4-chlorobenzylamine in 10 mL of tetrahydrofuran is added dropwise. The reaction is allowed to warm slowly to room temperature and stirred for 18 h. The reaction mixture is concentrated in vacuo. The residue is taken up in 100 mL of dichloromethane and filtered. The filtrate is chromatographed twice, eluting with 5% methanol/dichloromethane. Fractions homogeneous by TLC are combined and concentrated in vacuo to yield a pale yellow solid. The solid is recrystallized from ethyl acetate to yield 0.298 g of the title compound as a white crystalline solid.

Physical characteristics are as follows: Mp 189–190° C.

$^1$H NMR (DMSO) δ 12.96, 10.28, 8.92, 8.46, 8.08, 7.79, 7.43–7.36, 4.58.

$^{13}$C NMR (DMSO) δ 175.4, 164.0, 145.0, 138.7, 138.5, 131.3, 129.1, 128.3, 127.3, 120.5, 116.7, 111.7, 41.4.

IR (Nujol) 3185, 3077, 3028, 1647, 1614, 1600, 1570, 1534, 1478, 1319, 1170, 1143 cm$^{-1}$.

MS (EI) m/z 380 (M$^+$), 362, 240, 213, 184, 140, 125.
Anal Found: C, 56.74; H, 3.44; N, 7.35; Cl, 9.04.

EXAMPLE 2

7-Amino-N-[(4-chlorophenyl)methyl]-4-hydroxy-3-quinolinecarboxamide

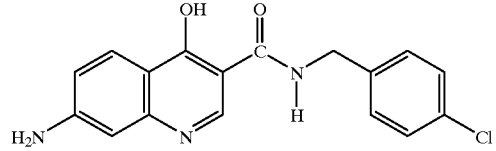

A suspension of 0.60 mL of 4-chlorobenzylamine and 0.200 g of ethyl 4-hydroxy-7-nitro-3-quinoline carboxylate is heated to 180° C. for 1 h. The reaction is cooled to room temperature. Ethyl acetate is added and the resulting solid is collected and washed with ethyl acetate to yield 0.071 g of the title compound as a tan solid.

Physical characteristics are as follows:
Mp 244–245° C. (dec).

$^1$H NMR (DMSO) δ 12.10. 10.63, 8.44, 7.85, 7.37, 7.31, 6.67, 6.53, 6.13, 4.49.

$^{13}$C NMR (DMSO) δ 175.9, 165.6, 153.4, 142.8, 141.9, 139.3, 131.8, 129.6, 128.8, 127.1, 116.9, 114.8, 109.8, 97.9, 41.7.

IR (mull) 3480, 3357, 2748, 2726, 1650, 1586, 1553, 1528, 1506, 1494, 1480, 1281, 789, 737, 621 cm$^{-1}$.

MS (EI) m/z 327 (M$^+$), 329, 327, 188, 187, 186, 160, 140, 132, 125, 104.

HRMS (EI) Found 327.0778.

EXAMPLE 3

N-[(4-Chlorophenyl)methyl]-8-fluoro-4,6-dihydroxy-3-quinoline-carboxamide

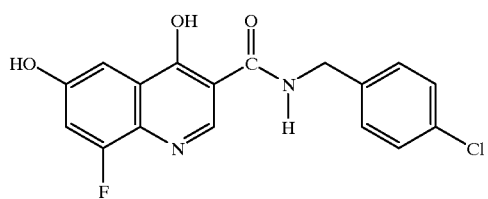

To a mixture of 10% Pd/C and 2.0 g of 3-fluoro-4-nitrophenol in 10 mL of tetrahydrofuran and 10 mL of methanol is added 4.817 g of ammonium formate. After the reaction stirred at room temperature for 1 h, it is filtered through celite and condensed. To the residue is then added 2.57 mL of diethylethoxymethylenemalonate and 10 mL xylene. The mixture is heated to 135° C. for 1 h with a Dean-Stark trap to remove formed ethanol. The reaction is cooled. The resulting solid is collected, washed with hexanes, and dried. The solid is then dissolved in 50 mL of diphenyl ether and heated to 250° C. for 3 h with a Dean-Stark trap to collect ethanol. The solution is cooled and diluted with hexanes. The resulting solid is collected and dried to yield 0.527 g. A solution of 0.415 g of that solid in 4 mL of 4-chlorobenzylamine is heated to 180° C. for 1 h. The solution is cooled and diluted with diethyl ether. The resulting solid is collected and recrystallized from acetone/hexanes to yield 0.226 g of the title compound as a tan solid.

Physical characteristics are as follows:

Mp 310–313° C.

$^1$H NMR (DMSO) δ 12.73, 10.34, 8.51, 7.35, 7.18, 4.52.

IR (mull) 3195, 3127, 3097, 3068, 1651, 1639, 1612, 1538, 1493, 1399, 1352, 283, 1193, 1142, 797 cm$^{-1}$.

MS (EI) m/z 346 (M$^+$), 348, 346, 207, 206, 179, 151, 150, 142, 140, 125.

EXAMPLE 4

6-Bromo-N-[(4-chlorophenyl)methyl]-8-fluoro-3-quinolinecarboxamide

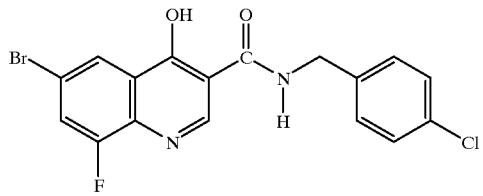

A mixture of 9.50 g of 4-bromo-2-fluoroaniline and 10.81 g diethylethoxymethylene malonate is heated to 130° C. in a flask equipped with a Dean-Stark trap to collect formed ethanol. The mixture is then cooled to 75° C. and diluted with hexanes. The resulting solid is collected and dried. The solid is then dissolved in 60 mL diphenyl ether and heated to 250° C. for 2 h in a flask equipped with a Dean-Stark trap to collect the ethanol. The solution is allowed to cool to room temperature and the resulting solid is collected, washed with hexanes and dried to yield 8.69 g. This material (0.49 g) and 5 mL of 4-chlorobenzylamine are heated at 180° C. for 1 h. The reaction is cooled and poured into 80 mL diethyl ether. The resulting solid is filtered and recrystallized from ethyl acetate/hexanes to give the title compound as an off-white solid (0.35 g).

Physical characteristics are as follows:

Mp 254–255° C.

$^1$H NMR (DMSO) d 10.16, 8.61, 8.11, 8.03, 7.38, 7.33, 4.52.

IR (mull) 3168, 3075, 1650, 1611, 1590, 1572, 1547, 1524, 1489, 1347, 1297, 1283, 1238, 1182, 804 cm$^{-1}$.

MS (ES-) 408.9 (M-H$^+$).

Anal. Found: C, 49.84; H, 3.05; N, 6.70; Cl, 8.87.

EXAMPLE 5

N-[(4-Chlorophenyl)methyl]-8-fluoro-4-hydroxy-6-iodo-3-quinolinecarboxamide

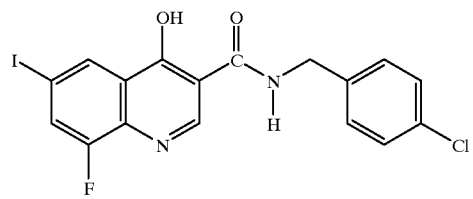

A mixture of 11.85 g of 2-fluoro-4-iodoaniline and 10.81 g of diethylethoxymethylene malonate is heated to 130° C. in a flask equipped with a Dean-Stark trap to collect formed ethanol. The mixture is then cooled to 75° C. and diluted with hexanes. The resulting solid is collected and dried. The solid is then dissolved in 60 mL diphenyl ether and heated to 250° C. for 3 h in a flask equipped with a Dean-Stark trap to collect the ethanol. The solution is allowed to cool to room temperature and the resulting solid is collected and dried to yield 11.73 g. This material (0.55 g) and 3 mL of 4-chlorobenzylamine are heated at 180° C. for 1 h. The reaction is cooled and poured into 75 mL diethyl ether. The resulting solid is filtered and recrystallized from ethyl acetate/hexanes to give the title compound as an off-white solid (0.45 g).

Physical characteristics are as follows:

Mp 268–270° C.

$^1$H NMR (DMSO) d 10.17, 8.59, 8.29, 8.05, 7.37, 7.33, 4.51.

IR (mull) 3180, 3078, 3059, 3004, 1647, 1607, 1551, 1524, 1489, 1344, 1297, 1285, 1240, 1183, 805 cm$^{-1}$.

MS (ES-) 454.9 (M-H$^+$).

HRMS (FAB) found 456.9628.

EXAMPLE 6

N-[(4-Chlorophenyl)methyl]-4-hydroxy-3-quinolinecarboxamide

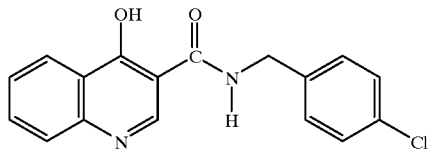

A mixture of 0.50 g of ethyl 4-hydroxy-3-quinolinecarboxylate (J. Amer. Chem. Soc., 68, 1264 (1946)) and 5.0 mL of 4-chlorobenzylamine is stirred 18 h at 200° C. The mixture is cooled to 25° C. and it is diluted with 25 mL of hexanes. After stirring for an additional 1 h the solid precipitate is collected by filtration and washed with 10 mL of hexanes. It is dried at 20 torr and 45° C. for 18 h. The yield is 0.28 g.

Physical characteristics are as follows:

Mp 245–48° C.

$^1$H NMR (DMSO) δ 10.58, 8.76, 8.23, 7.74–7.66, 7.45–7.20, 4.53.

MS (EI) m/z 312 (M+), 173, 172, 145, 142, 140, 125, 117, 116, 89.

Anal. Found: C, 64.42; H, 4.34; N, 8.79.

PREPARATION 1

Ethyl 4-hydroxy-6-(trifluoromethoxy)-3-quinolinecarboxylate

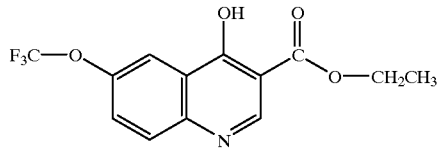

A mixture of 4-(trifluoromethyl)aniline (4.14 g) and 5.2 mL of diethyl ethoxymethylenemalonate is stirred 2 h at 130° C. The solid which formed upon cooling to 25° C. is washed with hexanes and dried in a stream of air. It is further dried at 20 torr and 34° C. for 18 h to give the condensation product as 5.09 g of a solid. This solid (5.0 g) is suspended in 20 mL of diphenyl ether and the mixture is refluxed for 1 h. The mixture is cooled to 25° C. and diluted with 100 mL of hexanes. After stirring for 20 min the solid is collected by filtration and dried at 20 torr and 45° C. for 18 h. The ester is obtained as 1.8 g of a solid.

Physical characteristics are as follows:

MS (EI) m/z 301 (M+), 302, 256, 255, 254, 228, 227, 186, 158, 69.

Anal. Found: C, 51.83; H, 3.38; N, 4.66.

EXAMPLE 7

N-[(4-Chlorophenyl)methyl]-4-hydroxy-7-methoxy-3-quinoline-carboxamide

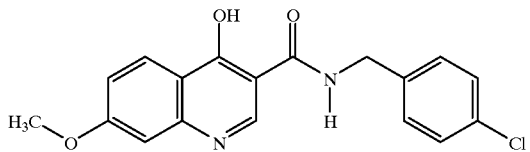

A mixture of 0.50 g of ethyl 4-hydroxy-7-methoxy-3-quinolinecarboxylate (J. Amer. Chem. Soc., 68, 1268 (1946)) and 3.0 mL of 4-chlorobenzylamine is stirred 1 h at 200° C. The mixture is cooled to 25° C. and it is diluted with 25 mL of hexanes. After stirring for an additional 1 h the solid precipitate is collected by filtration and washed with 10 mL of hexanes. It is dried in a stream of air and then it is suspended in 20 mL of glacial acetic acid. The mixture is heated until the solid completely dissolved and the resulting solution is diluted with 200 mL of distilled water. The mixture is allowed to cool to 25° C. and the solid is collected by filtration. It is washed with a small volume of 10% aqueous acetic acid and then it is dried at torr and 45° C. for 18 h. The yield is 0.39 g.

Physical characteristics are as follows:

Mp 230–35° C.

¹H NMR (DMSO) δ 12.5, 10.48, 8.67, 8.12, 7.42–7.31, 7.06–7.03, 4.51, 3.86.

MS (EI) m/z 342 (M+), 344, 203, 202, 201, 176, 175, 140, 132, 125.

Anal. Found: C, 62.45; H, 4.55; N, 8.00.

EXAMPLE 8

N-[(4-Chlorophenyl)methyl]-4-hydroxy-5,7-bis(trifluoromethyl)-3-quinolinecarboxamide

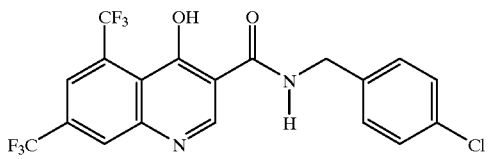

A mixture of 0.35 g of ethyl 4-hydroxy-5,7-bis(trifluoromethyl)-3-quinolinecarboxylate (FR 2537140) and 3.0 mL of 4-chlorobenzylamine is stirred 1 h at 200° C. The mixture is cooled to 25° C. and it is diluted with 25 mL of hexanes. After stirring for an additional 1 h the solid precipitate is collected by filtration and washed with 10 mL of hexanes. It is dried in a stream of air and then it is suspended in 20 mL of glacial acetic acid. The mixture is heated until the solid is completely dissolved and the resulting solution is diluted with 200 mL of distilled water. The mixture is allowed to cool to 25° C. and the solid is collected by filtration. It is washed with a small volume of 10% aqueous acetic acid and then it is dried at torr and 45° C. for 18 h. The yield is 0.23 g.

Physical characteristics are as follows:

Mp 115–118° C.

¹H NMR (DMSO) δ 13.09, 10.10, 8.93, 8.38, 8.02, 7.40–7.32, 4.53.

MS (EI) m/z 448 (M+), 450, 449, 288, 281, 142, 141, 140, 127, 125.

Anal. Found: C, 50.08; H, 2.75; N, 5.94, Cl, 7.43.

EXAMPLE 9

N-[(4-Chlorophenyl)methyl]-7-fluoro-4-hydroxy-3-quinolinecarboxamide

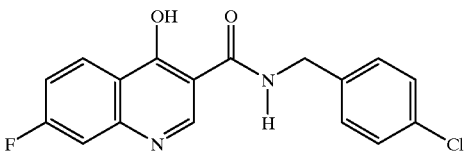

To a 0° C. solution of 4-chlorobenzylamine (0.52 mL) in 5 mL of toluene is added 2.13 mL of a 2.0 M solution of trimethylaluminum in toluene. The solution is stirred for 5 min at 0° C. and then a suspension of 0.50 g of ethyl 7-fluoro-4-hydroxy-3-quinolinecarboxylate (J. Med. Chem., 20, 1001 (1977)) in 5 mL of toluene is added. The solution is stirred at 0° C. for an additional 10 min and then it is stirred 18 h at 90° C. The mixture is cooled to 25° C. and it is poured onto a mixture of a large excess of 3 M hydrochloric acid and ice. After stirring the mixture vigorously for 30 min it is filtered. The solid is dissolved in 50 mL of warm glacial acetic acid and distilled water is added to the resulting solution until it is cloudy. The mixture is then allowed to stand for several hours at 5° C. Filtration of this mixture gives the desired amide as 150 mg of a solid.

Physical characteristics are as follows:

Mp 248–59° C.

¹H NMR (DMSO) δ 12.79, 10.30, 8.78, 8.29, 7.47, 7.41–7.32, 4.54.

MS (EI) m/z 330 (M+), 332, 190, 163, 142, 140, 135, 127, 125, 107.

Anal. Found: C, 61.69; H, 3.79; N, 8.38.

EXAMPLE 10

N-[(4-Chlorophenyl)methyl]-6-fluoro-4-hydroxy-3-quinoline-carboxamide

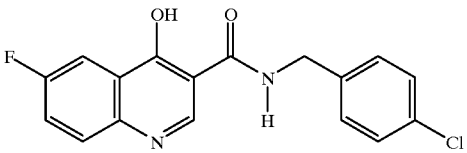

To a 0° C. solution of 4-chlorobenzylamine (0.52 mL) in 5 mL of toluene is added 2.13 mL of a 2.0 M solution of trimethylaluminum in tolune. The solution is stirred for 5 min at 0° C. and then a suspension of 0.50 g of ethyl 6-fluoro-4-hydroxy-3-quinolinecarboxylate (J. Amer. Chem. Soc., 69, 371 (1947)) in 5 mL of toluene is added. The solution is stirred at 0° C. for an additional 10 min and then it is stirred 18 h at 90° C. The mixture is cooled to 25° C. and it is poured onto a mixture of a large excess of 3 M hydrochloric acid and ice. After stirring the mixture vigorously for 30 min it is filtered. The solid is dissolved in 50 mL of warm glacial acetic acid and distilled water is added to the resulting solution until it is cloudy. The mixture is then allowed to stand for several hours at 5° C. Filtration of this mixture gives the desired amide as 390 mg of a solid.

Physical characteristics are as follows:

Mp 264° C.

$^1$H NMR (DMSO) δ 12.95, 10.35, 8.76, 7.86, 7.81–7.76, 7.70–7.63, 7.39–7.32, 4.53.

MS (EI) m/z 330 (M+), 332, 190, 163, 142, 140, 134, 127, 125, 107.

Anal. Found: C, 61.77; H, 3.75; N, 8.39; Cl, 10.70.

EXAMPLE 11

N-[(4-Chlorophenyl)methyl]-4-hydroxy-7-methyl-3-quinoline-carboxamide

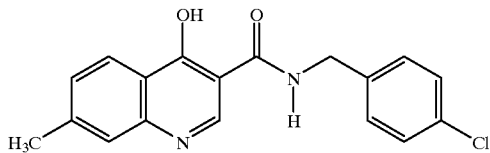

A mixture of 0.50 g of ethyl 4-hydroxy-7-methyl-3-quinolinecarboxylate (J. Indian Chem. Soc., 31 (1954)) and 5.0 mL of 4-chlorobenzylamine is stirred 1 hour at 200° C. The mixture is cooled to 25° C. and it is diluted with 25 mL of hexanes. After stirring for an additional 1 h the solid precipitate is collected by filtration and washed with 10 mL of hexanes. It is dried in a stream of air and then it is suspended in 20 mL of glacial acetic acid. The mixture is heated until the solid is completely dissolved and the resulting solution is diluted with 200 mL of distilled water. The mixture is allowed to cool to 25° C. and the solid is collected by filtration. It is washed with a small volume of 10% aqueous acetic acid and then it is dried at torr and 45° C. for 18 h. The yield is 0.23 g.

Physical characteristics are as follows:

Mp>255° C.

$^1$H NMR (DMSO) δ 12.55, 10.45, 8.70, 8.12, 7.44, 7.42–7.32, 7.29, 4.53, 2.46.

MS (EI) m/z 326 (M+), 328, 187, 186, 160, 159, 140, 130, 125, 77.

Anal. Found: C, 65.96; H, 4.66; N, 8.55.

EXAMPLE 12

N-[(4-Chlorophenyl)methyl]-8-fluoro-4-hydroxy-3-quinoline-carboxamide

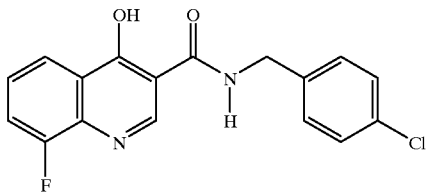

A mixture of 0.50 g of ethyl 8-fluoro-4-hydroxy-3-quinolinecarboxylate (J. Med. Chem., 22, 816 (1979)) and 3.0 mL of 4-chlorobenzylamine is stirred 1 hour at 200° C. The mixture is cooled to 25° C. and it is diluted with 25 mL of hexanes. After stirring for an additional 1 h the solid precipitate is collected by filtration and washed with 10 mL of hexanes. It is dried in a stream of air and then it is suspended in 20 mL of glacial acetic acid. The mixture is heated until the solid is completely dissolved and the resulting solution is diluted with 200 mL of distilled water. The mixture is allowed to cool to 25° C. and the solid is collected by filtration. It is washed with a small volume of 10% aqueous acetic acid and then it is dried at torr and 45° C. for 18 h. The yield is 0.52 g.

Physical characteristics are as follows:

Mp 226–28° C.

$^1$H NMR (DMSO) δ 12.90, 10.28, 8.63, 8.05, 7.73–7.68, 7.49–7.45, 7.40–7.34, 4.54.

MS (EI) m/z 330 (M+), 332, 331, 190, 163, 142, 141, 140, 135, 134.

Anal. Found: C, 61.75; H, 3.63; N, 8.45.

EXAMPLE 13

N-[(4-Chlorophenyl)methyl]-4-hydroxy-6-nitro-3-quinoline-carboxamide

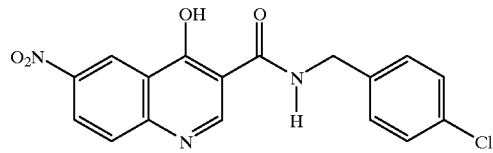

A mixture of 0.65 g of ethyl 4-hydroxy-6-nitro-3-quinolinecarboxylate (J. Amer. Chem. Soc., 68, 1264 (1946)) and 5.0 mL of 4-chlorobenzylamine is stirred 1 hour at 200° C. The mixture is cooled to 25° C. and it is diluted with 25 mL of hexanes. After stirring for an additional 1 h the solid precipitate is collected by filtration and washed with 10 mL of hexanes. It is dried in a stream of air and then it is suspended in 20 mL of glacial acetic acid. The mixture is heated until the solid is completely dissolved and the resulting solution is diluted with 200 mL of distilled water. The mixture is allowed to cool to 25° C. and the solid is collected by filtration. It is washed with a small volume of 10% aqueous acetic acid and then it is dried at torr and 45° C. for 18 h. The yield is 0.41 g.

Physical characteristics are as follows:

Mp>250° C.

$^1$H NMR (DMSO) δ 13.10, 10.11, 8.96, 8.87, 8.51, 7.89, 7.41–7.35, 4.56.

MS (EI) m/z 357 (M+), 359, 190, 171, 144, 142, 140, 127, 125, 89.

Anal. Found: C, 57.14; H, 3.50; N, 11.64.

EXAMPLE 14

N-[(4-Chlorophenyl)methyl]-5,6,7,8-tetrafluoro-4-hydroxy-3-quinolinecarboxamide

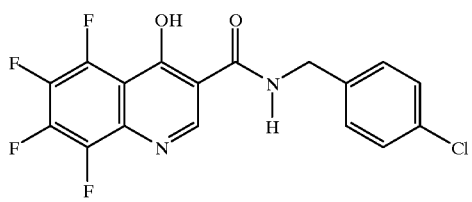

To a 0° C. solution of 4-chlorobenzylamine (0.080 mL) in 5 mL of toluene is added 0.70 mL of a 2.0 M solution of trimethylaluminum in toluene. The solution is stirred for 5 min at 0° C. and then a suspension of 0.20 g of ethyl 5,6,7,8-tetrafluoro-4-hydroxy-3-quinolinecarboxylate (U.S. Pat. No. 4,940,710) in 5 mL of toluene is added. The solution is stirred at 0° C. for an additional 10 min and then it is stirred 3 h at 90° C. The mixture is cooled to 25° C. and it is poured onto a mixture of 10 mL of 3 M hydrochloric acid and 10 mL of crushed ice. After stirring the mixture vigorously for 20 min it is filtered. The solid is dissolved in 50 mL of warm glacial acetic acid and distilled water is added to the resulting solution until it is cloudy. The mixture is then allowed to stand for several h at 5° C. Filtration of this mixture gives the desired amide as 0.12 g of a solid.

Physical characteristics are as follows:

Mp 241–43° C.

$^1$H NMR (DMSO) δ 13.13, 8.58, 7.42–7.31, 4.52.

MS (EI) m/z 384 (M+), 386, 244, 217, 189, 188, 142, 140, 127, 125, 77.

Anal. Found: C, 52.70; H, 2.51; N, 7.10.

EXAMPLE 15

N-[(4-Chlorophenyl)methyl]-6,7,8-trifluoro-4-hydroxy-3-quinolinecarboxamide

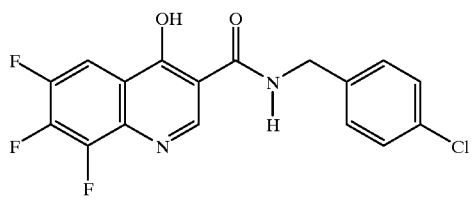

To a 0° C. solution of 4-chlorobenzylamine (0.45 mL) in 5 mL of toluene is added 1.84 mL of a 2.0 M solution of trimethylaluminum in toluene. The solution is stirred for 5 min at 0° C. and then 0.20 g of ethyl 6,7,8-trifluoro-4-hydroxy-3-quinolinecarboxylate (Tetrahedron 48, 29 (1992)) is added. The solution is stirred at 0° C. for an additional 30 min and then it is stirred 18 h at 25° C. The mixture is poured onto a mixture of 50 mL of 3 M hydrochloric acid and 50 mL of crushed ice. The mixture is extracted with three successive 75 mL portions of ethyl acetate. The combined extracts are dried (MgSO$_4$) and the solvent is evaporated at reduced pressure. The residue is dissolved in a small volume of ethyl acetate and hexanes is added until the solution becomes cloudy. The mixture is then allowed to stand for 1 h. Filtration of this mixture gives the desired amide as 0.25 g of a solid.

Physical characteristics are as follows:

Mp 245–50° C.

$^1$H NMR (DMSO) δ 13.20, 10.10, 8.64, 8.03–7.90, 7.44–7.31, 4.54.

MS (EI) m/z 366 (M+), 368, 226, 199, 171, 170, 143, 142, 141, 140, 125.

Anal. Found: C, 55.47; H, 2.91; N, 7.53.

PREPARATION 2

6,7,8-Trifluoro-4-hydroxy-3-quinolinecarboxylic acid

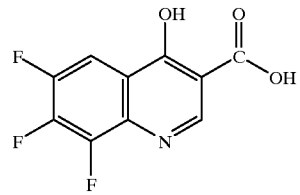

A mixture of 5.0 g of ethyl 6,7,8-trifluoro-4-hydroxy-3-quinolinecarboxylate (Tetrahedron, 48, 6135–6150 (1992)), 146 mL of tetrahydrofuran, 146 mL of methanol, and 74 ml of a 1.0 M aqueous solution of lithium hydroxide is stirred for four days at 25° C. The solution is neutralized with 16 mL of 3 M hydrochloric acid and the volume of the resulting mixture is reduced to 30 mL by evaporation at reduced pressure. The solid precipitate which forms is collected by filtration and partitioned between ethyl acetate and water. The aqueous phase is washed several times with ethyl acetate and the combined organic extracts are dried with magnesium sulfate. The solution is filtered and the solvent is removed from the filtrate by evaporation at reduced pressure. The title compound is obtained as 3.22 g of a solid.

Physical characteristics are as follows:

$^1$H NMR (400 MHz, DMSO) δ 8.72, 7.75.

MS (ES-): m/z 242 (M-H$^+$).

EXAMPLE 16

6,7,8-Trifluoro-4-hydroxy-3-quinolinecarboxylic acid 2-(4-chlorophenyl)hydrazide

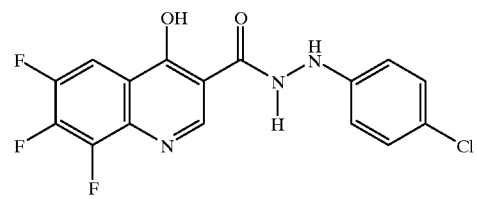

To a solution of 1.0 g of 6,7,8-trifluoro-4-hydroxy-3-quinolinecarboxylic acid (J. Amer. Chem. Soc., 68, 1264 (1946)). (The sample used in this procedure was shown by Karl Fisher titration to be a hydrate containing 0.4 equivalents of water.) in 15 mL of a 99:1 (v/v) mixture of dimethylformamide and triethylamine is added 1.01 g of carbonyldiimidazole. The mixture is stirred for 3 days and then it is transferred to a volumetric flask and diluted with dimethylformamide to a total volume of 25 mL. To 1.22 mL of this solution is added 39 mg of 4-chlorophenyl-hydrazine hydrochloride. The mixture is stirred 18 h at 25° C. and then 15 mL of distilled water is added. The precipitate is collected by filtration and dried in a stream of air. This procedure gives the title compound as 45 mg of a solid.

Physical characteristics are as follows:

Mp 210–216° C. (dec).

$^1$H NMR (DMSO) δ 13.36, 11.03, 8.63, 8.19, 8.04, 7.17, 6.75.

MS (ES–): m/z 366.1 (M–H$^+$).

Anal. Found: C, 50.62; H, 2.87; N, 11.24.

PREPARATION 3
4-(Phenylmethyl)thio-3-trifluoromethylaniline

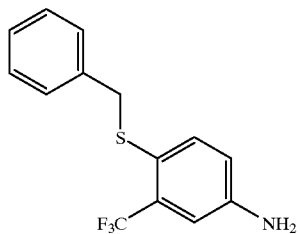

A solution of 338 g of stannous chloride dihydrate in 340 mL of concentrated hydrochloric acid is added to a stirred slurry of 104 g of 4-(phenylmethyl)thio-3-trifluoromethylnitrobenzene (J. Med. Chem., 845 (1978)) in 100 mL of concentrated hydrochloric acid. The mixture is heated on a steam bath during the addition and for one hour after the addition is complete. The mixture is cooled in ice, and the solid is filtered, washed with water, and dried in a stream of air. The solid is dissolved in a mixture of 500 mL of 0° C. 6 M aqueous sodium hydroxide solution and extracted into diethyl ether. The ether extract is washed with distilled water and then with brine. It is dried over sodium sulfate and filtered. The solvent is evaporated to give 91 g of a solid. This solid is recrystallized from methanol to give 39.7 g of the title compound.

Physical characteristics are as follows:

Mp 75–76.5° C.

Anal. Found: C, 59.59; H, 4.16; N, 4.79; S, 11.68.

PREPARATION 4
4-Hydroxy-6-[(phenylmethyl)thio]-7-(trifluoromethyl)-3-quinolinecarboxylic acid

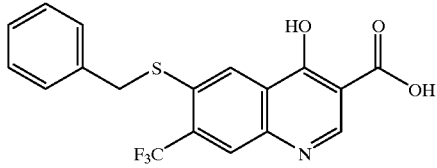

A mixture of 54 g of diethyl ethoxymethylenemalonate and 71.0 g of 4-(phenylmethyl)-3-trifluoromethylaniline is stirred at 100–160° C. until no further evolution of ethanol is observed. The mixture is diluted with 750 mL of phenyl ether and the mixture is refluxed for one hour. The solution is cooled to 25° C. and it is diluted with an equal volume of petroleum ether. The mixture is filtered and the solid is washed with petroleum ether to give 95 g of a light brown solid. A mixture of 81.5 g of this solid and 1.0 L of 2 N aqueous sodium hydroxide solution is refluxed for 4 h. The cooled mixture is neutralized with concentrated hydrochloric acid. The solid is collected by filtration and dried at reduced pressure to give 65.7 g of the title compound as a solid.

Physical characteristics are as follows:

Mp 225–235° C.

Anal. Found: C, 57.20; H, 3.43; N, 3.58; S, 8.33.

PREPARATION 5
5,8-Difluoro-4-hydroxy-3-quinolinecarboxylic acid

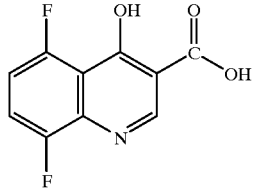

To a suspension of 6.0 g of ethyl 5,8-difluoro-4-hydroxy-3-quinolinecarboxylate (Magn. Reson. Chem., 34, 972–978 (1996)) in 400 mL of a 1:1 (v/v) mixture of methanol and tetrahydrofuran is added 100 mL of a 1.0 M aqueous solution of lithium hydroxide. After three days an additional 20 mL of 1.0 M aqueous lithium hydroxide solution is added and the mixture is warmed to 50° C. After an additional three days the solution is cooled to 25° C. and it is diluted with 15 mL of glacial acetic acid. The volume of the solution is reduced by two-thirds by evaporation at reduced pressure. The precipitate is collected by filtration and it is washed with four successive 150 mL portions of distilled water. The solid is dried at 80° C. and 20 torr for 24 h. This procedure yields the title compound as 4.96 g of an off-white solid.

Physical characteristics are as follows:

Mp>240° C.

$^1$H NMR (DMSO) δ 8.61, 7.87–7.79, 7.37–7.26.

MS (ES–) m/z 224 (M–H$^+$).

EXAMPLE 17
N-[(4-Chlorophenyl)methyl]-5,8-difluoro-4-hydroxy-3-quinolinecarboxamide

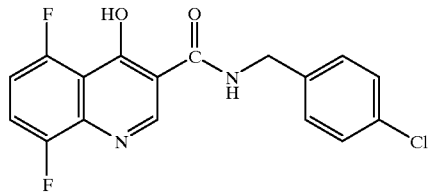

To a mixture of 0.25 g of 5,8-difluoro-4-hydroxy-3-quinolinecarboxylic acid and 10 mL of dimethyformamide is added 0.20 g of carbonyldiimidazole. The mixture is stirred 18 h at 50° C. and then it is cooled to 25° C. The mixture is treated with 0.10 mL of distilled water and stirred for 5 min. To the resulting solution is added 0. 15 mL of 4-chlorobenzylamine. After stirring for 18 hours the solvent is evaporated at reduced pressure and the residue is dissolved in 10 mL of refluxing glacial acetic acid. Hot (100° C.) water is added dropwise until the solution becomes cloudy, and the mixture is allowed to cool to 25° C. The precipitate is collected by filtration and it is washed with two successive 5 mL portions of 50% aqueous acetic acid. It is dried for 18 h at 20 torr and 90° C. This procedure yields the title compound as 173 mg of a white powder.

Physical characteristics are as follows:
Mp 259–260° C.
$^1$H NMR (400 MHz, DMSO) δ 8.56, 7.70, 7.39, 7.35, 7.17, 4.52.
HRMS (FAB) found 349.0564.
Anal. Found: C, 57.89; H, 3.23; N, 7.85.

PREPARATION 6
7,8-Difluoro-4-hydroxy-3-quinolinecarboxylic acid

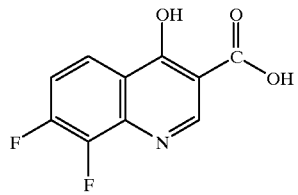

To a suspension of 2.0 g of ethyl 7,8-difluoro-4-hydroxy-3-quinolinecarboxylate (Magn. Reson. Chem., 34, 972–978 (1996)) in 160 mL of a 1:1 (v/v) mixture of methanol and tetrahydrofuran is added 40 mL of a 1.0 M aqueous solution of lithium hydroxide. After three days the volume of the solution is reduced by two-thirds by evaporation at reduced pressure. Twenty percent aqueous acetic acid is added to the solution until further addition causes no additional precipitate to form. The precipitate is collected by filtration and it is washed with three successive 50 mL portions of distilled water. The solid is dried at 75° C. and 20 torr for 18 h. This procedure yields the title compound as 1.54 g of a white solid.
Physical characteristics are as follows:
Mp>240° C.
$^1$H NMR (DMSO) δ 8.69, 8.38–8.20, 8.62–8.73.
MS (ES–) m/z 224 (M–H$^+$).

EXAMPLE 18

N-[(4-Chlorophenyl)methyl]-7,8-difluoro-4-hydroxy-3-quinoline-carboxamide

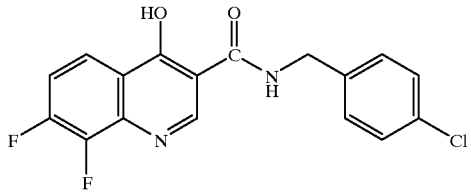

To a mixture of 0.25 g of 7,8-difluoro-4-hydroxy-3-quinolinecarboxylic acid and 10 mL of dimethyformamide is added 0.20 g of carbonyldiimidazole. The mixture is stirred 18 h at 50° C. and then it is cooled to 25° C. The mixture is treated with 0.10 mL of distilled water and stirred for 5 min. To the resulting solution is added 0.15 mL of 4-chlorobenzylamine. After stirring for 18 hours the solvent is evaporated at reduced pressure and the residue is dissolved in 10 mL of refluxing glacial acetic acid. Hot (100° C.) water is added dropwise until the solution becomes cloudy, and the mixture is allowed to cool to 25° C. The precipitate is collected by filtration and it is washed with two successive 5 mL portions of 50% aqueous acetic acid. It is dried for 18 h at 20 torr and 90° C. This procedure yields the title compound as 280 mg of a white powder.

Physical characteristics are as follows:
Mp 247–248° C.
$^1$H NMR (DMSO) δ 8.62, 8.12–8.03, 7.53, 7.38, 7.34, 4.53.
HRMS (FAB) found 349.0561.
Anal. Found: C, 56.35; H, 3.45; N, 7.31.

PREPARATION 7
5,7-Difluoro-4-hydroxy-3-quinolinecarboxylic acid

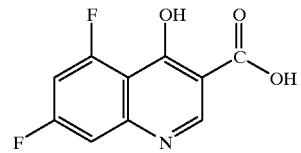

To a suspension of 8.0 g of ethyl 5,7-difluoro-4-hydroxy-3-quinolinecarboxylate (Magn. Reson. Chem., 34, 972–978 (1996)) in 600 mL of a 1:1 (v/v) mixture of methanol and tetrahydrofuran is added 150 mL of a 1.0 M aqueous solution of lithium hydroxide. After three days an additional 35 mL of 1.0 M aqueous lithium hydroxide solution is added and the mixture is warmed to 50° C. After an additional three days the solution is cooled to 25° C. and it is diluted with 20 mL of glacial acetic acid. The volume of the solution is reduced by two-thirds by evaporation at reduced pressure. The precipitate is collected by filtration and it is washed with four successive 150 mL portions of distilled water. $^1$H-NMR analysis of this material revealed the presence of a small amount of the methyl ester of the desired acid, so it is redissolved in a mixture of 260 mL of tetrahydrofuran, 260 mL of methanol, and 130 mL of 1.0 N aqueous lithium hydroxide solution. The mixture is stirred 48 h at 50° C. and then it is cooled to 25° C. It is treated with 25 mL of glacial acetic acid and the volume of the solution is reduced by two-thirds by evaporation at reduced pressure. The precipitate is collected by filtration and it is washed with four successive 150 mL portions of distilled water. It is dried at 80° C. and 20 torr for three days. This procedure gives the title compound as 4.82 g of an off-white solid.
Physical characteristics are as follows:
$^1$H NMR (DMSO) δ 8.89, 7.50–7.37.
MS (ES–) m/z 224 (M–H$^+$).

PREPARATION 8
6,8-Difluoro-4-hydroxy-3-quinolinecarboxylic acid

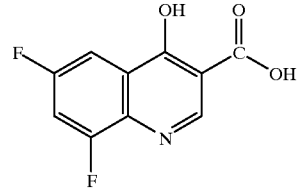

To a suspension of 5.0 g of ethyl 6,8-difluoro-4-hydroxy-3-quinolinecarboxylate (Magn. Reson. Chem., 34, 972–978 (1996)) in 400 mL of a 1:1 (v/v) mixture of methanol and tetrahydrofuran is added 100 mL of a 1.0 M aqueous solution of lithium hydroxide. After three days an additional 25 mL of 1.0 M aqueous lithium hydroxide solution is added and the mixture is warmed to 50° C. After an additional two days the solution is cooled to 25° C. and it is stirred for one additional day. It is diluted with 25 mL of glacial acetic acid.

The volume of the solution is reduced by two-thirds by evaporation at reduced pressure. The precipitate is collected by filtration and it is washed with four successive 150 mL portions of distilled water. It is dried at 80° C. and 20 torr for three days. This procedure gives the title compound as 4.0 g of a white solid.

Physical characteristics are as follows:
$^1$H NMR (DMSO) δ 8.64, 8.00, 7.80.
MS (ESI−) m/z 224 (M−H$^+$).

EXAMPLE 20

N-[(4-Chlorophenyl)methyl]-4-hydroxy-8-methoxy-3-quinoline-carboxamide

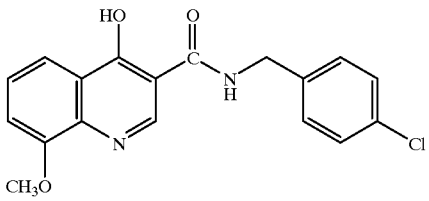

To a mixture of 0.50 g of 4-hydroxy-8-methoxy-3-quinolinecarboxylic acid (J. Amer. Chem. Soc., 68, 1268 (1946)) and 10 mL of dimethylformamide is added 0.41 g of carbonyldiimidazole. The mixture is stirred 20 h at 37° C. and then it is cooled to ° C. The mixture is treated with 0.25 mL of distilled water and stirred for 5 min. To the resulting solution is added 0.31 mL of 4-chlorobenzylamine. After stirring for 18 hours the mixture is warmed to 40° C. and stirred an additional 24 h. The solution is then cooled to 25° C. and it is diluted with 10 mL of distilled water. After minutes the precipitate is collected by filtration and it is washed with two successive 5 mL portions of 10% aqueous acetic acid. It is dried for 18 h in a stream of air at 25° C. This procedure yields the title compound as 485 mg of a tan solid.

Physical characteristics are as follows:
Mp>240° C.
$^1$H NMR (DMSO) δ 8.59, 7.86, 7.54–7.32, 4.53, 4.02.
MS (ES−) m/z 341 (M−H$^+$, 70%), 343 (M+2−H$^+$, 25%).
HRMS (EI) found 342.0766.
Anal. Found: C, 62.45; H, 4.53; N, 8.09.

EXAMPLE 21

6-Chloro-N-[(4-chlorophenyl)methyl]-4-hydroxy-3-quinoline-carboxamide

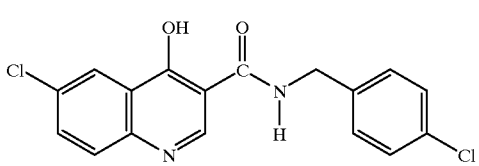

To a mixture of 0.365 g of 6-chloro-4-hydroxy-3-quinolinecarboxylic acid (J. Amer. Chem. Soc., 68, 1264 (1946)) and 5 mL of dimethylformamide is added 0.29 g of carbonyldiimidazole. The mixture is stirred 18 h at 60° C. and then it is cooled to 25° C. To the resulting solution is added 0.22 mL of 4-chlorobenzylamine. After stirring for 18 hours the mixture is diluted with 10 mL of distilled water.

After 30 minutes the precipitate is collected by filtration and it is washed with two successive mL portions of water. It is then washed with 5 mL of diethyl ether. It is dried for 48 h at 85° C. and 20 torr. This procedure yields the title compound as 251 mg of an off-white solid.

Physical characteristics are as follows:
Mp>245° C.
$^1$H NMR (DMSO) δ 8.78, 8.16, 7.80, 7.74, 7.42–7.32, 4.54.
MS (ES−) m/z 345 (M−H$^+$).
HRMS (EI) found 346.0265.
Anal. Found: C, 58.02; H, 3.54; N, 7.94; Cl, 20.33.

EXAMPLE 22

N-[(4-Chlorophenyl)methyl]-4-hydroxy-6-methyl-3-quinoline-carboxamide

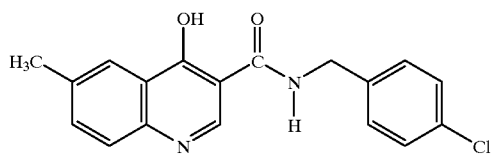

A mixture of 230 mg of ethyl 4-hydroxy-6-methyl-3-quinolinecarboxylate (J. Chem. Soc., 893 (1948)) and 0.7 mL of 4-chlorobenzylamine is stirred for 1 h at 210 ° C. The mixture is cooled to 25° C. and it is diluted with 1.5 mL of toluene. The mixture is filtered and the filtrant is dissolved in a minimum volume of refluxing glacial acetic acid. The hot solution is treated with distilled water dropwise until it becomes cloudy, and it is allowed to cool to 25° C. The precipitate is collected by filtration and it is washed with a small amount of dilute aqueous acetic acid. The solid is dried for 48 h at 20 torr and 85° C. This procedure gives the title compound as 47 mg of a light tan solid.

Physical characteristics are as follows:
Mp>245° C.
$^1$H NMR (DMSO) δ 8.71, 8.02, 7.59, 7.39, 7.35, 4.54, 2.43.
HRMS (EI) found 326.0829.
Anal. Found: C, 65.50; H, 4.71; N, 8.55.

EXAMPLE 23

N-[(4-Chlorophenyl)methyl]-4-hydroxy-6-methoxy-3-quinoline-carboxamide

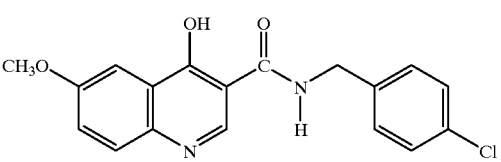

A mixture of 320 mg of ethyl 4-hydroxy-6-methoxy-3-quinolinecarboxylate (J. Amer. Chem. Soc., 68, 1204 (1946)) and 1.0 mL of 4-chlorobenzylamine is stirred for 1 h at 210° C. The mixture is cooled to 25° C. and it is diluted with 2.0 mL of toluene. The mixture is filtered and the filtrant is dissolved in a minimum volume of refluxing glacial acetic acid. The hot solution is treated with distilled water dropwise until it becomes cloudy, and it is allowed to cool to 25° C. The precipitate is collected by filtration and it is washed with a small amount of dilute aqueous acetic acid. It is dried in a stream of air and then it is dissolved in 7 mL of refluxing acetonitrile. The solution is allowed to cool to 25° C. and after an additional 2 h the precipitate is collected by filtration. The solid is dried for 48 h at torr and 85° C. This procedure gives the title compound as 64 mg of a light tan solid.

Physical characteristics are as follows:

Mp 221–222° C.

$^1$H NMR (DMSO) δ 8.64, 7.69–7.61, 7.43–7.30, 4.54, 3.85.

MS (ES−) m/z 341 (M−H$^+$).

HRMS (EI) found 342.0772.

Anal. Found: C, 62.60; H, 4.44; N, 8.10.

PREPARATION 9

6-Cyano-4-hydroxy-3-quinolinecarboxylic acid

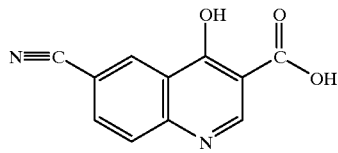

To a suspension of 5.15 g ethyl 6-cyano-4-hydroxy-3-quinolinecarboxylate (FR 2002888) in 212 mL of a 1:1 (v/v) mixture of methanol and tetrahydrofuran is added 53 mL of a 1.0 M aqueous solution of lithium hydroxide. After 24 h an additional 50 mL of 1.0 M aqueous lithium hydroxide solution is added and the mixture is stirred for 24 additional hours. It is neutralized by dropwise addition of 3.0 N hydrochloric acid. The volume of the solution is reduced by two-thirds by evaporation at reduced pressure. The precipitate is collected by filtration and it is washed several portions of distilled water. This procedure gives the title compound as 3.39 g of a white solid.

Physical characteristics are as follows:

$^1$H NMR (DMSO) δ 8.85, 8.55, 7.87, 7.79.

MS (ES−) m/z 213 (M−H$^+$, 100%).

EXAMPLE 24

N-[(4-Chlorophenyl)methyl]-6-cyano-4-hydroxy-3-quinoline-carboxamide

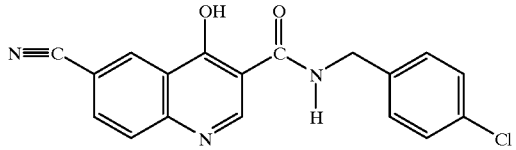

A suspension of 0.25 g of 6-cyano-4-hydroxy-3-quinolinecarboxylic acid in 5 ml of thionyl chloride is treated with one drop of dimethylformamide. The mixture is stirred 24 h at 25° C. and then the excess thionyl chloride is evaporated in a stream of nitrogen. The final traces of thionyl chloride are removed at high vacuum (0.05 torr) and the solid is suspended in 5 ml of dichloromethane. The suspension is treated with 0.46 mL of 4-chlorobenzylamine and the resulting mixture is stirred for two weeks at 25° C. The mixture is partitioned between 50 ml of ethyl acetate and 50 mL of a solution prepared by diluting a saturated aqueous solution of sodium dihydrogen phosphate with an equal volume of distilled water. The organic phase is washed with an additional 50 mL of this buffer and then it is washed with brine. The solution is dried (MgSO$_4$) and the solvent is evaporated at reduced pressure. The residual oil is treated with 10 mL of diethyl ether which causes the oil to crystallize. The solid is collected by filtration and it is washed with a minimum volume of ethyl acetate. The solid is dissolved in 1.5 mL of refluxing glacial acetic acid and the resulting solution is diluted with 3 mL of distilled water. The mixture is allowed to cool to 25° C. and the pale yellow solid which precipitated is collected by filtration. The solid is washed with 1.0 mL of 50% aqueous acetic acid and it is dried in a stream of air. The title compound is thus obtained as 50 mg of a pale yellow solid.

Physical characteristics are as follows:

Mp>265° C.

$^1$H NMR (DMSO) δ 8.84, 8.59, 8.11, 7.84, 7.39, 7.35, 4.55.

MS (ES−) m/z 337 (M−H$^+$).

HRMS (EI) found 337.0621.

Anal. Found: C, 60.76; H, 3.83; N, 11.84.

EXAMPLE 25

7-(Acetylamino)-N-[(4-chlorophenyl)methyl]-4-hydroxy-3-quinolinecarboxamide

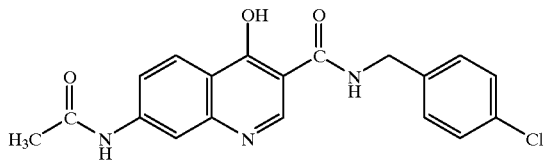

A solution of 100 mg of 7-amino-N-[(4-chlorophenyl)methyl]-4-hydroxy-3-quinolinecarboxamide in 1 mL of anhydrous pyridine is treated with 0.032 mL of acetic anhydride. After 24 h, an additional 0.005 mL of acetic anhydride is added and the mixture is stirred for an additonal 48 h. The mixture is diluted with 2 mL of distilled water and the precipitate is collected by filtration. It is washed with two 1 mL portions of distilled water and dried in a stream of air. It is dried at 20 torr/75°C./16 h. The product is obtained as 78 mg of a tan solid.

Physical characteristics are as follows:

Mp>250° C.

$^1$H NMR (DMSO) δ 12.65, 10.42, 10.45, 8.61, 8.27, 8.12, 7.42–7.28, 4.52, 2.10.

MS (EI) m/z 369 (M+), 371, 230, 229, 203, 202, 186, 160, 140, 125.

HRMS (EI) found 369.0878.

EXAMPLE 26

N-[(4-Chlorophenyl)methyl]-4-hydroxy-7-[(methylsulfonyl)-amino]-3-quinolinecarboxamide

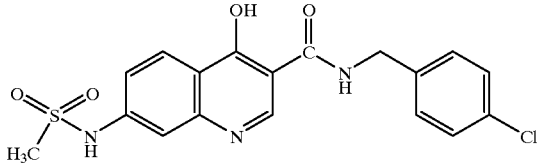

Methanesulfonyl chloride is added to a solution of 200 mg of 7-amino-N-r[(4-chlorophenyl)methyl]-4-hydroxy-3-quinolinecarboxamide in 1.0 mL of anhydrous pyridine. The mixture is stirred for 20 h and then it is diluted with 2 mL of distilled water. The precipitate is collected by filtration and it is washed with two 2 mL portions of distilled water. It is dried in a stream of air and then further dried at 70 ° C./20 torr/2 h. The product is obtained as 225 mg of a dark orange powder.

Physical characteristics are as follows:

Mp>220° C.

$^1$H NMR (400 MHz, DMSO) δ 12.63, 10.50, 10.41, 8.64, 8.15, 7.51, 7.40–7.29, 7.22, 4.52, 3.13.

MS (EI) m/z 405 (M+), 266, 265, 238, 187, 186, 159, 142, 140, 125.

Anal. Found: C, 57.02; H, 4.19; N, 11.24. (The presence of 1.0 equivalent of pyridine was confirmed by $^1$H-NMR.)

EXAMPLE 27

N-[(4-Chlorophenyl)methyl]-7-(dimethylamino)-4-hydroxy-3-quinolinecarboxamide

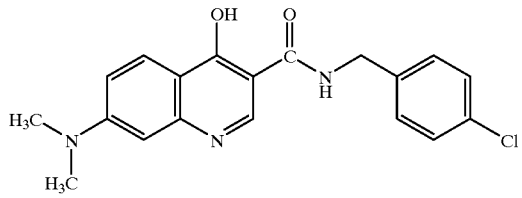

Sodium cyanoborohydride (96 mg) is added to a mixture of 100 mg 7-amino-N-[(4-chlorophenyl)methyl]-4-hydroxy-3-quinolinecarboxamide and 91 mg paraformaldehyde in 5 mL of acetic acid. After 2 days the mixture is diluted with 5 mL of distilled water (use of more water causes the product to precipitate as an oil). The mixture is stirred an additional 10 min and then the product is collected by filtration. It is washed with three 1 mL portions of 50% aqueous acetic acid and dried in a stream of air. It is dried at 20 torr/24 h/75° C. The product is obtained as mg of an off-white powder.

Physical characteristics are as follows:

Mp>240° C.

MS (EI) m/z 355 (M+), 357, 216, 215, 214, 189, 188, 187, 159, 132.

Anal. Found: C, 63.56; H, 5.13; N, 11.57.

EXAMPLE 28

6-Amino-N-[(4-chlorophenyl)methyl]-4-hydroxy-3-quinoline-carboxamide

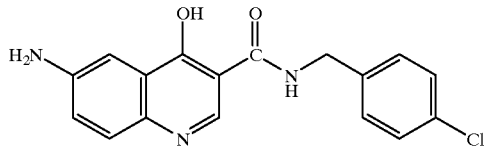

N-[(4-chlorophenyl)methyl]-4-hydroxy-6-nitro-3-quinolinecarboxamide (500 mg) is suspended in 50 mL of freshly degassed dimethylformamide and treated with 0.5 mL of 50% Raney nickel in water (Aldrich). The mixture is agitated under 45 psi hydrogen pressure for 24 h, and then it is filtered through celite. The solvent is removed by evaporation at reduced pressure and the residue is suspended in 5 mL of absolute ethanol and it is collected by filtration. After drying at 0.1 torr/100 ° C./1.5 h, the product is obtained as 387 mg of a pale yellow powder.

Physical characteristics are as follows:

Mp>225° C.

$^1$H NMR (DMSO) δ 8.51, 7.43–7.27, 7.30, 7.07, 5.52, 4.53.

MS (EI) m/z 327 (M+), 329, 188, 187, 186, 161, 160, 140, 131, 104.

HRMS (EI) found 327.0787.

Anal. Found: C, 61.55; H, 4.53; N, 12.71.

EXAMPLE 29

N-[(4-Chlorophenyl)methyl]-4-hydroxy-6-[(methylsulfonyl)-amino]-3-quinolinecarboxamide

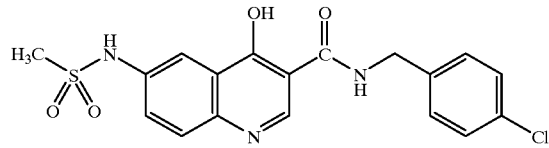

This compound is prepared from 6-amino-N-[(4-chlorophenyl)methyl]-4-hydroxy-3-quinolinecarboxamide using a procedure similar to that used to prepare N-[(4-chlorophenyl)methyl]-4-hydroxy-7-[(methylsulfonyl) amino]3-quinoline-carboxamide from 7-amino-N-[(4-chlorophenyl)methyl]-4-hydroxy-3-quinoline-carboxamide. The product is obtained as a tan powder.

Physical characteristics are as follows:

Mp>200° C.

$^1$H NMR (DMSO) δ 10.42, 8.71, 8.07, 7.70, 7.62, 7.39, 7.35, 4.54, 3.00.

MS (EI) m/z 405 (M+), 265, 264, 238, 186, 185, 159, 142, 140, 125.

HRMS (EI) found 405.0541.

Anal. Found: C, 52.31; H, 4.24; N, 9.97.

EXAMPLE 30

N-[(4-Chlorophenyl)methyl]-6-(dimethylamino)-4-hydroxy-3-quinolinecarboxamide

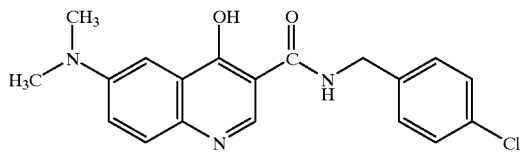

This compound is prepared from 6-amino-N-[(4-chlorophenyl)methyl]-4-hydroxy-3-quinolinecarboxamide using a procedure similar to that used to prepare N-[(4-chlorophenyl)methyl]-7-(dimethylamino)-4-hydroxy-3-quinolinecarboxamide from 7-amino-N-[(4-chlorophenyl)methyl]-4-hydroxy-3-quinolinecarboxamide (29805JT118). The product is obtained as a tan powder.

Physical characteristics are as follows:

Mp>225° C.

$^1$H NMR (DMSO) δ 8.58, 7.57, 7.43–7.28, 4.53, 2.98.

MS (EI) m/z 355 (M+), 357, 216, 215, 214, 188, 187, 173, 159, 145.

HRMS (EI) found 355.1093.

Anal. Found: C, 61.03; H, 5.03; N, 10.85.

EXAMPLE 31

6-(Acetylamino)-N-[(4-chlorophenyl)methyl]-4-hydroxy-3-quinolinecarboxamide

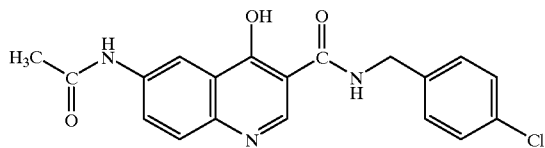

This compound is prepared from 6-amino-N-[(4-chlorophenyl)methyl]-4-hydroxy-3-quinolinecarboxamide using a procedure similar to that used to prepare 7-(acetylamino)-N-[(4-chlorophenyl)methyl]-4-hydroxy-3-quinolinecarboxamide from 7-amino-N-[(4-chlorophenyl)methyl]-4-hydroxy-3-quinolinecarboxamide. The product is obtained as a tan powder.

Physical characteristics are as follows:

Mp>220° C.

$^1$H NMR (DMSO) δ 8.67, 8.48, 7.96, 7.64, 7.41–7.32, 4.54, 2.07.

MS (EI) m/z 369 (M+), 230, 229, 228, 203, 202, 186, 160, 140, 125.

Anal. Found: C, 61.38; H, 4.47; N, 11.06.

EXAMPLE 32

N-[(4-Chlorophenyl)methyl]-4-hydroxy-7-(1-pyrrolyl)-3-quinolinecarboxamide

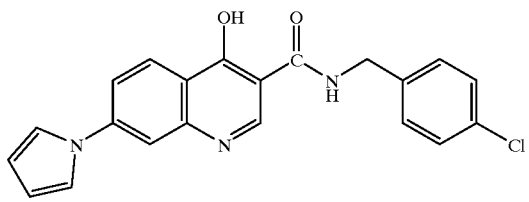

A mixture of 100 mg of 7-amino-N-[(4-chlorophenyl)methyl]-4-hydroxy-3-quinolinecarboxamide and 0.043 mL 2,5-dimethoxytetrahydrofuran in 1 mL of acetic acid is refluxed for four hours. (The mixture rapidly turned very dark.) It is cooled to 25° C. and the precipitate is collected by filtration. It is washed with three 1 mL portions of acetic acid and dried in a stream of air. After drying at 75° C. the product is obtained as 20 mg of a brown powder.

Physical characteristics are as follows:

Mp>200° C.

$^1$H NMR (400 MHz, DMSO) δ 8.77, 8.27, 7.74, 7.73, 7.48, 7.42–7.32, 6.37, 4.54.

MS (EI) m/z 377 (M+), 238, 237, 236, 211, 210, 154, 142, 140, 125.

HRMS (EI) found 377.0918.

Anal. Found: C, 65.15; H, 4.42; N, 10.51.

EXAMPLE 33

N-[(4-Chlorophenyl)methyl]-4-hydroxy-7-[(phenylsulfonyl)-amino]-3-quinolinecarboxamide

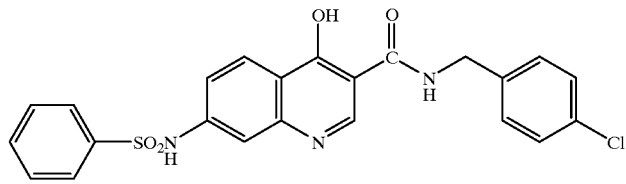

A solution of 40 mg of 6-amino-N-[(4-chlorophenyl)methyl]-4-hydroxy-3-quinolinecarboxamide in 1 mL of anhydrous pyridine is treated with 16.9 μL of benzenesulfonyl chloride. The mixture is stirred 3 h at 25° C. and then 24 h at 50° C. The reaction mixture is diluted with 2 mL of distilled water and the solid which precipitated is collected by filtration. It is washed with two 1 mL portions of distilled water and dried for 16 h at 20 torr and 75° C. The yield is 36 mg.

Physical characteristics are as follows:

Mp>200° C.

¹H NMR (DMSO) δ 8.62, 8.06, 8.87, 7.67–7.52, 7.46, 7.40–7.30, 7.15, 4.52.

MS (EI) m/z 467 (M+), 327, 301, 300, 187, 186, 159, 142, 140, 125, 77.

Anal. Found: C, 59.91; H, 4.24; N, 9.79. (The presence of 0.4 equivalent of pyridine was confirmed by ¹H-NMR.)

EXAMPLE 34

N-[(4-Chlorophenyl)methyl]-4-hydroxy-7-[[(phenylmethyl)-sulfonyl]amino]-3-quinolinecarboxamide

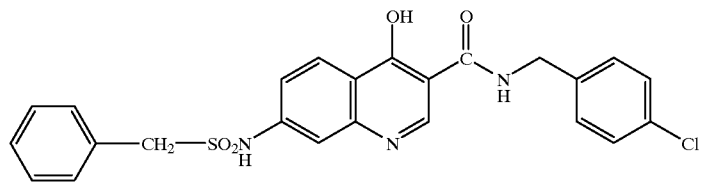

This compound is prepared by the procedure used to prepare the title compound of Example No. 33 above, except that 25 mg of α-toluenesulfonyl chloride is used in place of the benzenesulfonyl chloride. The yield is 48 mg.

Physical characteristics are as follows:

Mp>200° C.

¹H NMR (DMSO) δ 8.65, 8.13, 7.52, 7.42–7.22, 7.19, 4.61, 4.54.

MS (EI) m/z 481 (M+), 314, 187, 186, 160, 159, 140, 125, 106, 91, 77.

Anal. Found: C, 61.11; H, 4.50; N, 9.73. (The presence of 0.5 equivalent of pyridine was confirmed by ¹H-NMR.)

EXAMPLE 35

N-[(4-Chlorophenyl)methyl]-7-[[(4-chlorophenyl)sulfonyl]amino]-4-hydroxy-3-quinolinecarboxamide

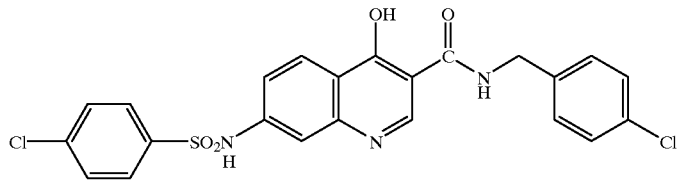

This compound is prepared by the procedure used to prepare the title compound of Example No. 33 above, except that 28 mg of 4-chlorobenzenesulfonyl chloride is used in place of the benzenesulfonyl chloride. The yield is 52 mg.

Physical characteristics are as follows:

Mp>200° C.

¹H NMR (DMSO) δ 8.57, 8.08, 7.85, 7.66, 7.46, 7.42–7.27, 7.16, 4.51.

MS (EI) m/z 501 (M+), 336, 334, 187, 186, 159, 142, 140, 131, 125, 111.

PREPARATION 10

8-Fluoro-4-hydroxy-3-quinolinecarboxylic acid

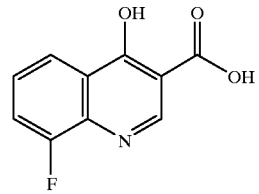

To a suspension of 3.53 g of ethyl 8-fluoro-4-hydroxy-3-quinolinecarboxylate (J. Med. Chem., 22, 816 (1979)) in 150 mL of tetrahydrofuran and 150 mL of methanol is added 3.14 g of lithium hydroxide hydrate as a solution in 75 mL of water. The mixture is heated at 55° C. overnight. The reaction is cooled to room temperature and concentrated under reduced pressure to remove volatiles. The aqueous phase is cooled to 0° C. and treated dropwise with 6N hydrochloric acid until pH 4. The resulting precipitate is collected by filtration, washed with dilute pH 4 phosphate buffer and air-dried. The residue is crystallized from dimethylformamide-water and dried in vacuo to afford 2.75 g of the title compound.

Physical characteristics are as follows:

¹H NMR (DMSO) δ 14.9, 13.6, 8.6, 8.1, 7.8, 7.6.

MS (ES–) m/z 206 (M–H⁺).

PREPARATION 11
(8-Fluoro-4-hydroxy-3-quinolinoyl)-1H-imidazole

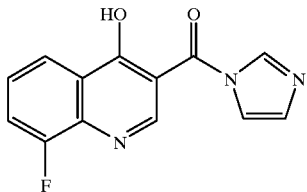

To a flame-dried flask under an atmosphere of argon is added 1.04 g of 8-fluoro-4-hydroxy-3-quinolinecarboxylic acid, 0.9 g of 1,1'-carbonyldiimidazole and 50 mL of dry tetrahydrofuran. The mixture is heated to reflux overnight. The reaction is cooled to room temperature, treated with an additional 0.15 g of 1,1-carbonyldiimidazole and heating is resumed. After overnight reflux, the suspension is cooled to room temperature and the resulting precipitate collected by filtration. The solid is washed with tetrahydrofuran, diethyl ether and hexanes, and dried in vacuo to afford 1.34 g of the crude title compound which is used without additional purification.

Physical characteristics are as follows:

$^1$H-NMR (DMSO): δ 8.4, 8.2, 8.0, 7.7, 7.6, 7.4, 7.0.
MS (ES−) m/z 256 (M−H$^+$).

EXAMPLE 36

8-Fluoro-4-hydroxy-3-quinolinecarboxylic acid 2-(4-chlorophenyl) hydrazide

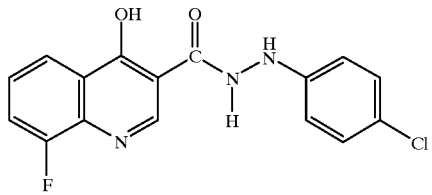

Physical characteristics are as follows:

$^1$H NMR (DMSO) δ 13.0, 11.2, 8.6, 8.2, 8.1, 7.7, 7.5, 7.2, 6.7.
MS (ES−) m/z 330 (M−H$^+$).

EXAMPLE 38

N-[(4-Chlorophenyl)methyl]-8-fluoro-4-hydroxy-6-methyl-3-quinolinecarboxamide

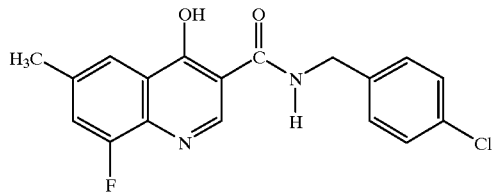

A mixture of 2-fluoro-4-methylaniline (5.0 g) and diethyl ethoxymethylene-malonate (8.64 g) is heated to 130° C. for 2 h with removal of ethanol by a Dean-Stark trap. The mixture is cooled to 75° C. and diphenyl ether (50 mL) is added. The solution is heated to 250° C. for 2 h with removal of ethanol by a Dean-Stark trap, then cooled to room temperature. The resulting solid is collected, washed with hexanes and dried to yield 5.564 g of ethyl 8-fluoro-4-hydroxy-6-methylquinoline-3-carboxylate. A mixture of this ester (0.50 g) and 4-chlorobenzylamine (3.0 mL) are heated at 180° C. for 1 hour. The reaction is cooled and poured into 50 mL of diethyl ether. The resulting solid is filtered, dried, and purified by trituration in acetone to give the desired product (0.54 g).

Physical characteristics are as follows:

Mp 278–279° C. dec.

$^1$H NMR (300 MHz, DMSO-d$_6$) δ 12.37, 10.30, 8.57, 7.82, 7.55, 7.37, 7.33, 4.53, 2.43.

IR (mull) 3086, 3008, 1665, 1614, 1580, 1543, 1512, 1493, 1484, 1432, 1268, 991, 796, 661, 651 cm$^{-1}$.

MS (electrospray) 345.1 (M+H), 367.1 (M+Na), 343.1 (M−H).

Anal.Found: C, 62.38; H, 4.05; N, 8.04; Cl, 10.35.

EXAMPLE 39

N-[(4-Chlorophenyl)methyl]-4-hydroxy-7-iodo-3-quinolinecarboxamide

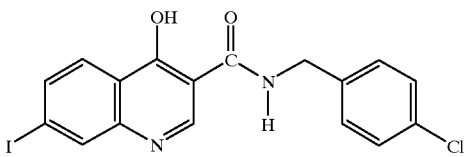

3-Iodoaniline (8.50 mL) and diethyl ethoxymethylenemalonate (14.30 mL) are heated at 130° C. for 1 hour. The reaction is cooled to room temperature and 70 mL diphenyl ether is added. The solution is heated at 250° C. for 1.5 hours with removal of ethanol by a Dean-Stark trap. The reaction is cooled to room temperature and the resulting solid filtered, washed with hexanes, and dried. The solid is triturated in ethyl acetate to give 12.82 g of ethyl 4-hydroxy-7-iodoquinoline-3-carboxylate. A mixture of this ester (0.35 g) and 4-chlorobenzylamine (3.0 mL) are heated at 180° C. for 1 hour. The reaction is cooled to 70° C. and poured into 50 mL diethyl ether. A tan solid which crystallizes slowly out of diethyl ether is obtained. The solid is recrystallized from ethyl acetate/hexanes to give the desired product (0.22 g).

Physical characteristics are as follows:

Mp 248–250° C.

$^1$H NMR (300 MHz, DMSO-d$_6$) δ 12.60, 10.29, 8.74, 8.07, 7.95, 7.76, 7.38, 7.33, 4.52.

IR (mull) 3343, 3245, 3200, 3149, 3064, 1640, 1623, 1603, 1552, 1530, 1513, 1492, 1352, 1191, 791 cm$^{-1}$.

MS (electrospray) 438.9 (M+H).

HRMS (EI) found 437.9637.

EXAMPLE 40

N-[(4-Chlorophenyl)methyl]-4-hydroxy-6-iodo-3-quinoline-carboxamide

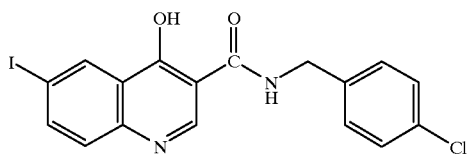

4-Iodoaniline (8.60 g) and diethyl ethoxymethylenemalonate (7.90 mL) are heated at 130° C. for 1 hour. The reaction is cooled to room temperature and 60 mL diphenyl ether is added. The solution is heated at 250° C. for 1.5 hours with removal of ethanol by a Dean-Stark trap. The reaction is cooled to room temperature and the resulting solid is filtered, washed with hexanes, and dried to yield 11.20 g of ethyl 4-hydroxy-6-iodoquinoline-3-carboxylate. A mixture of this ester (0.58 g) and 4-chlorobenzylamine (4.0 mL) are heated at 180° C. for 1.5 hours. The reaction is cooled and poured into 50 mL diethyl ether. The resulting solid is filtered, triturated in ethyl acetate, and filtered again to give the desired product (0.50 g).

Physical characteristics are as follows:

Mp 297–299° C.

$^1$H NMR (300 MHz, DMSO-$d_6$) δ 12.71, 10.27, 8.76, 8.50, 8.02, 7.50, 7.38, 7.33, 4.52.

IR (mull) 3151, 3078, 3039, 1631, 1610, 1572, 1563, 1545, 1527, 1512, 1491, 1433, 1351, 1303, 799 cm$^{-1}$.

MS (electrospray) 438.9 (M+H), 460.9 (M+Na), 436.9 (M−H).

Anal. Found: C, 46.61; H, 2.81; N, 6.34; Cl, 8.19.

EXAMPLE 41

N-[(4-Chlorophenyl)methyl]-6-(cyanomethyl)-4-hydroxy-3-quinolinecarboxamide

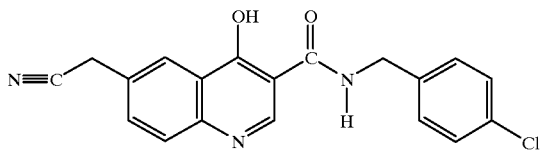

A suspension of 4-aminobenyl cyanide (6.61 g) and diethyl ethoxymethylene-malonate (10.1 mL) is heated to 95° C. for 1 hour. The reaction is cooled to room temperature and poured into 50 mL hexanes to wash away impurities. The desired enamine intermediate formed upon cooling and is filtered and collected. In a 3-necked roundbottom connected to a Dean-Stark trap, 75 mL of diphenyl ether is added to the enamine and the solution is heated at 250° C. for 2 hours. The crude product is washed with hot MeOH and dried to yield 3.40 g of ethyl 6-cyanomethyl-4-hydroxyquinoline-3-carboxylate as an orange solid. A mixture of this ester (0.50 g) and p-chlorobenzylamine (3.5 mL) are heated at 180° C. for 1 hour. The reaction is cooled to room temperature and diluted with CH$_2$Cl$_2$ and ether. The solvents are evaporated. The residue is chromatographed on silica, eluting with 3% MeOH in CH$_2$Cl$_2$. Fractions homogenous by TLC are combined, condensed and recrystallized with EtOAc/hexanes to yield 0.162 g of the desired product as a light yellow solid.

Physical characteristics are as follows:

Mp 244–246° C.

$^1$H NMR (300 MHz, DMSO) δ 10.39, 8.75, 8.22, 7.73, 7.39, 7.34, 4.54, 4.21.

IR (mull) 3084, 3060, 3039, 3018, 1644, 1626, 1616, 1578, 1548, 1530, 1490, 1294, 804, 800, 723 cm$^{-1}$.

MS (EI) m/z 351 (M+), 353, 351, 211, 184, 156, 155, 142, 140, 127, 125.

HRMS (FAB) found 352.0863.

EXAMPLE 42

N-[(4-Chlorophenyl)methyl]-4,5-dihydroxy-3-quinolinecarboxamide

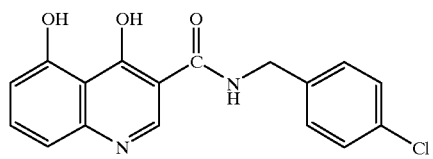

A mixture of 3-aminophenol (5.457 g) and diethyl ethoxymethylenemalonate (10.81 g) is heated to 130° C. for 2 h with removal of ethanol by a Dean-Stark trap. The reaction is cooled to 80° C. and 50 ml of diphenyl ether is added. The mixture is heated to 250° C. for 30 min with removal of ethanol by a Dean-Stark trap. The solution is cooled to 80° C. and the resulting solid is collected and washed with hexanes. A portion of this solid is adsorbed onto silica and chromatographed, eluting with 5% MeOH/CH$_2$Cl$_2$. Fractions homogeneous by TLC are combined and concentrated in vacuo to yield ethyl 4,5-dihydroxyquinoline-3-carboxylate as a gold solid. A mixture of this ester (0.125 g) and 4-chlorobenzylamine (0.379 g) are heated to 180° C. for 1 h. The solution is cooled to room temperature. The crude reaction is chromatographed on silica, eluting with 2% MeOH/CH$_2$Cl$_2$. Fractions homogeneous by TLC are combined and concentrated in vacuo. The residue is sonicated with CH$_2$Cl$_2$/hexanes. The resulting solid is collected and dried to yield 0.050 g of the desired product as a pale-yellow solid.

Physical characteristics are as follows:

Mp 235–238° C.

$^1$H NMR (300 MHz, DMSO) δ 13.71, 13.04, 9.72, 8.87, 7.59, 7.38, 7.34, 7.08, 6.71, 4.52.

$^{13}$C NMR (75 MHz, DMSO) d 181.0, 164.1, 161.4, 145.3, 140.6, 139.1, 135.3, 131.8, 129.7, 128.8, 113.5, 110.4, 110.2, 108.5, 42.0.

IR (mull) 3184, 3118, 3042, 1654, 1630, 1561, 1531, 1493, 1328, 1286, 1248, 1210, 819, 740, 604 cm$^{-1}$.

MS (EI) m/z 328 (M$^+$), 330, 328, 188, 161, 142, 140, 133, 125, 104, 77.

Anal. Found: C, 61.75; H, 4.07; N, 8.21; Cl, 11.04.

EXAMPLE 43

7,8-Dichloro-N-[(4-chlorophenyl)methyl]-4-hydroxy-3-quinolinecarboxamide

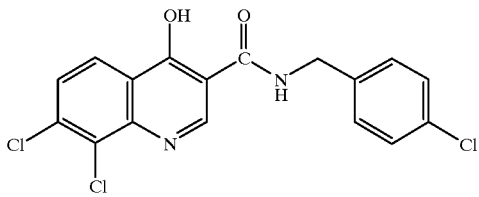

2,3-Dichloroaniline (7.83 g) and diethyl ethoxymethylenemalonate (9.76 g) are heated at 130° C. for 1.5 hours. The reaction is cooled to 60° C. and the solution poured into hexanes. The intermediate enamine is collected and dried. The solid is added to 70 mL diphenyl ether and heated to 250° C. for 1.5 hours with removal of ethanol with a Dean-Stark trap. The reaction is cooled to room temperature. The product is collected by filtration, washed thoroughly with hexanes, and dried to yield 11.32 g of ethyl 7,8-dichloro-4-hydroxyquinoline-3-carboxylate. A mixture of this ester (0.48 g) and 4-chlorobenzylamine (1.0 mL) are heated at 180° C. for 1 hour. The reaction is cooled to room temperature and diethyl ether is added. The resulting solid is filtered, washed twice with diethyl ether, and dried. The solid is adsorbed onto silica and purified by Biotage Flash 40S chromatography (eluent 2% MeOH:CH$_2$Cl$_2$). The product-containing fractions are evaporated to give a white solid (0.12 g).

Physical characteristics are as follows:

Mp 295–297° C.

$^1$H NMR (300 MHz, DMSO-d$_6$) δ 12.43, 10.12, 8.65, 8.18, 7.68, 7.37, 7.34, 4.52.

IR (mull) 3204, 3094, 3077, 3026, 1663, 1603, 1586, 1553, 1526, 1492, 1443, 1330, 1272, 1095, 786 cm$^{-1}$.

MS (EI) m/z 380 (M$^+$), 382, 380, 242 240, 215, 213, 142, 141, 140, 125.

HRMS (EI) found 379.9857.

EXAMPLE 44

N-[(4-Chlorophenyl)methyl]-4,6-dihydroxy-3-quinoline-carboxamide

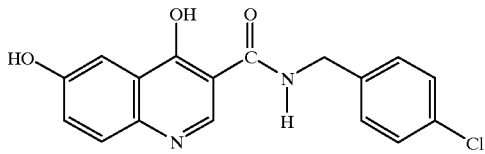

A mixture of 4-aminophenol (5.457 g) and diethyl ethoxymethylenemalonate (10.81 g) is heated to 130° C. for 2 h with removal of ethanol by a Dean-Stark trap. The reaction is cooled to room temperature. Diphenyl ether (50 mL) is added and the mixture is heated to 250° C. for 45 min with removal of ethanol by a Dean-Stark trap. The solution is cooled to 80° C. and the resulting solid is collected and washed with hexanes. The solid is suspended in 250 mL MeOH and brought to a boil. The insoluble material is filtered and the filtrate is adsorbed onto silica and chromatographed, eluting with 5% MeOH/CH$_2$Cl$_2$ then with 10% MeOH/CH$_2$Cl$_2$. Fractions homogeneous by TLC are combined and concentrated in vacuo to yield 0.644 g of ethyl 4,6-dihydroxyquinoline-3-carboxylate. A mixture of this ester (0.500 g) and 4-chlorobenzylamine (1.518 g) are heated to 180° C. for 1 h. The solution is cooled to room temperature and diluted with CH$_2$Cl$_2$. The resulting solid is collected and chromatographed on silica, eluting with 3% MeOH/CH$_2$Cl$_2$. Fractions homogeneous by TLC are combined and concentrated in vacuo. The residue is sonicated with CH$_2$Cl$_2$/hexanes. The resulting solid is collected and dried to afford 0.372 g of the desired product as a white solid.

Physical characteristics are as follows:

Mp 319–320° C.

$^1$H NMR (300 MHz, DMSO) δ 12.58, 10.52, 9.97, 8.63, 7.54, 7.38, 7.33, 7.23, 4.53.

$^{13}$C NMR (75 MHz, DMSO) d 175.9, 165.4, 155.4, 142.4, 139.3, 133.0, 131.8, 129.7, 128.8, 128.1, 123.2, 121.1, 109.7, 108.3, 41.8.

IR (mull) 3214, 3114, 3084, 3062, 3042, 1634, 1618, 1540, 1493, 1444, 1356, 1296, 1233, 1223, 800 cm$^{-1}$.

MS (EI) m/z 328 (M$^+$), 330, 328, 189, 188, 187, 161, 142, 140, 133, 125.

Anal. Found: C, 61.92; H, 3.82; N, 8.44; Cl, 10.78.

EXAMPLE 45

N-[(4-Chlorophenyl)methyl]-4,8-dihydroxy-3-quinoline-carboxamide

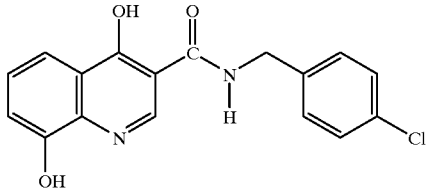

A mixture of 2-aminophenol (5.457 g) and diethyl ethoxymethylenemalonate (10.81 g) is heated to 130° C. for 2 h with removal of ethanol by a Dean-Stark trap. The reaction is cooled to room temperature. Diphenyl ether (50 mL) is added and the mixture is heated to 240° C. for 90 min with removal of ethanol by a Dean-Stark trap. The solution is cooled to room temperature and the resulting solid is collected and washed with hexanes. The crude solid is recrystallized from acetone to yield 0.650 g of ethyl 4,8-dihydroxyquinoline-3-carboxylate. A mixture of this ester (0.500 g) and 4-chlorobenzylamine (1.518 g) are heated to 180° C. for 1 h. The solution is cooled to room temperature and diluted with CH$_2$Cl$_2$. The resulting solid is collected and chromatographed on silica, eluting with 3% MeOH/CH$_2$Cl$_2$. Fractions homogeneous by TLC are combined and concentrated in vacuo. The residue is sonicated with CH$_2$Cl$_2$/hexanes. The resulting solid is collected and dried to afford 0.349 g of the desired product as an off-white solid.

Physical characteristics are as follows:

Mp 319–320° C.

$^1$H NMR (300 MHz, DMSO) δ 10.46, 8.57, 7.65, 7.38, 7.33, 7.26, 7.15, 4.52.

$^{13}$C NMR (75 MHz, DMSO) d 176.6, 165.2, 147.7, 143.1, 139.2, 131.8, 129.8, 29.7, 128.8, 127.9, 125.5, 115.9, 115.5, 111.0, 41.8.

IR (mull) 3144, 3080, 3041, 1651, 1624, 1606, 1538, 1490, 1479, 1359, 1280, 211, 1194, 1016, 772 cm$^{-1}$.

MS (EI) m/z 328 (M+), 330, 328, 188, 187, 161, 140, 127, 125, 104, 89.

HRMS (EI) found 328.0627.

EXAMPLE 46

8-Chloro-N-[(4-chlorophenyl)methyl]-4-hydroxy-3-quinolinecarboxamide

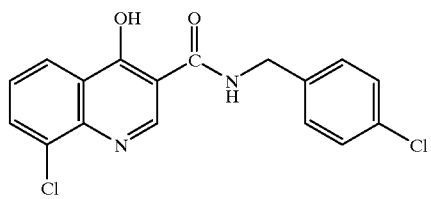

Ethyl 8-chloro-4-hydroxyquinoline-3-carboxylate (1.21 g) and 4-chlorobenzyl-amine (1.8 mL) are heated at 180° C. for 2 hours. The reaction is cooled to room temperature and the resulting solid filtered, washed thoroughly with diethyl ether and methylene chloride, and dried to give the desired product (1.44 g).

Physical characteristics are as follows:

Mp 279–281° C.

$^1$H NMR (300 MHz, DMSO-d$_6$) δ 12.25, 10.20, 8.65, 8.20, 7.94, 7.45, 7.37, 7.34, 4.52.

IR (mull) 3217, 3190, 1660, 1600, 1558, 1551, 1527, 1492, 1442, 1433, 1331, 1281, 803, 749, 726 cm$^{-1}$.

MS (EI) m/z 346 (M+), 348, 346, 206, 181, 179, 151, 142, 140, 125, 89.

Anal. Found: C, 58.86; H, 3.61; N, 8.05; Cl, 18.81.

EXAMPLE 47

N-[(4-Chlorophenyl)methyl]-4-hydroxy-6-[[(1-phenyl-1H-pyrazol-5-yl)amino]sulfonyl]-3-quinolinecarboxamide

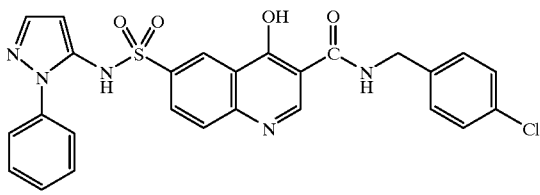

A solution of sulfapyridine (6.23 g) and diethyl ethoxymethylenemalonate (5.406 g) is heated at 135° C. for 1 h. The mixture is cooled to room temperature. Diphenyl ether (50 mL) is added and the mixture is heated to 250° C. for 30 min. The mixture is cooled to room temperature and poured into 250 mL hexanes. An oily residue formed and the solvents are decanted off. The residue is taken up in CH$_2$Cl$_2$. Hexanes are added and a solid formed which is collected and dried. The solid is chromatographed on silica, eluting with 5% MeOH/CH$_2$Cl$_2$. Fractions homogeneous by TLC are combined and concentrated in vacuo to yield 0.254 g of the desired ester as a pale-yellow solid. A mixture of this ester (0.200 g) and 4-chrlorobenzylamine (0.28 mL) are heated to 180° C. for 1 h. The reaction is cooled to room temperature and diluted with CH$_2$Cl$_2$. The resulting solid is collected, dried and chromatographed on silica, eluting with 5% MeOH/CH$_2$Cl$_2$. Fractions homogeneous by TLC are combined and concentrated in vacuo. The resulting solid is recrystallized from acetone/hexanes to yield 0.031 g of the desired product as a tan solid.

Physical characteristics are as follows:

Mp 185–187° C.

IR (mull) 3251, 3089, 3066, 1652, 1624, 1612, 1598, 1553, 1521, 1502, 1338, 1166, 760, 692, 683 cm$^{-1}$.

MS (FAB) m/z 534 (MH+), 536, 535, 534, 160, 142, 139, 125, 123, 105, 103.

HRMS (FAB) found 534.1023.

EXAMPLE 48

N-[(4-Chlorophenyl)methyl]-8-cyano-4-hydroxy-3-quinoline-carboxamide

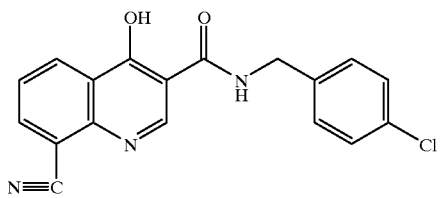

Anthranilonitrile (8.23 g) and diethyl ethoxymethylenemalonate (14 mL) are heated at 130° C. for 1 hour. The reaction is cooled to 60° C., poured into 50 mL hexanes, and the resulting enamine intermediate filtered and dried. The enamine is added to 60 mL diphenyl ether and heated to 250° C. for 1 hour with removal of ethanol by a Dean-Stark trap. The reaction is cooled to room temperature and the orange-brown solid filtered, washed thoroughly with hexanes, and dried to give ethyl 8-cyano-4-hydroxyquinoline-3-carboxylate (5.69 g). A mixture of this ester (1.00 g) is added to 60 mL 1:1 THF:MeOH. Lithium hydroxide (1.0 M solution, 16 mL) is added dropwise and the reaction mixture heated at 40° C. overnight. The reaction is poured into 20 mL acetic acid. The volume is reduced by half on the rotary evaporator after which a solid precipitated. The solid is filtered, washed with water, and dried. An additional crop of the desired acid is obtained by further reducing the volume of the filtrate. The crops are combined to yield 0.72 g of 8-cyano-4-hydroxyquinoline-3-carboxylic acid. The acid (0.24 g) and carbonyldiimidazole (0.20 g) are added to 10 mL freshly distilled tetrahydrofuran and heated at reflux overnight. The reaction is cooled to room temperature and 4-chlorobenzylamine (0.13 mL) is added dropwise. The reaction is stirred at room temperature for 24 hours, then at reflux for 6 hours. The reaction is cooled and a white solid filtered and dried to give the desired product (0.17 g).

Physical characteristics are as follows:

Mp 287–289° C.

$^1$H NMR (300 MHz, DMSO-d$_6$) δ 10.76, 10.13, 8.64, 8.51, 8.30, 7.58, 7.37, 7.34, 4.52.

IR (mull) 3193, 1666, 1615, 1606, 1594, 1573, 1556, 1521, 1487, 1435, 1327, 1287, 805, 755, 737 cm$^{-1}$.

MS (electrospray) 338.1 (M+H), 336.1 (M−H).

HRMS (EI) found 337.0639.

Anal. Found: C, 61.52; H, 3.56; N, 12.13; Cl, 10.08.

EXAMPLE 49

N-[(4-Chlorophenyl)methyl]-4-hydroxy-8-nitro-3-quinoline-carboxamide

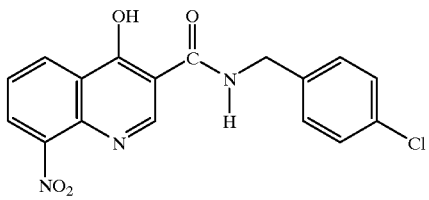

A mixture of 2-nitroaniline (6.907 g) and diethyl ethoxymethylenemalonate (10.812 g) is heated to 130° C. for 2 h with removal of ethanol by a Dean-Stark trap. The mixture is cooled to 80° C. Diphenyl ether (60 mL) is added and the mixture is heated to 250° C. for 2 h. The solution is cooled to room temperature. The resulting solid is collected, washed with hexanes and dried to yield 3.447 g of ethyl 4-hydroxy-8-nitroquinolone-3-carboxylate as a gold solid. To a mixture of this ester (1.2 g) in 66 mL of 1:1 MeOH:THF is added 18 mL of 1M LiOH. The reaction is maintained at 40° C. overnight. The reaction mixture is cooled to room temperature, then diluted with 35 mL glacial acetic acid. The resulting precipitate is collected, washed with $H_2O$ and hot isopropanol, and dried to yield 0.639 g of 4-hydroxy-8-nitroquinoline-3-carboxylic acid as a yellow solid. A mixture of this acid (0.20 g) and p-chlorobenzylamine (0.10 mL) are dissolved in 25 mL xylenes and heated to reflux. $PCl_3$ (0.037 mL) is added dropwise and the mixture is refluxed for 4 hours. The reaction mixture is cooled to room temperature and $H_2O$ is added to quench excess $PCl_3$. An orange solid precipitates, which is collected, washed with ether, and dried. The crude product is recrystallized with hot MeOH to yield 0.0367 g of the desired product as a yellow solid.

Physical characteristics are as follows:

Mp 275–278° C. (dec).

$^1$H NMR (300 MHz, DMSO-$d_6$) δ 10.08, 8.82, 8.70, 7.65, 7.39, 7.35, 4.54.

IR (mull) 3261, 3231, 1667, 1592, 1567, 1550, 1502, 1434, 1321, 1267, 1260, 1182, 782, 745, 725 cm$^{-1}$.

MS (EI) m/z 357 (M$^+$), 357, 217, 200, 190, 171, 144, 142, 140, 89, 53.

HRMS (FAB) found 358.0600.

EXAMPLE 50

7-Amino-N-[(4-chlorophenyl)methyl]-4-hydroxy-8-methyl-3-quinolinecarboxamide

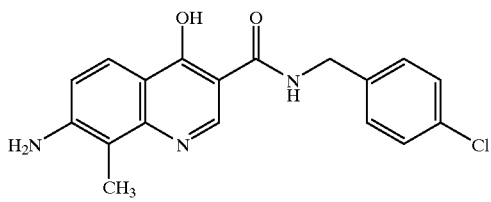

2-Methyl-3-nitroaniline (10.17 g) and diethyl ethoxymethylenemalonate (13.65 mL) are reacted at 130° C. for 2 hours. The reaction is cooled to room temperature and 80 mL diphenyl ether is added. The solution is heated to 250° C. for 1 hour with removal of ethanol by a Dean-Stark trap. The reaction is cooled to room temperature and the resulting ethyl 4-hydroxy-8-methyl-7-nitroquinoline-3-carboxylate is filtered, washed thoroughly with hexanes, and dried (7.82 g). Ethyl 4-hydroxy-8-methyl-7-nitroquinoline-3-carboxylate (0.40 g) and 4-chlorobenzylamine (2.0 mL) are heated at 180° C. for 1 hour. The reaction is cooled to room temperature and poured into 50 mL diethyl ether. The resulting solid is filtered and dried. The solid is then triturated in ethyl acetate, filtered, and dried to give the desired product (0.12 g).

Physical characteristics are as follows:

Mp 256–258° C.

$^1$H NMR (300 MHz, DMSO-$d_6$) δ 11.44, 10.62, 8.42, 7.82, 7.37, 7.32, 6.77, 5.89, 4.49, 2.15.

IR (mull) 3349, 3234, 3029, 1653, 1623, 1619, 1571, 1553, 1517, 1493, 1422, 1409, 1299, 1273, 800 cm$^{-1}$.

MS (EI) m/z 341 (M$^+$), 341, 216, 202, 201, 200, 175, 174, 146, 145, 144.

HRMS (FAB) found 342.1020.

Anal.Found: C, 60.47; H, 4.66; N, 11.48; Cl, 9.24.

EXAMPLE 51

N-[(4-Chlorophenyl)methyl]-6-cyano-8-fluoro-4-hydroxy-3-quinolinecarboxamide

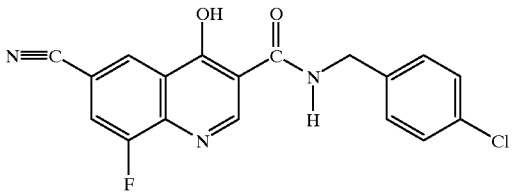

N-[(4-chlorophenyl)methyl]-8-fluoro-4-hydroxy-6-iodo-3-quinolinecarboxamide of Example No. 5 (0.19 g), Pd(PPh$_3$)$_4$ (0.10 g), and KCN (0.06 g) are heated at 60° C. in 60 mL freshly distilled tetrahydrofuran. The reaction is cooled to room temperature. The solid in the reaction mixture is filtered. Thin layer chromatography shows the desired product in the filtrate and the solid. Both are dissolved in a MeOH:CH$_2$Cl$_2$ mixture and adsorbed onto silica. The residue is chromatographed eluting with 3% MeOH:CH$_2$Cl$_2$ (1 L), followed by 4% MeOH:CH$_2$Cl$_2$ (1 L), and 5% MeOH:CH$_2$Cl$_2$ (1 L). The product-containing fractions are evaporated to give an off-white solid (0.08 g).

Physical characteristics are as follows:

Mp>300° C.

$^1$H NMR (300 MHz, DMSO-$d_6$) δ 13.23, 10.03, 8.63, 8.41, 8.26, 7.37, 7.33, 4.53.

IR (mull) 3079, 3063, 3019, 1653, 1634, 1608, 1597, 1574, 1565, 1520, 1493, 1301, 1287, 1272, 806 cm$^{-1}$.

MS (EI) m/z 355 (M$^+$), 355, 215 188 160 159, 142, 141, 140, 132, 125.

HRMS (EI) found 355.0548.

EXAMPLE 52

6-(Aminothioxomethyl)-N-[(4-chlorophenyl)methyl]-8-fluoro-4-hydroxy-3-quinolinecarboxamide

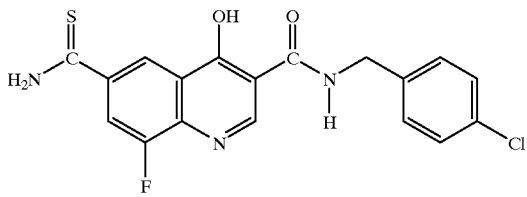

N-[(4-Chlorophenyl)methyl]-6-cyano-8-fluoro-4-hydroxy-3-quinoline-carboxamide (0.32 g) is dissolved in 15 mL dimethyl formamide. Triethylamine (0.25 mL) is added and the reaction mixture heated to 95° C. H₂S is bubbled in the reaction for 2.5 hours. After this period, the reaction is cooled to 35° C. and stirred overnight. The reaction is diluted with 50 mL water and the resulting yellow solid is filtered and dried. The solid is dissolved in a mixture of ethyl acetate and methanol and adsorbed onto silica. Purification by Biotage Flash 40S chromatography (eluent 3% MeOH:CH₂Cl₂ (1 L) followed by 5% MeOH:CH₂Cl₂ (1 L) affords the desired product as a yellow solid (0.17 g).

Physical characteristics are as follows:

Mp 247–248° C.

¹H NMR (300 MHz, DMSO-d₆) δ 13.0, 10.19, 10.10, 9.78, 8.61, 8.16, 7.37, 7.34, 4.54.

IR (mull) 3303, 3194, 3084, 3062, 3023, 1653, 1630, 1612, 1555, 1524, 1486, 1435, 1283, 1187, 806 cm⁻¹.

MS (EI) m/z 389 (M⁺), 389, 355, 222, 215, 188, 160, 142, 141, 140, 125.

Anal. Found: C, 54.91; H, 3.76; N, 10.17.

EXAMPLE 53

N-[(4-Chlorophenyl)methyl]-8-fluoro-4-hydroxy-6-(3-hydroxy-1-propynyl)-3-quinolinecarboxamide

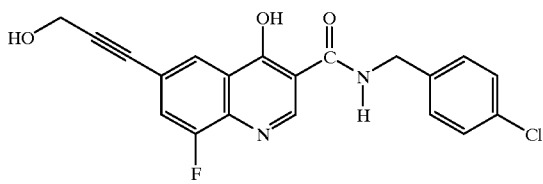

To a mixture of N-[(4-chlorophenyl)methyl]-8-fluoro-4-hydroxy-6-iodo-3-quinolinecarboxamide of Example 5 (0.466 g) in 15 mL diethylamine is added CuI (0.010 g) and (Ph₃P)₂PdCl₂ (0.035 g). Propargyl alcohol (0.058 mL) is then added and the reaction is stirred overnight at room temperature. The diethylamine is removed in vacuo. The residue is partitioned between EtOAc and water. The insoluble material is filtered off and saved. The organic layer is washed with brine, dried and condensed. The residue is combined with the insoluble material and adsorbed onto silica and chromatographed, eluting with 3% MeOH/CH₂Cl₂. Fractions homogeneous by TLC are combined and condensed to yield 0.192 g of the desired product as a tan solid.

Physical characteristics are as follows:

Mp 277–279° C.

¹H NMR (300 MHz, DMSO) δ 13.02, 10.15, 8.59, 8.00, 7,76, 7.40, 7.33, 5.41, 4.52, 4.32.

IR (mull) 3137, 3070, 3008, 1661, 1632, 1608, 1577, 1550, 1520, 1495, 1307, 1289, 1198, 1017, 802 cm⁻¹.

MS (EI) m/z 384 (M⁺), 386, 384, 271, 244, 217, 142, 141, 140, 125, 60.

HRMS (FAB) found 385.0773.

EXAMPLE 54

8-Fluoro-4-hydroxy-6-iodo-3-quinolinecarboxylic acid 2-(4-chlorophenyl)hydrazide

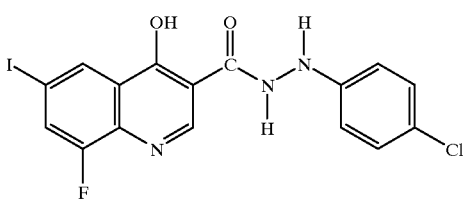

To a solution of ethyl 8-fluoro-4-hydroxy-6-iodoquinolone-3-carboxylate (1.5 g) in 60 mL of 1:1 MeOH:THF is added 16 mL of 1M LiOH. The reaction is maintained at 40° C. overnight. The reaction mixture is cooled to room temperature, then diluted with 40 mL glacial acetic acid. The resulting precipitate is collected, washed with H₂O, and dried to yield 0.890 g of 8-fluoro-6-iodoquinoline-3-carboxylic acid as a white solid. This acid (0.25 g) and 1,1'-carbonyldiimidazole (0.146 g) are dissolved in mL anhydrous THF and heated at 65° C. for 3 days. After the reaction mixture is cooled to room temperature, 4-chlorophenylhydrazine (0.161 g) and diisopropylethylamine (0.16 mL) are added. The reaction mixture is heated at 65° C. overnight to solubilize the reactants. The mixture is cooled to room temperature and partitioned between EtOAc and H₂O. The aqueous layer is extracted with EtOAc (2×). The combined organic layers are washed with brine (1×), dried over Na₂SO₄, and condensed. The crude product is recrystallized with EtOAc/hexanes to yield 0.13g of the desired product as an off-white solid.

Physical characteristics are as follows:

Mp 179–182° C.

¹H NMR (300 MHz, DMSO-d₆) δ 13.12, 11.05, 8.58, 8.37, 8.20, 8.12, 7.16, 6.72.

IR (mull) 3211, 3170, 3075, 1660, 1611, 1598, 1560, 1524, 1491, 1345, 1291, 1243, 868, 823, 802 cm⁻¹.

MS (EI) m/z 457 (M⁺), 459, 457, 316, 189, 162, 161, 144, 142, 133, 107.

HRMS (FAB) found 457.9566.

EXAMPLE 55

8-Fluoro-4-hydroxy-6-methyl-3-quinolinecarboxylic acid 2-(4-chlorophenyl)hydrazide

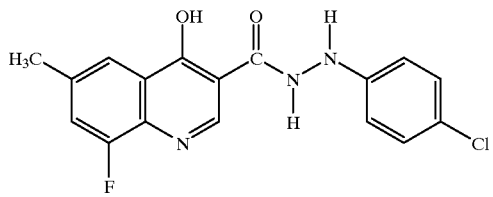

To a solution of ethyl 8-fluoro-4-hydroxy-6-methylquinolone-3-carboxylate (0.50 g) in 30 mL of 1:1 MeOH:THF is added 8 mL of 1M LiOH. The reaction is maintained at 40° C. overnight. The reaction mixture is cooled to room temperature, then diluted with 20 mL glacial acetic acid. The resulting precipitate is collected, washed with H$_2$O, and dried to yield 0.382 g of 8-fluoro-4-hydroxy-6-methyl-3-quinolinecarboxylic acid as a white solid. To a solution of this acid (0.23 g) and 4-chlorophenylhydrazine (0.21 g) in 10 mL DMF is added triethylamine (0.16 m), EDC (0.24 g), and HOBt (0.16 g). The mixture is stirred at room temperature for 3 days. Upon diluting the reaction mixture with 100 mL H$_2$O, an orange solid precipitates. The crude product is adsorbed onto silica and chromatographed eluting with 4% MeOH in CHCl$_2$. Fractions homogenous by TLC are condensed and recrystallized from EtOAc/hexanes to yield 0.0181 g of the desired product as a white solid.

Physical characteristics are as follows:
Mp 256–258° C.
$^1$H NMR (300 MHz, DMSO-d$_6$) δ 12.94, 11.20, 8.55, 8.19, 7.90, 7.61, 7.17, 6.73, 2.46.
HRMS (FAB) found 346.0747.

EXAMPLE 56

7-Chloro-N-((4-chlorophenyl)methyl)-4-hydroxy-3-quinoline-carboxamide

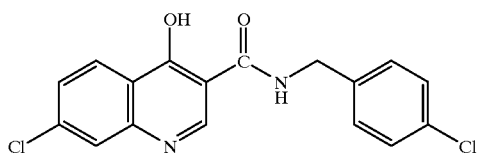

7-Chloro-4-hydroxy-3-quinolinecarboxylic acid (500 mg) (Org. Syn. Coll. 3:272–275 (1955)) is dissolved in N,N-dimethylformamide (20 mL) and to the mixture is added 1,1'-carbonyl diimidazole (399 mg). The mixture is heated at 50° C. for 20 h and then allowed to cool to rt. The mixture is treated with water (200 mL) and then after 5 min, 4-chlorobenzylamine (300 mL) is added. The mixture is allowed to stir at rt for 2 days and then is poured into water (50 mL) and the resulting white precipitate is filtered. The crude product is recrystallized (acetic acid, water) to afford 481 mg of the title compound as a white solid.

Physical characteristics are as follows:
Mp 237–9° C.
$^1$H NMR (300 MHz, DMSO) δ 12.70, 10.29, 8.79, 8.22, 7.74, 7.49, 7.37, 4.52.
$^{13}$C NMR (100 MHz, DMSO) δ 176.04, 164.73, 144.95, 140.34, 139.09, 137.72, 131.85, 129.65, 128.79, 128.12, 125.72, 125.25, 118.67, 111.74, 41.90.

IR (mull) 3065, 2954, 2854, 1657, 1625, 1613, 1570, 1536, 1492, 1461, 1356, 1200, 1096, 1079, 1016, 908, 799 cm$^{-1}$.

Anal. Found: C, 58.50; H, 3.78; N, 7.87.
MS (ESI–) for C$_{17}$H$_{12}$Cl$_2$N$_2$O$_2$ m/z 345 (M–H)$^-$.

EXAMPLE 57

6-Bromo-N-((4-chlorophenyl)methyl)-4-hydroxy-3-quinoline-carboxamide

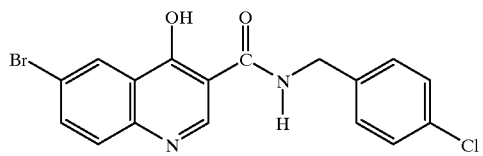

A mixture of 4-bromoaniline (3.44 g) and diethyl ethoxymethylenemalonate (4.0 mL) is heated at 135° C. for 2 h. The resulting mixture is diluted with diphenyl ether (40 mL) and heated to reflux with a Dean-Stark trap for 1 h. The mixture is allowed to cool to rt and is then poured into hexane (50 mL). The solvent is decanted, and the solid is triturated with hexane (25 mL) and diethyl ether/hexane (1/1, 2×25 mL) and filtered to afford 5.52 g of the quinolinecarboxylate ethyl ester. The ester (592 mg) and 4-chlorobenzylamine (2.43 mL) are heated at 190° C. for 1 h. The resulting mixture is diluted with toluene (5 mL) and allowed to cool to rt. The crude product is filtered, washed with toluene (2 mL) followed by hexane (2×5 mL), and then recrystallized (acetic acid, water) to afford 640 mg of the title compound as a white solid.

Physical characteristics are as follows:
Mp 282–3° C.
$^1$H NMR (300 MHz, DMSO) δ 12.84, 10.26, 8.78, 8.30, 7.90, 7.66, 7.37, 4.33.
$^{13}$C NMR (100 MHz, DMSO) δ 175.27, 164.70, 144.67, 139.10, 138.53, 135.55, 131.83, 129.67, 128.80, 128.02, 127.95, 122.08, 118.17, 111.54, 41.89.
IR (mull) 3049, 2924, 2855, 1665, 1632, 1572, 1546, 1515, 1492, 1471, 1352, 1291, 1195, 1090, 1017, 846, 827, 816, 799, 647 cm$^{-1}$.
Anal. Found: C, 51.85; H, 3.24; N, 7.09; Br, 20.40; Cl, 9.01.
MS (ESI–) for C$_{17}$H$_{12}$BrClN$_2$O$_2$ m/z 389 (M–H)$^-$.

EXAMPLE 58

N-((4-Chlorophenyl)methyl)-4-hydroxy-6-phenyl-3-quinoline-carboxamide

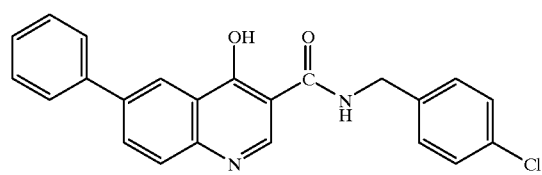

A mixture of 4-aminobiphenyl (0.846 g) and diethyl ethoxymethylenemalonate (1.0 mL) is heated at 135° C. for 2 h. The resulting mixture is diluted with diphenyl ether (25 mL) and heated to reflux with a Dean-Stark trap for 0.5 h.

The mixture is allowed to cool to rt and is then poured into hexane (50 mL). The solid is filtered, washed with hexane (15 mL) and hexane/diethyl ether (1/1, 2×15 mL), and recrystallized (DMF) to afford 1.35 g of the quinolinecarboxylate ethyl ester. The resulting ester (500 mg) and 4-chlorobenzylamine (2.07 mL) are heated at 190° C. for 1 h. The mixture is diluted with toluene (5 mL) and allowed to cool to rt. The crude product is filtered, washed with toluene (2 mL) followed by hexane (2×5 mL), and then recrystallized (acetic acid, water) to afford 359 mg of the title compound as a light-yellow solid.

Physical characteristics are as follows:

Mp 255–7° C.

$^1$H NMR (300 MHz, DMSO) δ 12.79, 10.43, 8.77, 8.45, 8.08, 7.78, 7.73 7.50, 7.38, 4.55.

$^{13}$C NMR (100 MHz, DMSO) δ 176.59, 165.05, 144.13, 139.51, 139.91, 137.21, 131.85, 129.65, 128.81, 128.28, 127.26, 126.88, 123.12, 120.31, 111.29, 41.91.

IR (mull) 3336, 3166, 3062, 2924, 1656, 1639, 1625, 1576, 1515, 1479, 1422, 1364, 1305, 1206, 1095, 1017, 822, 789, 763, 701 cm$^{-1}$.

Anal. Found: C, 70.72; H, 4,54; N, 7.18; Cl, 9.04.

MS (ESI–) for $C_{23}H_{17}ClN_2O_2$ m/z 387 (M–H)$^-$.

EXAMPLE 59

8-Chloro-N-((4-chlorophenyl)methyl)-4-hydroxy-5-trifluoro-methyl-3-quinolinecarboxamide

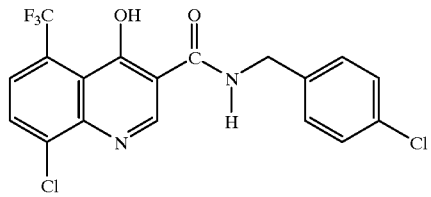

A mixture of 2-chloro-5-trifluoromethylaniline (3.91 g) and diethyl ethoxymethylenemalonate (4.0 mL) is heated at 190° C. for 2 h and is then diluted with diphenyl ether (30 mL). The mixture is allowed to cool to rt, filtered, and the white solid is washed with hexane (2×10 mL) to afford 1.632 g of the diethyl amino-methylenemalonate. The resulting intermediate (2.63 g) is suspended in diphenyl ether (30 mL) and heated to reflux with a Dean-Stark trap for 3 h. The mixture is allowed to cool to rft and is then poured into hexane (50 mL). The solid is filtered and then washed with hexane (20 mL) and hexane/diethyl ether (1/1, 20 mL) to afford 1.273 g of the quinolinecarboxylate ethyl ester. Te he ester (4 00 mg) and 4-chlorobenzylamine (1.52 mL) are heated at 190° C. for 1 h. The resulting mixture is diluted with toluene (4 mL), allowed to cool to rt, and then poured into hexane (50 mL). The solvent is decanted and the remaining oil is crystallized (acetic acid, water) to afford 285 mg of the title compound as a brown solid.

Physical characteristics are as follows:

Mp 270–1° C.

$^1$H NMR (300 MHz, DMSO) δ 12.33, 10.06, 8.68, 8.10, 7.86, 7.36, 4.52.

$^{13}$ NMR (100 MHz, DMSO) δ 175.05, 164.07, 144.36, 139.12, 138.20, 132.42, 131.85, 129.84, 128.77, 128.44, 126.70 (q), 125.84, 125.20, 122.22, 113.75, 42.00.

IR (mull) 3187, 3091, 2925, 2855, 1657, 1604, 1567, 1531, 1462, 1417, 1377, 1366, 1348, 1307, 1272, 1210, 1158, 1139, 1128, 1106, 854, 841, 802, 726 cm$^{-1}$.

Anal. Found: C, 52.12; H, 2.78; N, 6.70; Cl, 16.85.

MS (ESI–) for $C_{18}H_{11}Cl_2F_3N_2O_2$ m/z 412 (M–H)$^-$.

EXAMPLE 60

N-((4-Chlorophenyl)methyl)-4-hydroxy-6,8-dimethoxy-3-quinolinecarboxamide

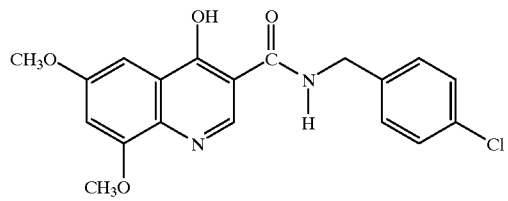

A mixture of 2,4-dimethoxyaniline (3.06 g) and diethyl ethoxymethylenemalonate (4.0 mL) is heated at 135° C. for 2 h. The resulting mixture is diluted with diphenyl ether (40 mL) and heated to reflux with a Dean-Stark trap for 1 h. The mixture is allowed to cool to rt and is then poured into hexane (50 mL). The solid is filtered, washed with hexane (25 mL) and hexane/diethyl ether (1/1 , 30 L) to afford 4.68 g of the quinolinecarboxylate ethyl ester. A mixture of the ethyl ester (500 mg) and 4-chlorobenzylamine (2.19 mL) are heated at 190° C. for 1 h. The resulting mixture is diluted with toluene (5 mL) and allowed to cool to rt. The crude product is filtered, washed with toluene (2 mL) followed by hexane (2×5 mL), and then recrystallized (acetic acid, water) to afford 270 mg of the title compound as a white solid.

Physical characteristics are as follows:

Mp 270–1° C.

$^1$H NMR (300 MHz, DMSO) δ 12.30, 10.50, 8.49, 7.35, 7.18, 6.98, 4.52, 4.00, 3.84.

$^{13}$C NMR (100 MHz, DMSO) δ 175.61, 165.17, 157.58, 150.50, 141.86, 139.09, 131.85, 129.62, 128.82, 128.18, 125.31, 110.66, 103.91, 96.35, 57.05, 55.97, 41.88.

IR (mull) 3171, 3129, 3092, 2925, 2855, 1712, 1623, 1551, 1455, 1421, 1396, 1375, 1307, 1287, 1199, 1157, 1146, 1070, 1053, 1032, 801 cm$^{-1}$.

Anal. Found: C, 60.89; H, 4.72; N, 7.40; Cl, 9.49.

MS (ESI+) for $C_{19}H_{17}ClN_2O_4$ m/z 373 (M+H)$^+$.

EXAMPLE 61

N-((4-Chlorophenyl)methyl)-4-hydroxy-6,7-dimethoxy-3-quinolinecarboxamide

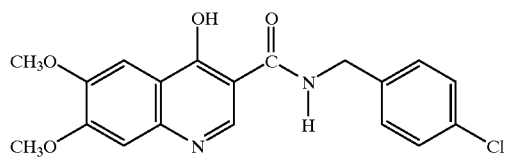

A mixture of 6,7-dimethoxy-4-hydroxy-3-quinoline carboxylate ethyl ester (J. Am. Chem. Soc., 68, 1264 (1946)) (139 mg) and 4-chlorobenzylamine (0.61 mL) are heated at 190° C. for 1 h. The resulting mixture is diluted with toluene (1.5 mL) and allowed to cool to rt. The crude product is purified by column chromatography (dichloromethane/methanol; 100/1, 100/5) and recrystallization (acetic acid, water) to afford 26 mg of the title compound as a white solid.

Physical characteristics are as follows:

Mp 184° C.

$^1$H NMR (300 MHz, DMSO) δ 12.50, 10.62, 8.63, 7.56, 7.37, 7.10, 4.52, 3.88, 3.84.

IR (mull) 3392, 3223, 3069, 2924, 2854, 1648, 1613, 1544, 1503, 1459, 1408, 1377, 1274, 1220, 1114, 1030, 799 cm$^{-1}$.

HRMS (FAB) Found, 373.0952.

MS (ESI–) [for $C_{19}H_{17}ClN_2O_4$]m/z 371 (M–H)$^-$.

EXAMPLE 62

N-((4-Chlorophenyl)methyl)-4-hydroxy-5-methyl-3-quinoline-carboxamide

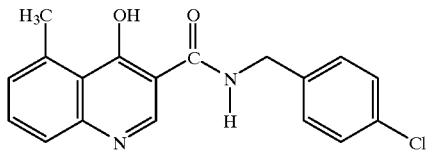

A mixture of 2-chloro-5-methylaniline (2.83 g) and diethyl ethoxymethylenemalonate (4.04 mL) is heated at 135° C. for 2 h. The resulting mixture is diluted with diphenyl ether (40 mL) and heated to reflux with a Dean-Stark trap for 1 h. The mixture is allowed to cool to rt and is then poured into hexane (50 mL). The solid is filtered and is washed with hexane (20 mL) and hexane/diethyl ether (1/1, 2×30 mL) to afford 4.89 g of the 8-chloro-6-methyl-quinolinecarboxylate ethyl ester. The ethyl ester (2.0 g) is dissolved in acetic acid (150 mL) along with NaOAco3 H$_2$O (1.12 g) and 5% palladium on carbon (750 mg). The mixture is placed under hydrogen pressure (28 psi) in a Parr hydrogenator for 3 h. The mixture is filtered through a plug of celite, concentrated in vacuo, and suspended in water (10 mL). The crude product is filtered, washed with water, and recrystallized (DMF) to afford 964 mg of the 5-methyl-quinolinecarboxylate ethyl ester. The resulting ester (463 mg) and 4-chlorobenzylamine (2.43 mL) are heated at 190° C. for 1 h. The resulting mixture is diluted with toluene (5 mL) and allowed to cool to rt affording a white solid. The crude product is filtered, washed with toluene (2 mL) followed by hexane (4 mL), and then recrystallized successively from acetic acid/water then ethyl acetate to afford 426 mg of the title compound as a white solid.

Physical characteristics are as follows:

Mp 205-6° C.

$^1$H NMR (300 MHz, DMSO) δ 12.50, 10.46, 8.64, 7.55, 7.47, 7.37, 7.15, 4.51, 2.83.

$^{13}$C NMR (100 MHz, DMSO) δ 179.47, 165.26, 143.30, 141.17, 140.60, 139.33, 132.26, 131.80, 129.75, 128.77, 127.97, 125.04, 117.56, 112.18, 41.84, 24.21

IR (mull) 3404, 2924, 2855, 1645, 1628, 1604, 1574, 1545, 1498, 1467, 1459, 1342, 1224, 1170, 1097, 1016, 816, 783, 75 cm$^{-1}$.

HRMS (FAB) Found, 326.0803.

MS (ESI–) for $C_{18}H_{15}ClN_2O_2$ m/z 325 (M–H)$^-$.

PREPARATION 12

6-(1,1-dimethylethyl)-4-hydroxy-3-quinolinecarboxylic acid, ethyl ester

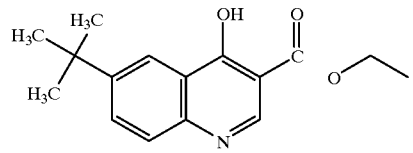

A 100-mL, round-bottomed flasked fitted with a Dean Stark trap and a reflux condensor is charged with 4-t-butylaniline (5.3 mL) and diethylethoxymethylene malonate (6.8 mL). The reaction mixture is warmed to 140° C. for 1.5 h. The mixture is then allowed to cool to room temperature, and 50 mL of diphenylether is added. The resulting mixture is warmed to 250° C. for 1.5 h. The solution is allowed to cool to room temperature, then poured into toluene and hexane. A solid slowly precipitates and is collected by filtration to give 0.678 g of the title compound as a white solid.

Physical characteristics are as follows:

Mp 262–64° C.

$^1$H NMR (300 MHz, DMSO-d$_6$) δ 8.49, 8.11, 7.78, 7.54, 4.19, 1.32, 1.26 ppm.

$^{13}$C NMR (75 MHz, DMSO-d$_6$) δ 173.6, 165.0, 147.4, 144.6, 137.1, 130.6, 126.9, 120.9, 118.8, 109.6, 59.6, 34.7, 31.1, 14.5 ppm.

IR (mull) 3182, 3095, 3054, 3019, 1700, 1633, 1584, 1572, 1531, 1493, 1291, 1255, 1189, 1119, 606 cm$^{-1}$.

MS (EI) m/z 273 (M+), 274, 273, 258, 228, 227, 213, 212, 184, 144, 115.

Anal. found: C, 70.46; H, 7.11; N, 5.03.

EXAMPLE 63

N-[(4-Chlorophenyl)methyl]-6-(1,1-dimethylethyl)-4-hydroxy-3-quinolinecarboxamide

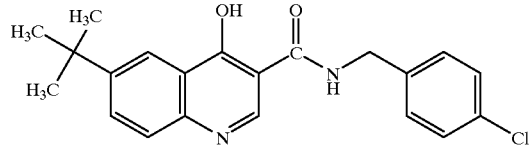

A solution of the title compound of Preparation 12 (0.350 g) in 1.6 mL of p-chlorobenzylamine is warmed to 190° C. for 1.5 h. The reaction mixture is then allowed to cool to room temperature and poured into toluene and hexane. A precipitate forms, which is collected-by filtration to give 0.255 g of the title compound as a white solid.

Physical characteristics are as follows:

Mp 266° C.

$^1$H NMR (300 MHz, DMSO-d$_6$) δ 10.50, 8.71, 8.19, 7.85, 7.63, 7.40–7.33, 4.53, 1.33 ppm.

$^{13}$C NMR (75 MHz, DMSO-d$_6$) δ 176.0, 164.7, 147.4, 143.3, 138.6, 137.2, 131.3, 130.8, 129.1 (2), 128.3 (2), 125.5, 120.3, 118.9, 110.3, 41.3, 34.5, 30.7 (3) ppm.

IR (mull) 3163, 3054, 3009, 1634, 1616, 1563, 1548, 1523, 1490, 1359, 1351, 1300, 839, 831, 804 cm$^{-1}$.

MS (EI) m/z 368 (M+), 370, 368, 229, 228, 212, 202, 201, 186, 140, 125.

Anal. found: C, 68.22; H, 5.60; N, 7.45.

EXAMPLE 64

N-[(4-Chlorophenyl)methyl]-7,8-dihydro-4-hydroxy-6H-cyclopent a[g]quinoline-3-carboxamide

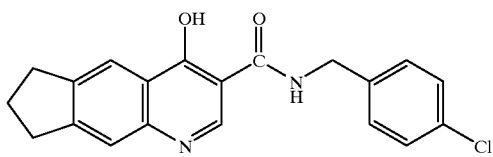

The title compound is prepared according to the procedures described in Preparation 12 and Example 63, substituting 5-aminoindan for 4-t-butylaniline. Crystallization from $CH_2Cl_2$/EtOAc/hexane/$Et_2O$ gives 0.03 g of the title compound as a brown solid.

Physical characteristics are as follows:

Mp 260–261° C. (decomposition).

$^1$H NMR (300 MHz, DMSO-$d_6$) δ 12.6, 10.51, 8.66, 8.03, 7.49, 7.40–7.32, 4.52, 3.01–2.93, 2.10–2.03 ppm.

$^{13}$C NMR (75 MHz, DMSO-$d_6$) δ 176.5, 165.3, 150.7, 143.3, 142.3, 139.3, 138.7, 131.8, 129.7, 128.8, 125.6, 120.3, 114.3, 110.6, 41.8, 32.9, 32.2, 25.9 ppm.

IR (mull) 3243, 3216, 3170, 3089, 3025, 1645, 1620, 1578, 1551, 1531, 1518, 1492, 1436, 1230, 797 cm$^{-1}$.

MS (EI) m/z 352 (M+), 354, 352, 213, 212, 211, 186, 185, 184, 140, 125.

Anal. found: C, 67.77; H, 4.94; N, 7.96.

EXAMPLE 65

N-[(4-Chlorophenyl)methyl]-1,4-dihydro-8-(methylthio)-4-oxo-3-quinolinecarboxamide

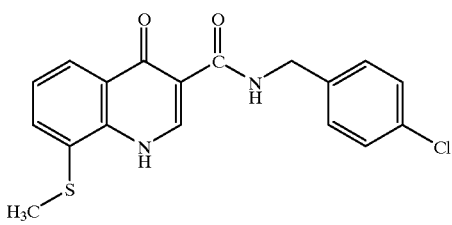

The title compound is prepared according to the procedures described in Preparation 12 and Example 63, substituting 2-(methylmercapto)aniline for 4-t-butylaniline. This procedure gives 0.355 g of the title compound as a white solid.

Physical characteristics are as follows:

Mp 225–228° C.

$^1$H NMR (300 MHz, CDCl$_3$) δ 10.33, 8.94, 8.38, 7.90, 7.43, 7.33–7.28, 4.64, 2.48 ppm.

$^{13}$C NMR (75 MHz, DMSO-$d_6$) δ 175.7, 164.7, 145.1, 138.7, 132.1, 131.2, 130.5, 129.1, 128.4, 128.2, 126.6, 124.4, 123.4, 110.6, 41.3, 16.6 ppm.

IR (mull) 3236, 3210, 3184, 1657, 1609, 1577, 1558, 1529, 1491, 1440, 1329, 1286, 800, 774, 747 cm$^{-1}$.

MS (EI) m/z 358 (M+), 360, 358, 219, 218, 203, 192, 191, 176, 142, 140.

Anal found: C, 60.28; H, 4.32; N, 7.85; Cl, 9.98; S, 8.81.

EXAMPLE 66

N-[(4-Chlorophenyl)methyl]-9-hydroxythiazolo[5,4-f]quinoline-8-carboxamide

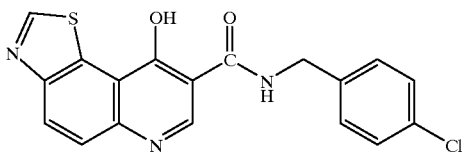

The title compound is prepared according to the procedures described in Preparation 12 and Example 63, substituting 6-aminobezothiazole for 4-t-butylaniline. This procedure gives 0.342 g of the monohydrate of the title compound as a pale yellow solid.

Physical characteristics are as follows:

Mp 193° C. (decomposition).

$^1$H NMR (300 MHz, DMSO-$d_6$) δ 10.44, 9.47, 8.88, 8.42, 7.90, 7.38, 4.57 ppm.

13C NMR (75 MHz, DMSO-$d_6$) δ 173.8, 164.5, 158.0, 150.3, 143.9, 138.8, 131.2, 130.3, 129.2, 128.8, 128.4, 128.2, 127.2, 120.8, 118.9, 111.0, 41.3 ppm.

IR (mull) 3236, 3189, 3156, 3062, 1647, 1618, 1571, 1547, 1492, 1359, 1313, 1292, 1093, 819, 802 cm$^{-1}$.

MS (EI) m/z 369 (M+), 371, 369, 229, 202, 174, 173, 146, 142, 140, 125.

MS (EI) 369.0343.

Anal. found: C, 55.81; H, 3.67; N, 10.64.

EXAMPLE 72

N-[(4-Chlorophenyl)methyl]-4-hydroxy-6-[(phenylmethyl)thio]-7-(trifluoromethyl)-3-quinolinecarboxamide

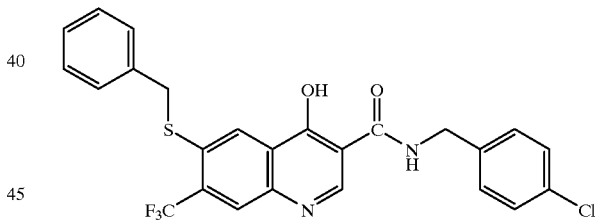

A mixture of 0.15 g of 4-hydroxy-6-[(phenylmethyl)thio]-7-(trifluoromethyl)-3-quinolinecarboxylic acid and 1.2 mL of dimethylformamide is treated with 0.075 g of carbonyldiimidazole. The mixture is stirred 20 h at 35–40° C. The solution is cooled to 25° C. and it is treated with 0.075 mL of distilled water and then it is stirred for 10 min. The solution is treated with 0.053 mL of 4-chlorobenzylamine and it is stirred for 18 h. The mixture is diluted with 1.0 mL of distilled water and then it is decanted from a dark, oily precipitate. This precipitate is treated with 1 mL of glacial acetic acid and the mixture is shaken for 5 min. The solid which formed is collected by filtration and it is washed with a few mL of 50% aqueous acetic acid. The solid is dried in a stream of air to give 48 mg of the title compound.

Physical characteristics are as follows:

Mp 185–188° C.

$^1$H NMR (DMSO) δ 8.86, 8.33, 8.10, 7.53–7.18, 4.55, 4,39.

Anal. Found: C, 58.63; H, 3.62; N, 5.43.

EXAMPLE 75

N-[(4-Chlorophenyl)methyl]-8-fluoro-4-hydroxy-6-(2-thiophenyl)-3-quinolinecarboxamide

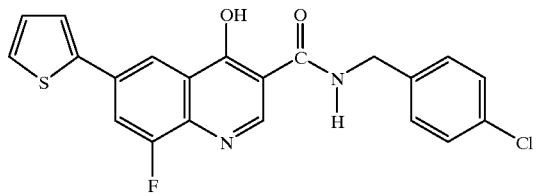

To a solution of the title comound of Example 5 in 12.5 mL dioxane and 0.5 mL HMPA are added 2-(tributylstannyl) thiophene (0.64 mL) and $PdCl_2(PPh_3)_2$ (84.2 mg). The mixture is stirred at 100° C. for 2 days. The reaction mixture is cooled to room temperature, then filtered to remove excess palladium. Upon diluting the filtrate with $CH_2Cl_2$ and $H_2O$, a white solid precipitates. The solid is filtered and dried to yield 0.262 g of the desired product.

Physical characteristics are as follows:

MP 298–301° C.

$^1$H NMR (300 MHz, DMSO) δ 10.26, 8.59, 8.16, 8.10, 7.69, 7.63, 7.37, 7.16, 4.54.

IR (mull) 3158, 3073, 3020, 1657, 1612, 1574, 1554, 1531, 1516, 1490, 1303, 1287, 846, 804, 696 $cm^{-1}$.

MS (ESI–) for $C_{21}H_{14}ClFN_2O_2S$ m/z 410.9 (M–H)$^-$.

Anal. Found: C, 60.92; H, 3.63; N, 6.86.

EXAMPLE 76

N-((4-Chlorophenyl)methyl)-4-hydroxy-5-trifluoromethyl-3-quinolinecarboxamide

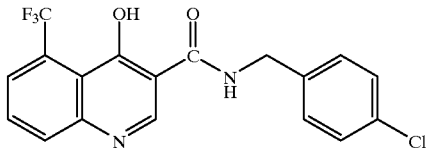

N-((4-Chlorophenyl)methyl)-8-chloro-4-hydroxy-5-trifluromethyl-3-quinoline-carboxamide (2.00 g) from Example No. 59 is dissolved in glacial acetic acid (100 mL) along with NaOAc•3H$_2$O (937 mg) and 5% palladium on carbon (666 mg). The mixture is placed under hydrogen pressure (25 psi) in a Parr hydrogenator for 3 h. The reaction mixture is filtered through a plug of celite, concentrated, suspended in water (30 mL), and filtered. The resulting solid (500 mg) and 4-chlorobenzylamine (2.13 mL) are then heated at 190° C. for 1 h. The crude product is purified by column chromatography (dichloromethane/methane, 50/1) to afford 62 mg of the title compound as a white solid.

Physical characteristics are as follows:

Mp 224–226° C.

$^1$H NMR (DMSO-d$_6$) δ 12.92, 10.26, 8.79, 8.00, 7.88, 7.36, 4.52.

$^{13}$C NMR (DMSO-d$_6$) δ 175.3, 164.7, 143.9, 141.7, 139.3, 132.4, 131.8, 129.8, 128.8, 127.5, 125.3, 123.5, 122.6, 113.1, 41.9.

IR (mull) 3072, 1651, 1627, 1611, 1563, 1544, 1492, 1438, 1309, 1288, 1224, 1153, 1131, 1120, 826 $cm^{-1}$.

MS (ESI–) for $C_{18}H_{12}ClF_3N_2O_2$ m/z 379 (M–H)$^{-1}$.

Anal. Found ($C_{18}H_{12}ClF_3N_2O_2$•$H_2O$): C, 53.82; H, 3.60; N, 6.91; Cl, 8.82; F, 14.57.

EXAMPLE 77

N-((4-Chlorophenyl)methyl)-8-fluoro-4-hydroxy-6-(2-methyl-phenyl)-3-quinolinecarboxamide

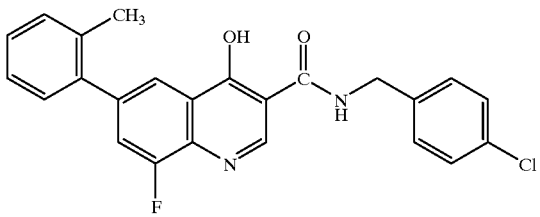

6-Iodo-8-fluoro-4-hydroxy-3-quinolinecarboxylic acid ethyl ester (903 mg) from Example No. 5 and o-tolueneboronic acid (374 mg) are dissolved in DMF (50 mL) and at 50° C. a solution of barium hydroxide octahydrate (1.18 g) in water (5 mL) is added followed by palladium tetrakistriphenylphosphine (58 mg). The mixture is heated at 80° C. for 20 h, allowed to cool to rt, poured into water (200 mL), and extracted with ethyl acetate (3×100 mL). The organic layer is washed with brine (25 mL), dried (MgSO$_4$), and concentrated. The solid is then triturated with MTBE, and filtered to afford 382 mg of 6-(2-methylphenyl)-8-fluoro-4-hydroxy-3-quinoline-carboxylic acid ethyl ester. The crude ester is mixed with 4-chlorobenzylamine (380 mg) and is heated to 190° C. for 1 h. The mixture is diluted with toluene (4 mL), allowed to cool to rt, poured into a mixture of 50% acetic acid (10 mL) and 1 N hydrochloric acid (25 mL), and is extracted with ethyl acetate (3×25 mL). The organic layer is dried (MgSO$_4$) and allowed to crystallize. Recrystallization from acetic acid/water affords 166 mg of the title compound.

Physical characteristics are as follows:

Mp 259–265° C.

$^1$H NMR (DMSO-d$_6$) δ 12.99, 10.26, 8.64, 7.93, 7.79, 7.40–7.26, 4.53, 2.25.

$^{13}$C NMR (DMSO-d$_6$) δ 175.8, 164.6, 152, 144.1, 139.1, 138.3, 135.4, 131.9, 131.1, 130.1, 129.7, 128.8, 128.6, 128.2, 127.8, 126.7, 121.4, 118.9, 112.0, 41.9, 20.5.

IR (mull) 3143, 3060, 3020, 1656, 1612, 1551, 1521, 1490, 1309, 1284, 1206, 1187, 805, 799, 751 $cm^{-1}$.

MS (ESI–) for $C_{24}H_{18}ClFN_2O_2$ m/z 419 (M–H)$^-$.

Anal. Found: C, 68.36; H, 4.47; N, 6.67; Cl, 8.46.

EXAMPLE 78

N-((4-Chlorophenyl)methyl)-6,7-difluoro-4-hydroxy-8-(tetrahydro-2H-pyran-4-oxy)-3-quinolinecarboxamide

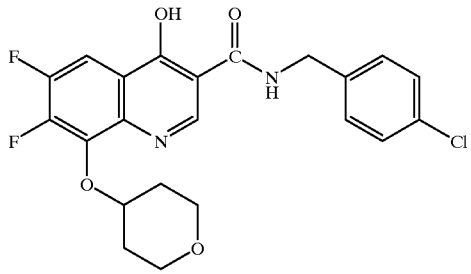

N-((4-Chlorophenyl)methyl)-4-hydroxy-6,7,8-trifluoro-3-quinolinecarboxamide (366 mg) from Example No. 15 and sodium hydride (60% dispersion, 40 mg) are dissolved in DMF (10 mL) and to the mixture is added tetrahydro-2H-pyran-4-ol (114 μL). Additional sodium hydride (60 mg) is added and the mixture is heated at 140° C. for 1 h. The reaction mixture is allowed to cool to rt, poured into water (30 mL), acidified with 1 N hydrochloric acid (20 mL), and extracted with ethyl acetate (3×25 mL). The organic layer is washed with brine (10 mL), dried (MgSO$_4$), and concentrated. The resulting solid is triturated with heptane (10 mL) and filtered to afford 153 mg of the title compound as a white solid.

Physical characteristics are as follows:

Mp 287° C. dec.

$^1$H NMR (DMSO-d$_6$) δ 12.20, 10.21, 8.62, 7.82, 7.39–7.31, 4.62, 4.52, 3.90, 3.35, 2.00–1.70.

$^{13}$C NMR (DMSO-d$_6$) δ 175.2, 164.5, 148.8, 146.09, 144.5, 139.0, 135.3, 132.0, 131.9, 129.6, 128.8, 122.7, 111.2, 106.4, 80.49, 65.34, 41.92, 32.7.

IR (mull) 3192, 3084, 1649, 1611, 1583, 1576, 1535, 1485, 1306, 1279, 1171, 1108, 1089, 1007, 802, cm$^{-1}$.

MS (ESI−) for C$_{22}$H$_{19}$ClF$_2$N$_2$O$_4$ m/z 447 (M−H)$^-$.

Anal. Found: C, 58.57; H, 4.50; N, 6.16; Cl, 7.67.

EXAMPLE 79

N-((4-Chlorophenyl)methyl)-6,7-difluoro-4-hydroxy-8-methoxy-3-quinolinecarboxamide

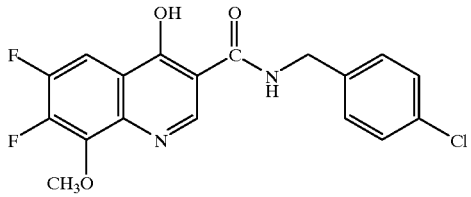

N-((4-Chlorophenyl)methyl)-4-hydroxy-6,7,8-trifluoro-3-quinolinecarboxamide (366 mg) from Example No. 15 and sodium hydride (60% dispersion, 40 mg) are dissolved in DMF (10 mL) and to the mixture is added methanol (200 μL). Additional sodium hydride (40 mg) is added, and the mixture is heated at 140° C. for 1 h. The reaction mixture is allowed to cool to rt, poured into water (50 mL), acidified with acetic acid (10 mL), and is filtered. The crude product is purified by column chromatography (hexane/2-propanol, 95/5) to afford 68 mg of the title compound as a white solid.

Physical characteristics are as follows:

Mp 248–251° C.

$^1$H NMR (DMSO-d$_6$) δ 12.60, 10.21, 8.59, 7.78, 7.39–7.31, 4.51, 4.14.

$^{13}$C NMR (DMSO-d$_6$) δ 175.1, 164.5, 150.0, 145.4, 144.2, 139.0, 138.1, 131.9, 131.0, 129.7, 128.8, 122.6, 111.2, 105.7, 62.8, 41.9.

IR (mull) 1658, 1635, 1617, 1585, 1579, 1560, 1546, 1486, 1439, 1309, 1287, 1117, 1105, 1085, 799 cm$^{-1}$.

MS (ESI−) for C$_{18}$H$_{13}$ClF$_2$N$_2$O$_3$ m/z 377 (M−H)$^-$.

Anal. Found: C, 56.75; H, 3.67; N, 7.30; Cl, 9.33.

EXAMPLE 80

N-((4-Chlorophenyl)methyl)-7,8-dimethoxy-6-fluoro-4-hydroxy-3-quinolinecarboxamide

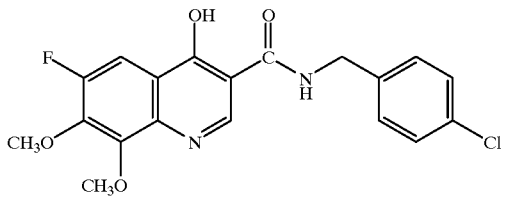

N-((4-Chlorophenyl)methyl)-4-hydroxy-6,7,8-trifluoro-3-quinolinecarboxamide (366 mg) from Example No. 15 and sodium hydride (60% dispersion, 160 mg) are dissolved in DMF (10 mL) and to the mixture is added methanol (200 μL). The mixture is heated at 140° C. for 1 h. The reaction mixture is allowed to cool to rt, poured into water (40 mL), acidified with acetic acid (10 mL), and is filtered. The crude product is recrystalized from acetic acid/water and then from toluene to afford 174 mg of the title compound as a white solid.

Physical characteristics are as follows:

Mp 228–229° C.

$^1$H NMR (DMSO-d$_6$) δ 12.38, 10.28, 8.56, 7.67, 7.36, 4.51, 4.02.

$^{13}$C NMR (DMSO-d$_6$) δ 175.3, 164.7, 153.7, 143.9, 143.8, 142.4, 139.1, 131.9, 131.3, 129.7, 128.8, 122.1, 110.8, 105.9, 62.3, 62.2, 41.9.

IR (mull) 1656, 1628, 1610, 1597, 1568, 1544, 1438, 1428, 1307, 1282, 1105, 1081, 1016, 799, 726 cm$^{-1}$.

MS (ESI+) for C$_{19}$H$_{16}$ClFN$_2$O$_4$ m/z 389 (M+H)$^+$.

Anal. Found: C, 58.19; H, 4.13; N, 7.14; Cl, 9.06.

PREPARATION 13
N-((4-Chlorophenyl)methyl)-1,4-dihydro-4-oxo-6,7,8-trifluoro-1-(2-(trimethylsilyl)ethoxy)methyl-3-quinolinecarboxamide

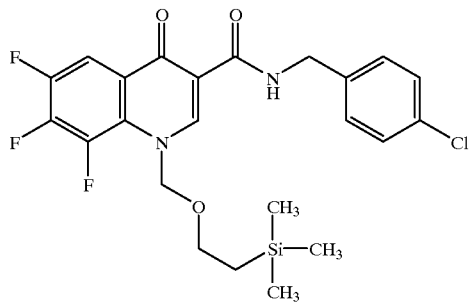

N-((4-Chlorophenyl)methyl)-4-hydroxy-6,7,8-trifluoro-3-quinolinecarboxamide (6.00 g) from Example No. 15 is suspended in DMF (100 mL) and sodium hydride (60% dispersion, 720 mg) is added. The mixture is allowed to stir at rt for 15 min and then 2-(trimethylsilyl)ethoxymethyl chloride (2.90 mL) is added. After 3.5 h, the reaction mixture is poured into a mixture of water (200 mL) and sat aq. ammonium chloride (100 mL) and is extracted with ethyl acetate (2×100 mL, 200 mL). The organic layer is washed with brine (50 mL), dried (MgSO$_4$), and concentrated. The crude solid is recrystallized from ethanol to afford 5.943 g of the title compound as a white solid.

Physical characteristics are as follows:
Mp 141–143° C.
$^1$H NMR (DMSO-d$_6$) δ 9.96, 9.02, 8.10, 7.40–7.32, 5.83, 4.53, 3.57, 0.82, −0.13.
$^{13}$C NMR (DMSO-d$_6$) δ 174.1, 163.7, 151.0, 148.2, 143.2, 142.2, 138.9, 131.9, 129.7, 128.8, 126.5, 124.4, 110.7, 108.7, 85.8, 66.2, 42.1, 17.5, −1.0.
IR (mull) 1660, 1607, 1591, 1581, 1569, 1542, 1492, 1485, 1418, 1248, 1125, 1104, 1056, 849, 805 cm$^{-1}$.
MS (ESI+) for C$_{23}$H$_{24}$ClF$_3$N$_2$O$_3$Si m/z 497 (M+H)$^+$.
Anal. Found: C, 55.51; H, 4.84; N, 5.59; Cl, 7.14.

EXAMPLE 81

N-((4-Chlorophenyl)methyl)-6,8-difluoro-4-hydroxy-7-(4-(hydroxymethyl)phenoxy)-3-quinolinecarboxamide

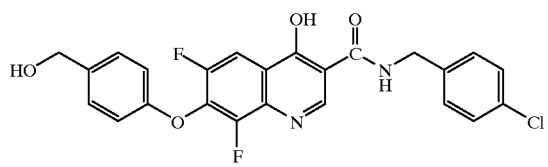

N-((4-Chlorophenyl)methyl)-4-oxo-6,7,8-trifluoro-1-(2-(trimethylsilyl)ethoxy) methyl-3-quinolinecarboxamide (1.00 g) from Preparation No. 13 and 4-hydroxymethyl phenol (500 mg) are dissolved in DMF (20 mL). Sodium hydride (60% dispersion, 80 mg) is added and the mixture is heated to 140° C. for 1 h. The reaction mixture is allowed to cool to rt, is poured into sat. aq. ammonium chloride (100 mL), and is extracted with ethyl acetate (3×50 mL). The organic layer is washed with brine (10 mL), dried (MgSO$_4$), and concentrated. The crude product is purified by column chromatography (heptane/ethyl acetate, 1/1; 1/5) followed by recrystallization to afford 145 mg of the title compound as a white solid.

Physical characteristics are as follows:
Mp 235–240° C.
$^1$H NMR (DMSO-d$_6$) δ 13.10, 10.20, 8.65, 7.92, 7.41–7.28, 7.05, 5.19, 4.55, 4.46.
$^{13}$C NMR (DMSO-d$_6$) δ 174.8, 164.4, 156.2, 152.6, 146.1, 144.5, 139.0, 138.5, 134.4, 131.9, 129.7, 128.8, 128.6, 127.6, 115.5, 111.5, 107.4, 62.7, 42.0.
IR (drift) 3056, 1651, 1612, 1579, 1574, 1563, 1557, 1543, 1505, 1483, 1310, 1236, 1200, 1038, 791 cm$^{-1}$.
MS (ESI−) for C$_{24}$H$_{17}$ClF$_2$N$_2$O$_4$ m/z 469 (M−H)$^-$.
Anal. Found: C, 60.82; H, 3.76; N, 5.78; Cl, 7.38.

EXAMPLE 82

N-((4-Chlorophenyl)methyl)-6,8-difluoro-4-hydroxy-7-methoxy-3-quinolinecarboxamide

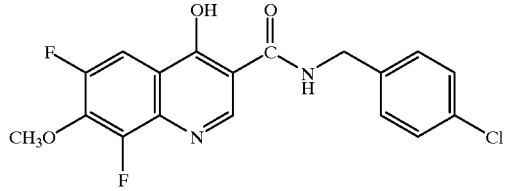

N-((4-Chlorophenyl)methyl)-4-oxo-6,7,8-trifluoro-1-(2-(trimethylsilyl)ethoxy) methyl-3-quinolinecarboxamide (1.00 g) from Preparation No. 13 and methanol (163 μL) are dissolved in DMF (20 mL). Sodium hydride (60% dispersion, 80 mg) is added and the mixture is heated to 140° C. for 1 h. The mixture is allowed to cool to rt, is poured into sat. aq. ammonium chloride (100 mL), and is extracted with ethyl acetate (3×50 mL). The organic layer is washed with brine (10 mL), dried (MgSO$_4$), and concentrated. The crude product is purified by column chromatography (heptane/ethyl acetate, 4/1; 3/1) to afford N-((4-chlorophenyl)methyl)-6,8-difluoro-7-methoxy-4-oxo-1-(2-(trimethylsilyl)ethoxy)methyl-3-quinolinecarboxamide. The resulting crude amide is suspended in ethanol (15 mL), heated to 85° C., and to the mixture is added 50% aq. hydrochloric acid (5 mL). The mixture is heated an additional 1.5 h and allowed to cool to rt. The reaction mixture is neutralized with solid sodium bicarbonate and filtered. The solids are washed with ethanol (10 mL) followed by ethyl acetate (20 mL), and the combined filtrates are concentrated to afford a tan solid. The crude product is purified by recrystallization from acetic acid/water followed by column chromatography (heptane/2-propanol, 95/5) to afford 27 mg of the title compound.

Physical characteristics are as follows:
Mp 217–219° C.
$^1$H NMR (DMSO-d$_6$) δ 12.94, 10.23, 8.61, 7.79, 7.41–7.33, 4.54, 4.14.
IR (drift) 3060, 2987, 2956, 1653, 1609, 1568, 1561, 1539, 1488, 1435, 1311, 1290, 1237, 1038, 799 cm$^{-1}$.
Anal. Found: C, 56.87; H, 3.59; N, 7.56.
HRMS (FAB) found 379.0655.

EXAMPLES 83–85

N-((4-Chlorophenyl)methyl)-6,8-difluoro-4-hydroxy-7-(2-(methoxy)ethoxy)-3-quinolinecarboxamide;

N-((4-chlorophenyl)methyl)-6,7-difluoro-4-hydroxy-8-(2-(methoxy)ethoxy)-3-quinolinecarboxamide; and N-((4-chlorophenyl)methyl)-7,8-di(2-(methoxy)ethoxy)-6-fluoro-4-hydroxy-3-quinolinecarboxamide N-((4-Chlorophenyl)methyl)-4-hydroxy-6,7,8-trifluoro-3-quinolinecarboxamide (500 mg) from Example No. 15 and sodium hydride (60% dispersion, 163 mg) are dissolved in DMF (10 mL) and to the mixture is added 2-methoxyethanol (536 μL). The mixture is heated at 140° C. for 1 h. The reaction mixture is allowed to cool to rt, poured into 20% aq. acetic acid (25 mL), and is filtered. The crude products are purified by column chromatography to afford 28 mg of the 6,8-difluoro-7-(2-(methoxy)ethoxy)-derivative (Example 83); 124 mg of the 6,7-difluoro-8-(2-(methoxy)ethoxy)-derivative (Example 84); and 194 mg of the 6-fluoro-7,8-di-(2-(methoxy)ethoxy)-derivative (Example 85).

83) N-((4-Chlorophenyl)methyl)-6,8-difluoro-4-hydroxy-7-(2-(methoxy)ethoxy)-3-quinolinecarboxamide

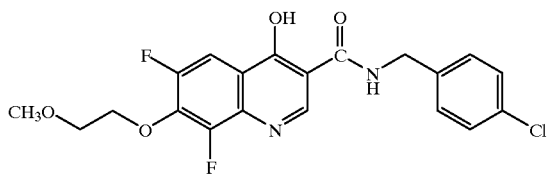

Physical characteristics are as follows:

Mp 193–198° C.

$^1$H NMR (DMSO-d$_6$) δ 12.90, 10.20, 8.58, 7.77, 7.35, 4.52, 4.43, 3.66, 3.27.

IR (mull) 3196, 3056, 1650, 1608, 1569, 1542, 1485, 1310, 1282, 1237, 1109, 1096, 1034, 1016, 794 cm$^{-1}$.

HRMS (FAB) found 423.0915.

84) N-((4-Chlorophenyl)methyl)-6,7-difluoro-4-hydroxy-8-(2-(methoxy)ethoxy)-3-quinolinecarboxamide

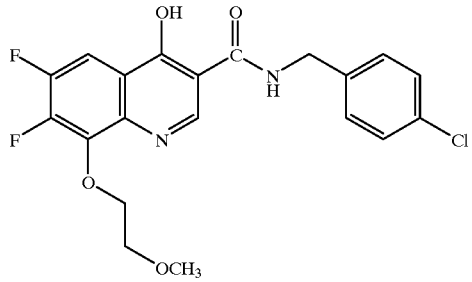

Physical characteristics are as follows:

Mp 167–168° C.

$^1$H NMR (DMSO-d$_6$) δ 12.30, 10.22, 8.63, 7.79, 7.36, 4.52, 4.46, 3.72, 3.23.

$^{13}$C NMR (DMSO-d$_6$) δ 175.2, 164.5, 148.9, 145.6, 144.4, 139.0, 137.4, 131.9, 131.3, 129.7, 128.8, 122.6, 111.2, 106.0, 74.3, 71.2, 58.5, 41.9.

IR (mull) 3217, 3067, 2814, 1648, 1617, 1573, 1546, 1488, 1310, 1288, 1130, 1106, 1091, 1070, 807 cm$^{-1}$.

HRMS (FAB) found 423.0919.

85) N-((4-Chlorophenyl)methyl)-6-fluoro-7,8-di(2-(methoxy)ethoxy)-4-hydroxy-3-quinolinecarboxamide

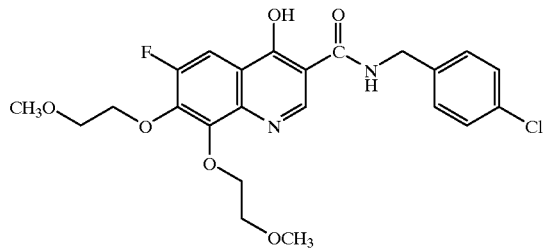

Physical characteristics are as follows:

Mp 160–161.5° C.

$^1$H NMR (DMSO-d$_6$) δ 12.00, 10.29, 8.61, 7.67, 7.36, 4.51, 4.38, 4.32, 3.70, 3.65, 3.28, 3.24.

$^{13}$C NMR (DMSO-d$_6$) δ 175.4, 164.8, 153.8, 143.9, 142.9, 141.6, 139.1, 131.9, 131.6, 129.7, 128.8, 122.1, 110.7, 105.8, 73.6, 73.4, 71.5, 71.3, 58.6, 58.5, 41.9.

IR (mull) 1660, 1631, 1611, 1574, 1564, 1538, 1495, 1307, 1293, 1195, 1111, 1100, 1062, 1044, 794 cm$^{-1}$.

MS (ESI–) for $C_{23}H_{24}ClFN_2O_6$ m/z 477 (M–H)$^-$.

Anal. Found: C, 57.69; H, 5.02; N, 5.85; Cl, 7.47.

EXAMPLE 86

N-((4-Chlorophenyl)methyl)-6,8-difluoro-4-hydroxy-7-(1-methylethoxy)-3-quinolinecarboxamide

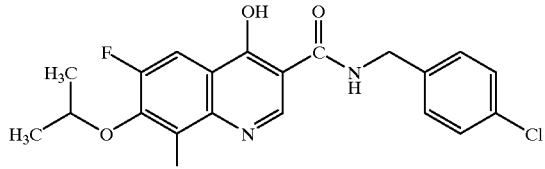

N-((4-Chlorophenyl)methyl)-4-hydroxy-6,7,8-trifluoro-3-quinolinecarboxamide (500 mg) from Example No. 15 and sodium hydride (60% dispersion, 109 mg) are dissolved in DMF (10 mL) and to the mixture is added 2-propanol (115 μL). After being heated for 1 h, additional sodium hydride (50 mg) is added, and the mixture is heated for an additional 1 h. The reaction mixture is allowed to cool to rt, poured into sat. aq. ammonium chloride (25 mL), and is filtered. The crude product is purified by column chromatography (dichloromethane/methanol, 100/1) to afford 62 mg of the title compound as a white solid.

Physical characteristics are as follows:

Mp 207–209° C.

$^1$H NMR (DMSO-d$_6$) δ 12.90, 10.20, 8.58, 7.78, 7.40–7.31, 4.63, 4.52, 1.32.

IR (mull) 3240, 3173, 3091, 3037, 1641, 1610, 1573, 1549, 1538, 1311, 1280, 1105, 1024, 797, 723 cm$^{-1}$.

MS (ESI–) for $C_{20}H_{17}ClF_2N_2O_3$ m/z 405 (M–H)$^-$.

Anal. Found: C, 59.02; H, 4.13; N, 6.89; Cl, 8.76.

EXAMPLE 87

N-(4-Chlorobenzyl)-8-fluoro-4-hydroxy-6-(1,3-thiazol-2-yl)-3-quinolinecarboxamide

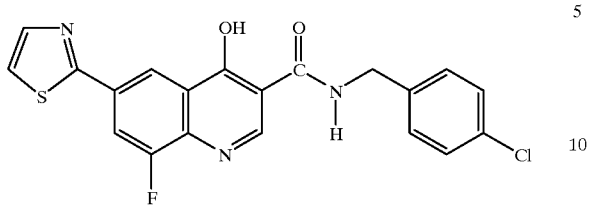

To a suspension of the title compound of Example 52 (0.14 g) and p-toluenesulfonic acid (0.0084 g) in 2 mL acetic acid is added bromoacetaldehyde diethyl acetal (0.08 mL).

The reaction is heated at 100° C. for approximately 45 minutes. The reaction is cooled to room temperature and diluted with 30 mL ethyl acetate. The solid is filtered and dried to give the desired product (0.11 g).

Physical characteristics are as follows:

MP 296–298° C.

$^1$H NMR (300 MHz, DMSO-d$_6$) δ 13.08, 10.18, 8.60, 8.49, 8.19, 7.98, 7.87, 7.38, 7.35, 4.54.

IR (mull) 3069, 1659, 1634, 1611, 1577, 1558, 1529, 1494, 1411, 1352, 1302, 1194, 1016, 800, 651 cm$^{-1}$.

MS (EI) m/z 413 (M$^+$), 415, 413, 274, 273, 247, 246, 218, 142, 140, 58.

HRMS (FAB) found 414.0495.

EXAMPLE 88

N-(4-Chlorobenzyl)-6,8-difluoro-4-hydroxy-7-[(2-methoxyethyl)amino]-3-quinolinecarboxamide

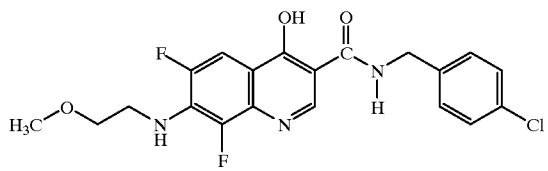

A solution of the title compound of Example 15 (0.32 g) and 2-methoxy-ethylamine (2.0 mL) are heated at 90° C. overnight. The reaction is then cooled to room temperature. Dichloromethane is added and the residue is adsorbed onto silica. A Biotage Flash 40S silica gel column (eluent 2.5% MeOH:CH$_2$Cl$_2$) affords the desired product as an oil which is crystallized with CH$_2$Cl$_2$:hexanes (0.21 g).

Physical characteristics are as follows:

MP 208–209° C.

$^1$H NMR (300 MHz, DMSO-d$_6$) δ 12.47, 10.34, 8.46, 7.57, 7.37, 7.32, 6.24, 4.50, 3.54, 3.49, 3.23.

IR (mull) 3387, 3347, 1653, 1608, 1584, 1553, 1527, 1510, 1494, 1441, 1314, 1131, 1090, 1016, 794 cm$^{-1}$.

MS (EI) m/z 421 (M$^+$), 423, 421, 282, 281, 255, 254, 235, 209, 180, 140.

HRMS (EI) found 421.0993.

EXAMPLE 89

N-(4-Chlorobenzyl)-6-(5-cyano-1-pentynyl)-8-fluoro-4-hydroxy-3-quinolinecarboxamide

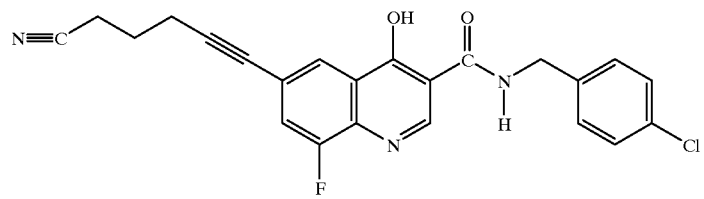

To a solution of the title compound of Example 5 (0.35 g), CuI (0.042 g), and Pd(PPh$_3$)$_2$Cl$_2$ (0.012 g) in 10 mL diethylamine is added 5-hexynenitrile (0.085 mL). The reaction is stirred overnight. The reaction is then partitioned between ethyl acetate and water. The organic layer is washed twice with water, dried over MgSO$_4$, filtered, and adsorbed onto silica. A Biotage Flash 40S (eluent 3% MeOH:CH$_2$Cl$_2$) affords the desired product. The product is recrystallized from CH$_2$Cl$_2$—MeOH/hexanes. A second crop of crystals is obtained by concentration of the filtrate. The total yield of the title compound is 0.21 g.

Physical characteristics are as follows:

MP 208–210° C.

$^1$H NMR (300 MHz, DMSO-d$_6$) δ 12.99, 10.17, 8.59, 8.01, 7.77, 7.37, 7.33, 4.52, 2.65, 2.57, 1.85.

IR (mull) 3192, 3076, 3057, 1651, 1636, 1607, 1576, 1543, 1516, 1492, 1350, 1304, 1283, 1198, 804 cm$^{-1}$.

MS (EI) m/z 421 (M$^+$), 423, 421, 281, 255, 254, 200, 171, 142, 140, 125.

HRMS (EI) found 421.0982.

EXAMPLE 90

N-(4-Chlorobenzyl)-8-fluoro-4-hydroxy-6-(2-pyridinyl)-3-quinolinecarboxamide

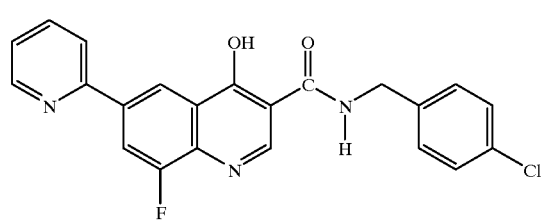

To a solution of the title compound of Example 5 (0.844 g) in 12.5 mL dioxane and 0.5 mL HMPA are added 2-(tributylstannyl)pyridine (0.74 g) and PdCl$_2$(PPh$_3$)$_2$ (84.2 mg). The mixture is stirred at 100° C. for 2 days. The reaction mixture is cooled to room temperature, then filtered to get rid of excess palladium. Upon diluting the filtrate with water, a yellow solid precipitates. The crude product is dissolved in MeOH, adsorbed onto silica, and chromatographed eluting with 2% MeOH in CH$_2$Cl$_2$. Fractions homogenous by TLC are combined, condensed and recrystallized from EtOAc/hexanes to yield 0.207 g of the desired product as a white solid.

Physical characteristics are as follows:

MP 304–305° C.;

$^1$H NMR (300 MHz, DMSO) δ 13.01, 10.29, 8.77, 8.70, 8.65, 8.40, 8.11, 7.93, 7.38, 4.55.

IR (mull) 3074, 1662, 1639, 1590, 1576, 1543, 1508, 1492, 1317, 1288, 1223, 808, 802, 786, 684 cm$^{-1}$.

MS (ESI)$^-$ for C$_{22}$H$_{15}$ClFN$_3$O$_2$ m/z 406.0 (M–H)$^-$.

Anal. Found: C, 64.48; H, 3.80; N, 10.26.

EXAMPLE 91

4-Hydroxy-6-iodo-3-quinolinecarboxylic acid 2-(4-chlorophenyl)hydrazide

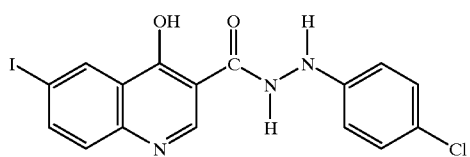

Ethyl 4-hydroxy-6-iodo-3-quinolonecarboxylate (1.4 g) is dissolved in 60 mL of 1:1 MeOH:THF and 16 mL 1M LiOH. The reaction is heated at 40° C. overnight. Upon diluting the reaction mixture with 25 mL acetic acid, a white precipitate forms. The solid is filtered, washed with water, and dried to obtain 1.09 g of the desired acid as a white solid.

The acid from above (250 mg) and 1.1'-carbonyldiimidazole (154.4 mg) are dissolved in 25 mL anhydrous THF and heated at 65° C. for 2 days. After the reaction mixture is cooled to room temperature, 4-chlorobenzylamine (170.5 mg) and diisopropylethylamine (0.17 mL) are added. The reaction mixture is heated at 65° C. overnight to solubilize the reactants and an additional 20 mL THF is also added. The mixture is cooled to room temperature and partitioned between EtOAc and H$_2$O. The aqueous layer is extracted with EtOAc (2×). The combined organic layers are washed with brine (1×), dried over Na$_2$SO$_4$, and condensed. The crude solid is recrystallized with EtOAc/hexanes and filtered to obtain a product of very low yield. After storing the filtrate in the freezer for 1 month, a pure solid precipitates and is filtered to yield 25.5 mg of the desired product as a pink solid.

Physical characteristics are as follows:

MP 250–252° C.;

$^1$H NMR (300 MHz, DMSO) δ 12.94, 11.19, 8.77, 8.55, 8.18, 8.06, 7.54, 7.16, 6.72.

HRMS (FAB) found 439.9673.

EXAMPLE 92

N-(4-Chlorobenzyl)-8-fluoro-4-hydroxy-6-[2-(2-pyridinyl)ethynyl]-3-quinolinecarboxamide

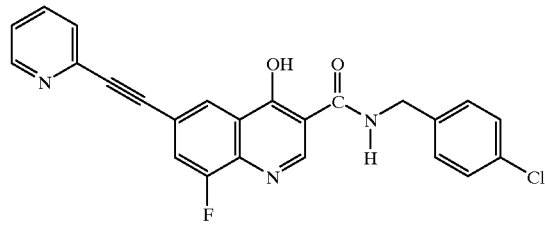

A solution of the title compound of Example 5 (540.3 mg), 2-ethynyl pyridine (0.172 g), PdCl$_2$(PPh$_3$)$_2$ (21.1 mg), and 0.75 mL Et$_3$N in 3 mL DMF is heated at 90° C. for 1 hr. The reaction mixture is cooled to room temperature and diluted with H$_2$O. A tan solid precipitates, which is collected, dissolved in a mixture of CH$_2$Cl$_2$ and MeOH, and adsorbed onto silica. The crude product is chromatographed eluting with 2% MeOH in CH$_2$Cl$_2$. Fractions homogenous by TLC are combined, condensed and recrystallized from hot MeOH/CH$_2$Cl$_2$ and hexanes to yield 0.302 g of the desired product as a white solid.

Physical characteristics are as follows:

MP 275–277° C.;

$^1$H NMR (300 MHz, DMSO) δ 13.09, 10.17, 8.62, 8.18, 7.98, 7.87, 7.70, 7.41, 4.56.

IR (mull) 3064, 3027, 1684, 1613, 1591, 1561, 1532, 1519, 1494, 1484, 1435, 1295, 1248, 801, 772 cm$^{-1}$.

HRMS (EI) found 431.0823.

EXAMPLE 94

N-(4-Chlorobenzyl)-8-fluoro-4-hydroxy-6-(4-hydroxy-1-butynyl)-3-quinolinecarboxamide

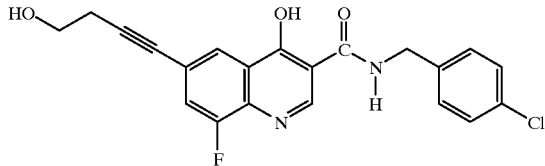

To a mixture of the title compound of Example 5 (0.457 g), copper iodide (0.010 g) and dichlorobis(triphenylphosphine)palladium (II) (0.035 g) in 15 mL diethylamine is added 3-butyne-1-ol (0.076 mL). The reaction is allowed to stir overnight. The solvents are evaporated and the residue is chromatographed on silica, eluting with 3% MeOH/CH$_2$Cl$_2$ to yield 0.279 g of the desired product as a tan solid.

Physical characteristics are as follows:

MP 253–255° C.;

IR (mull) 3197, 3068, 1654, 1630, 1609, 1575, 1556, 1521, 1493, 1305, 1292, 1195, 1030, 1016, 804 cm$^{-1}$.

$^1$H NMR (300 MHz, DMSO) δ 12.99, 10.18, 8.61, 7.99, 7.75, 7.37, 4.54, 3.61, 2.60.

MS (EI) m/z 398 (M$^+$), 400, 398, 258, 232, 231, 200, 171, 142, 140, 125.

HRMS (EI) found 398.0831.

EXAMPLE 95

N-(4-Chlorobenzyl)-8-fluoro-4-hydroxy-6-(3-methoxy-1-propynyl)-3-quinolinecarboxamide

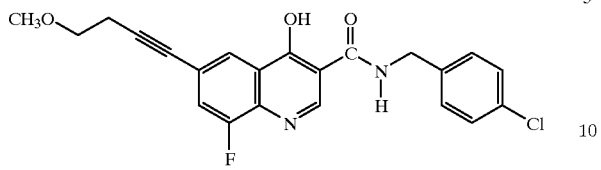

A solution of the title compound of Example 5 (540.3 mg), methyl propargyl ether (0.14 mL), PdCl$_2$(PPh$_3$)$_2$ (21.1 mg), and 0.75 mL Et$_3$N in 3 mL DMF is heated at 90° C. for 1 hr. The reaction mixture is cooled to room temperature and partitioned between EtOAc and H$_2$0. The aqueous layer is washed with EtOAc (4×). The combined organic layers are dried over Na$_2$SO$_4$ and condensed to obtain a dark residue. The residue is diluted with MeOH, adsorbed onto silica, and chromatographed eluting with 2% MeOH in CH$_2$Cl$_2$. Fractions homogenous by TLC are combined, condensed and recrystallized from EtOAc/hexanes to yield 0.218 g of the desired product as a white solid.

Physical characteristics are as follows:

MP 222–224° C.;

$^1$H NMR (300 MHz, DMSO) δ 13.03, 10.16, 8.62, 8.05, 7.84, 7.38, 4.55, 4.37, 3.33.

IR (mull) 1655, 1635, 1610, 1585, 1572, 1564, 1543, 1536, 1517, 1490, 1305, 1287, 1185, 1093, 805 cm$^{-1}$.

MS (EI) m/z 398 (M$^+$), 400, 398, 258, 231, 200, 171, 142, 141, 140, 125.

Anal. Found: C, 63.01; H, 4.23; N, 6.99.

EXAMPLE 96

N-(4-Chlorobenzyl)-8-fluoro-4-hydroxy-6-(3-hydroxy-1-butynyl)-3-quinolinecarboxamide

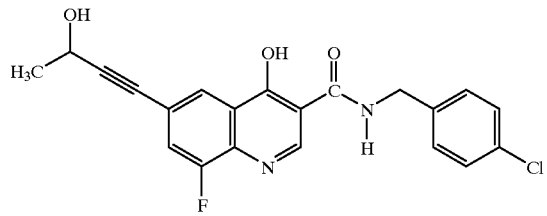

A solution of the title compound of Example 5 (540.3 mg), 3-butyn-2-ol (0.13 mL), PdCl$_2$(PPh$_3$)$_2$ (21.1 mg), and 0.75 mL Et$_3$N in 3 mL DMF is heated at 90° C. for 1 hr. The reaction mixture is cooled to room temperature and partitioned between EtOAc and H$_2$O. The aqueous layer is washed with EtOAc (3×). The combined organic layers are dried over Na$_2$SO$_4$ and condensed to obtain a brown residue. The residue is diluted with MeOH, adsorbed onto silica, and chromatographed eluting with 2.5 % MeOH in CH$_2$Cl$_2$. Fractions homogenous by TLC are combined, condensed and recrystallized from EtOAc/hexanes to yield 0.207 g of the desired product as a creme-colored solid.

Physical characteristics are as follows:

MP 232–234° C.;

$^1$H NMR (300 MHz, DMSO) δ 13.01, 10.17, 8.60, 7.98, 7.73, 7.38, 5.55, 4.60, 4.55, 1.38.

IR (mull) 3153, 3113, 3061, 1652, 1637, 1610, 1579, 1562, 1546, 1514, 1491, 1305, 1285, 1001, 804 cm$^{-1}$.

MS (EI) m/z 398 (M$^+$), 400, 398, 258, 231, 216, 188, 187, 142, 140, 125.

Anal. Found: C, 62.92; H, 4.22; N, 6.96.

EXAMPLE 97

6-(4-Bromo-2-thienyl)-N-(4-chlorobenzyl)-8-fluoro-4-hydroxy-3-quinolinecarboxamide

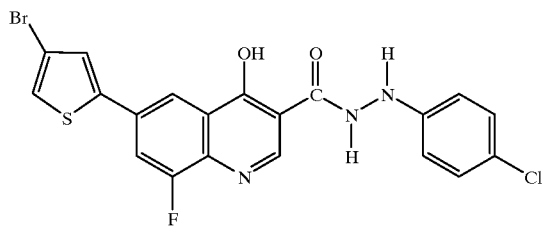

To a solution of the title compound of Example 5 (0.684 g) and PdCl$_2$(PPh$_3$)$_2$ (68.8 mg) in 10.1 mL dioxane and 0.41 mL HMPA is added 2-(tributylstannyl)-4-bromothiophene (0.732 g). The reaction is maintained at 100° C. overnight. The reaction mixture is cooled to room temperature, then filtered to get rid of excess palladium. The filtrate is diluted with H$_2$0 and extracted with CH$_2$Cl$_2$ (3×) in a sep funnel. The combined organic layers are washed with brine (1×), dried over Na$_2$SO$_4$, and condensed to obtain a yellow solid. The crude product is dissoved in a mixture of CH$_2$Clr!/MeOH, adsorbed onto silica, and chromatographed eluting with 2% MeOH in CH$_2$Cl$_2$. The product is recrystallized with EtOAc/hexanes to yield 0.358 g of the desired product as a yellow solid.

MP 281–283° C.

$^1$H NMR (300 MHz, DMSO) δ 13.00, 10.22, 8.61, 8.17, 7.75, 7.36, 4.53.

IR (mull) 3140, 3114, 3089, 3059, 3019, 1652, 1638, 1611, 1577, 1550, 1530, 1515, 1490, 1305, 804 cm$^{-1}$.

MS (EI) m/z 490 (M$^+$), 492, 490, 352, 350, 325, 323, 142, 141, 140, 125.

Anal. Found: C, 51.42; H, 2.85; N, 5.68.

EXAMPLE 98

N-(4-Chlorobenzyl)-8-fluoro-6-(hydrazinocarbothioyl)-4-hydroxy-3-quinolinecarboxamide

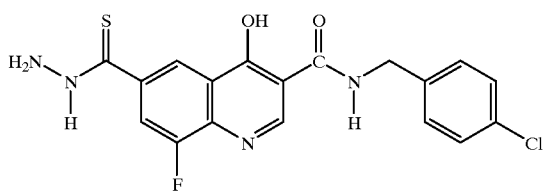

To a suspension of the title compound of Example 52 (0.60 g) in 20 mL 1:1 THF:CH$_2$Cl$_2$ at room temperature is added methyl triflate (0.2 mL). The reaction is stirred for 45 minutes after which time everything goes into solution. Pyridine (0.38 mL) is added and then H$_2$S is bubbled in for 1 hour. Nitrogen is then purged through the reaction for 30 minutes. Hydrazine monohydrate (0.28 mL) is added dropwise to the reaction mixture. The reaction is stirred for 1 hour after which time the solution turned from an orange to a pale yellow color and a precipitate is observed. The solid in the reaction is filtered and dried to give the desired product (0.26 g).

Physical characteristics are as follows:

MP 317–319° C.

$^1$H NMR (300 MHz, DMSO-d$_6$) δ 10.27, 8.62, 8.49, 8.05, 7.38, 7.34, 4.54, 4.07, 3.30.

IR (mull) 3238, 3199, 3164, 3044, 3019, 1656, 1615, 1578, 1558, 1524, 1491, 1314, 1280, 898, 810 cm$^{-1}$.

MS (FAB) m/z 405 (MH$^+$), 407, 406, 405, 404, 388, 125, 87, 73, 71, 55.

HRMS (FAB) found 405.0590.

EXAMPLE 99

N-(4-Chlorobenzyl)-8-fluoro-4-hydroxy-6-(4-hydroxybutyl)-3-quinolinecarboxamide

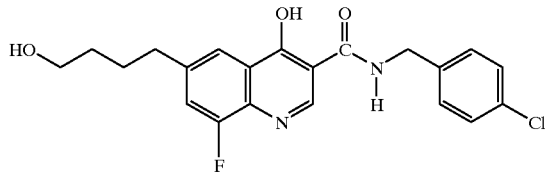

A solution of the title compound of Example 94 (0.180 g), Pd/Ba$_2$SO$_4$ (10%, 75.3 mg), and pyridine (5 mL) in EtOAc (25 mL) is maintained under an atmosphere of H$_2$ (balloon) for 3 hrs, then filtered over celite. The crude product is recrystallized from EtOAc/hexanes to afford 81.6 mg of the desired product as an off-white solid.

Physical characteristics are as follows:

MP 210–212° C.;

$^1$H NMR (300 MHz, DMSO) δ 12.83, 10.33, 8.61, 7.86, 7.61, 7.38, 4.55, 4.38, 3.38, 2.71, 1.63, 1.41.

IR (mull) 3246, 3196, 3161, 3082, 1662, 1641, 1615, 1577, 1544, 1507, 1491, 1306, 1266, 804, 685 cm$^{-1}$.

MS (EI) m/z 402 (M$^+$), 404, 402, 263, 262, 236, 235, 176, 147, 142, 140.

Anal. Found: C, 62.48; H, 4.95; N, 6.88.

EXAMPLE 100

N-(4-Chlorobenzyl)-8-fluoro-4-hydroxy-6-(5-methyl-1,3,4-thiadiazol-2-yl)-3-quinolinecarboxamide

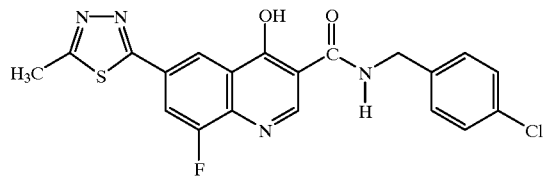

A solution of the title compound of Example 98 (0.24 g) and acetyl chloride (0.05 mL) in 10 mL freshly distilled THF is heated at 65° C. for 1 hour. The reaction is cooled to room temperature and concentrated to give a yellow solid. The solid is triturated in diethyl ether, filtered, and dried to give the desired thiadiazole (0.20 g).

Physical characteristics are as follows:

MP 292–294° C.

$^1$H NMR (300 MHz, DMSO-d$_6$) δ 13.13, 10.14, 8.63, 8.43, 8.25, 7.38, 7.35, 4.54, 2.79.

IR (drift) 3077, 3058, 3040, 3024, 2945, 1673, 1616, 1585, 1550, 1527, 1489, 1444, 1277, 1199, 798 cm$^{-1}$.

MS (EI) m/z 428 (M$^+$), 428, 289, 288, 262, 261, 233, 142, 141, 140, 125.

HRMS (FAB) found 429.0583.

EXAMPLE 101

N-(4-Chlorobenzyl)-4-hydroxy-7-(3-hydroxy-1-propynyl)-3-quinolinecarboxamide

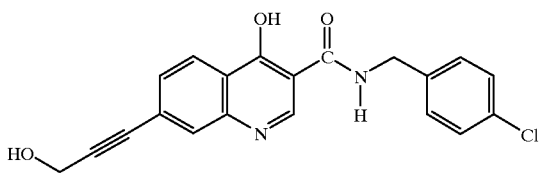

To a mixture of the title compound of Example 39 (0.439 g), copper iodide (0.010 g) and dichlorobis(triphenylphosphine)palladium (II) (0.035 g) in 15 mL diethylamine is added propargyl alcohol (0.058 mL). The reaction is allowed to stir overnight. The solvents are evaporated and the residue is chromatographed on silica, eluting with 3% MeOH/CH$_2$Cl$_2$ to yield 0.271 g of the desired product as a tan solid.

Physical characteristics are as follows:

MP 218–220° C.;

$^1$H NMR (300 MHz, DMSO) δ 12.72, 19,36, 1.80, 8.21, 7.72, 7.46, 7.38, 4.55, 4.37, 3.17.

IR (mull) 3066, 3055, 3006, 1651, 1634, 1595, 1575, 1531, 1496, 1320, 1242, 1031, 869, 833, 797 cm$^{-1}$.

MS (EI) m/z 366 (M$^+$), 368, 366, 227, 226, 200, 199, 142, 140, 125, 115.

HRMS (FAB) found 367.0840.

EXAMPLE 102

7-(Aminocarbothioyl)-N-(4-chlorobenzyl)-4-hydroxy-3-quinoline-carboxamide

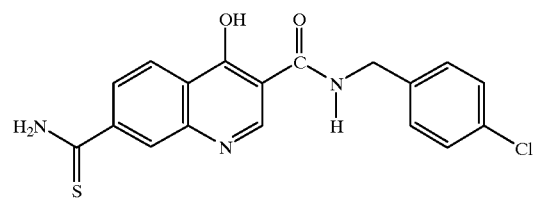

To a solution of the title compound Example 39 (1.0 g) in 30 mL freshly distilled tetrahydrofuran is added KCN (0.30 g) and Pd(PPh3)$_4$ (0.49 g). The reaction is heated at 60° C. overnight. The reaction is cooled to room temperature and the solvents removed. The residue is dissolved in a mixture of MeOH/CH$_2$Cl$_2$/EtOAc and adsorbed onto silica. Purification by a Biotage Flash 40S silica gel column (eluent 2% MeOH/CH$_2$Cl$_2$) affords the desired product as a yellow solid (0.52 g).

A solution of the solid obtained above (0.52 g) and NEt₃ (0.44 mL) in 10 mL DMF is heated to 95° C. H₂S is bubbled into the reaction mixture for approximately 4 hours. The bubbler is removed and the reaction allowed to stir at 30° C. over 3 days. Water is added to the reaction and the resulting solid is filtered and dried. This solid is confirmed to be starting material so the solid is re-dissolved in DMF and subjected to the same reaction conditions. The solid obtained after water is added to the reaction mixture contains desired product. The solid is dissolved in MeOH/CH₂Cl₂ and adsorbed onto silica. A Biotage Flash 40S silica gel column (eluent 2.5% MeOH:CH₂Cl₂ (1 L) followed by 4% MeOH:CH₂Cl₂ (1 L)) affords the desired product (0.38 g).

Physical characteristics are as follows:

MP 255–256° C.

$^1$H NMR (300 MHz, DMSO-d₆) δ 12.87, 10.34, 10.15, 9.78, 8.77, 8.22, 8.12, 7.78, 7.38, 7.35, 4.53.

IR (mull) 3291, 3210, 1666, 1660, 1639, 1617, 1609, 1558, 1531, 1514, 1492, 1354, 1309, 1297, 621 cm$^{-1}$.

MS (ESI) 372.1 (M+H)$^+$, 394.0 (M+Na)$^+$, 370.0 (M−H)$^-$.

HRMS (FAB) found 372.0573.

Anal. Found: C, 56.83; H, 3.87; N, 10.90.

EXAMPLE 103

N-(4-Chlorobenzyl)-8-fluoro-4-hydroxy-6-(3-methoxypropyl)-3-quinolinecarboxamide

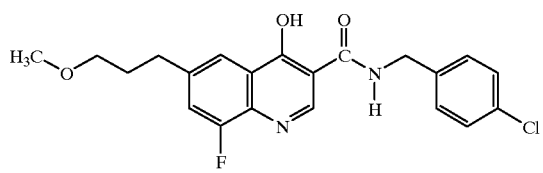

A mixture of the title compound of Example 95 (0.113 g) and Pd/C (10%, 22.6 mg) is dissolved in 3:1 CH₂Cl₂:MeOH. The reaction mixture is placed under the Parr hydrogenator at 25 psi H₂ and monitored with the OAMS for complete reduction of the acetylene. The reaction is complete in 1 hr and is filtered over celite. The filtrate is condensed to obtain a white solid. The product is recrystallized with EtOAc/hexanes to yield 32.0 mg of the desired product.

Physical characteristics are as follows:

MP 189–192° C.;

$^1$H NMR (300 MHz, DMSO) δ 12.82, 10.30, 8.58, 7.83, 7.61, 7.38, 7.33, 4.53, 3.30, 3.21, 2.75, 1.82.

IR (drift) 3079, 3014, 2963, 2935, 2892, 2854, 2826, 1660, 1613, 1575, 1541, 1507, 1306, 1266, 804 cm$^{-1}$.

EXAMPLE 104

N-(4-Chlorobenzyl)-8-fluoro-4-hydroxy-6-[(Z)-4-hydroxy-1-butenyl]-3-quinolinecarboxamide

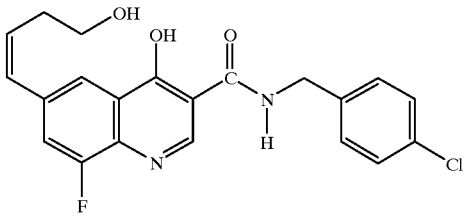

A solution of the title compound of Example 94 (0.393 g), pyridine (3 mL), and Pd/C (10%, 80.0 mg) in 3:1 CH₂Cl₂:MeOH is maintained under an atmosphere of H₂ (balloon) for 3 hrs. More Pd/C (10%, 40 mg) is added and the reaction mixture is placed under the Parr hydrogenator at 25 psi H₂ for an additional 3 hrs. The reaction mixture is filtered over celite. The filtrate is condensed and then placed under high vac to remove residual pyridine. The crude product is recrystallized with EtOAc/hexanes to afford 0.218g of the desired product as a tan solid.

Physical characteristics are as follows:

MP 195–197° C.;

$^1$H NMR (300 MHz, DMSO) δ 12.92, 10.28, 8.61, 7.97, 7.68, 7.36, 6.56, 5.83, 4.68, 4.52, 3.52, 2.50.

IR (drift) 3181, 3076, 3059, 3014, 2932, 1651, 1610, 1548, 1519, 1490, 1347, 1307, 1283, 808, 798 cm$^{-1}$.

HRMS (FAB) found 401.1082.

Anal. Found: C, 62.56; H, 4.64; N, 6.91.

EXAMPLE 105

N-(4-Chlorobenzyl)-6-(5-cyanopentyl)-8-fluoro-4-hydroxy-3-quinolinecarboxamide

MS (ESI)$^-$ for C₂₁H₂₀ClFN₂O₃ m/z 401.0 (M−H)$^-$.

Anal. Found: C, 63.09; H, 5.16; N, 6.89.

To a suspension of the title compound of Example 89 (0.11 g) in 25 mL EtOAc is added triethylamine (0.08 mL) and pyridine (5 mL) to aid dissolution. After 10% Pd/C (50 mg) is added, the reaction is placed under a hydrogen balloon. After 2 hours, the reaction is complete and subsequently filtered over Celite. The filter cake is washed with ethyl acetate. The filtrate is concentrated to give a tan solid which is further dried on the vacuum pump to afford the desired product (0.088 g).

Physical characteristics are as follows:

MP 213–215° C.

$^1$H NMR (300 MHz, DMSO-d$_6$) δ 12.98, 10.33, 8.60, 7.87, 7.64, 7.40, 7.36, 4.55, 2.74, 2.48, 1.58, 1.37.

IR (drift) 3194, 3158, 3060, 2935, 1651, 1613, 1568, 1558, 1544, 1524, 1489, 1304, 1288, 804, 724 cm$^{-1}$.

MS (ESI) 426.0 (M+H)$^+$, 424.0 (M−H)$^-$.

HRMS (FAB) found 426.1371.

Anal. Found: C, 64.95; H, 5.17; N, 9.69.

pleted in 1 hr and filtered over celite to remove the palladium. The filtrate is condensed to obtain a white solid. The product is recrystallized with EtOAc/hexanes to yield 32.0 mg of the desired product.

Physical characteristics are as follows:

MP 219–222° C.;

$^1$H NMR (300 MHz, DMSO) δ 12.85, 10.33, 8.60, 7.86, 7.61, 7.41, 7.36, 4.55, 4.32, 2.77, 1.68, 1.51.

IR (drift) 2977, 2962, 2942, 1647, 1614, 1561, 1525, 1490, 1303, 1287, 1207, 1199, 808, 798, 724 cm$^{-1}$.

HRMS (FAB) found 417.1382.

Anal. Found: C, 63.65; H, 5.53; N, 6.69.

EXAMPLE 107

N-(4-Chlorobenzyl)-8-fluoro-4-hydroxy-6-(5-hydroxy-1-pentynyl)-3-quinolinecarboxamide

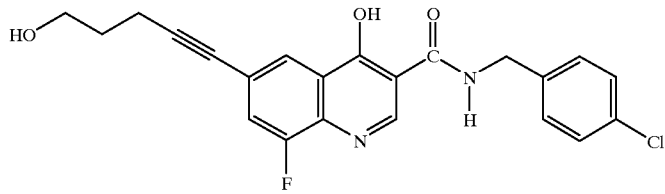

EXAMPLE 106

N-(4-Chlorobenzyl)-8-fluoro-4-hydroxy-6-(3-hydroxy-3-methylbutyl)-3-quinolinecarboxamide

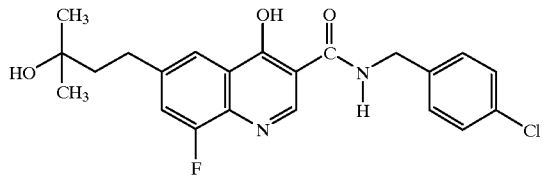

To a mixture of the title compound of Example 5 (0.457 g), copper iodide (0.010 g) and dichlorobis(triphenylphosphine)palladium (II) (0.035 g) in 15 mL diethylamine is added 2-methyl-3-butyne-2-ol (0.097 mL). The reaction is allowed to stir overnight. The solvents are evaporated and the residue is chromatographed on silica, eluting with 3% MeOH/CH$_2$Cl$_2$ to yield 0.248 g of the desired product as a white solid.

The acetylene from above (0.190 g) is dissolved in 3:1 CH$_2$Cl$_2$:MeOH. To this is added 10% Pd/C and Pd/C (38.0 mg). The reaction mixture is placed under the Parr hydrogenator at 25 psi H$_2$ and monitored with the OAMS for complete reduction of the acetylene. The reaction is com- A solution of the title compound of Example 5 (540.3 mg), 4-pentyn-1-ol (0.16 mL), PdCl$_2$(PPh$_3$)$_2$ (21.1 mg), and 0.75 mL Et$_3$N in 3 mL DMF is heated at 90° C. for 1 hr. The reaction mixture is cooled to room temperature and partitioned between EtOAc and H$_2$O. The aqueous layer is washed with EtOAc (3×). The combined organic layers are dried over Na$_2$SO$_4$ and condensed to obtain a red-brown residue. The residue is diluted with CH$_2$Cl$_2$ and chromatographed eluting with 2% MeOH in CH$_2$Cl$_2$. Fractions homogenous by TLC are combined, condensed and recrystallized from EtOAc/hexanes to yield 0.296 g of the desired product as a white solid.

Physical characteristics are as follows:

MP 208–209° C.;

$^1$H NMR (300 MHz, DMSO) δ 13.00, 10.19, 8.61, 7.98, 7.73, 7.41, 7.36, 4.54, 3.52, 2.51, 1.71 (m, 2 H).

IR (drift) 3290, 2966, 2934, 1659, 1610, 1574, 1563, 1558, 1543, 1538, 1523, 1303, 1031, 869, 804 cm$^{-1}$.

MS (ESI)$^-$ for C$_{22}$H$_{18}$ClFN$_2$O$_3$ m/z 411.1 (M−H)$^-$.

Anal. Found: C, 63.65; H, 4.41; N, 6.62.

EXAMPLE 108

6-{3-[Benzyl(methyl)amino]propyl}-N-(4-chlorobenzyl)-8-fluoro-4-hydroxy-3-quinolinecarboxamide

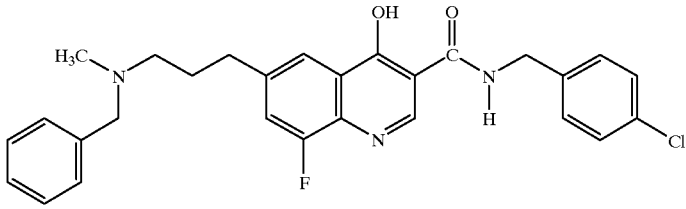

To a solution of the title compound of Example 5 (0.37 g), CuI (0.058 g), and Pd(PPh$_3$)$_2$Cl$_2$ (0.011 g) in 10 mL diethylamine is added N-methyl-N-propargylbenzylamine (0.15 mL). The reaction is stirred overnight. The reaction is partitioned between ethyl acetate and H$_2$O. The organic layer is washed twice with water, dried over MgSO$_4$, filtered, and adsorbed onto silica. A Biotage Flash 40S column (eluent 2.5% MeOH:CH$_2$Cl$_2$ (1 L) followed by 3% MeOH:CH$_2$Cl$_2$ (1 L)) affords the intermediate acetylene which is further recrystallized with CH$_2$Cl$_2$/Hexanes (0.25 g).

The product from above (0.16 g) is suspended in 25 mL EtOAc. Triethylamine (0.1 mL) followed by pyridine (2 mL) is added to affect dissolution. After addition of 10% Pd/C (60 mg), the reaction is placed under hydrogen balloon and stirred at room temperature. After 1.5 hours, the reaction is complete and is subsequently filtered over Celite. The filtrate is concentrated to give a liquid which is crystallized with EtOAc/Hexanes to give the desired product as a white solid (0.056 g).

Physical characteristics are as follows:

MP 161–162° C.

$^1$H NMR (300 MHz, DMSO-d$_6$) δ 10.35, 8.59, 7.84, 7.56, 7.37, 7.33, 7.26, 4.52, 3.46, 2.72, 2.35, 2.11, 1.81.

IR (drift) 3160, 3060, 2935, 1651, 1634, 1613, 1573, 1567, 1548, 1525, 1489, 1285, 805, 724, 699 cm$^{-1}$.

MS (ESI) 492.0 (M+H)$^+$, 490.0 (M−H)$^-$.

HRMS (FAB) found 492.1839.

EXAMPLE 109

Methyl 3-{[(4-chlorobenzyl)amino]carbonyl}-8-fluoro-4-hydroxy-6-quinolinecarboxylate

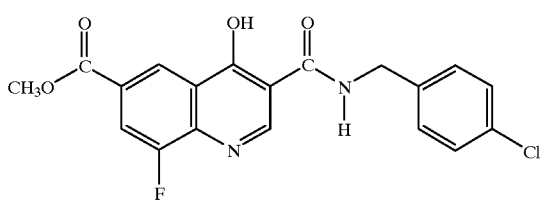

A solution of the title compound of Example 5 (1.0 g), Et$_3$N (0.61 mL), MeOH (3.55 mL), Pd(OAc)$_2$ (13.7 mg), 1,3-bis(diphenylphosphino)propane (25.2 mg) in 12 mL DMSO is stirred at room temperature until everything dissolves. CO(g) is slowly bubbled through for 3 hrs and the reaction is maintained at 70° C. overnight. CO(g) is bubbled into the reaction mixture for an additional 4 hrs the following day. The reaction is cooled to room temperature and diluted with H$_2$O. The white solid that precipitates is collected, while the filtrate is partitioned against CH$_2$Cl$_2$. The aqueous layer is washed with CH$_2$Cl$_2$ (3×). The combined organic layers are dried over Na$_2$SO$_4$ and condensed to obtain an orange residue. The residue is placed under high vac to remove residual DMSO. The previously collected solid is combined with the residue, dissolved in MeOH, and adsorbed onto silica. The crude product is chromatographed eluting with 2% MeOH in CH$_2$Cl$_2$. Fractions homogenous by TLC are combined, condensed and recrystallized with EtOAc/hexanes to yield 0.418g of the desired product as a white solid.

Physical characteristics are as follows:

MP 288–290° C.;

$^1$H NMR (300 MHz, DMSO) δ 13.17, 10.09, 8.63, 8.58, 8.04, 7.39, 7.34, 4.54, 3.30.

IR (drift) 3071, 1727, 1660, 1634, 1611, 1576, 1557, 1527, 1496, 1311, 1288, 1234, 1191, 803, 765 cm$^{-1}$.

HRMS (FAB) found 389.0706.

Anal. Found: C, 58.64; H, 3.84; N, 7.24.

EXAMPLE 110

N-(4-Chlorobenzyl)-8-fluoro-4-hydroxy-6-(3-hydroxypropyl)-3-quinolinecarboxamide

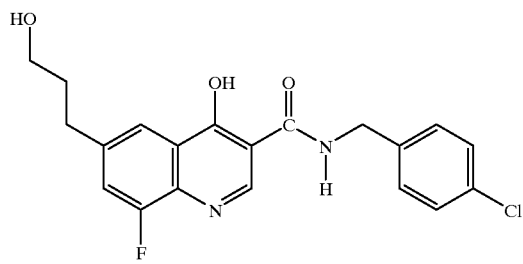

A suspension of the title compound of Example 53 (0.300 g) and 10% Pd/C (0.03 g) in 25 mL of 3:1 CH$_2$Cl$_2$/MeOH is hydrogenated at atmospheric pressure overnight. The reaction is filtered through celite. The filtrate is condensed. The crude product is recrystallized from EtOAc/hexanes to yield 0.200 g of the desired product as a pale-yellow solid.

Physical characteristics are as follows:

MP 224–226° C.;

$^1$H NMR (300 MHz, DMSO) δ 12.8, 10.33, 8.60, 7.86, 7.61, 7.38, 4.53, 3.42, 30 3.32, 2.77, 1.76.

IR (drift) 3045, 2950, 2931, 2886, 1651, 1611, 1582, 1563, 1557, 1537, 1532, 1492, 1301, 1015, 808 cm$^{-1}$.

MS (FAB) m/z 389 (MH$^+$), 391, 390, 389, 248, 139, 125, 123, 105, 91, 86.

HRMS (FAB) found 389.1060.

EXAMPLE 111

N-(4-Chlorobenzyl)-4-hydroxy-7-(3-hydroxypropyl)-3-quinoline-carboxamide

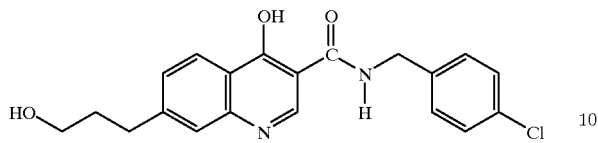

A mixture of the title compound of Example 101 (0.190g) and Pd/C (10%, 37.9 mg) is dissolved in 3:1 $CH_2Cl_2$:MeOH. The reaction mixture is placed under the Parr hydrogenator at 25 psi $H_2$ and monitored with the OAMS for complete reduction of the acetylene. The reaction is filtered and fresh catalyst is added each time the reaction is taken off the Parr. The reaction is completed in 3½ hrs and filtered over celite to remove the palladium. The filtrate is condensed to obtain a residue. The residue is dissolved in MeOH, adsorbed onto silica, and chromatographed eluting with 4% MeOH in $CH_2Cl_2$. Fractions homogenous by TLC are combined, condensed and recrystallized with EtOAc/hexanes to yield 91.4 mg of the desired product as a white solid.

Physical characteristics are as follows:

MP 166–168° C.;

$^1$H NMR (300 MHz, DMSO) δ 12.60, 10.46, 8.71, 8.15, 7.45, 7.36, 4.53, 3.41, 2.75, 1.75.

IR (drift) 3284, 2946, 1652, 1635, 1612, 1582, 1562, 1539, 1492, 1474, 1053, 20 860, 849, 795, 753 cm$^{-1}$.

HRMS (FAB) found 371.1155.

Anal. Found: C, 64.47; H, 5.14; N, 7.46.

EXAMPLE 112

Ethyl (E)-3-(3-{[(4-chlorobenzyl)amino]carbonyl}-8-fluoro-4-hydroxy-6-quinolinyl)-2-propenoate

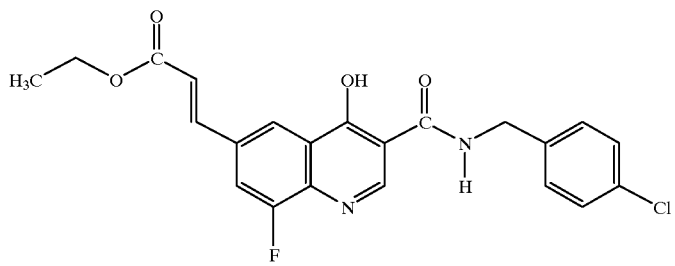

A mixture of the title compound of Example 5 (1.05 g), triethylamine (6 mL), ethyl acrylate (0.3 mL), palladium acetate (5.1 mg) and tris(o-tolyl)phosphine (42 mg) in DMF (5 mL) is heated to 100° C. for 24 h in a pressure-safe tube. The reaction is partitioned between $CH_2Cl_2$ and water. The aqueous layer is extracted with $CH_2Cl_2$ (3×). The combined organic layers are filtered, dried over $Na_2SO_4$, filtered and condensed. The crude product is purified by trituration with hot EtOAc to yield 0.461 g of the desired product as a tan solid.

Physical characteristics are as follows:

MP 278–280° C.;

$^1$H NMR (300 MHz, DMSO) δ 13.01, 10.23, 8.61, 8.21, 7.78, 7.40, 6.78, 4.55, 4,21, 1.27.

MS(ESI−) for $C_{22}H_{18}ClFN_2O_4$ m/z 427.1 (M−H)$^-$.

EXAMPLE 113

(E)-3-(3-{[(4-Chlorobenzyl)amino]carbonyl}-8-fluoro-4-hydroxy-6-quinolinyl)-2-propenoic acid

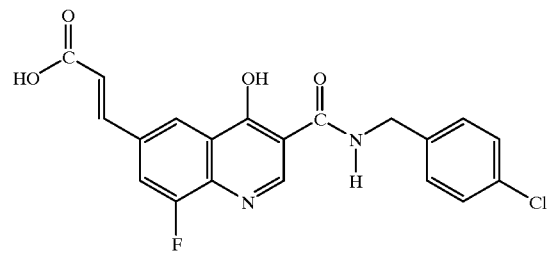

A mixture of the title compound of Example 5 (0.913 g), acrylic acid (0.17 mL), palladium acetate (4 mg) and triethylamine (0.70 mL) in 5 mL DMF is heated to 100° C. for 24 h in a pressure-safe tube. The reaction is cooled and diluted with 50 mL of a 10% aqueous HCl solution. The resulting solid is collected, dried and recrystallized from EtOH to yield 0.564 g of the desired product as a tan solid.

Physical characteristics are as follows:

MP 296–298° C.;

$^1$H NMR (300 MHz, DMSO) δ 13.05, 10.23, 8.60, 8.21, 7.71, 7.39, 6.67, 4.56.

MS(ESI−) for $C_{20}H_{14}ClFN_2O_4$ m/z 399.1 (M−H)$^-$.

EXAMPLE 114

3-(3-{[(4-Chlorobenzyl)amino]carbonyl}-8-fluoro-4-hydroxy-6-quinolinyl)propanoic acid

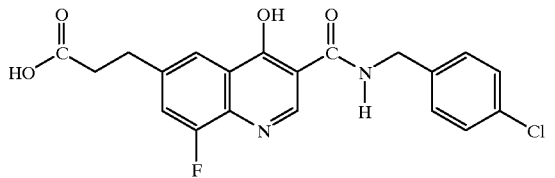

To a mixture of the title compound of Example 113 (0.250 g) and triethylamine (0.09 mL) in 100 mL of 3:1 CH$_2$Cl$_2$MeOH is added 10% Pd/C (0.050 g). The mixture is hydrogenated at 30 psi H$_2$ for 6 h. The reaction is filtered through celite and the filtrate is condensed. The crude product is dissolved in DMF (~25 mL) and acidified with 1 N HCl (25 mL). The resulting solid is collected, dried and recrystallized from EtOH to yield 0.152 g of the desired product as a white solid.

Physical characteristics are as follows:

MP 284–286° C.;

$^1$H NMR (300 MHz, DMSO) δ 12.85, 12.19, 10.32, 8.60, 7.89, 7.69, 7.40, 7.36, 4.55, 2.96, 2.62.

MS(ESI−) for C$_{20}$H$_{16}$ClFN$_2$O$_4$ m/z 401.0 (M−H)$^-$.

EXAMPLE 115

5-(3-{[(4-Chlorobenzyl)amino]carbonyl}-8-fluoro-4-hydroxy-6-quinolinyl)-4-pentynoic acid

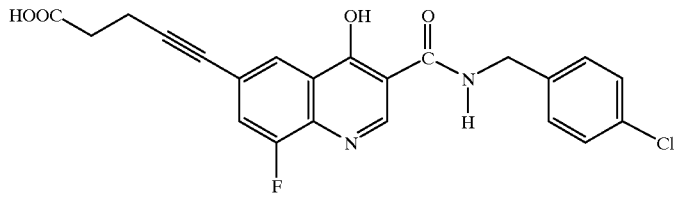

To a mixture of the title compound of Example 5 (0.457 g), copper iodide (0.010 g) and dichlorobis(triphenylphosphine)palladium (II) (0.035 g) in 15 mL diethylamine is added 4-pentynoic acid (0.098 g). The reaction is allowed to stir overnight. The solvents are evaporated and the residue is chromatographed on silica, eluting with 10% MeOH/CH$_2$Cl$_2$. Fractions homogeneous by TLC are combined and condensed. The residue is recrysallized from acetone/hexanes to yield 0.057 g of the desired product as a tan solid.

Physical characteristics are as follows:

MP 148–155° C. (dec);

$^1$H NMR (300 MHz, DMSO) δ 12.9, 12.3, 10.19, 8.61, 7.97, 7.71, 7.38, 4.55, 2.68, 2.56.

IR (drift) 1660, 1656, 1650, 1645, 1633, 1607, 1579, 1574, 1567, 1563, 1557, 25 1552, 1538, 1524, 1519 cm$^{-1}$.

MS (FAB) m/z 427 (MH$^+$), 581, 429, 428, 427, 371, 286, 127, 125, 71, 57.

HRMS (FAB) found 427.0856.

EXAMPLE 116

N-[(4-Chlorophenyl)methyl]-9]hydroxy-3H-pyrazolo [4,3-f]quinoline-8-carboxamide (Formula E-3, wherein R$_3$=R$_4$=H, R$_1$ and R$_2$ are together diazole. Refer to Chart E.)

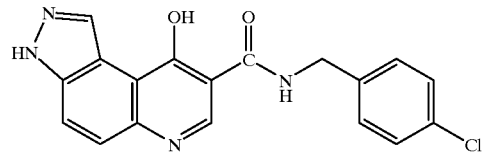

The title compound is prepared according to the procedures described in Preparation 12 and Example 63, substituting 5-aminoindazole for 4-t-butylaniline. This procedure gives 0.137 g of the title compound as a brown solid.

Physical characteristics are as follows:

mp 268–271° C.

$^1$H NMR (300 MHz, DMSO-d$_6$) δ 13.66, 10.80, 8.87, 8.78, 8.01, 7.69, 7.41, 4.60 ppm.

$^{13}$C NMR (75 MHz, DMSO-d$_6$) δ 175.7, 164.7, 141.0, 138.8, 135.7, 131.2, 129.2, 128.9, 128.7, 128.2, 128.0, 119.1, 118.3, 117.0, 112.2, 41.3 ppm.

IR (mull) 3202, 3045, 1647, 1626, 1580, 1542, 1491, 1409, 1260, 1093, 946, 10 817, 801, 761, 710 cm$^{-1}$.

MS (EI) m/z 352 (M+), 352, 213, 212, 211, 185, 156, 140, 129, 127, 125.

HRMS (EI) found 352.0726.

% Water (KF): 3.80.

Anal. found: C, 59.00; H, 4.07; N, 14.90.

EXAMPLE 117

N-(4-Chlorobenzyl)-4-hydroxy-6-iodo-8-methoxy-3-quinolinecarboxamide

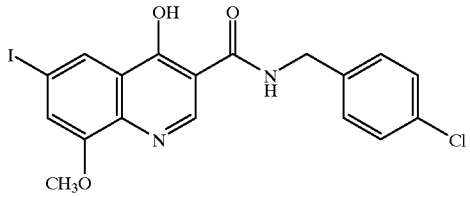

N-(4-Chlorobenzyl)-8-fluoro-4-hydroxy-6-iodo-3-quinolinecarboxamide (2.95 g) from Example No. 5 and sodium hydride (60% dispersion, 520 mg) is suspended in DMF (60 mL) and to the mixture is added methanol (288 μL). After being heated for 1 h at 135° C., additional sodium hydride (200 mg) is added, and the mixture is heated for an additional 1 h. The reaction mixture is allowed to cool to rt and then is poured into saturated aqueous ammonium chloride (200 mL). The resulting precipitate is filtered and washed with water (20 mL), tert-butyl methyl ether (20 mL), and heptane (20 mL). The crude product is purified by column chromatography (heptane/2-propanol, 9/1; 4/1) to afford 1.68 g (56%) of the title compound as a white solid. Recrystallization (acetic acid, water) affords a hydrate ($1H_2O$).

Physical characteristics are as follows:

Mp 241–243° C.

$^1$H NMR (DMSO-$d_6$) δ 12.43, 10.28, 8.57, 8.09, 7.61, 7.41–7.34, 4.53, 4.04.

$^{13}$C NMR ($CF_3CO_2D$) δ 173.3, 167.3, 149.0, 141.4, 134.8, 133.2, 129.8, 129.2, 129.0, 124.9, 124.5, 122.5, 106.7, 94.4, 56.4, 44.0.

IR (drift) 3072, 1646, 1612, 1594, 1558 (s), 1530 (s), 1492, 1306, 1298, 1255, 1202, 1082, 851, 846, 804 (s) $cm^{-1}$.

MS (ESI–) for m/z 467 (M–H)⁻.

Anal. Found for $C_{18}H_{14}ClIN_2O_3 \cdot H_2O$: C, 44.39; H, 3.46; N, 5.76; Cl, 7.34.

Water (KF): 3.67.

EXAMPLE 118

N-(4-Chlorobenzyl)-4-hydroxy-6-(3-hydroxy-1-propynyl)-8-methoxy-3-quinolinecarboxamide

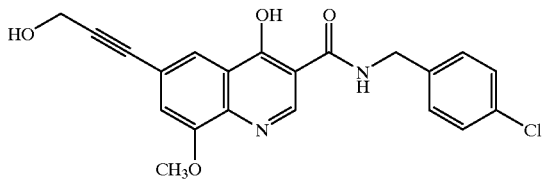

N-(4-Chlorobenzyl)-4-hydroxy-6-iodo-8-methoxy-3-quinolinecarboxamide (469 mg) from Example No. 117, copper (I) iodide (57 mg), and bis(triphenylphosphine)-palladium (II) chloride (35 mg) are suspended in diethylamine (15 mL). Propargyl alcohol (70 µL) is added and the mixture is allowed to stir at rt for 16 h. The reaction mixture is poured into water (50 mL) and extracted with ethyl acetate (2×50 mL). The organic layer is washed with saturated aqueous ammonium chloride (3×10 mL) and brine (10 mL). The aqueous layer is back-extracted with ethyl acetate (20 mL). The combined organic layers are dried ($MgSO_4$) and concentrated. The crude product is purified by column chromatography (dichloromethane/methanol, 50/1; 33/1; 25/1; 20/1) to afford 289 mg (73%) of the title compound as a white solid.

Physical characteristics are as follows:

Mp 207–208° C.

$^1$H NMR (DMSO-$d_6$) δ 12.45, 10.3, 8.58, 7.79, 7.42–7.34, 5.38, 4.53, 4.34, 4.05.

$^{13}$C NMR (DMSO-$d_6$) δ 178.0, 167.1, 151.8, 145.9, 141.5, 134.2, 132.6, 132.1, 131.2, 129.6, 122.5, 121.7, 117.0, 114.4, 93.3, 86.1, 59.5, 52.3, 44.3.

IR (drift) 3196 (b), 3157 (b), 3074, 2234 (w), 1649, 1603, 1568, 1562, 1523 (s), 1491, 1314, 1200, 1089, 1021, 805 $cm^{-1}$.

MS (ESI–) m/z 395 (M–H)⁻.

Anal. Found for $C_{21}H_{17}ClN_2O_4$: C, 63.26; H, 4.35; N, 7.07; Cl, 8.94.

EXAMPLE 119

N-(4-Chlorobenzyl)-4-hydroxy-8-methoxy-6-(3-methoxy-1-propynyl)-3-quinolinecarboxamide

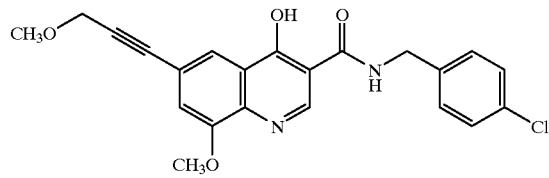

N-(4-chlorobenzyl)-4-hydroxy-6-iodo-8-methoxy-3-quinolinecarboxamide (469 mg) from Example No. 117, copper (I) iodide (57 mg), and bis(triphenylphosphine)-palladium (II) chloride (35 mg) are suspended in diethylamine (15 mL). Methyl propargyl ether (101 µL) is added and the mixture is allowed to stir at rt for 64 h. The reaction mixture is poured into water (50 mL) and extracted with ethyl acetate (2×50 mL). The organic layer is washed with saturated aqueous ammonium chloride (3×10 mL) and brine (10 mL). The aqueous layer is back-extracted with ethyl acetate (20 mL). The combined organic layers are dried ($MgSO_4$) and concentrated. The crude product is purified by column chromatography (heptane/2-propanol, 12/1; 10/1; 5/1) to afford 188 mg (46%) of the title compound as a white solid.

Physical characteristics are as follows:

Mp 211–213° C.

$^1$H NMR (DMSO-$d_6$) δ 12.47, 10.30, 8.58, 7.82, 7.42–7.32, 4.54, 4.37, 4.05, 3.36.

$^{13}$C NMR ($CF_3CO_2D$) δ 174.1, 167.3, 149.2, 141.5, 134.8, 133.2, 130.2, 129.0, 128.9, 125.1, 121.6, 118.9, 117.1, 106.5, 86.2, 84.9, 59.7, 56.8, 56.2, 43.9.

IR (drift) 2231 (w), 1988 (w), 1931 (w), 1652 (s), 1608, 1571, 1551 (s), 1524 (s), 1354, 1307, 1289, 1192, 1095, 1083, 804 $cm^{-1}$.

MS (ESI–) m/z 409 (M–H)⁻.

Anal. Found for $C_{22}H_{19}ClN_2O_4$: C, 64.25; H, 4.81; N, 6.84; Cl, 8.60.

EXAMPLE 120

N-(4-Chlorobenzyl)-4-hydroxy-6-(3-hydroxypropyl)-8-methoxy-3-quinolinecarboxamide

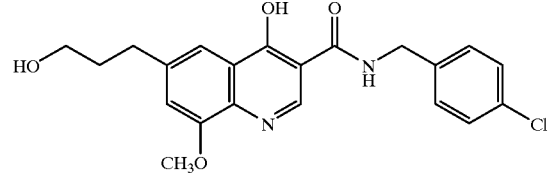

N-(4-Chlorobenzyl)-4-hydroxy-6-(3-hydroxy-1-propynyl)-8-methoxy-3-quinolinecarboxamide (397 mg) from Example No. 118 is dissolved in methanol/dichloromethane (1/1, 80 mL) and palladium on carbon (5%, 80 mg) are —added. The mixture is placed under a hydrogen atmosphere (23 psi) for 1 h, filtered through celite, and concentrated. The crude product is purified by column chromatography (dichloromethane/methanol, 50/1 to 20/1) to afford 251 mg (63%) of the title compound as a white solid.

Physical characteristics are as follows:

Mp 201–204° C.

$^1$H NMR (DMSO-d$_6$) δ 12.28, 10.47, 8.56, 7.60, 7.41–7.39, 7.24, 4.54, 4.50, 4.43, 4.03, 2.75, 1.78.

$^{13}$C NMR (CF$_3$CO$_2$D) δ 176.3, 165.2, 149.2, 142.8, 140.0, 139.2, 131.9, 129.6, 128.8, 128.5, 127.3, 115.6, 113.6, 111.2, 60.5, 56.8, 41.9, 34.6, 32.4.

IR (drift) 3315, 3170 (b), 3047 (b), 2938, 1651, 1608, 1569, 1554, 1531 (s), 1490, 1292, 1266, 1090, 1059, 802 cm$^{-1}$.

MS (ESI−) m/z 399 (M−H)$^-$.

Anal. Found for C$_{21}$H$_{21}$ClN$_2$O$_4$: C, 62.87; H, 5.59; N, 7.02.

EXAMPLE 121

N-(4-Chlorobenzyl)-4-hydroxy-6-(3-hydroxy-1-propynyl)-8-(trifluoromethyl)-3-quinolinecarboxamide

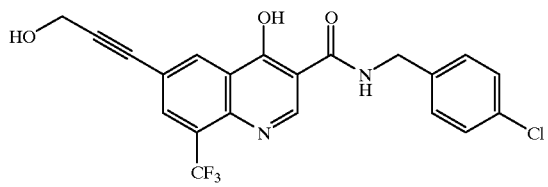

A mixture of 4-bromo-2-trifluoromethylaniline (10.0 g) and diethyl ethoxymethylenemalonate (8.42 mL) is heated to 135° C. for 2 h. The reaction mixture is diluted with diphenylether (50 mL) and heated to reflux with removal of ethanol by a Dean-Start trap for 30 min. The resulting precipitate was poured into heptane, filtered, and recrystallized (DMF) to afford 6.66 g (44%) of the 6-bromo-8-trifluoromethylquinoline ethyl ester. A mixture of the quinoline ethyl ester (5.0 g) and 4-chlorobenzylamine (8.4 mL) are heated to 190° C. for 1 h. The mixture is diluted with toluene (25 mL), allowed to cool to rt, and filtered. The crude product is recrystallized (HOAc) to afford 5.35 g (85%) of the amide. The resulting amide (2.30 g), bis(triphenyl-phosphine)palladium (II) chloride (175 mg), and triethylamine (5.0 mL) are dissolved in DMF (50 mL). Propargyl alcohol (2.5 mL) is added over 20 h at 90° C. The reaction mixture was allowed to cool to rt, poured into aq. ammonium chloride (200 mL) and extracted with ethyl acetate (4×50 mL). The organic layer is washed with sat. aqueous brine (10 mL). The aqueous layer is back-extracted with ethyl acetate (20 mL). The combined organic layers are dried (MgSO$_4$) and concentrated. The crude product is purified by column chromatography (dichloromethane/methanol, 100/1; 50/1; 100/3; 25/1) and recrystallization (HOAc) to afford 928 mg (43%) of the title compound as a tan solid.

Physical characteristics are as follows:

Mp 256° C. dec.

$^1$H NMR (DMSO-d$_6$) δ 12.18, 10.05, 8.67, 8.49, 8.15, 7.42–7.34, 5.45, 4.55, 4.36.

$^{13}$C NMR (CF$_3$CO$_2$D) δ 175.1, 163.9, 145.5, 138.9, 134.9, 133.5, 133.3, 131.9, 129.7, 128.8, 127.9, 123.3, 118.8, 118.7, 112.7, 92.7, 81.8, 49.9, 42.0.

IR (drift) 1661 (s), 1609, 1587, 1559, 1519, 1463, 1293, 1212, 1193, 1168, 1132 (s), 1114, 1017, 914, 802 cm$^{-1}$.

MS (FAB) m/z 435 (MH)$^+$.

Anal. Found for C$_{21}$H$_{14}$ClF$_3$N$_2$O$_3$·2H$_2$O: C, 53.63; H, 3.69; N, 6.04; Cl, 7.54.

EXAMPLE 122

N-(4-Chlorobenzyl)-4-hydroxy-6-(3-hydroxy-1-propynyl)-8-(trifluoromethoxy)-3-quinolinecarboxamide

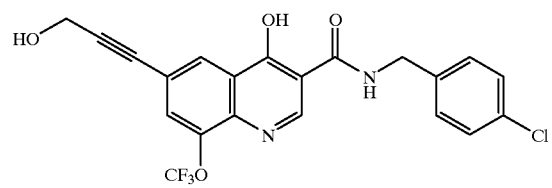

A mixture of 4-bromo-2-trifluoromethoxyaniline (10.0 g) and diethyl ethoxymethylenemalonate (7.9 mL) is heated to 135° C. for 2 h. The reaction mixture is diluted with diphenylether (90 mL) and heated to reflux with removal of ethanol by a Dean-Start trap for 30 min. The resulting precipitate is poured into heptane and filtered to afford 10.83 g (73%) of the 6-bromo-8-trifluoromethoxyquinoline ethyl ester. A mixture of the quinoline ethyl ester (5.0 g) and 4-chlorobenzylamine (12.0 mL) are heated to 190° C. for 1 h. The mixture is diluted with toluene (25 mL), allowed to cool to rt, and filtered. The crude product is recrystallized (HOAc, water) to afford 5.03 g (80%) of the amide. The resulting amide (469 mg), bis(triphenylphosphine)palladium (II) chloride (175 mg), and triethylamine (5.0 mL) are dissolved in DMF (50 mL). Propargyl alcohol (2.5 mL) is added over 20 h at 90° C. The reaction mixture was allowed to cool to rt, poured into aq. ammonium chloride (200 mL) and extracted with ethyl acetate (4×50 mL). The organic layer is washed with sat. aqueous brine (10 mL). The aqueous layer is back-extracted with ethyl acetate (20 mL). The combined organic layers are dried (MgSO$_4$) and concentrated. The crude product is purified by column chromatography (dichloromethane/methanol, 100/1; 50/1; 100/3) to afford 580 mg (26%) of the title compound as a white solid.

Physical characteristics are as follows:

Mp 262° C. dec.

$^1$H NMR (DMSO-d$_6$) δ 12.89, 10.12, 8.64, 8.20, 7.86, 7.42–7.34, 5.42, 4.55, 4.35.

$^{13}$C NMR (CF$_3$CO$_2$D) δ 175.7, 167.4, 144.1, 139.1, 134.8, 133.3, 131.5, 129.2, 129.1, 127.3, 126.3, 123.6, 123.2, 120.6, 107.3, 84.8, 84.1, 55.5, 44.1.

IR (drift) 1936 (w), 1657 (s), 1602, 1574, 1544, 1517 (s), 1279 (s), 1268, 1223 (s), 1212 (s), 1183, 1161 (s), 1048, 1020, 802 cm$^{-1}$.

MS (ESI−) m/z 449 (M−H)$^-$.

Anal. Found for C$_{21}$H$_{14}$ClF$_3$N$_2$O$_4$: C, 55.86; H, 3.16; N, 6.09; Cl, 7.96.

EXAMPLE 123

N-(4-Chlorobenzyl)-4-hydroxy-6-(3-hydroxypropyl)-8-(trifluoromethyl)-3-quinolinecarboxamide

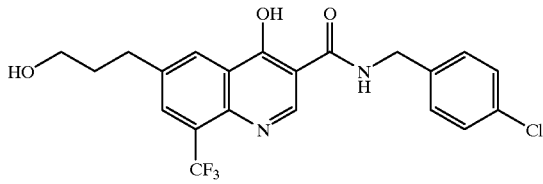

N-(4-Chlorobenzyl)-4-hydroxy-6-(3-hydroxy-1-propynyl)-8-(trifluoromethyl)-3-quinolinecarboxamide (397 mg) from Example No. 121 is dissolved in methanol/dichloromethane (1/1, 87 mL) and palladium on carbon (5%, 80 mg) are added. The mixture is placed under a hydrogen atmosphere (28 psi) for 1 h, filtered through celite, and concentrated. The crude product is purified by column chromatography (dichloromethane/methanol, 100/1 to 100/3) to afford 43 mg (10%) of the title compound as a white solid.

Physical characteristics are as follows:

Mp 249–250° C.

$^1$H NMR (DMSO-$d_6$) δ 12.03, 10.20, 8.67, 8.38, 8.06, 7.42–7.34, 4.57–4.50, 3.42, 2.85, 1.79.

IR (drift) 1656 (s), 1613, 1579, 1553 (s), 1526 (s), 1461, 1427, 1371, 1345, 1295, 1209, 1187, 1155, 1121 (s) cm$^{-1}$.

MS (ESI-) m/z 399 (M-H)$^-$.

Anal. Calcd for $C_{21}H_{18}ClF_3N_2O_3$: C, 57.48; H, 4.13; N, 6.38; Cl, 8.08. Found: C, 57.18; H, 4.14; N, 6.18; Cl, 7.93.

EXAMPLE 124

N-(4-Chlorobenzyl)-4-hydroxy-8-(2-hydroxyethoxy)-6-(3-hydroxypropyl)-3-quinolinecarboxamide

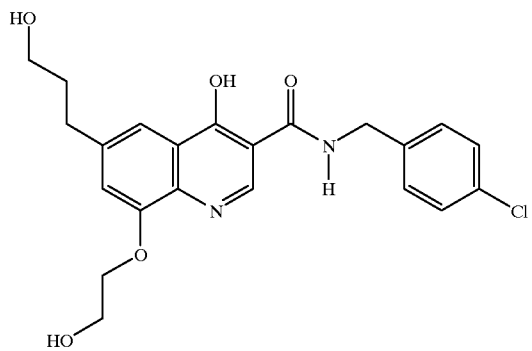

To a suspension of N-[(4-chlorophenyl)methyl]-8-fluoro-4-hydroxy-6-iodo-3-quinolinecarboxamide from Example No. 5 (2.28 g) in DMF (75 mL) is added sodium hydride (60% oil dispersion; 0.600 g) followed by addition of 2-benzyloxyethanol (1.42 mL). The reaction is heated to 135° C. and stirred for 1 h. The reaction mixture is cooled to room temperature and poured into saturated aqueous ammonium chloride (200 mL). The aqueous layer is extracted with dichloromethane (4×100 mL). The combined organic layers are washed with brine (50 mL), dried with MgSO$_4$, filtered, and concentrated in vacuo. The resulting yellow solid is purified by column chromatography (dichloromethane/methanol, 98/2). Fractions homogeneous by TLC are combined and concentrated in vacuo to yield a yellow solid which is recrystallized from ethanol to yield 1.568 g (53%) of the intermediate amide as an off-white solid. To a suspension of this material (1.149 g) in diethylamine (24 mL) are added copper iodide (0.111 g) and Pd(PPh$_3$)$_2$Cl$_2$ (0.069 g) followed by addition of propargyl alcohol (0.16 mL). The reaction is stirred at room temperature for 3 d. The reaction mixture is concentrated in vacuo and partitioned between H$_2$O (50 mL) and dichloromethane (50 mL). The aqueous layer is extracted with dichloromethane (3×50 mL). Combined organic layers are washed with saturated aqueous ammonium chloride (50 mL), dried with MgSO$_4$, filtered and concentrated in vacuo. The resulting brown solid is purified by column chromatography (dichloromethane/methanol, 98/2). Fractions homogeneous by TLC are combined and concentrated in vacuo to yield a tan solid which is recrystallized from ethanol to yield 0.181 g (18%) of the propargyl compound as a tan, crystalline solid. This material (0.400 g) is dissolved in 1/1 dichloromethane/methanol (50 mL) and hydrogenated over 10% Pd/C (80 mg) at 35 psi for 3.5 h. The reaction mixture is filtered through a Celite pad, and the filtrate is concentrated in vacuo. The resulting yellow oil is purified by column chromatography (dichloromethane/-methanol, 98/2). Fractions homogeneous by TLC are combined and concentrated in vacuo to yield a white solid which is recrystallized from ethyl acetate/methanol to yield 0.090 g (27%) of the title compound as a white solid.

Physical characteristics are as follows:

Mp 250–252° C.

$^1$H NMR (300 MHz, DMSO-$d_6$) δ 12.10, 10.49, 8.61, 7.60, 7.42–7.34, 7.24, 4.56, 4.49, 4.24, 3.44, 2.74, 1.77.

$^{13}$C NMR (75 MHz, DMSO-$d_6$) δ 176.3, 165.1, 148.5, 142.8, 140.0, 139.2, 131.8, 129.7, 128.8, 128.7, 127.4, 115.6, 114.4, 111.3, 71.3, 60.4, 59.9, 41.9, 34.6, 32.4.

IR (drift) 3234, 1661, 1649, 1613, 1572, 1550, 1532 (s), 1491, 1311, 1301, 1267, 1096, 1076, 1059, 806, cm$^{-1}$.

MS (ESI-) for m/z 429 (M-H)$^-$.

Anal. Found: C, 61.41; H, 5.47; N, 6.51; Cl, 7.53.

EXAMPLE 125

N-(4-Chlorobenzyl)-4-hydroxy-6-(3-hydroxy-1,1-dimethylpropyl)-3-quinolinecarboxamide

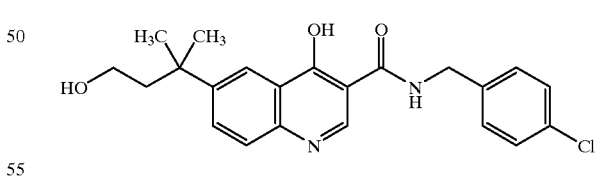

To a suspension of 3-methyl-3-(4-nitrophenyl)butanoic acid (16.2 g) (J. Amer. Chem. Soc. 1981, 103, 7768–7773. and J. Amer. Chem. Soc. 1948, 370–371.) in THF (70 mL) is added 103 mL of a 1.0 M borane/THF solution. The reaction is stirred at room temperature for 18 h. The reaction is poured into H$_2$0 (500 mL). The aqueous layer is saturated with potassium carbonate and extracted with dichloromethane (3×500 mL). The combined organic layers are dried with MgSO$_4$, filtered and concentrated in vacuo to yield 16.16 g of the alcohol as a yellow solid. The alcohol (9.41 g) is dissolved in THF (100 mL). Sodium hydride (60% oil dispersion; 5.40 g) is added followed by addition of benzyl bromide (16.0 mL). The reaction is stirred at room temperature for 18 h. The reaction mixture is partitioned between H₂O (400 mL) and dichloromethane (400 mL). The aqueous layer is extracted with dichloromethane (2×400 mL). The combined organic layers are washed with brine (400 mL), dried with MgSO₄, filtered, and concentrated in vacuo. The resulting yellow oil is purified by column chromatography to yield 8.86 g (64%) of the benzyl protected compound as a yellow oil. This material (8.51 g) is suspended in 1/1 conc. HCl/ethanol (200 mL) and SnCl₂•2H₂O (19.22 g) is added. The reaction is heated to 70° C. and is stirred for 2 h. The reaction mixture is cooled to room temperature, and H₂O (400 mL) is added. The aqueous layer is adjusted to pH12 with ammonium hydroxide and then extracted with dichloromethane (2×400 mL). The combined organic layers are dried with MgSO₄, filtered, and concentrated in vacuo. The resulting brown oil is purified by column chromatography (dichloromethane; dichloromethane/methanol, 98/2) to yield 1.306 g (17%) of the amine as a yellow oil. This material (1.306 g) is combined with diethylethoxylmethylenemalonate (0.98 mL) and heated to 120° C. for 2 h. The reaction mixture is purified by column chromatography (dichloromethane; dichloromethane/methanol, 98/2) to yield 2.044 g (96%) of the malonate intermediate as a yellow oil. This material (2.007 g) is dissolved in diphenyl ether (10 mL) and heated to reflux with removal of ethanol via a Dean-Stark trap for 30 min. The reaction is cooled to room temperature and heptane and ethyl acetate are added. The reaction mixture is allowed to stand at room temperature overnight. The resulting precipitate is filtered off and triturated with ethyl acetate to yield the 0.572 g (32%) of the ester as an off-white solid. The ester (0.517 g) and 4-chlorobenzylamine (1.60 mL) are combined and heated to 190 ° C. for 1 h. The reaction is cooled to room temperature and ethyl acetate and heptane are added. The mixture is allowed to stand in the freezer for 3 d. The resulting precipitate is filtered off and recrystallized from ethyl acetate/heptane to yield 0.479 g (75%) of the amide as an off-white solid. This material (0.402 g) is dissolved in 25% dichloromethane/methanol (60 mL) and hydrogenated over 10% Pd/C (80 mg) at psi for 45 min. The reaction mixture is filtered through a Celite pad and the filtrate is concentrated in vacuo. The resulting yellow oil is purified by column chromatography (dichloromethane; dichloromethane/methanol, 99/1; dichloromethane/methanol, 98/2). Fractions homogeneous by TLC are combined and concentrated in vacuo to yield a white solid which is recrystallized from ethyl acetate/methanol to yield 0.163 g (50%) of the title compound as a white, crystalline solid.

Physical characteristics are as follows:

Mp 184–192° C.

¹H NMR (300 MHz, DMSO-d₆) δ 12.69, 10.51, 8.75, 8.17, 7.85, 7.67, 7.44–7.25, 4.57, 4.27, 3.19, 1.86, 1.34.

¹³C NMR (75 MHz, DMSO-d₆) δ 176.6, 165.2, 165.1, 146.5, 143.7, 139.9, 139.1, 137.6, 131.9, 131.6, 129.6, 128.9, 128.8, 127.8, 127.3, 126.1, 121.6, 119.4, 111.1, 111.0, 58.2, 46.7, 42.6, 37.1, 29.5.

IR (drift) 3059, 2966, 2947, 2919, 2885, 2424 (w), 2315 (w), 1985 (w), 1933, 1647 (s), 1616, 1579, 1552 (s), 1527 (s), 1493, cm⁻¹.

HRMS (FAB) Found 399.1480.

Anal. Found: C, 66.88; H, 6.18; N, 7.05; Cl, 6.63.

EXAMPLE 126

N-[(4-Chlorophenyl)methyl]-8-fluoro-4-hydroxy-6-[3-(methylthio)-1-propynyl]-3-quinolinecarboxamide

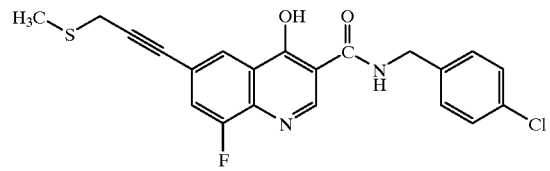

A mixture of N-[(4-Chlorophenyl)methyl]-8-fluoro-4-hydroxy-6-iodo-3-quinolinecarboxamide from Example No. 5 (1.57 g), propargyl methyl sulfide (0.355 g, 4.12 mmol), copper iodide (0.125 g), and dichlorobis (triphenylphosphine)palladium (II) (0.462 g) in diethylamine (38 mL) are stirred at room temperature overnight. An additional 0.092 g of propargyl methyl sulfide is added, and the mixture is stirred another 5 h. The reaction mixture was then concentrated in vacuo, and the residue is suspended in water (100 mL) and extracted with three portions of EtOAc. The combined organic layers are then dried over MgSO₄, filtered, and concentrated in vacuo. Column chromatography (elution with 5–10%MeOH/CH₂Cl₂) yielded the title compound as a solid.

Physical characteristics are as follows:

Mp 259–261° C.

¹H NMR (300 MHz, DMSO-d₆) δ 13.00, 10.20–10.17, 8.60, 8.00, 7.77, 7.40–7.32, 4.52, 3.63, 2.22 ppm.

IR (drift) 3195, 3175, 3165, 3154, 3076, 3062, 1645, 1604, 1582, 1549, 1524, 1492, 1306, 1285, 801 cm⁻¹.

MS (EI) m/z 414 (M⁺), 414, 274, 247, 200, 171, 142, 140, 125, 106, 77.

HRMS (EI) calcd for C₂₁H₆₁ClFN₂O₂S 414.0605, found 414.0608.

EXAMPLE 127

N-[(4-Chlorophenyl)methyl]-6-[3-(ethylthio)-1-propynyl]-8-fluoro-4-hydroxy-3-quinolinecarboxamide

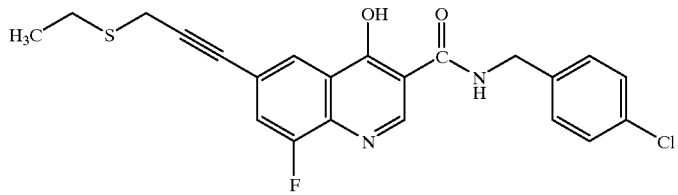

A mixture of N-[(4-chlorophenyl)methyl]-8-fluoro-4-hydroxy-6-iodo-3-quinolinecarboxamide from Example No. 5 (1.5 g), propargyl ethyl sulfide (1.04 g, 10.4 mmol), copper iodide (0.125 g), and dichlorobis(triphenylphosphine)-palladium(II) (0.462 g) in diethylamine are stirred at room temperature overnight. The reaction mixture is then concentrated in vacuo, and the residue is suspended in water (100 mL) and extracted with four 50-mL portions of EtOAc. The combined organic layers are then dried over $MgSO_4$, filtered, and concentrated in vacuo. Column chromatography (elution with 5-10%MeOH/$CH_2Cl_2$) yielded the title compound as a solid.

Physical characteristics are as follows:

Mp 232–233° C.

$^1$H NMR (400 MHz, DMSO-$d_6$) δ 13.10, 10.21–10.18, 8.61, 8.00, 7.78, 7.42–7.35, 4.55, 3.69, 2.73, 1.27 ppm.

IR (drift) 3159, 3081, 3059, 2936, 1653, 1609, 1568, 1546, 1520, 1489, 1304, 1285, 1185, 808, 724 cm$^{-1}$.

MS (EI) m/z 430 (M$^+$), 370, 263, 229, 228, 201, 172, 142, 140, 127, 125.

Anal. found: C, 61.17; H, 4.62; N, 6.44.

EXAMPLE 128

N-[(4-Chlorophenyl)methyl]-8-fluoro-4-hydroxy-6-[(1Z)-3-(methylthio)-1-propenyl]-3-quinolinecarboxamide

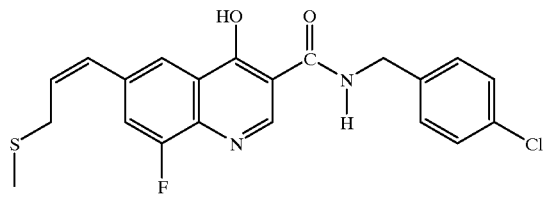

A mixture of N-[(4-Chlorophenyl)methyl]-8-fluoro-4-hydroxy-6-[3-(methylthio)-1-propynyl]-3-quinolinecarboxamide from Example 126 (0.226 g) and Pd/C (10%, 0.032 g) in 3:1 $CH_2Cl_2$/MeOH (20 mL) are placed on a Parr hydrogenator under 38 psi of $H_2$ and shaken for 2 h. Another 0.060 g of Pd/C is added, and the resulting Physical characteristics are as follows:

Mp 201–202° C.

$^1$H NMR (300 MHz, DMSO-$d_6$) δ 12.92, 10.25–10.22, 8.60, 7.99, 7.67, 7.40–7.33, 6.65, 5.92–5.83, 4.53, 3.39, 2.02 ppm.

IR (drift) 3196, 3157, 3081, 3059, 2937, 1650, 1610, 1569, 1544, 1521, 1490, 1298, 1287, 807, 799 cm$^{-1}$.

MS (EI) n/z 416 (M$^+$), 418, 416, 372, 371, 370, 278, 276, 251, 249, 228.

Anal found: C, 60.27; H, 4.40; N, 6.72.

EXAMPLE 129

N-[(4-Chlorophenyl)methyl]-6-[(1Z)-3-(ethylthio)-1-propenyl]-8-fluoro-4-hydroxy-3-quinolinecarboxamide

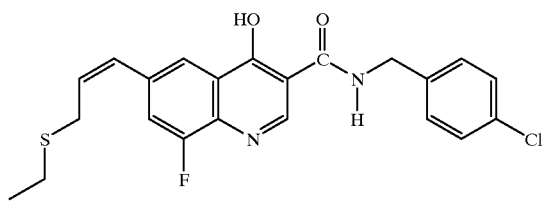

A mixture of N-[(4-Chlorophenyl)methyl]-6-[3-(ethylthio)-1-propynyl]-8-fluoro-4-hydroxy-3-quinolinecarboxamide from Example No. 127 (0.15 g) and Pd/C (10%, 0.06 g) in 3:1 $CH_2Cl_2$/MeOH (20 mL) are placed on a Parr hydrogenator under 40 psi of $H_2$ and shaken for 3 h. The reaction mixture is then filtered through Celite and concentrated in vacuo. Crystallization from MeOH affords the title compound as a solid.

Physical characteristics are as follows:

Mp 203–205° C.

$^1$H NMR (400 MHz, DMSO-$d_6$) δ 12.98, 10.29–10.26, 8.62, 8.02, 7.72, 7.42–7.36, 6.66, 5.93–5.87, 4.55, 3.46, 2.54–2.49, 1.06 ppm.

IR (drift) 3159, 3081, 3059, 2936, 1653, 1609, 1568, 1546, 1520, 1489, 1304, 1285, 1185, 808, 724 cm$^{-1}$.

MS (EI) m/z 430 (M$^+$), 370, 263, 229, 228, 201, 172, 142, 140, 127, 125.

Anal. found: C, 61.17; H, 4.62; N, 6.44.

EXAMPLE 130

N-[(4-Chlorophenyl)methyl]-8-fluoro-4-hydroxy-6-[3-(methylthio)propyl]-3-quinolinecarboxamide

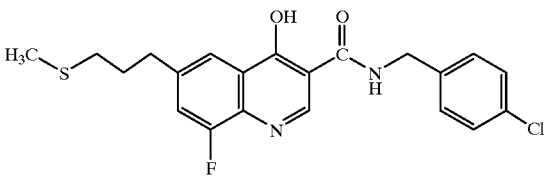

A mixture of N-[(4-Chlorophenyl)methyl]-8-fluoro-4-hydroxy-6-[3-(methylthio)-1-propynyl]-3- quinolinecarboxamide from Example No. 126 (0.07 g) and Pd/C (10%, 0.120 g) in 3:1 $CH_2Cl_2$/MeOH (20 mL) was placed on a Parr hydrogenator under 45 psi of $H_2$ and shaken for 4 h. Another 0.08 g of Pd/C was added, and the resulting mixture is shaken for 2 h. The reaction mixture is then filtered through Celite, 0.120 g of fresh catalyst was added, and the resulting mixture was shaken under $H_2$ for 6 h. The reaction mixture is then filtered through Celite and concentrated in vacuo. Crystallization from EtOH gave 0.015 g of the title compound as a solid.

Physical characteristics are as follows:

Mp 178–180° C.

$^1$H NMR (400 MHz, DMSO-$d_6$) δ 12.90, 10.35–10.32, 8.61, 7.88, 7.66, 7.42–7.35, 4.55, 2.84–2.81, 2.49–2.45, 2.05, 1.91–1.87 ppm.

MS (EI) m/z 418 ($M^+$), 278, 251, 203, 147, 142, 140, 125, 91, 77, 61.

Anal. found: C, 60.22; H, 4.87; N, 6.59.

EXAMPLE 131

3-(3-{[(4-Chlorobenzyl)amino]carbonyl}-8-fluoro-4-hydroxy-6-quinolinyl)-2-propynyl formate

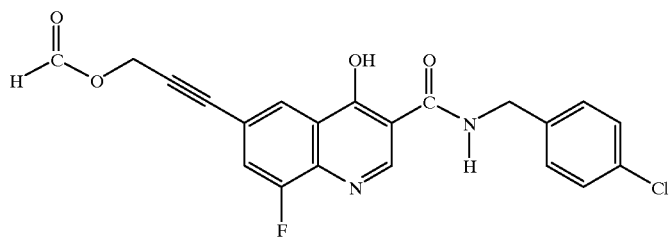

A solution of N-(4-chlorobenzyl)-8-fluoro-4-hydroxy-6-(3-hydroxy-1-propynyl)-3-quinolinecarboxamide from Example No. 53 (0.15 g) in 6 mL formic acid is heated at 100° C. for 6 hours. Once the reaction is cooled to room temperature, it is partitioned between $CH_2Cl_2$ and water. The organic layer is washed with water, saturated $NaHCO_3$, and water again. The organic layer is dried over $MgSO_4$, filtered and concentrated under reduced pressure to give a residue which is crystallized with $CH_2Cl_2$/hexanes to give the product (0.070 g, 44%).

Physical characteristics are as follows:

MP 231–233° C.

$^1$H NMR (300 MHz, DMSO-$d_6$) 13.05, 10.14, 8.62, 8.34, 8.06, 7.84, 7.40, 7.36, 5.08, 4.54.

IR (drift) 1732, 1656, 1651, 1608, 1579, 1574, 1567, 1563, 1557, 1548, 1538, 1519, 1186, 1160, 805 $cm^{-1}$.

MS (ESI) for m/z 411.1 $(M-H)^-$.

HRMS (FAB) Found 413.0726.

EXAMPLE 132

N-(4-Chlorobenzyl)-8-fluoro-4-hydroxy-6-(3-hydroxybutyl)-3-quinolinecarboxamide

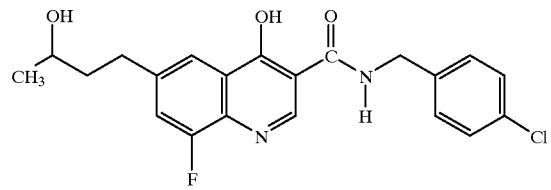

A mixture of N-(4-chlorobenzyl)-8-fluoro-4-hydroxy-6-(3-hydroxy-1-butynyl)-3-quinolinecarboxamide from Example No. 96 (173.7 mg) and Pd/C (10%, 34.7 mg) was dissolved in 3:1 $CH_2Cl_2$:MeOH. The reaction mixture was placed under the Parr hydrogenator and monitored with the OAMS for complete reduction of the acetylene. The reaction was completed in 1 hr and filtered over celite to remove the palladium. The filtrate was condensed to obtain a yellow solid. The crude product was recrystallized with EtOAc/hexanes to yield 123.8 mg (71%) of the desired product as an off-white solid.

Physical characteristics are as follows:

MP 216–218 C;

$^1$H NMR (300 MHz, DMSO) 12.83, 10.33, 8.60, 7.87, 7.61, 7.38, 4.55, 4.51, 3.57, 2.77, 1.66, 1.09.

IR (drift) 3197, 3157, 3092, 3062, 2966, 2934, 1649, 1614, 1550, 1525, 1489, 1303, 1288, 806, 724 $cm^{-1}$.

MS (ESI) 403.0 $(M+H)^+$, 401.1 $(M-H)^-$.

Anal. Found: C, 62.27; H, 5.22; N, 6.86.

EXAMPLE 133

N-(4-Chlorobenzyl)-6-[(E)-2-cyanoethenyl]-8-fluoro-4-hydroxy-3-quinolinecarboxamide

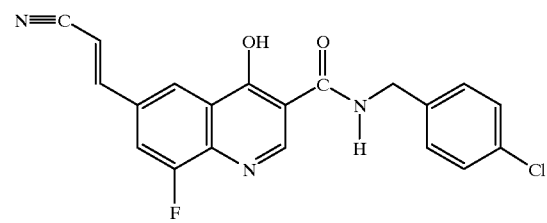

A sealed tube was charged with N-(4-chlorobenzyl)-8-fluoro-4-hydroxy-6-iodo-3-quinolinecarboxamide from Example 5 (0.76 g), Pd(OAc)$_2$ (0.0070 g), P(o-tolyl)$_3$ (0.033 g), acrylonitrile (0.14 mL), NEt$_3$ (0.59 mL), and DMF (4 mL). The tube was capped tightly and heated at 100° C.

overnight behind a blast shield. The reaction was cooled to room temperature and poured into 20 mL 1N HCl. The resulting solid was filtered, dissolved in hot EtOH, and adsorbed onto silica. Chromatography on a Biotage Flash 40S column (eluent 1.5% MeOH:CH$_2$Cl$_2$ (2 L) followed by 2.5% MeOH:CH$_2$Cl$_2$ (1 L) and 3% MeOH:CH$_2$Cl$_2$ (1 L)) afforded the desired product as a tan solid (0.47 g, 74%).

Physical characteristics are as follows:

MP 285–287° C.

$^1$H NMR (300 MHz, DMSO-d$_6$) 13.07, 10.20, 8.62, 8.25, 8.13, 7.85, 7.40, 7.36, 6.63, 4.56.

IR (drift) 3080, 3059, 3016, 1654, 1611, 1577, 1544, 1517, 1492, 1305, 1289, 1196, 1184, 804, 725 cm$^{-1}$.

MS (ESI) for m/z 382.0 (M+H)$^+$, 404.0 (M+Na)$^+$, 380.0 (M−H)$^−$.

Anal. Found: C, 60.82; H, 3.77; N, 10.58.

EXAMPLE 134

N-(4-Chlorobenzyl)-4-hydroxy-6-(3-hydroxy-1-propynyl)-3-quinolinecarboxamide

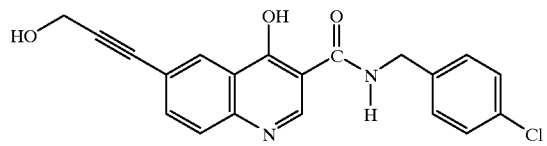

To a mixture of N-(4-chlorobenzyl)-4-hydroxy-6-iodo-3-quinolinecarboxamide from Example 40 (0.494 g) in Et$_2$NH (12.9 mL) is added CuI (10.8 mg) and (Ph$_3$P)$_2$PdCl$_2$ (39.7 mg). DMF (2 mL) is added to solubilize the reactants. To this solution is added propargyl alcohol (0.066 mL) and the reaction is stirred at room temperature for 2 days. The reaction mixture is concentrated to remove Et$_2$NH. The resulting residue is partitioned between CH$_2$Cl$_2$ (3×) and H$_2$O. A brown solid precipitated from the CH$_2$Cl$_2$ layer is filtered and collected to obtain pure product as indicated by NMR. The organic layers are combined, dried over Na$_2$SO$_4$, and concentrateed to obtain a brown residue. The residue was placed under high vac to remove residual DMF. The residue was adsorbed onto silica and chromatographed eluting with 2% MeOH in CH$_2$Cl$_2$ and 3% MeOH in CH$_2$Cl$_2$. Fractions homogenous by TLC were combined, condensed and recrystallized with EtOAc/hexanes to obtain a creme solid. The two crops yielded 325.4 mg (79%) of the desired product as a tan solid.

Physical characteristics are as follows:

MP 248–250 C;

$^1$H NMR (300 MHz, DMSO) 12.85, 10.31, 8.78, 8.22, 7.78, 7.70, 7.38, 5.39, 4.55, 4.33.

IR (drift) 3161, 3073, 3003, 2960, 2914, 1656, 1614, 1557, 1517, 1487, 1299, 1014, 1006, 826, 805 cm$^{-1}$.

MS (ESI) 367.0 (M+H)$^+$, 365.1 (M−H)$^−$.

Anal. Found: C, 65.23; H, 4.24; N, 7.60.

EXAMPLES 135 AND 136

EXAMPLE 135

N-[(4-Chlorophenyl)methyl]-1,4-dihydro-6-[(1Z)-3-hydroxy-1-propenyl]-4-oxo-3-quinolinecarboxamide

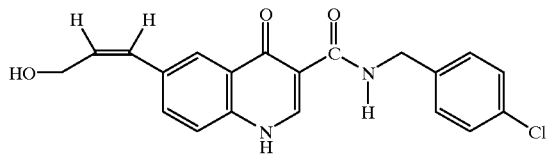

EXAMPLE 136

N-[(4-Chlorophenyl)methyl]-1,4-dihydro-6-[(1E)-3-hydroxy-1-propenyl]-4-oxo-3-quinolinecarboxamide

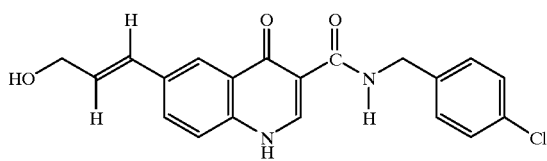

A mixture of N-(4-chlorobenzyl)-4-hydroxy-6-(3-hydroxy-1-propynyl)-3-quinolinecarboxamide from Example 134 (5.48 g) and Pd/C (10%, 0.55 g) in 3:1 CH$_2$Cl$_2$/MeOH (150 mL) are placed on a Parr hydrogenator under 50 psi of H$_2$ and shaken for 4 h. Another 0.30 g of Pd/C was added, and the resulting mixture was shaken for 2 h. The reaction mixture is then filtered through Celite, 0.55 g of fresh catalyst is added, and the resulting mixture is shaken under H$_2$ for 3 h. The reaction mixture is then filtered through Celite and concentrated in vacuo. Trituration from CHCl$_3$/MeOH affords a solid which is purified by HPLC chromatography on a 0.46×25 cm Chiralcel OD-H column eluting with EtOH at a rate of 0.3 mL/min to give 0.383 g of N-[(4-chlorophenyl)methyl]-1,4-dihydro-6-[(1Z)-3-hydroxy-1-propenyl]-4-oxo-3-quinolinecarboxamide (cis title compound), and 0.492 g of N-[(4-chlorophenyl)methyl]-1,4-dihydro-6-[(1E)-3-hydroxy-1-propenyl]-4-oxo-3-quinolinecarboxamide (trans title compound). Crystallization of the cis isomer from ethyl acetate gave 0.29 g of the title cis compound as a solid. Crystallization of the trans isomer from CH$_2$Cl$_2$/MeOH gave 0.289 g of the title trans compound as a solid.

Physical characteristics of N-[(4-Chlorophenyl)methyl]-1,4-dihydro-6-[(1Z)-3-hydroxy-1-propenyl]-4-oxo-3-quinolinecarboxamide (EXAMPLE 135) are as follows:

Mp 188–191° C.

$^1$H NMR (400 MHz, DMSO-d$_6$) δ 12.77, 10.47–10.41, 8.75, 8.05, 7.71–7.65, 7.42–7.36, 6.58, 5.91, 4.98, 4.56, 4.30 ppm.

IR (drift) 3257, 3249, 3210, 3166, 3083, 3063, 3018, 2971, 2941, 1646, 1616, 1552, 1525, 1489, 798 cm$^{-1}$.

MS (EI) n/z 368 (M+), 228, 201, 154, 142, 140, 127, 125, 115, 89, 77.

HRMS (FAB) calcd for C$_{20}$H$_{17}$ClN$_2$O$_3$+H 369.1006, found 369.0996.

Physical characteristics of N-[(4-Chlorophenyl)methyl]-1,4-dihydro-6-[(1E)-3-hydroxy-1-propenyl]-4-oxo-3-quinolinecarboxamide (EXAMPLE 136) are as follows:

Mp 212–215° C.

¹H NMR (400 MHz, DMSO-d₆) δ 12.74, 10.45, 8.73, 8.16, 7.92, 7.66, 7.42–7.33, 6.72, 6.54–6.47, 4.92, 4.56, 4.17 ppm.

IR (drift) 3078, 3059, 3053, 3026, 3010, 2971, 2928, 1651, 1615, 1576, 1552, 1525, 1490, 1297, 802 cm⁻¹.

MS (EI) m/z 368 (M+), 228, 201, 198, 142, 140, 127, 125, 89, 77, 73.

HRMS (FAB) calcd for $C_{20}H_{17}ClN_2O_3$+H 369.1006, found 369.0993.

EXAMPLE 137

N-(4-Chlorobenzyl)-8-fluoro-4-hydroxy-6-[(Z)-3-hydroxy-1-propenyl]-3-quinolinecarboxamide

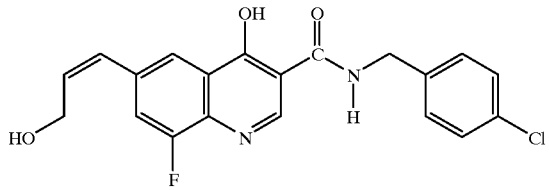

To a solution of N-(4-chlorobenzyl)-8-fluoro-4-hydroxy-6-(3-hydroxy-1-propynyl)-3-quinolinecarboxamide from Example No. 53 (0.24 g) in 60 mL 3:1 CH₂Cl₂:MeOH was added a spatula tip of 5% Pd/CaCO₃. The reaction was placed under hydrogen balloon atmosphere. After 2 hours, the Pd catalyst was filtered over Celite, new catalyst added to the filtrate and the reaction again placed under a hydrogen balloon. This regeneration of catalyst was repeated 8 times and the reaction monitored by MS until complete. The reaction mixture was filtered over celite and the filter cake washed thoroughly with MeOH and CH₂Cl₂. The filtrate was concentrated under reduced pressure to give a tan solid which was a 2:1 mixture of desired product and over-reduced material as shown by NMR. This mixture was further purified by HPLC (Cyclobond 2000) to give the desired product (0.072 g, 30%).

Physical characteristics are as follows:

MP 234–235° C.

¹H NMR (300 MHz, DMSO-d₆) 12.94, 10.27, 8.61, 7.86, 7.65, 7.40, 7.36, 6.56, 5.94, 5.0, 4.55, 4.28.

IR (drift) 3078, 3059, 3016, 1654, 1610, 1554, 1521, 1293, 1282, 1190, 1031, 1021, 889, 805, 798 cm⁻¹.

MS (ESI) for m/z 387.0 (M+H)⁺, 409.0 (M+Na)⁺, 385.1 (M−H)⁻.

HRMS (FAB) Found 387.0917.

Anal. Found: C, 61.31; H, 4.36; N, 7.05.

EXAMPLE 138

N-(4-Chlorobenzyl)-6-(2-cyanoethyl)-8-fluoro-4-hydroxy-3-quinolinecarboxamide

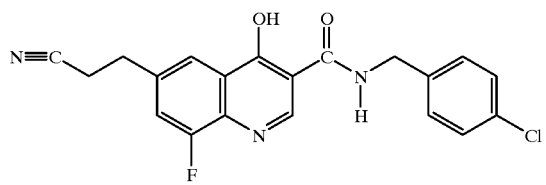

To a solution of N-(4-chlorobenzyl)-6-[(E)-2-cyanoethenyl]-8-fluoro-4-hydroxy-3-quinolinecarboxamide from Example No. 133 (0.13 g) and Et₃N in 50 mL 3:1 CH₂Cl₂:MeOH was added 10% Pd/C (0.040 g). The reaction was placed under hydrogen balloon atmosphere for 4 hours. The reaction was filtered over Celite, the filter cake rinsed thoroughly with methanol, and the filtrate concentrated under reduced pressure to give a yellow solid. The solid was recrystallized with CH₂Cl₂/MeOH/hexanes to give the desired product as an off-white solid (0.084 g, 63%).

Physical characteristics are as follows:

MP 273–274° C.

¹H NMR (300 MHz, DMSO-d₆) 12.89, 10.31, 8.62, 7.99, 7.73, 7.40, 7.36, 4.56, 3.05, 2.90.

IR (drift) 3201, 3062, 2948, 1650, 1613, 1569, 1524, 1490, 1431, 1300, 1285, 1267, 1199, 804, 724 cm⁻¹.

MS (ESI) for m/z 382.1 (M−H)⁻.

HRMS (FAB) Found 384.0889.

Anal. Found: C, 60.46; H, 4.19; N, 10.40.

EXAMPLE 139

N-(4-Chlorobenzyl)-8-fluoro-4-hydroxy-6-(3-oxopropyl)-3-quinolinecarboxamide

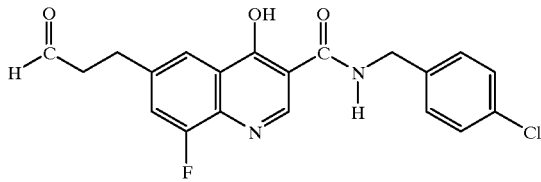

To a solution of N-(4-chlorobenzyl)-8-fluoro-4-hydroxy-6-iodo-3-quinolinecarboxamide from Example No. 5 (0.39 g), CuI (0.043 g), and Pd(PPh₃)₂Cl₂ (0.013 g) in 10 mL diethylamine was added propiolaldehyde diethyl acetal (0.13 mL). The reaction was stirred at room temperature overnight. The reaction was partitioned between EtOAc and water. The organic layer was washed twice with water, then dried over MgSO₄, filtered and adsorbed onto silica. A Biotage Flash 40S chromatography column (eluent 3% MeOH:CH₂Cl₂ (1 L)) afforded the acetylenic intermediate as a solid which was further purified by recrystallization from CH₂Cl₂/hexanes (0.17 g, 42%). The product from above (0.099 g) was dissolved in 30 mL EtOAc (0.5 mL pyridine added to aid dissolution). Et₃N (0.030 mL) followed by 10% Pd/C (0.030 g) was added and the reaction placed under hydrogen balloon atmosphere. After 3.5 h, the reaction was filtered over Celite. The filter cake was rinsed thoroughly with EtOAc. The filtrate was concentrated under reduced pressure to give a residue which was recrystallized with CH$_2$Cl$_2$/hexanes. The intermediate straight-chain acetal was obtained as a white solid (0.063 g, 62%). The product from above (0.11 g) was stirred in a solution of 20 mL 1:1 3N HCl:THF. The reaction was allowed to stir overnight. The reaction was partitioned between EtOAc and H$_2$O. A solid which did not dissolve in either layer was filtered (A). The aqueous layer was then extracted 2× with EtOAc and 1× with CH$_2$Cl$_2$. The combined organic layers were dried over MgSO$_4$, filtered and concentrated under reduced pressure to give a white solid (B). Both solid A and solid B are desired product as evidenced by NMR. The total yield of product was 0.056 g (58%).

Physical characteristics are as follows:

MP 242–244° C.

$^1$H NMR (300 MHz, DMSO-d$_6$) 12.83, 10.31, 9.72, 8.60, 7.89, 7.65, 7.40, 7.36, 4.55, 3.01, 2.87.

IR (drift) 3196, 3158, 3090, 3061, 2940, 1722, 1646, 1614, 1569, 1525, 1489, 1302, 1288, 805, 724 cm$^{-1}$.

HRMS (FAB) Found 387.0891.

Anal. Found: C, 61.11; H, 4.38; N, 6.94.

EXAMPLE 140

N-(4-Chlorobenzyl)-4-hydroxy-7-(4-hydroxybutyl)-3-quinolinecarboxamide

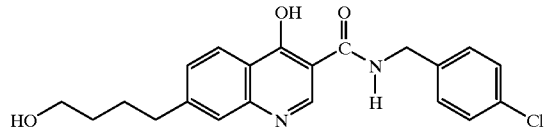

A solution of N-(4-chlorobenzyl)-4-hydroxy-7-iodo-3-quinolinecarboxamide from Example No. 39 (0.646 g), 3-butyn-1-ol (0.16 mL), PdCl$_2$(PPh$_3$)$_2$ (26.0 mg), and 0.93 mL DMF was heated at 90° C. for 1 hr. The reaction mixture was cooled to room temperature and partitioned between EtOAc and H$_2$O. An orange solid precipitated from the organic layer and was filtered and collected to obtain pure product as indicated by NMR. The aqueous layer was washed with EtOAc (3×). The combined organic layers were dried over Na$_2$SO$_4$ and condensed to obtain an orange-brown residue. The residue was adsorbed onto silica and chromatographed eluting with 4% MeOH in CH$_2$Cl$_2$. Fractions homogenous by TLC were combined, condensed, and recrystallized from EtOAc/hexanes to obtain a white solid. The two crops yielded 0.412 g (74%) of the desired product as an orange and white solid. A mixture of the acetylene from above (300 mg) and Pd/C (10%, 60.0 mg) was dissolved in 3:1 CH$_2$Cl$_2$:MeOH. The reaction mixture was placed under the Parr hydrogenator and monitored with the OAMS for complete reduction of the acetylene. After 1 hr OAMS showed that complete reduction had not been achieved. The old palladium catalyst was replaced with fresh palladium catalyst (60.0 mg) and placed under the Parr hydrogenator for another hour. The reaction was completed in a total of 2 hrs and filtered over celite to remove the palladium. The filtrate was condensed to obtain a yellow solid. The crude product was adsorbed onto silica and chromatographed eluting with 4% MeOH in CH$_2$Cl$_2$. Fractions homogenous by TLC were condensed and recrystallized with EtOAc/hexanes to yield 186.2 mg (61%) of the desired product as a white solid.

Physical characteristics are as follows:

MP 189–191 C;

$^1$H NMR (300 MHz, DMSO) 12.60, 10.47, 8.71, 8.15, 7.46, 7.37, 4.55, 4.36, 3.42, 2.74, 1.67, 1.46.

IR (drift) 3271, 3265, 3246, 3216, 3088, 3067, 3026, 1652, 1609, 1559, 1536, 1491, 1475, 797, 751 cm$^{-1}$.

MS (ESI) 385.1 (M+H)$^+$, 383.1 (M–H)$^-$.

Anal. Found: C, 65.27; H, 5.68; N, 7.23.

EXAMPLE 141

N-(4-Chlorobenzyl)-8-fluoro-4-hydroxy-6-(hydroxymethyl)-3-quinolinecarboxamide

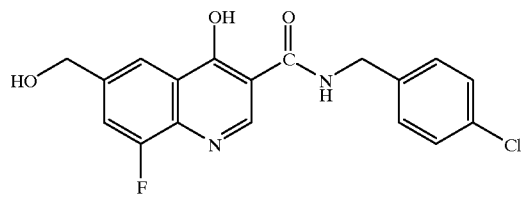

Methyl 3-{[(4-chlorobenzyl)amino]carbonyl}-8-fluoro-4-hydroxy-6-quinolinecarboxylate from Example No. 109 (150 mg) was dissolved in distilled THF (45 mL). The solution was heated to 35° C. to get the starting material into solution, then cooled to 18° C. for addition of LiAlH$_4$ (27.0 mg). After 2 hours additional LiAlH$_4$ (27.0 mg) was added because not much progress was seen in complete conversion to product. Complete conversion to product was achieved in 6 1/2 hrs. The reaction was quenched by adding 0.1 mL H$_2$O, 0.1 mL 15% NaOH, and 0.1 mL to the reaction mixture. The reaction mixture was filtered to get rid of the aluminum salt that had precipitated. The filtrate was condensed to obtain a green residue. The green residue was adsorbed onto silica and chromatographed eluting with 2% MeOH in CH$_2$Cl$_2$ and 3% MeOH in CH$_2$Cl$_2$. Fractions homogenous by TLC were condensed to yield 76.8 mg (55%) of the desired product as a white solid.

Physical characteristics are as follows:

MP 263–265 C;

$^1$H NMR (300 MHz, DMSO) 12.85, 10.32, 8.62, 8.03, 7.63, 7.41, 7.36, 5.49, 4.62, 4.55.

IR (drift) 3082, 2939, 1658, 1614, 1575, 1543, 1514, 1495, 1346, 1301, 1292, 1265, 891, 800, 679 cm$^{-1}$.

MS (ESI) 361.1 (M+H)$^+$, 359.1 (M–H)$^-$.

Anal. Found: C, 59.76; H, 4.00; N, 7.85.

EXAMPLE 142

3-(3-{[(4-Chlorobenzyl)amino]carbonyl}-8-fluoro-4-hydroxy-6-quinolinyl)propyl methanesulfonate

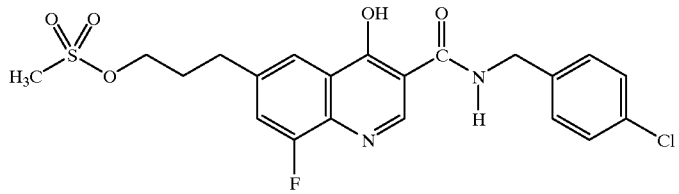

To a solution of N-(4-chlorobenzyl)-8-fluoro-4-hydroxy-6-(3-hydroxypropyl)-3-quinolinecarboxamide from Example No. 110 (0.13 g) in 10 mL DMF is added $NEt_3$ (0.05 mL) and a spatula tip of DMAP. Methanesulfonyl chloride (0.030 mL) is added dropwise and the reaction is allowed to stir at room temperature overnight. The reaction is partitioned between EtOAc and $H_2O$. The aqueous layer is extracted 3× with EtOAc. The organics are combined, dried over $MgSO_4$, filtered, and concentrated under reduced pressure to give a yellow liquid. The residue is dissolved in $CH_2Cl_2$, adsorbed onto silica and chromatographed on a Biotage Flash 40S column (eluent 1% $MeOH:CH_2Cl_2$ (1 L) followed by 3% $MeOH:CH_2Cl_2$ (2 L)) to afford the desired product as a white solid which is further purified by recrystallization with $CH_2Cl_2$/hexanes. (0.045 g, 0.097 mmol, 29%).

Physical characteristics are as follows:

MP 200–201 C $^1$H NMR (300 MHz, DMSO-$d_6$) 12.86, 10.33, 8.61, 7.90, 7.66, 7.40, 7.36, 4.55, 4.21, 3.18, 2.84, 2.03.

IR (drift) 1651, 1612, 1569, 1550, 1523, 1360, 1350, 1301, 1284, 1170, 980, 936, 838, 807, 725 $cm^{-1}$.

MS (ESI) for m/z 467.0 $(M+H)^+$, 488.9 $(M+Na)^+$, 465.0 $(M-H)^-$.

HRMS (EI) Found 466.0764.

EXAMPLE 143

N-(4-Chlorobenzyl)-8-fluoro-6-(3-fluoro-1-propynyl)-4-hydroxy-3-quinolinecarboxamide

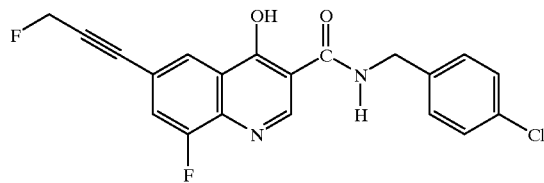

To a 3-necked round bottomed flask connected to a condenser and bulb-to-bulb distillation apparatus is added N-(4-chlorobenzyl)-8-fluoro-4-hydroxy-6-iodo-3-quinolinecarboxamide from example No. 5 (1.2 g), $PdCl_2$ $(PPh_3)_2$ (92.6 mg), and CuI (25.1 mg) in 30 mL $Et_2NH$. The solution was cooled with a dry ice/acetone bath and propargyl flouride is distilled into the reaction mixture. After distillation of propargyl fluoride into the reaction mixture, the dry ice/acetone bath is replaced with an ice water bath to allow the reaction mixture to warm to 0° C. and then to room temperature overnight. The reaction mixture is stripped to get rid of $Et_2NH$ and the resulting residue is partitioned between $CH_2Cl_2$ (3×) and water. The combined organic layers are dried over $Na_2SO_4$ and condensed to afford a residue. The residue is chromatographed eluting with 1% MeOH in $CH_2Cl_2$. Fractions homogenous by TLC are combined, condensed, and recrystallized with EtOAc/hexanes to yield a sample consisting of starting material and product. The solid is resubjected to the reaction conditions and purification process two times. Complete conversion to product is almost achieved. The final solid is purified by HPLC to yield 151.2 mg (15%) of the desired product as an off-white solid.

Physical characteristics are as follows:

MP 278–280 C;

$^1$H NMR (300 MHz, DMSO) 13.07, 10.14, 8.63, 8.10, 7.89, 7.40, 7.36, 5.47, 5.31, 4.55.

IR (drift) 3067, 2923, 1656, 1629, 1607, 1576, 1551, 1520, 1493, 1306, 1294, 1198, 988, 885, 801 $cm^{-1}$.

MS (ESI) 387.1 $(M+H)^+$, 385.1 $(M-H)^-$.

Anal. Found: C, 61.54; H, 3.26; N, 7.18.

EXAMPLE 144

N-(4-Chlorobenzyl)-4-hydroxy-6-(3-hydroxypropyl)-3-quinolinecarboxamide

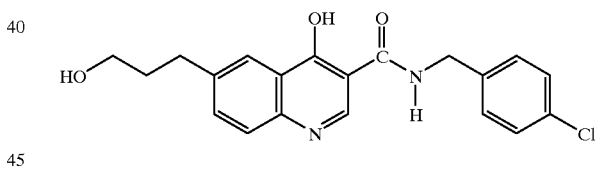

A mixture of N-(4-chlorobenzyl)-4-hydroxy-6-(3-hydroxy-1-propynyl)-3-quinolinecarboxamide from Example No. 134 (231.0 mg) and Pd/C (10%, 46.2 mg) are dissolved in 40 mL 3:1 $CH_2Cl_2$:MeOH. The reaction mixture is placed under the Parr hydrogenator at 26 psi and monitored with the OAMS for complete reduction of the acetylene. The reaction is complete in 25 min and filtered over celite to remove the palladium. The filtrate is condensed to obtain a solid. The solid is suspended in ether, filtered, and collected to yield 31.8 mg (14%) of the desired product as a white solid.

Physical characteristics are as follows:

MP 192–194 C;

$^1$H NMR (300 MHz, DMSO) 12.68, 10.49, 8.72, 8.05, 7.63, 7.38, 4.55, 4.53, 3.42, 2.76, 1.76.

IR (drift) 3238, 3164, 2934, 2888, 2861, 1660, 1621, 1575, 1539, 1488, 1365, 845, 823, 806, 677 $cm^{-1}$.

MS (ESI) 371.1 $(M+H)^+$, 369.1 $(M-H)^-$.

Anal. Found: C, 64.69; H, 5.16; N, 7.55.

EXAMPLE 145

3-(3-{[(4-Chlorobenzyl)amino]carbonyl}-8-fluoro-4-hydroxy-6-quinolinyl)propyl 2-bromoacetate

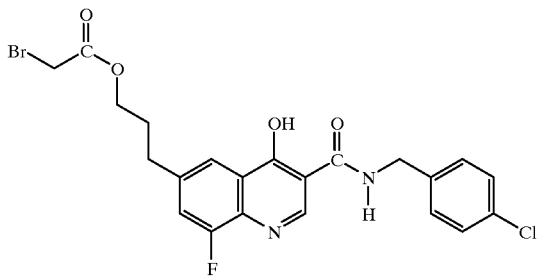

A solution of N-(4-chlorobenzyl)-8-fluoro-4-hydroxy-6-(3-hydroxypropyl)-3-quinolinecarboxamide from Example 110 (0.23 g), Et$_3$N (0.090 mL), and catalytic DMAP (5–10 mol %) in 20 mL DMF is cooled to 0° C. Bromoacetyl bromide (0.050 mL) is added in one portion. The reaction is stirred at 0° C. for 20 minutes, then at room temperature for 1.5 h. Once the reaction was complete, it is partitioned between CH$_2$Cl$_2$ and H$_2$O. The aqueous layer is extracted 3× with CH$_2$Cl$_2$. The organics are combined, dried over Na$_2$SO$_4$, filtered, and concentrated under reduced pressure to give a liquid which subsequently crystallizes to an off-white solid when it is dried on the vacuum pump overnight. The solid is triturated in CH$_2$Cl$_2$/hexanes, filtered, and dried to give the desired product (0.27 g, 0.53 mmol, 91%).

Physical characteristics are as follows:

MP 197–199° C. dec.

$^1$H NMR (300 MHz, DMSO-d$_6$) 12.85, 10.31, 8.60, 7.89, 7.65, 7.40, 7.36, 4.55, 4.16, 4.13, 2.82, 1.97.

IR (drift) 3060, 2946, 1722, 1650, 1613, 1569, 1544, 1523, 1489, 1300, 1283, 1268, 1198, 805, 724 cm$^{-1}$.

MS (ESI) for m/z 509.0 (M+H)$^+$, 531.0 (M+Na)$^+$, 507.1 (M–H)$^-$.

Anal. Found: C, 51.77; H, 3.77; N, 5.49.

EXAMPLE 146

3-(3-{[(4-Chlorobenzyl)amino]carbonyl}-8-fluoro-4-hydroxy-6-quinolinyl)propyl 2-[(tert-butoxycarbonyl)amino]-3-methylbutanoate

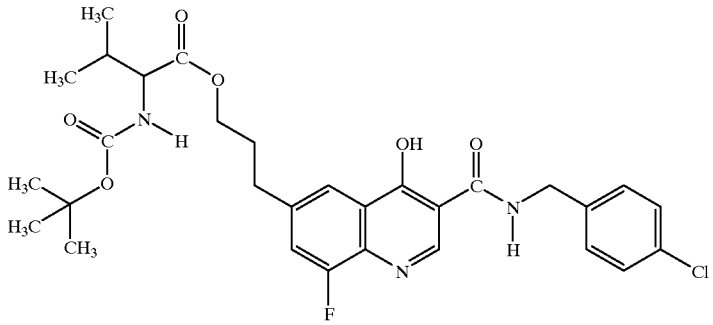

N-Boc-valine (0.13 g) is added to a solution of N-(4-chlorobenzyl)-8-fluoro-4-hydroxy-6-(3-hydroxypropyl)-3-quinolinecarboxamide from example 110 (0.15 g), EDC hydrochloride (0.11 g), and DMAP (0.016 g) in 4 mL pyridine. The reaction is stirred at room temperature overnight. The solvent is removed in vacuo and the residue partitioned between CH$_2$Cl$_2$ and H$_2$O. The organic layer is washed once with water, and once with brine. The organic layer is then dried over Na$_2$SO$_4$, filtered, and concentrated in vacuo to give a yellow liquid. The residue is adsorbed onto silica and purified by chromatography on a Biotage Flash 40S column (eluent 1% MeOH:CH$_2$Cl$_2$ (1 L) followed by 2% MeOH:CH$_2$Cl$_2$ (2 L)). The product is obtained as a white solid which is further purified by recrystallization with CH$_2$Cl$_2$/hexanes (0.17 g, 74%).

Physical characteristics are as follows:

MP 164–165 C $^1$H NMR (300 MHz, DMSO-d$_6$) 12.85, 10.32, 8.61, 7.89, 7.63, 7.39, 7.36, 7.17, 4.55, 4.06, 3.83, 2.8, 1.93, 1.38, 0.88, 0.86.

IR (drift) 2967, 1734, 1714, 1652, 1613, 1569, 1550, 1524, 1492, 1366, 1302, 1286, 1183, 1159, 804 cm$^{-1}$.

MS (ESI) for m/z 587.9 (M+H)$^+$, 610.0 (M+Na)$^+$, 586.0 (M–H)$^-$.

EXAMPLE 147

3-(3-([(4-Chlorobenzyl)amino]carbonyl}-8-fluoro-4-hydroxy-6-quinolinyl)propyl 2-morpholinoacetate

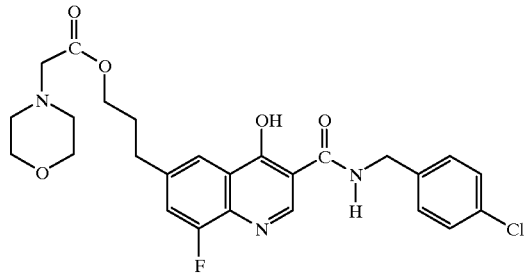

Morpholine (0.03 mL) is added to a solution of 3-(3-{[(4-chlorobenzyl)amino]-carbonyl}-8-fluoro-4-hydroxy-6-quinolinyl)propyl 2-bromoacetate from Example No. 145 (0.10 g) and Et$_3$N (0.040 mL) in 5 mL DMF. The reaction is stirred at room temperature after which time reaction is complete. The reaction is partitioned between CH$_2$Cl$_2$ (50 mL) and H$_2$O (25 mL). The organic layer is washed twice with H$_2$O, and once with brine. The aqueous layers are combined and back-extracted with CH$_2$Cl$_2$. The organics are combined, dried over Na$_2$SO$_4$, filtered, and concentrated in vacuo to give a yellow liquid. The liquid is re-dissolved in CH$_2$Cl$_2$ and adsorbed onto silica. Chromatography on a Biotage Flash 40S column (eluent 1% MeOH:CH$_2$Cl$_2$ (1 L), followed by 2% MeOH:CH$_2$Cl$_2$ (2 L) and 5% MeOH:CH$_2$Cl$_2$ (1 L)) affords the desired product as a white solid (0.070 g, 68%).

Physical characteristics are as follows:

MP 165–167 C $^1$H NMR (300 MHz, DMSO-d$_6$) 12.85, 10.44, 8.63, 7.87, 7.60, 7.40, 7.35, 4.55, 4.06, 3.56, 3.20, 2.80, 2.47, 1.95.

MS (ESI) for m/z 516.1 (M+H)$^+$, 538.0 (M+Na)$^+$, 514.1 (M−H)$^-$.

EXAMPLE 148

3-(3-{[(4-Chlorobenzyl)amino]carbonyl}-8-fluoro-4-hydroxy-6-quinolinyl)propyl 2-(dimethylamino)acetate

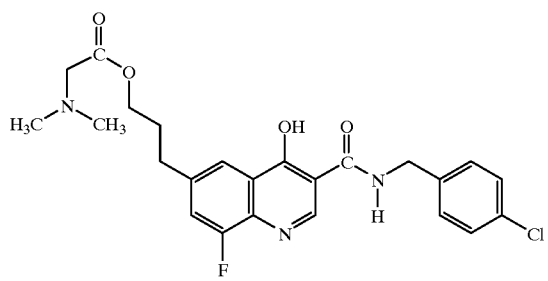

To a solution of N-(4-chlorobenzyl)-8-fluoro-4-hydroxy-6-(3-hydroxypropyl)-3-quinolinecarboxamide from Example No. 110 (0.23 g), EDC hydrochloride (0.22 g), and DMAP (0.022 g) in 7 mL pyridine is added N,N-dimethylglycine (0.12 g). The reaction is allowed to stir at room temperature overnight. The solvent is removed in vacuo and the residue partitioned between CH$_2$Cl$_2$ and water. The organic layer is washed once with water, once with brine, dried over Na$_2$SO$_4$, filtered, and concentrated in vacuo. The residue is adsorbed onto silica and purified by chromatography on a Biotage Flash 40S column (eluent 1.5% MeOH:CH$_2$Cl$_2$ (1 L), 2.5% MeOH:CH$_2$Cl$_2$ (1 L), and 4% MeOH:CH$_2$Cl$_2$ (1 L)). The product-containing fractions are concentrated in vacuo to give a white solid which is further triturated in EtOH, filtered, washed with hexanes, and dried. (0.14 g, 51%).

Physical characteristics are as follows:

MP 173–175 C $^1$H NMR (300 MHz, DMSO-d$_6$) 12.80, 10.32, 8.61, 7.87, 7.64, 7.40, 7.36, 4.55, 4.06, 3.16, 2.80, 2.24, 1.95.

IR (drift) 3200, 2940, 1727, 1652, 1613, 1572, 1546, 1524, 1489, 1300, 1286, 1268, 1198, 1185, 805 cm$^{-1}$.

MS (ESI) for m/z 474.1 (M+H)$^+$, 496.0 (M+Na)$^+$, 472.1 (M−H)$^-$.

Anal. Found: C, 59.93; H, 5.32; N, 8.57.

EXAMPLE 149

3-(3-{[(4-Chlorobenzyl)amino]carbonyl}-8-fluoro-4-hydroxy-6-quinolinyl)propyl 2-amino-3-methylbutanoate

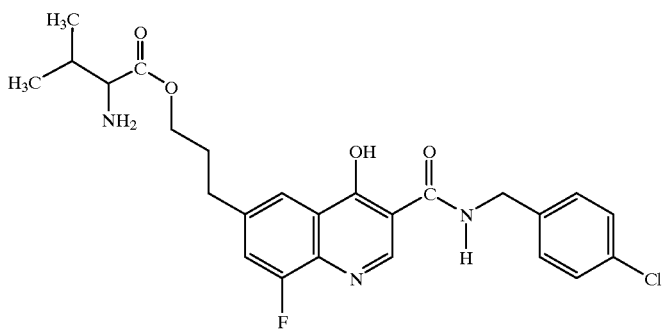

3-(3-{[(4-Chlorobenzyl)amino]carbonyl}-8-fluoro-4-hydroxy-6-quinolinyl)propyl 2-[(tert-butoxycarbonyl)amino]-3-methylbutanoate from Example No. 146 (0.13 g) is stirred in a mixture of 4 mL trifluoroacetic acid and 7 mL CH$_2$Cl$_2$ at 0° C. for approximately 1.5 h. Once the reaction is complete, the mixture is partitioned between CH$_2$Cl$_2$ and saturated NaHCO$_3$. After the TFA is neutralized, any undissolved material is filtered off. The organic layer is washed once with water. The combined aqueous layers are back-extracted with CH$_2$Cl$_2$ and EtOAc. The organics are combined, dried over Na$_2$SO$_4$, filtered, and concentrated in vacuo to give a white solid. The solid is recrystallized from a minimal amount of EtOH. (0.040 g, 0.082 mmol, 35%).

Physical characteristics are as follows:

MP 198–199 C $^1$H NMR (300 MHz, DMSO-d$_6$) 10.46, 8.63, 7.87, 7.59, 7.40, 7.36, 4.55, 4.07, 3.22, 2.81, 1.92, 0.88, 0.84.

IR (drift) 3197, 2958, 1729, 1651, 1613, 1569, 1549, 1525, 1489, 1300, 1285, 1198, 1182, 806, 724 cm$^{-1}$.

MS (ESI) for m/z 488.0 (M+H)$^+$, 486.1 (M–H)$^-$.

Anal. Found: C, 60.40; H, 5.54; N, 8.33.

EXAMPLE 150

3-(3-{[(4-Chlorobenzyl)amino]carbonyl}-8-fluoro-4-hydroxy-6-quinolinyl)-2-propynyl phenylcarbamate

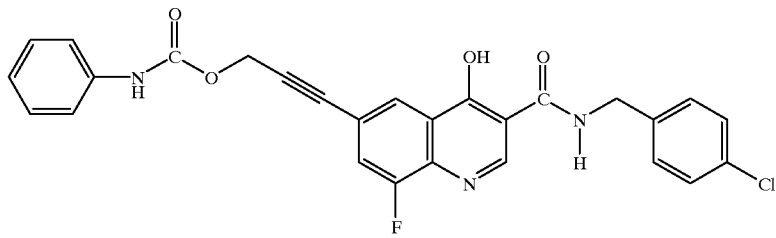

A solution of N-(4-chlorobenzyl)-8-fluoro-4-hydroxy-6-iodo-3-quinolinecarboxamide from Example No. 5 (400 mg), propynyl N-phenyl carbamate (217.2 mg), PdCl$_2$(PPh$_3$)$_2$ (15.4 mg), and 0.56 mL Et$_3$N in 2.22 mL anhydrous DMF is heated at 90° C. for 1 hr. The reaction mixture is cooled to room temperature and partitioned between EtOAc and H$_2$O. The aqueous layer is washed with EtOAc (3×). The combined organic layers are dried over Na$_2$SO$_4$ and condensed to obtain a red-brown residue. The residue is chromatographed eluting with 2% MeOH in CH$_2$Cl$_2$. Fractions homogenous by TLC are combined and condensed to afford 121.6 mg (28%) of the title compound as a yellow solid.

Physical characteristics are as follows:

Mp 227–229° C.

$^1$H NMR (300 MHz, DMSO) 13.07, 10.15, 9.90, 8.63, 8.06, 7.83, 7.48, 7.33, 7.02, 5.07, 4.55.

IR (drift) 3274, 3197, 1713, 1661, 1611, 1577, 1552, 1521, 1498, 1445, 1316, 1234, 1060, 765, 751 cm$^{-1}$.

MS (ESI) 503.9 (M+H)$^+$, 502.0 (M–H)$^-$.

Anal. Found: C, 64.10; H, 3.78; N, 8.27.

EXAMPLE 151

N-(4-Chlorobenzyl)-4-hydroxy-6-propyl-3-quinolinecarboxamide

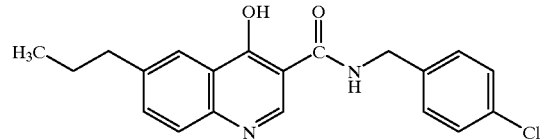

A mixture of N-(4-chlorobenzyl)-4-hydroxy-6-(3-hydroxy-1-propynyl)-3-quinolinecarboxamide from Example No. 134 (500 mg) and Pd/C (10%, 100 mg) is dissolved in 80 mL 3:1 CH$_2$Cl$_2$:MeOH. The reaction mixture is placed under the Parr hydrogenator at 30 psi and monitored by mass spectroscopy for complete reduction of the acetylene. The old palladium catalyst is replaced with fresh palladium catalyst each time the reaction is taken off the Parr. The reaction mixture is filtered over celite to remove the palladium. The filtrate is condensed. The crude solid is adsorbed onto silica and chromatographed eluting with 2% MeOH in CH$_2$Cl$_2$. Fractions homogenous by TLC are combined and condensed to afford 16.3 mg (3%) of the title compound as a white solid.

Physical characteristics are as follows:

Mp 225–227° C.

$^1$H NMR (300 MHz, DMSO) 12.68, 10.49, 8.73, 8.04, 7.63, 7.38, 4.55, 2.71, 1.64, 0.90.

MS (ESI) 355.1 (M+H)$^+$, 353.1 (M–H)$^-$.

Anal. Found: C, 67.38; H, 5.25; N, 7.98.

EXAMPLE 152

N-(4-Chlorobenzyl)-4-hydroxy-6-(3-hydroxy-1-butynyl)-3-quinolinecarboxamide

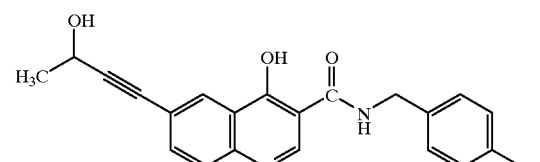

A solution of N-(4-chlorobenzyl)-4-hydroxy-6-iodo-3-quinolinecarboxamide from Example No. 40 (800 mg), 3-butyn-2-ol (0.20 mL), PdCl$_2$(PPh$_3$)$_2$ (32.3 mg), and 1.16 mL Et$_3$N in 4.64 mL anhydrous DMF is heated at 90° C. for 1 hr. The reaction mixture is cooled to room temperature and partitioned between EtOAc and H$_2$O. The aqueous layer is washed with EtOAc (3×). The combined organic layers are dried over Na$_2$SO$_4$ and condensed to obtain a red-brown residue. The residue is chromatographed eluting with 3% MeOH in CH$_2$Cl$_2$. Fractions homogenous by TLC are combined and condensed to afford 139.2 mg (20%) of the title compound as a brown solid.

Physical characteristics are as follows:

Mp 180–182° C.

$^1$H NMR (300 MHz, DMSO) 12.84, 10.31, 8.77, 8.20, 7.72, 7.38, 5.52, 4.62, 4.55, 1.40.

IR (drift) 3243, 3053, 2992, 2977, 2961, 1656, 1614, 1555, 1518, 1486, 1300, 1091, 917, 825, 805 cm$^{-1}$.

MS (ESI) 381.1 (M+H)$^+$, 379.1 (M–H)$^-$.

EXAMPLE 153

N-(4-Chlorobenzyl)-8-fluoro-4-hydroxy-6-[(E)-3-oxo-1-butenyl]-3-quinolinecarboxamide

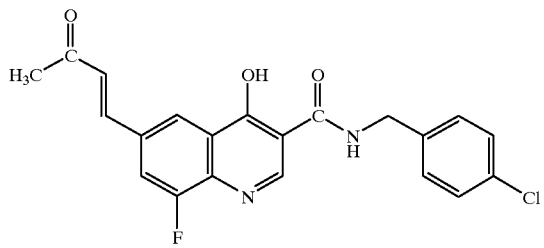

A solution of N-(4-chlorobenzyl)-8-fluoro-4-hydroxy-6-iodo-3-quinolinecarboxamide from Example No. 5 (1.0 g), Pd(OAc)$_2$ (9 mg), P(o-tolyl)$_3$ (45.7 mg), methyl vinyl ketone (0.23 mL), and Et$_3$N (0.78 mL) in 5.28 mL anhydrous DMF is heated in a sealed tube at 100° C. overnight. The reaction mixture is cooled to room temperature and then cooled in an ice bath. The cooled reaction mixture is poured into 20 mL ice cold 1N HCl. A brown solid precipitated and is collected. The crude product is adsorbed onto silica and chromatographed eluting with 2% MeOH in CH$_2$Cl$_2$. Fractions homogenous by TLC are combined and condensed to afford 453.4 mg (52%) of the title compound as a yellow solid.

Physical characteristics are as follows:

Mp 286–289° C.

$^1$H NMR (300 MHz, DMSO) 13.02, 10.22, 8.62, 8.30, 8.19, 7.79, 7.39, 6.93, 4.57, 2.37.

IR (drift) 1692, 1651, 1609, 1577, 1514, 1352, 1314, 1306, 1262, 1241, 1195, 1182, 1132, 984, 804 cm$^{-1}$.

MS (ESI) 399.1 (M+H)$^+$, 397.1 (M–H)$^-$.

Anal. Found: C, 62.84; H, 4.12; N, 6.93.

EXAMPLE 154

N-(4-Chlorobenzyl)-8-fluoro-4-hydroxy-6-(5-hydroxypentyl)-3-quinolinecarboxamide

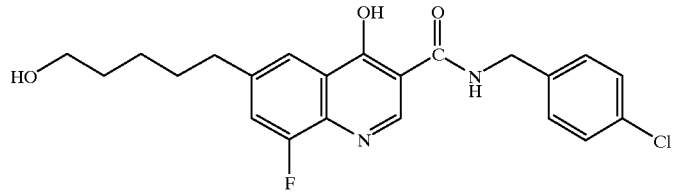

A mixture of N-(4-chlorobenzyl)-8-fluoro-4-hydroxy-6-(5-hydroxy-1-pentynyl)-3-quinolinecarboxamide from Example 107 (230 mg) and Pd/C (10%, 46.0 mg) is dissolved in 3:1 CH$_2$Cl$_2$:MeOH. The reaction mixture is placed under the Parr hydrogenator at 38 psi H$_2$ and monitored by mass spectroscopy for complete reduction of the acetylene. The reaction is complete in 1½ h and filtered over celite to remove the palladium. The filtrate is condensed to afford 129.3 mg (56%) of the title compound as a white solid.

Physical characteristics are as follows:

Mp 193–195° C.

$^1$H NMR (300 MHz, DMSO) 12.83, 10.32, 8.60, 7.85, 7.62, 7.38, 4.55, 4.32, 3.37, 2.73, 1.62, 1.43, 1.33.

MS (ESI) 417.1 (M+H)$^+$, 415.2 (M–H)$^-$.

Anal. Found: C, 63.10; H, 5.31; N, 6.65.

EXAMPLE 155

3-(3{[(4-Chlorobenzyl)amino]carbonyl}-8-fluoro-4-hydroxy-6-quinolinyl)propyl 2,6-bis[(tert-butoxycarbonyl)amino]hexanoate

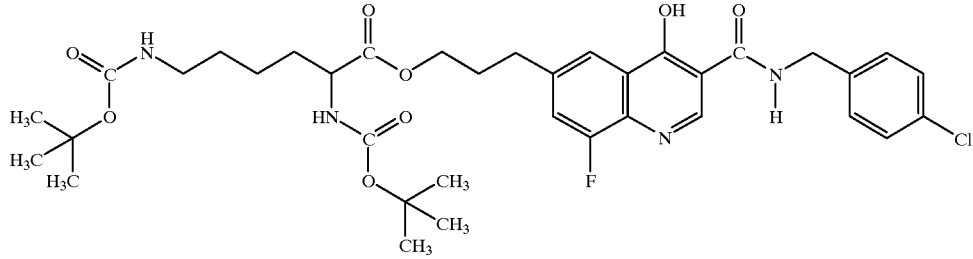

To a solution of N-[4-(chlorophenyl)methyl]-8-fluoro-4-hydroxy-6-(3-hydroxypropyl)-3-quinolinecarboxamide from Example No. 110 (0.21 g), EDC hydrochloride (0.22 g), and dimethylaminopyridine (0.030 g) in 5 mL pyridine is added di-Boc-lysine (0.38 g) in 4 mL pyridine. The reaction is stirred at room temperature for 24 hours. The solvent is removed in vacuo. The residue is partitioned between $CH_2Cl_2$ and water. The aqueous layer is extracted 3x with $CH_2Cl_2$. The organics are combined, dried over sodium sulfate, and filtered. The filtrate is concentrated in vacuo to give a clear residue which is re-dissolved in a mixture of $CH_2Cl_2$/MeOH and adsorbed onto silica. Purification by a Biotage Flash 40S silica gel column (eluent 1% MeOH/$CH_2Cl_2$ (2 L), 2% MeOH/$CH_2Cl_2$ (1 L), 2.5% MeOH/$CH_2Cl_2$ (1 L), 3% MeOH/$CH_2Cl_2$ (1 L)) affords the desired product as an oil. Dichloromethane and hexanes were added and the solvents are removed to give the product as a white solid (0.26 g, 67%).

Physical characteristics are as follows:

MP 125–126° C.

$^1$H NMR (300 MHz, DMSO-$d_6$) 12.85, 10.32, 8.60, 7.88, 7.62, 7.39, 7.35, 7.21, 6.75, 4.55, 4.05, 3.90, 2.88, 2.80, 1.93, 1.59, 1.37, 1.35.

IR (drift) 2976, 2933, 1710, 1654, 1613, 1569, 1549, 1524, 1366, 1349, 1300, 1284, 1268, 1250, 1173 cm$^{-1}$.

HRMS (FAB) Found 717.3081.

Anal. Found: C, 59.23; H, 6.43; N, 7.65.

EXAMPLE 156

3-(3-{[(4-Chlorobenzyl)amino]carbonyl}-8-fluoro-4-hydroxy-6-quinolinyl)propyl 2,6-diaminohexanoate, trifluoroacetic acid salt

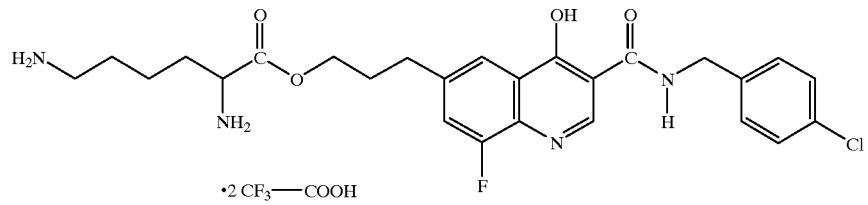

Trifluoroacetic acid (5 mL) is added to a solution of 3-(3{[(4-chlorobenzyl)-amino]-carbonyl}-8-fluoro-4-hydroxy-6-quinolinyl)propyl 2,6-bis [(tert-butoxycarbonyl)amino]-hexanoate from Example No. 155 (0.12 g) in dichloromethane (7 mL) cooled to 0° C. The reaction is stirred for 80 minutes while also being allowed to warm to room temperature. The solvents are removed in vacuo to give an oil which was crystallized with $CH_2Cl_2$/MeOH/hexanes. Once the solvents are removed, the product was obtained as a white solid (0.12 g, 93%).

Physical characteristics are as follows:

MP 151–154° C.

$^1$H NMR (300 MHz, DMSO-$d_6$) 10.28, 8.64, 7.91, 7.66, 7.40, 7.36, 4.56, 4.19, 4.03, 2.84, 2.77, 2.00, 1.78, 1.40.

IR (drift) 3052, 3036, 3028, 2998, 1744, 1675, 1646, 1614, 1568, 1551, 1522, 1203, 1135, 799, 723 cm$^{-1}$.

MS (ES) m/z 517.1 (M+H)$^+$, 515.1 (M–H)$^-$.

HRMS (FAB) Found 517.2018.

Anal. Found: C, 47.01; H, 4.43; N, 7.10.

EXAMPLE 157

N-(4-Chlorobenzyl)-4-hydroxy-6-(3-hydroxybutyl)-3-quinolinecarboxamide

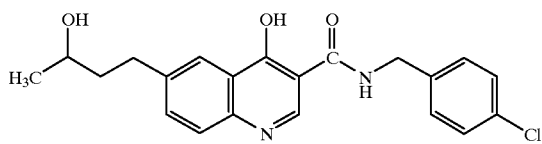

A mixture of N-(4-chlorobenzyl)-4-hydroxy-6-(3-hydroxy-1-butynyl)-3 -quinolinecarboxamide from Example No. 152 (106.3 mg) and Pd/C (10%, 21.3 mg) is dissolved in 40 mL 3:1 $CH_2Cl_2$:MeOH. The reaction mixture is placed under the Parr hydrogenator at 34 psi $H_2$ and monitored by mass spectroscopy for complete reduction of the acetylene. The old palladium catalyst is replaced with fresh palladium catalyst each time the reaction is taken off the Parr. In this case, the reaction is taken off the Parr twice. The reaction is complete in 130 min . The reaction mixture is filtered over celite to remove the palladium. The filtrate is condensed to obtain a solid. The crude product is adsorbed onto silica and chromatographed eluting with 4% MeOH in $CH_2Cl_2$. Fractions homogenous by TLC are combined and condensed to afford 30.0 mg (28%) of the title compound as a white solid.

Physical characteristics are as follows:

Mp 199–201° C.

$^1$H NMR (300 MHz, DMSO) 12.68, 10.49, 8.72, 8.05, 7.63, 7.38, 4.56, 4.50, 3.60, 2.77, 1.65, 1.09.

IR (drift) 3236, 3078, 3052, 3015, 2966, 2931, 2858, 1660, 1620, 1574, 1540, 1488, 1365, 822, 806 $cm^{-1}$.

MS (ESI) 385.2 $(M+H)^+$, 383.2 $(M-H)^-$.

Anal. Found: C, 65.27; H, 5.48; N, 7.16.

EXAMPLE 158

N-(4-Chlorobenzyl)-8-fluoro-4-hydroxy-6-(4-morpholinylmethyl)-3-quinolinecarboxamide

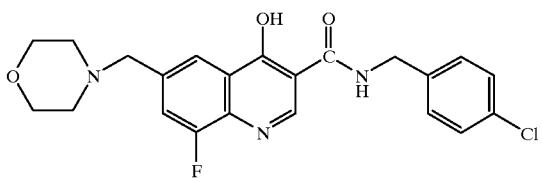

A solution of N-(4-chlorobenzyl)-8-fluoro-4-hydroxy-6-(hydroxymethyl)-3-quinolinecarboxamide from Example No. 141 (500 mg), collidine (0.21 mL), and DMAP (28.3 mg) in 25 mL DMF is cooled to 0° C. Methanesulfonyl chloride (0.12 mL) is added dropwise. The reaction is stirred at room temperature and monitored by mass spectroscopy for complete conversion to N-(4-chlorobenzyl)-6-(chloromethyl)-8-fluoro-4-hydroxy-3-quinolinecarboxamide (approx. 2–3 hrs and reaction mixture turns yellow). Morpholine (0.24 mL) is added. The reaction is monitored by mass spectroscopy for complete conversion. The product is precipitated by addition of 25 mL $H_2O$. The white solid is filtered and collected to afford 459.3 mg (78%) of the title compound.

Physical characteristics are as follows:

Mp 230–232° C. (dec). $^1$H NMR (300 MHz, DMSO) 12.87, 10.30, 8.62, 7.99, 7.65, 7.38, 4.56, 3.59, 2.39.

HRMS (FAB) Found 430.1329.

EXAMPLE 159

3-(3-{[(4-Chlorobenzyl)amino]carbonyl}-8-fluoro-4-hydroxy-6-quinolinyl)propyl phenylcarbamate

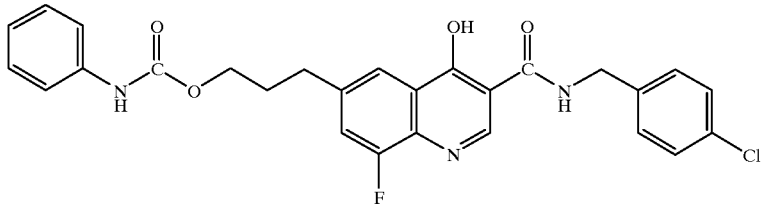

A mixture of 3-(3-{[(4-chlorobenzyl)amino]carbonyl}-8-fluoro-4-hydroxy-6-quinolinyl)-2-propynyl phenylcarbamate from Example No. 150 (100 mg) and Pd/C (10%, 20 mg) is dissolved in 80 mL 3:1 $CH_2Cl_2$:MeOH. The reaction mixture is placed under the Parr hydrogenator at 25 psi $H_2$ and monitored by mass spectroscopy for complete reduction of the acetylene. The old palladium catalyst is replaced with fresh palladium catalyst each time the reaction is taken off the Parr. The reaction is complete in 40 min . The reaction mixutre is filtered over celite to remove the palladium. The filtrate is condensed. The mixture is adsorbed onto silica and chromatographed eluting with 2% MeOH in $CH_2Cl_2$. Fractions homogenous by TLC are combined and condensed to afford 11.3 mg (11%) of the title compound as a white solid.

Physical characteristics are as follows:

Mp 182–183° C.

$^1$H NMR (300 MHz, DMSO) 12.86, 10.31, 9.60, 8.61, 7.91, 7.67, 7.39, 7.26, 6.97, 4.55, 4.09, 2.86, 2.00.

HRMS (FAB) Found 508.1450.

EXAMPLE 160

N-(4-Chlorobenzyl)-8-fluoro-4-hydroxy-6-(3-oxobutyl)-3-quinolinecarboxamide

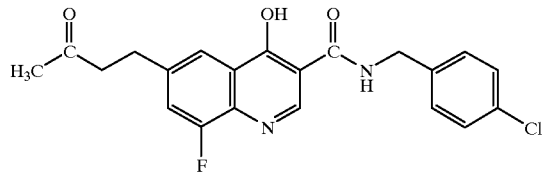

To a mixture of N-(4-chlorobenzyl)-8-fluoro-4-hydroxy-6-[(E)-3-oxo-1-butenyl]-3-quinolinecarboxamide from Example No. 153 (100 mg) and $Et_3N$ (0.35 mL) in 80 mL 3:1 $CH_2Cl_2$:MeOH is added Pd/C (10%, 20 mg). The reaction mixture is placed under the Parr hydrogenator at 29 psi $H_2$ and monitored by mass spectroscopy for complete reduction of the alkene. The old palladium catalyst is replaced with fresh palladium catalyst each time the reaction was taken off the Parr. In this case, the reaction is taken off the Parr once. The reaction is complete in 45 min. The reaction mixutre is filtered over celite to remove the palladium. The filtrate is concentrated. The crude mixture was separated by HPLC to afford 38.7 mg (8%) of the title compound as a yellow solid.

Physical characteristics are as follows:

Mp 218–222° C.

$^1$H NMR (300 MHz, DMSO) 12.67, 10.48, 8.62, 7.86, 7.56, 7.38, 4.55, 2.88, 2.10.

IR (drift) 2945, 1711, 1638, 1613, 1571, 1524, 1488, 1431, 1350, 1305, 1287, 1183, 805, 799, 724 $cm^{-1}$.

HRMS (FAB) Found 401.1067.

EXAMPLE 161

3-(3 [(4-Chlorobenzyl)amino]carbonyl}-4-hydroxy-6-quinolinyl)-2-propynyl 2,6-bis [(tert-butoxycarbonyl)amino]hexanoate

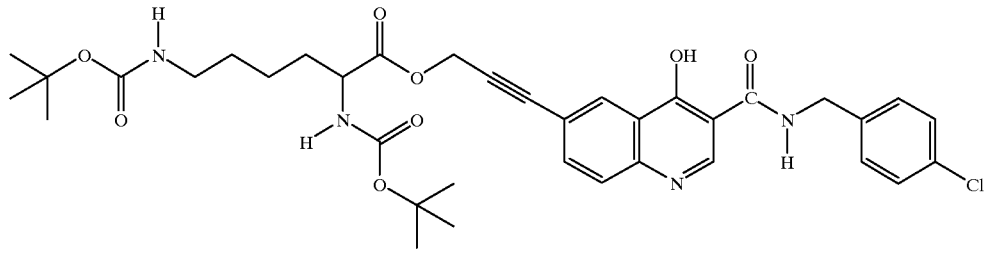

To a solution of N-(4-chlorobenzyl)-4-hydroxy-6-(3-hydroxy-1-propynyl)-3-quinolinecarboxamide from Example No. 134 (0.22 g), EDC hydrochloride (0.24 g), and dimethylaminopyridine (0.040 g) in 5 mL pyridine is added di-Boc-lysine (0.44 g) in 5 mL pyridine. The reaction is stirred at room temperature for 24 hours. The solvent is removed in vacuo. The residue is partitioned between dichloromethane and water. The aqueous layer is extracted 3× with $CH_2Cl_2$. The organics are combined, dried over sodium sulfate, filtered, and then adsorbed onto silica. Purification by a Biotage Flash 40 S silica gel column (eluent $CH_2Cl_2$ (1 L), 2% MeOH/$CH_2Cl_2$ (1 L), 4% MeOH/$CH_2Cl_2$ (1 L)) affords the desired product as a clear oil. The oil is dissolved in $CH_2Cl_2$, hexanes are added, and the solvents removed to give the product as a white solid (0.28 g, 66%).

Physical characteristics are as follows:

MP 148–150° C.

$^1$H NMR (300 MHz, DMSO-$d_6$) 12.86, 10.29, 8.78, 8.24, 7.78, 7.71, 7.40, 7.36, 7.29, 6.75, 5.02, 4.55, 3.97, 2.87, 1.64, 1.38, 1.36, 1.25, 0.86.

MS (ES) m/z 695.1 $(M+H)^+$, 717.1 $(M+Na)^+$, 693.1 $(M-H)^-$.

HRMS (FAB) Found 695.2826.

Anal. Found: C, 61.17; H, 6.63; N, 7.40.

EXAMPLE 162

3-(3-{[(4-Chlorobenzyl)amino]carbonyl}-4-hydroxy-6-quinolinyl)propynyl 2,6-diaminohexanoate, trifluoroacetic acid salt

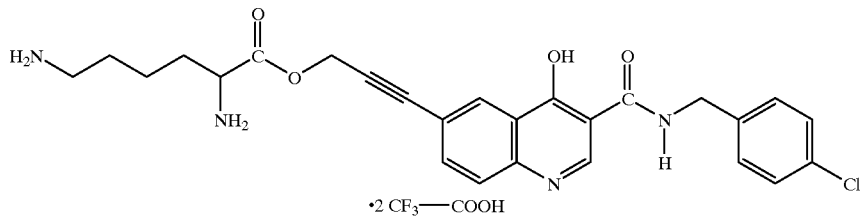

Trifluoroacetic acid (10 mL) is added to a solution of 3-(3[[(4-chlorobenzyl)-amino]carbonyl}-4-hdyroxy-6-quinolinyl)-2-propynyl-2,6-bis [(tert-butoxycarbonyl)-amino]hexanoate from Example No. 161 (0.60 g) in 20 mL $CH_2Cl_2$ cooled to 0° C. The reaction is stirred for 2 hours. The solvents are removed to give a pale yellow/orange oil. The oil is crystallized by addition of methanol and removal of the solvent in vacuo. The product is dried on the vacuum pump (0.41 g, 0.57 mmol, 66%).

Physical characteristics are as follows:

MP 128–130° C. (sublime)

$^1$H NMR (300 MHz, DMSO-$d_6$) 13.06, 10.26, 8.80, 8.57, 8.26, 7.84, 7.79, 7.75, 7.40, 7.36, 5.18, 4.55, 4.16, 2.76, 1.84, 1.57, 1.44.

IR (drift) 3047, 2994, 2984, 2954, 1676, 1649, 1614, 1551, 1516, 1487, 1203, 1135, 837, 799, 722 $cm^{-1}$.

MS (ES) m/z 495.1 $(M+H)^+$, 493.1 $(M-H)^-$.

HRMS (FAB) Found 495.1797.

% Water (KF): 2.07.

Anal. Found: C, 46.97; H, 4.07; N, 7.23.

EXAMPLE 163

N-(4-Chlorobenzyl)-4-hydroxy-6-[(2-hydroxyethoxy)methyl]-3-quinolinecarboxamide

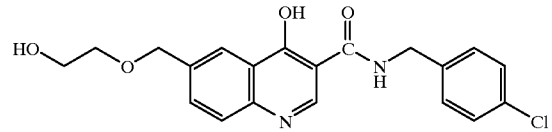

To a suspension of $Ag_2O$ (4.50 g) in 37 mL distilled $CH_2Cl_2$ is added 2-benzyloxyethanol (2.62 mL). The mixture is stirred at room temperature for 15–30 min. 4-Nitrobenzyl bromide (3.98 g) is added and the reaction is stirred at room temperature for 3 days. The reaction mixture is filtered over celite to remove the $Ag_2O$. The filtrate is condensed to obtain a yellow residue. The residue is chromatographed eluting with 7% EtOAc in hexanes. TLC plates are stained in polymolybdic acid to visualize the product. Fractions homogenous by TLC are combined and condensed to afford 4.46g (84%) of 1-{[2-(benzyloxy)ethoxy]methyl}-

4-nitrobenzene as a yellow residue. To a suspension of 1-{[2-(benzyloxy)ethoxy]-methyl}-4-nitrobenzene (~240 mg) in 11 mL EtOAc is added PtO₂ (48 mg). The reaction mixture is placed under the Parr hydrogenator at 21 psi H₂ and monitored by TLC for complete reduction of the nitro group. The reaction is complete in 25 min. The reaction mixture is filtered over celite to remove the catalyst. The filtrate is condensed to afford 4-((2-(benzyloxy)ethoxy)methyl)aniline as an orange residue contaminated with residual EtOAc. In a 3-necked roundbottom connected to a Dean-Stark trap, a suspension of 4-{[2-(benzyloxy)methyl}aniline (~0.384 g) and diethyl ethoxymethylenemalonate (0.32 mL) is refluxed for 2 hrs. The reaction is cooled to room temperature. Diphenyl ether (2.5 mL) is added and the reaction mixture is heated at 230° C. for 2 hrs. The reaction mixture is cooled to room temperature and diluted with a minimal amount of CH₂Cl₂ (~1 mL). The slurry is directly loaded onto a silica column and chromatographed eluting with 100% CH₂Cl₂, followed by 2% MeOH in CH₂Cl₂. Fractions homogenous by TLC are combined and condensed to afford 123.9 mg (21%) of ethyl 6-((2-(benzyloxy)ethoxy)methyl)-4-hydroxy-3-quinolinecarboxylate as a creme solid. A mixture of ethyl 6-{[2-(benzyloxy)ethoxy]methyl}-4-hydroxy-3-quinolinecarboxylate (250 mg) and Pd/C (10%, 50 mg) is dissolved in 20 mL 3:1 CH₂Cl₂:MeOH. The reaction mixture is placed under the Parr hydrogenator at 20 psi H₂ and monitored by mass spectroscopy for complete conversion to desired product. The old palladium catalyst is replaced with fresh palladium catalyst each time the reaction was taken off the Parr. In this case, the reaction is taken off the Parr once. The reaction is complete in 18½ hrs. The reaction mixture is filtered over celite to remove the palladium. The filtrate is condensed to yield a solid. The crude product is adsorbed onto silica and chromatographed eluting with 5% MeOH in CH₂Cl₂. Fractions homogenous by TLC are combined and condensed to afford 116.2 mg (61%) of ethyl 4-hydroxy-6-[(2-hydroxyethoxy)methyl]-3-quinolinecarboxylate as a white solid. Ethyl 4-hydroxy-6-[(2-hydroxyethoxy)methyl]-3-quinolinecarboxylate (134.2 mg) and p-chlorobenzylamine (0.84 mL) are heated neat at 180° C. for 1 hr. The reaction is cooled to room temperature and partitioned between CH₂Cl₂ and H₂O. The aqueous layer is extracted with CH₂Cl₂ (2×). The organic layers are combined, dried over Na₂SO₄, and condensed to afford a yellow residue. The residue is chromatographed eluting with 4% MeOH in CH₂Cl₂. Fractions homogenous by TLC are combined and condensed to yield 133.6 mg (75%) of the title compound as a white solid.

Physical characteristics are as follows:

Mp 180–182° C.

¹H NMR (300 MHz, DMSO) 12.68, 10.47, 8.76, 8.20, 7.71, 7.39, 4.66, 4.63, 4.56, 3.53.

IR (drift) 3248, 3176, 3086, 3053, 2933, 1646, 1610, 1568, 1531, 1490, 1360, 1108, 1090, 816, 797 cm⁻¹.

MS (ESI) 387.1 (M+H)⁺, 385.2 (M−H)⁻.

Anal. Found: C, 61.89; H, 4.94; N, 7.27.

EXAMPLE 164

N-(4-Chlorobenzyl)-4-hydroxy-6-{[2-hydroxy-1-(hydroxymethyl)ethoxy]methyl }-3-quinolinecarboxamide

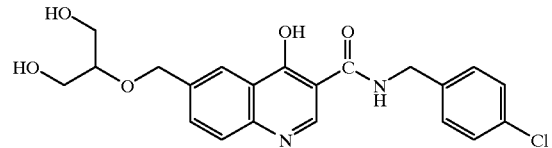

To a suspension of Arg₂O (5.12 g) in 37 mL distilled CH₂Cl₂ is added 1,3-dibenzyloxy-2-propanol (4.55 mL). The reaction is stirred at room temperature for 15–30 min. 4-Nitrobenzyl bromide (3.98 g) is added and the reaction is stirred at room temperature for 3 days. The reaction mixture is filtered over celite to remove the Arg₂O. The filtrate is condensed to obtain a yellow residue. The residue is diluted with a minimal amount of EtOAc (~1 mL) and chromatographed eluting with 7% EtOAc in hexanes. Fractions homogenous by TLC are combined and condensed to afford 4.69 g (63%) of 1-({2-benzyloxy)-1-[(benzyloxy)methyl]ethoxy}methyl)-4-nitrobenzene as a yellow residue. To a suspension of 1-{2-benzyloxy)-1-[(benzyloxy)methyl]ethoxy}-methyl)-4-nitrobenzene (4.69 g) in 15 mL EtOAc is added PtO₂ (938.3 mg). The reaction mixture is placed under the Parr hydrogenator at 20 psi H₂ and monitored by TLC for complete reduction of the nitro group. The reaction is complete in ~1 h. The reaction mixture is filtered over celite to remove the catalyst. The filtrate is condensed to afford 4-((2-benzyloxy)-1-[(benzyloxy)methyl]-ethoxy}methyl) aniline as an orange residue contaminated with residual EtOAc. In a 3-necked roundbottom connected to a Dean-Stark trap, a suspension of 4-((2-benzyloxy)-1-[(benzyloxy)methyl]ethoxy}methyl) aniline (2.539 g) and diethyl ethoxymethylenemalonate (1.36 mL) is refluxed for 2 h. The reaction is cooled to room temperature. Diphenyl ether (10 mL) is added and the reaction mixture is heated at 230° C. for 2 h. The reaction mixture is cooled to room temperature and diluted with a minimal amount of CH₂Cl₂ (~1–2 mL). The slurry is directly loaded onto a silica column and chromatographed eluting with 100% CH₂Cl₂, 1% MeOH in CH₂Cl₂, and 3% MeOH in CH₂Cl₂. The product elutes with 3% MeOH in CH₂Cl₂. Fractions homogenous by TLC are combined and condensed to afford 913.6 mg (27%) of ethyl 6-({2-(benzyloxy)-1-[(benzyloxy)methyl]ethoxy}methyl)-4-hydroxy-3-quinolinecarboxylate as a tan solid. A mixture of ethyl 6-({2-(benzyloxy)-1-[(benzyloxy)methyl]ethoxy}methyl)-4-hydroxy-3-quinolinecarboxylate (261.3 mg) and Pd/C (10%, 52.3 mg) is dissolved in 20 mL 3:1 CH₂Cl₂:MeOH. The reaction mixture is placed under the Parr hydrogenator at 25 psi H₂ and monitored by mass spectroscopy for complete conversion to desired product. The old palladium catalyst is replaced with fresh palladium catalyst each time the reaction is taken off the Parr. The reaction is complete in 40 h. The reaction mixture is filtered over celite to remove the palladium. The filtrate is condensed to yield a solid. The crude product is adsorbed onto silica and chromatographed eluting with 10% MeOH in CH₂Cl₂. Fractions homogenous by TLC are combined and condensed to afford 55.3 mg (33%) of ethyl 4-hydroxy-6-([2-hydroxy-1-(hydroxymethyl)ethoxy]methyl)-3-quinolinecarboxylate as a white solid. Ethyl 4-hydroxy-6-r([2-hydroxy-1-(hydroxymethyl)ethoxy]methyl}-3-quinolinecarboxylate (53.1 mg) and 4-chlorobenzylamine (0.30 mL) are heated neat at 180° C. for 1 h. The reaction is cooled to room temperature and partitioned between $CH_2Cl_2$ and $H_2O$ (2×). The organic layers are combined, dried over $Na_2SO_4$, and condensed to afford a yellow residue. The residue is chromatographed eluting with 5% MeOH in $CH_2Cl_2$. Fractions homogenous by TLC are combined and condensed to yield 18.8 mg (27%) of the title compound as a creme solid.

Physical characteristics are as follows:

Mp 182–184° C.;

$^1$H NMR (300 MHz, DMSO) 12.72, 10.47, 8.75, 8.21, 7.78, 7.67, 7.38, 4.75, 4.58, 3.48.

MS (ESI) 417.2 $(M+H)^+$, 415.2 $(M-H)^-$.

EXAMPLE 165

Methyl 3-{[(4-chlorobenzyl)amino]carbonyl}-4-hydroxy-6-quinolinecarboxylate

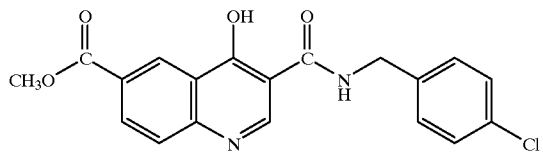

A solution of N-(4-chlorobenzyl)-4-hydroxy-6-iodo-3-quinolinecarboxamide from Example No. 40 (30.0 g), $Et_3N$ (19.1 mL), MeOH (110.6 mL), $Pd(OAc)_2$ (431 mg), and 1,3-bis (diphenylphosphino) propane (791.9 mg) in 375 mL anhydrous DMF is stirred at room temperature until everything dissolves. CO(g) is slowly bubbled through for 2 days and the reaction is maintained at 70° C. The reaction is cooled to room temperature. The product is precipitated by adding 160 mL 1N HCl to the reaction mixture. An orange solid precipitates and is collected. The solid is triturated with EtOAc, filtered, and washed with $CH_2Cl_2$ to afford 23.8 g (93%) of the title compound as an off-white solid.

Physical characteristics are as follows:

Mp 290–292° C.

$^1$H NMR (300 MHz, DMSO) 12.96, 10.26, 8.83, 8.25, 7.80, 7.39, 4.57, 3.9.

IR (drift) 3222, 1724, 1646, 1619, 1574, 1544, 1512, 1489, 1404, 1359, 1288, 1277, 1242, 1210, 738 cm$^{-1}$.

HRMS (FAB) Found 371.0794.

Anal. Found: C, 61.54; H, 3.88; N, 7.51.

EXAMPLE 166

N-(4-Chlorobenzyl)-4-hydroxy-6-(hydroxymethyl)-3-quinolinecarboxamide

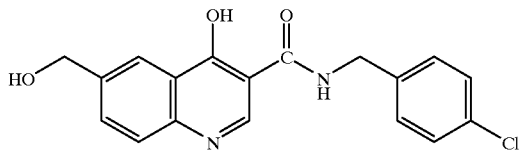

In a flame-dried 1 L 3-necked roundbottom, methyl 3-{[(4-chlorobenzyl)amino]-carbonyl}-4-hydroxy-6-quinolinecarboxylate from Example No. 165 (3.0 g) is dissolved in 700 mL distilled THF. The suspension is heated to 67° C. to solubilize the starting material. The reaction is allowed to cool to room temperature and then cooled in an ice bath to 10° C. Lithium aluminum hydride (552.2 mg) is added in one portion. The reaction is stirred at 25° C. and monitored by mass spectroscopy for conversion to desired product. The reaction is quenched by adding 2 mL $H_2O$, 2 mL 15% NaOH, and 2 mL $H_2O$ to the reaction mixture. The reaction mixture is filtered to remove the aluminum salt that had precipitated. The filtrate is condensed to obtain a yellow-green residue. The residue is adsorbed onto silica and chromatographed eluting with 2% MeOH in $CH_2Cl_2$ (1 L), 3% MeOH in $CH_2Cl_2$ (2 L), 4% MeOH in $CH_2Cl_2$ (2 L), 5% MeOH in $CH_2Cl_2$ (1 L), 6% MeOH in $CH_2Cl_2$ (1 L), and 7% MeOH in $CH_2Cl_2$ (2 L). The desired product elutes with 4–7% MeOH in $CH_2Cl_2$. Fractions homogenous by TLC are condensed to yield 1.85 g (67%) of the title compound as yellow crystals.

Physical characteristics are as follows:

Mp 288–289° C.;

$^1$H NMR (300 MHz, DMSO) 12.71, 10.48, 8.74, 8.21, 7.71, 7.66, 7.39, 5.38, 4.63, 4.56.

MS (ESI) 343.3 $(M+H)^+$, 341.3 $(M-H)^-$.

EXAMPLE 167

6-Chloro-N-[(4-chlorophenyl)methyl]-4-hydroxy-8-methyl-3-quinolinecarboxamide

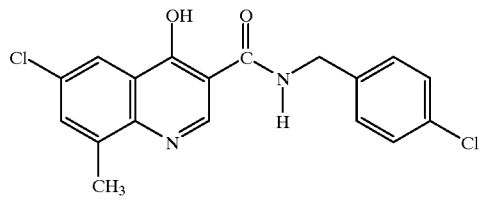

A mixture of 3.0 g of ethyl 6-chloro-4-hydroxy-8-methyl-3-quinolinecarboxylate (Maybridge Chemical Co.) and 7.0 mL of 4-chlorobenzylamine is stirred 3 h at 190° C. The mixture is cooled to 25° C. and is diluted with 35 mL of hexanes. The precipitate is collected by filtration and washed with 10 mL of hexanes. It is dried in a stream of air and then it was recrystallized from 30 mL of glacial acetic acid. It was dried at 20 torr and 100° C. for 20 h. The yield is 1.6 g (40%).

Physical properties are as follows:

Mp>230° C.

$^1$H NMR (400 MHz, DMSO-$d_6$) 12.0, 10.3, 8.61, 8.01, 7.68, 7.41–7.32, 4.52, 2.53.

MS (ES–) m/z 359 $(M-H)^-$.

HRMS (FAB): Calcd for $C_{18}H_{14}Cl_2N_2O_2+H_1$: 361.0510, found: 361.0502.

Anal. Found: C, 59.98; H, 3.96; N, 7.69.

PREPARATION 14

5,6,8-Trifluoro-4-hydroxy-3-quinolinecarboxylic acid

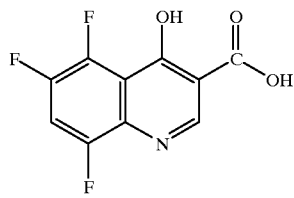

A mixture of 1.5 g ethyl 5,6,8-trifluoro-4-hydroxy-3-quinolinecarboxylate and 1.3 g sodium hydroxide in 70 mL of a 2:1 (v/v) mixture of distilled water and ethanol is refluxed for 4.5 h. The condenser is then removed and the volume of the solution is reduced by one third by distillation. To the resulting mixture is slowly and cautiously added 5 mL of glacial acetic acid. The mixture is allowed to cool to 25° C. and it is stored at this temperature for 18 h. The solid precipitate is collected by filtration and washed with with distilled water. It is dried in a stream of air and then dried for 3 days at 20 torr/120° C. This procedure yielded the title compound as 1.1 g (88%) of a white solid.

Physical properties are as follows:

Mp>230° C.

$^1$H NMR (400 MHz, DMSO-$d_6$) 8.56, 8.32–8.21.

MS (ES-): m/z 242 (M-H)$^-$.

HRMS (FAB): calcd for $C_{10}H_4F_3N_1O_3+H_1$ 244.0222, found 244.0228.

Anal. Found: C, 49.23; H, 1.75; N, 5.67.

EXAMPLE 168

N-[(4-Chlorophenyl)methyl]-5,6,8-trifluoro-4-hydroxy-3-quinolinecarboxamide

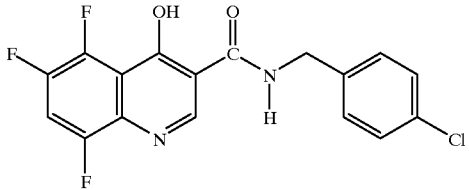

A mixture of 0.50 g 5,6,8-trifluoro-4-hydroxy-3-quinolinecarboxylic acid from preparation No. 14 and 0.366 g of carbonyldiimidazole in 8 mL of anhydrous dimethylacetamide is stirred for 2.5 h at 65° C. The mixture is cooled to 25° C. and 1 drop of distilled water was added to destroy the excess CDI. After stirring for 5 min 0.30 mL of 4-chlorobenzylamine was added. After stirring at 25° C. for 3 h the mixture is diluted with 10 mL of distilled water. The precipitate is collected by filtration and washed with three successive 10 mL aliquots of distilled water. The solid was dried in a stream of air and then at 120° C./20 torr/3 days. The yield is 0.49 g (65%) of a white solid.

Physical properties are as follows:

Mp>230° C.

$^1$H NMR (400 MHz, DMSO-$d_6$) 12.9, 10.96, 8.55, 8.13, 7.40–7.30, 4.51.

MS (ES-): m/z 365 (M-H)$^-$.

HRMS (FAB): calcd for $C_{17}H_{10}ClF_3N_2O_2+H_1$ 367.0461, found 367.0461;

PREPARATION 15

6,7-Difluoro-4-hydroxy-3-quinolinecarboxylic acid.

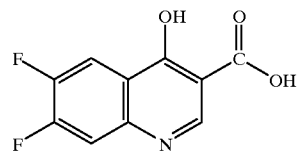

This compound was prepared using a procedure similar to that described in preparation No. 14.

Physical properties are as follows:

Mp>230° C.

$^1$H NMR (400 MHz, DMSO-$d_6$) 8.90, 8.15–8.06, 7.80–7.72.

MS (ES-) m/z 224 (M-H$^+$).

HRMS (FAB) calcd for $C_{10}H_5F_2NO_3+H$ 226.0316, found 226.0320.

Anal. Found: C, 52.16; H, 2.26; N, 5.93.

EXAMPLE 169

N-[(4-Chlorophenyl)methyl]-6,7-difluoro-4-hydroxy-3-quinolinecarboxamide

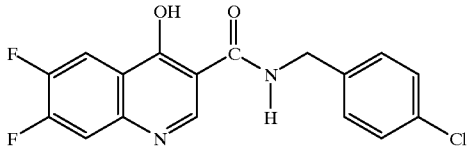

A mixture of 0.5 g of 6,7-difluoro-4-hydroxy-3-quinolinecarboxylic acid from preparation No. 15 and 0.435 g of carbonyldiimidazole in 8 mL of anhydrous dimethylacetamide is stirred 4 h at 65° C. The reaction mixture is cooled to 25° C. and 2 drops of distilled water is added. After an additional 10 min 0.34 mL of 4-chlorobenzylamine is added. The mixture is stirred 26 h at 25° C. and then diluted with 10 mL of distilled water. After standing for an additional 30 min the precipitate is collected by filtration and washed with three 10 mL portions of distilled water. The solid is dried in a stream of air and then at 20 torr/120° C./3 days. The yield is 0.51 g (70%) of a white solid.

Physical properties are as follows:

Mp>220° C.

HRMS (EI) calcd for $C_{17}H_{11}ClF_2N_2O_2+H$: 349.0555, found 349.0551.

Anal. Found for $C_{17}H_{11}ClF_2N_2O_2$ 0.3 $H_2O$: C, 64.13; H, 4.51; N, 8.29

PREPARATION 16

Ethyl 6-(cyanosulfanyl)-8-fluoro-4-hydroxy-3-quinolinecarboxylate.

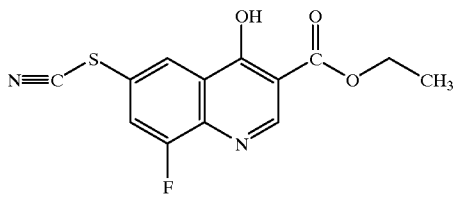

A mixture of 48 g of 4-(cyanosulfanyl)-2-fluoroaniline and 57.7 g of diethyl ethoxymethylenemalonate is stirred at 130° C. After 1.5 h the mixture is diluted with 200 mL of a 1:1 mixture of cyclohexane and toluene. The mixture is cooled to 0° C. and the precipitate collected by filtration. It is washed with two 75 mL portions of a 1:1 mixture of cyclohexane and toluene, dried in a stream of air, and then it dissolved in 400 mL of diphenyl ether. The mixture is refluxed for 1 h and then cooled to 25° C. It is diluted with 1 L of 1:1 toluene/cyclohexane and the precipitate collected by filtration. The solid is dried in a stream of air to give 20 g of the title compound.

Physical properties are as follows:

MS (ESI+) for $C_{13}H_{10}FN_2O_3S$ m/z 293 (M+H)+.

Anal. Found: C, 53.08; H, 3.19; N, 9.48.

PREPARATION 17

Ethyl 8-fluoro-4-hydroxy-6-sulfanyl-3-quinolinecarboxylate.

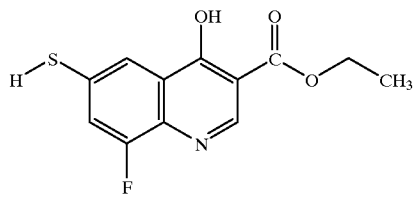

A mixture of 20 g of ethyl 6-(cyanosulfanyl)-8-fluoro-4-hydroxy-3-quinolinecarboxylate from preparation No. 16, 125 mL of DMF and 12.6 g of dithiothreitol is stirred for 5 h at 25° C. It is poured into 1 L of deoxygenated ice water and the precipitate collected by filtration, washed with two 200 mL portions of distilled water, and then dried in a stream of nitrogen. The title compound is obtained as 10.5 g of a white solid.

Physical properties are as follows:

MS (ESI+) for $C_{12}H_{11}FNO_3S$ m/z 268 (M+H)+.

Anal. Found for $C_{12}H_{10}FNO_3S$ 0.3 $H_2O$: C, 52.62; H, 3.55; N, 5.23.

PREPARATION 18

Ethyl 8-fluoro-4-hydroxy-6-(methylsulfanyl)-3-quinolinecarboxylate.

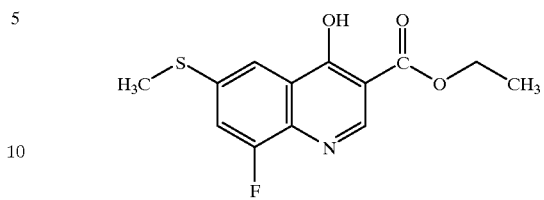

A suspension of 2.0 g of ethyl 8-fluoro-4-hydroxy-6-sulfanyl-3-quinolinecarboxylate from preparation No. 17 in 15 mL of DMF is deoxygenated in a stream of nitrogen. The mixture is treated with 0.56 mL of methyl iodide and then with 1.24 mL of triethylamine. After 20 min the mixture is poured into 15 mL of distilled water. The precipitate is collected by filtration, washed three times with water and then with methanol. It is dried in a stream of air to give 1.38 g of the title compound as a white powder.

Physical properties are as follows:

MS (ESI+) for $C_{13}H_{13}FNO_3S$ m/z 282 (M+H)+.

Anal. Found for $C_{13}H_{12}FNO_3S$ 0.1 $H_2O$: C, 55.08; H, 4.27; N, 5.04.

PREPARATION 19

Ethyl 8-fluoro-4-hydroxy-6-[(2-hydroxyethyl)sulfanyl]-3-quinolinecarboxylate.

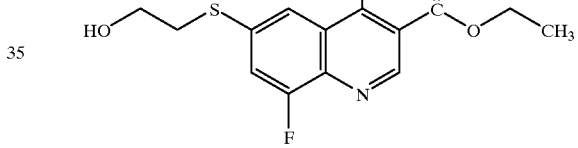

This compound is prepared using a procedure analogous to that described in preparation No. 17 except that a slight excess of 2-chloroethanol was used in place of methyl iodide and the reaction is allowed to proceed for 14 h prior to the mixture being poured into water.

Physical properties are as follows:

MS (ESI+) for $C_{14}H_{15}FNO_4S$ m/z 312 (M+H)+.

Anal. Found for $C_{14}H_{14}FNO_4S$ 0.3 $H_2O$: C, 53.38; H, 4.51; N, 4.62

PREPARATION 20

Ethyl 8-fluoro-4-hydroxy-6-{[(2-methoxyethoxy)methyl]sulfanyl-3-quinolinecarboxylate. [31565-JT-146.]

This compound is prepared using a procedure analogous to that described in preparation No. 18 except that a slight excess of methoxyethoxymethyl chloride is used in place of methyl iodide and the reaction allowed to proceed for 0.5 h prior to the mixture being poured into water.

Physical properties are as follows:

MS (ESI+) for $C_{16}H_{19}FNO_5S$ m/z 356 (M+H)+;

PREPARATION 21

Ethyl 8-fluoro-4-hydroxy-6-{[2-(4-morpholinyl)ethyl]sulfanyl-3-quinolinecarboxylate. [31565-JT-143.]

This compound is prepared using a procedure analogous to that described in preparation No.18 except that a slight excess of N-(2-chloroethyl)morpholine hydrochloride is used in place of methyl iodide and the reaction allowed to proceed for 18 h prior to the mixture being poured into water. The product is dissolved in ethyl acetate and filtered to remove an insoluble impurity. Evaporation of the filtrate gave the title compound.

Physical properties are as follows:

MS (ESI+) for $C_{18}H_{22}FN_2O_4S$ m/z 381 (M+H)+;

PREPARATION 22

Ethyl 8-fluoro-4-hydroxy-6-[(2-aminoethyl)sulfanyl)-3-quinolinecarboxylate, hydrobromide [31565-JT-140]

A suspension of 1.0 g of ethyl 8-fluoro-4-hydroxy-6-sulfanyl-3-quinolinecarboxylate from preparation No. 17 in 10 mL of DMF is deoxygenated in a stream of nitrogen. The mixture is treated with 0.85 g of 2-bromoethylamine hydrobromide and then with 0.57 mL of triethylamine. After 15 min the reaction mixture is diluted with 20 mL of ethyl acetate and filtered. The solid is washed with two 50 mL portions of ethyl acetate, then with two 30 mL portions of distilled water, and finally with two 30 mL portions of ethyl acetate. The solid is dried in a stream of air to provide the title compound as 0.42 g of a solid.

Physical properties are as follows:

MS (ESI+) for $C_{14}H_{16}FN_2O_3S$ m/z 311 (M+H)+.

Anal. Found for $C_{14}H_{15}FN_2O_3S$ HBr 0.5 $H_2O$: C, 42.30; H, 4.37; N, 6.80.

EXAMPLE 170

N-(4-Chlorobenzyl)-8-fluoro-4-hydroxy-6-(methylsulfanyl)-3-quinolinecarboxamide.

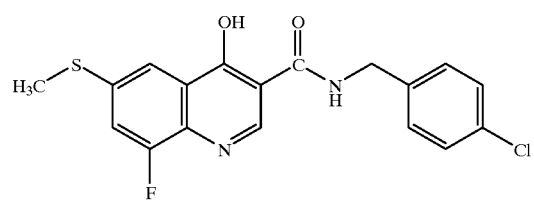

This compound was prepared from ethyl 8-fluoro-4-hydroxy-6-(methylsulfanyl)-3-quinolinecarboxylate (Preparation No. 18) using a procedure analogous to that described in Example No. 167.

Physical properties are as follows:

MS (ESI+) for $C_{18}H_{15}ClFN_2O_2S$ m/z 377 (M+H)+.

Anal. Found for $C_{18}H_{14}ClFN_2O_2S$ $H_2O$: C, 54.49; H, 3.91; N, 7.04.

EXAMPLE 171

N-(4-Chlorobenzyl)-8-fluoro-4-hydroxy-6-[(2-hydroxyethyl)sulfanyl)]-3-quinolinecarboxamide

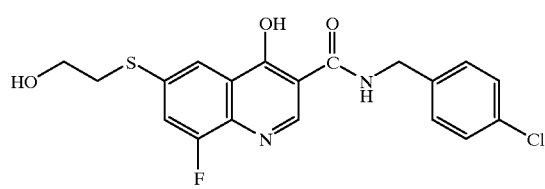

This compound is prepared from ethyl 8-fluoro-4-hydroxy-6-[(2-hydroxyethyl)sulfanyl)]-3-quinolinecarboxylate (Preparation No. 19) using a procedure analogous to that described in Example No. 167.

Physical properties are as follows:

MS (ESI+) for $C_{19}H_{17}ClFN_2O_3S$ m/z 407 (M+H)+.

Anal. Found for $C_{19}H_{16}ClFN_2O_3S \cdot 0.3 H_2O$: C, 55.08; H, 3.92; N, 6.78.

EXAMPLE 172

6-[(2-Aminoethyl)sulfanyl]-N-(4-chlorobenzyl)-8-fluoro-4-hydroxy-3-quinolinecarboxamide, hydrobromide

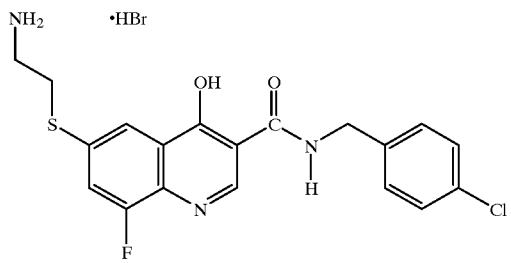

This compound is prepared from ethyl 8-fluoro-4-hydroxy-6-[(2-aminoethyl)-sulfanyl]-3-quinolinecarboxylate hydrobromide (Preparation No. 22) using a procedure analogous to that described in Example No. 167. The product is isolated by distilling off the excess 4-chlorobenzylamine at 1 torr and trituration of the crude product with methanol.

Physical properties are as follows:

MS (ESI+) for $C_{19}H_{18}ClFN_3O_2S$ m/z 406 (M+H)+.

Anal. Found for $C_{19}H_{17}ClFN_3O_2S$ 1.5 HBr: C, 42.95; H, 3.36; N, 7.64.

EXAMPLE 173

N-(4-Chlorobenzyl)-8-fluoro-4-hydroxy-6-{[(2-methoxyethoxy)-methyl]sulfanyl}-3-quinolinecarboxamide

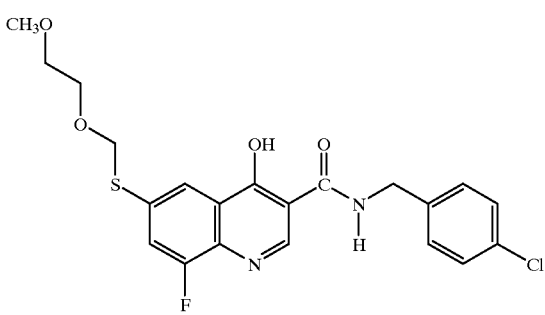

This compound is prepared from ethyl 8-fluoro-4-hydroxy-6-{[(2-methoxyethoxy)-methyl]sulfanyl-3-quinolinecarboxylate (Preparation No. 20) using a procedure analogous to that described in Example No. 167. The product is isolated by adding 2 mL of touene, 4 mL of hexanes, and 10 mL of 20% aqueous acetic acid to the cooled reaction mixture. The product is collected by filtration and purified by recrystallizing it from ethyl acetate/diethyl ether followed by a second crystallization from 2% acetic acid in methanol.

Physical properties are as follows:

MS (ESI+) for $C_{21}H_{21}ClFN_2O_4S$ m/z 451 (M+H)+;

EXAMPLE 174

N-(4-Chlorobenzyl)-8-fluoro-4-hydroxy-6-{[(2-(4-morpholinyl)-ethyl]sulfanyl}-3-quinolinecarboxamide

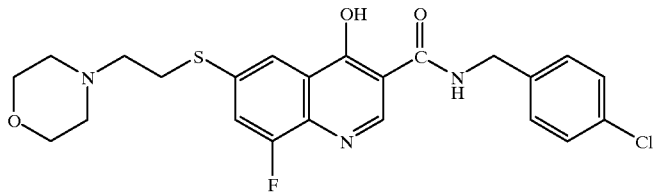

This compound is prepared from ethyl 8-fluoro-4-hydroxy-6-{[2-(4-morpholinyl)ethyl]sulfanyl-3-quinolinecarboxylate (Preparation 21) using a procedure analogous to that described in Example No. 167. The product is precipitated from the cooled reaction mixture by adding ethyl acetate and diethyl ether, collected by filtration, and washed with a small quanity of ether.

Physical properties are as follows:

Anal. Found: C, 57.52; H, 4.89; N, 8.69.

EXAMPLE 175

N-(4-Chlorobenzyl)-8-fluoro-4-hydroxy-6-(methylsulfinyl)-3-quinolinecarboxamide.

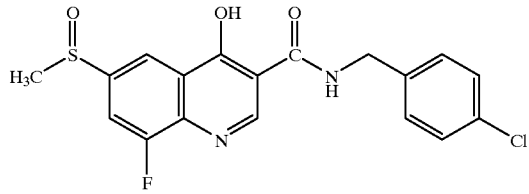

A suspension of 150 mg of N-(4-chlorobenzyl)-8-fluoro-4-hydroxy-6-(methylsulfanyl)-3-quinolinecarboxamide from Example No. 170 and 0.75 mL of DMF in 15 mL of chloroform is treated with 79 mg of m-chloroperbenzoic acid. After stirring for 10 min the mixture is treated with 10 mL of a concentrated aqeous solution of sodium bisulfite. After stirring an addtional 5 min the phases are separated and the organic layer is washed with 15 mL of a saturated aqueous solution of sodium bicarbonate. The organic layer is dried ($MgSO_4$) and the solvent was evaporated at reduced pressure. The residual solid is washed with a small volume of diethyl ether and dried to give 95 mg of a white solid.

Physical properties are as follows:

MS (ESI+) for $C_{18}H_{15}ClFN_2O_3S$ m/z 393 (M+H)$^+$.

Anal. Found for $C_{18}H_{14}ClFN_2O_3S$ 0.6 $H_2O$: C, 53.34; H, 3.61; N, 6.96.

EXAMPLE 176

N-(4-Chlorobenzyl)-8-fluoro-4-hydroxy-6-(methylsulfonyl)-3-quinolinecarboxamide.

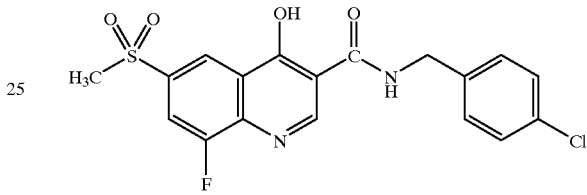

A mixture of 200 mg of N-(4-chlorobenzyl)-8-fluoro-4-hydroxy-6-(methylsulfanyl)-3-quinolinecarboxamide from Example No. 170, 20 mL of chloroform, 0.75 mL of DMF, and 200 mg of m-chloroperbenzoic acid is stirred at 25 ° C. After 18 h, an additional 140 mg of m-chloroperbenzoic acid is added and the mixture refluxed for 7 h. The cooled mixture is filtered and the solid is washed with two 5 mL portions of diethyl ether. It is recrystallized from 3 mL of acetic acid to give the title compound as 62 mg of a white powder.

Physical properties are as follows:

MS (ESI+) for $C_{18}H_{15}ClFN_2O_4S$ m/z 409 (M+H)$^+$.

Anal. Found for $C_{18}H_{14}ClFN_2O_4S$ 0.4 $H_2O$: C, 51.97; H, 3.59; N, 6.73.

EXAMPLE 177

N-(4-Chlorobenzyl)-8-fluoro-4-hydroxy-6-[(2-hydroxyethyl)sulfinyl]-3-quinolinecarboxamide.

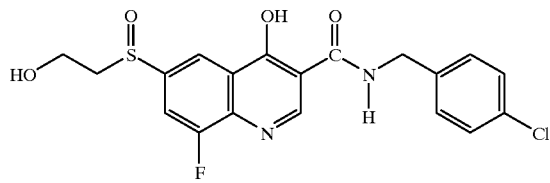

This compound was prepared from N-(4-chlorobenzyl)-8-fluoro-4-hydroxy-6-[(2-hydroxyethyl)sulfanyl]-3-quinolinecarboxamide (Example No. 171) and an equimolar amount of m-chloroperbenzoic acid according to a procedure similar to described in Example 175.

Physical properties are as follows:

MS (ESI+) for $C_{19}H_{17}ClFN_2O_4S$ m/z 423 (M+H)$^+$;

EXAMPLE 178

N-(4-Chlorobenzyl)-4-hydroxy-6-(2-thienyl)-3-quinolinecarboxamide

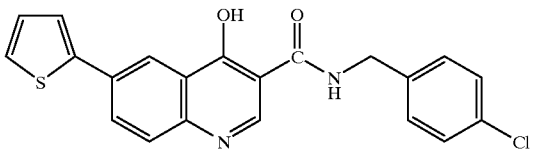

A deoxygenated mixture of 0.75 g of N-(4-chlorobenzyl)-4-hydroxy-6-iodo-3-quinolinecarboxamide from Example No. 40, 0.75 g of 2-(tributylstannyl)thiophene, 60 mg of bis(triphenylphosphine)palladium(II)dichloride, 7.5 mL of dioxane and 2.5 mL of DMPU is stirred for 2 h at 100° C. The cooled mixture is diluted with 20 mL of hexanes and 60 mL of distilled water. The mixture is stirred for 5 minutes and then filtered. The solid is washed with two 50 mL portions of distilled water and then with two 25 mL portions of methyl t-butyl ether. It is then dissolved in 20 mL of refluxing acetic acid, treated with 2 g of activated carbon and filtered through celite. The volume of the filtrate is reduced to 10 mL and the hot solution diluted with 10 mL of distilled water. Upon cooling, 0.3 g of the title compound precipitates and is collected by filtration.

Physical properties are as follows:

MS (ESI+) for $C_{21}H_{15}ClN_2O_2SNa$: m/z 417 (M+Na)$^+$.

Anal. Found for $C_{21}H_{15}ClN_2O_2S$ 0.2 $H_2O$: C, 63.25; H, 3.66; N, 7.02.

EXAMPLE 179

N-(4-Chlorobenzyl)-4-hydroxy-6-(2-hydroxyethoxy)-3-quinolinecarboxamide

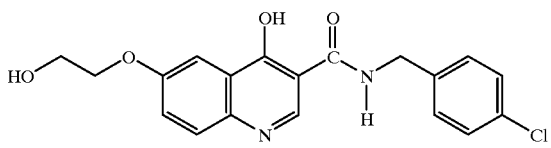

Sodium hydroxide (6.22 g) is added to a solution of p-nitrophenol (21.45 g) in DMF (300 mL) and stirred until the reagents are fully dissolved. After a dropwise addition of 2-chloroethanol (10.66 ml), the reaction mixture is heated to 100° C. for 72 hours. After filtering and evaporating the solvent under reduced pressure, the resulting oil is recrystallized in a methanol/water mixture and filtered to afford 21.62 g (92%) of 2-(4-nitrophenoxy)-1-ethanol. A mixture of 2-(4-nitrophenoxy)-1-ethanol (6.17 g) and palladium on carbon (0.08 g) in EtOH (120 mL) is hydrogenated in a 500 mL Parr jar at 33 psi for 18 hrs. Vacuum filtration through celite and evaporation under reduced pressure affords 5.00 g (96%) of 2-(4-aminophenoxy)-1-ethanol. This material is combined with diethyl ethoxymethylenemalonate (7 mL) and heated to 130° C. for 1 hr in a round bottom flask under a gentle stream of nitrogen. The mixture is cooled, diluted with 1:1 cyclohexane/toluene (20 mL), and filtered to afford 9.1 g (86%) of diethyl 2-{[4-(2-hydroxyethoxy)anilinorlmethylene}-malonate. A solution the resulting malonate (8.59 g) in acetic acid (15 mL) and acetic anhydride (4 mL) is heated to 60° C. for 36 hrs. The reaction mixture is diluted with water, extracted with ethyl acetate and washed with saturated sodium bicarbonate. Evaporation under reduced pressure leaves a brown oil which is recrystallized from 1:1 methanol/water and filtered to afford 7.09 g (73%) diethyl 2-({4-[2-(acetyloxy)ethoxy]anilino}methylene)malonate. Diethyl 2-({4-[2-(acetyloxy)ethoxy]anilino}methylene)malonate (6.55 g) is dissolved in diphenyl ether (75 mL) and refluxed at 250° C. for 1 hr. After the mixture is cooled and diluted with 250 mL toluene, the resulting precipitate is collected by filtration, washed with toluene and recrystallized from aqueous acetic acid. This procedure yielded 0.50 g (9%) of ethyl 6-[2-(acetyloxy)ethoxy]-4-hydroxy-3-quinolinecarboxylate. The resulting carboxylate ester (0.49 g) and 4-chlorobenzylamine (0.90 mL) are heated to 175° C. for 2 hrs. After the reaction mixture is cooled and diluted with xylenes, the dark solid is filtered. Recrystallization from acetic acid and water affords 0.150 g (26%) of the title compound as a beige solid.

Physical characteristics are as follows:

Mp 246–248° C.

$^1$H NMR (DMSO-d$_6$) 12.7, 10.5, 8.7, 7.6, 7.4, 4.89, 4.5, 4.1, 3.8.

MS (FAB) for m/z (M+H)$^+$: calcd 373.0955, found 373.0946.

PREPARATION 23

4-(Aminomethyl)benzonitrile

A mixture of 4-(bromomethyl)benzonitrile (7.1 g) and sodium azide (2.6 g) in DMF (40 mL) is stirred for 19 hrs. The reaction mixture is then diluted with water (150 mL) and extracted with ether (2×50 mL). The organic phases are combined, washed with water (50 mL) and brine (50 mL), and dried with MgSO$_4$. Filtration and evaporation of the solvent leaves 5.5 g of 4-(azidomethyl)benzonitrile as a clear, colorless oil.

Triphenylphosphine (7.67 g) is added to a solution of 4-(azidomethyl)-benzonitrile (4.19 g) in THF (30 mL) and stirred for 1 hr. Water (10 mL) is added, and the solution is stirred for 16 hrs. The reaction mixture is diluted with ether (50 mL) and extracted with HCl (3 N, 3×25 mL) and water (1×25 mL). The aqueous phases are combined and washed with ether (50 mL). Sodium hydroxide is added until the pH =12. After extracting with ether (2×50 mL), the solution is dried with MgSO$_4$ and filtered. The solvent is evaporated under reduced pressure. The resulting crude mixture is then purified via bulb to bulb distillation at 150° C. and 1 torr to afford 1.74 g (50%) of the title compound as a clear, colorless oil.

Physical characteristics are as follows:

$^1$H NMR (DMSO-d$_6$) 7.7, 7.5, 3.8, 1.9.

EXAMPLE 180

N-(4-Chlorobenzyl)-8-fluoro-4-hydroxy-6-(4-morpholinylcarbonyl)-3-quinolinecarboxamide

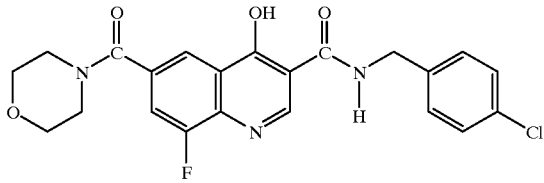

To a pressure tube containing N-[(4-chlorophenyl)methyl]-8-fluoro-4-hydroxy-6-iodo-3-quinolinecarboxamide of Example No. 5 (0.23 g), palladium (II) acetate (12 mg), and 1,3-bis(diphenylphosphino) propane (20 mg) is added DMF (5 mL), triethylamine (0.14 mL) and morpholine (0.13 mL). The reaction mixture is placed under an atmosphere of carbon monoxide gas, then tightly sealed and heated at 60° C. overnight. The reaction is cooled to room temperature and concentrated under reduced pressure. The residue is partioned between dichloromethane and aqueous phosphate buffer (0.1M, pH=4). The organic phase is washed with aqueous phosphate buffer (0.1M, pH=10), brine, dried ($Na_2SO_4$), filtered and concentrated under reduced pressure. The residue is chromatographed on silica eluting with 2% $MeOH:CH_2Cl_2$ to 8% $MeOH:CH_2Cl_2$. The product-containing fractions are evaporated to give 0.13 g of the title compound as a tan solid.

Physical characteristics are as follows:

$^1$H NMR (300 MHz, $CDCl_3$) 10.3, 8.7, 8.2, 7.6, 7.3, 4.6, 3.7

MS (ESI) m/z 444 (M+H$^+$).

EXAMPLE 181

$N^3$-(4-Chlorobenzyl)-8-fluoro-4-hydroxy-$N^6$-(2-hydroxyethyl)-3,6-quinolinedicarboxamide

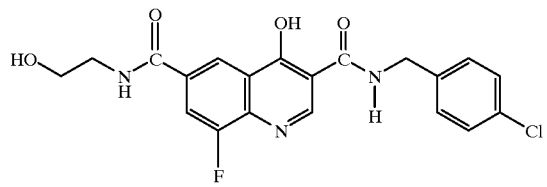

To a pressure tube containing N-[(4-chlorophenyl)methyl]-8-fluoro-4-hydroxy-6-iodo-3-quinolinecarboxamide of Example No. 5 (0.46 g) under an atmosphere of carbon monoxide gas is added DMF (4 mL). The suspension is treated with triethylamine (0.28 mL), palladium (II) acetate (23 mg), and 1,3-bis (diphenylphosphino)propane (41 mg). The mixture is treated with ethanolamine (0.24 mL), then tightly sealed and heated at 90° C. overnight with vigorous stirring. The reaction is cooled to room temperature and concentrated under reduced pressure. The residue is adsorbed onto silica and chromatographed on silica eluting with 3% $MeOH:CH_2Cl_2$ to 9% $MeOH:CH_2Cl_2$. The product-containing fractions are evaporated to give 0.12 g of the title compound as a tan solid.

Physical characteristics are as follows:

$^1$H NMR (300 MHz, DMSO-$d_6$) 10.2, 8.8, 8.6, 8.1, 7.4, 4.5, 3.5, 3.3

MS (ESI) m/z 418 (M+H$^+$).

EXAMPLE 182

$N^3$-(4-Chlorobenzyl)-8-fluoro-4-hydroxy-$N^6$,$N^6$-dimethyl-3,6-quinolinedicarboxamide

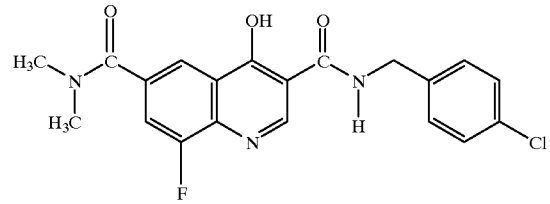

Using the procedure of Example No. 181, the following compound is also isolated.

Physical characteristics are as follows:

$^1$H NMR (300 MHz, DMSO-$d_6$) 13.0, 10.2, 8.7, 8.0, 7.8, 7.4, 4.5, 3.0

MS (ESI) m/z 402 (M+H$^+$).

EXAMPLE 183

$N^3$-(4-Chlorobenzyl)-8-fluoro-4-hydroxy-$N^6$-(4-hydroxyphenethyl)-3,6-quinolinedicarboxamide

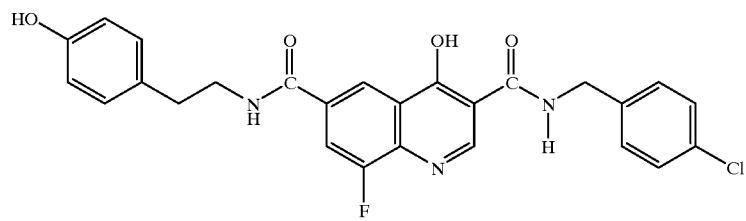

Using an analogous procedure to Example No. 181, the following compound is isolated from reaction with tyramine.

Physical characteristics are as follows:

$^1$H NMR (300 MHz, DMSO-$d_6$) 13.0, 10.2, 9.1, 8.7, 8.6, 8.0, 7.4, 7.0, 6.6, 4.5, 3.4, 2.7.

MS (ESI) m/z 494 (M+H$^+$).

EXAMPLE 184

N³-(4-Chlorobenzyl)-8-fluoro-4-hydroxy-3,6-quinolinedicarboxamide

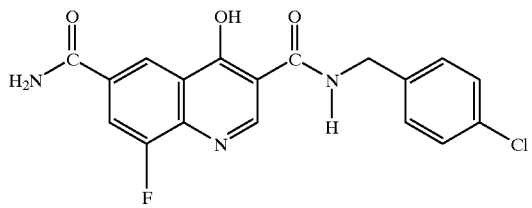

Using an analogous procedure to Example No. 181, the following compound is isolated from reaction with hydroxylamine in DMF.

Physical characteristics are as follows:

¹H NMR (300 MHz, DMSO-$d_6$) 13.0, 10.2, 8.6, 8.3, 8.1, 7.6, 7.4, 4.5

MS (ESI) m/z 374 (M+H⁺).

PREPARATION 24

3-{[(4-Chlorobenzyl)amino]carbonyl}-8-fluoro-4-hydroxy-6-quinolinecarboxylic acid

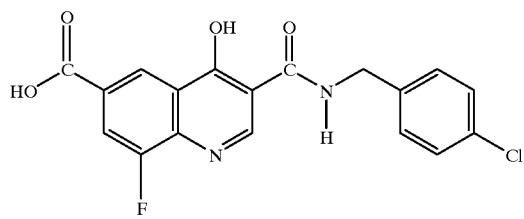

To a flask containing N-[(4-chlorophenyl)methyl]-8-fluoro-4-hydroxy-6-iodo-3-quinolinecarboxamide of Example No. 5 (0.91 g) and potassium carbonate (2.24 g) under an atmosphere of carbon monoxide gas is added N-methylpiperidine (9 mL). The reaction mixture is treated with palladium (II) acetate (0.5 g) followed by water (1 mL) and heated at 90° C. overnight. The reaction is cooled to room temperature and added to stirring diethyl ether (150 mL). The resulting precipitate is collected by filtration. The precipitate is dissolved in a small amount of methanol:acetonitrile, decanted and re-precipitated from diethyl ether. The resulting solid is collected by filtration and dried in vacuo to give 0.40 g of the title compound as a light green solid.

Physical characteristics are as follows:

¹H NMR (300 MHz, DMSO-$d_6$) 10.1, 8.6, 8.0, 7.4, 4.5

MS (ESI) m/z 375 (M+H⁺).

EXAMPLE 185

N³,N⁶-Bis(4-chlorobenzyl)-8-fluoro-4-hydroxy-3,6-quinolinedicarboxamide

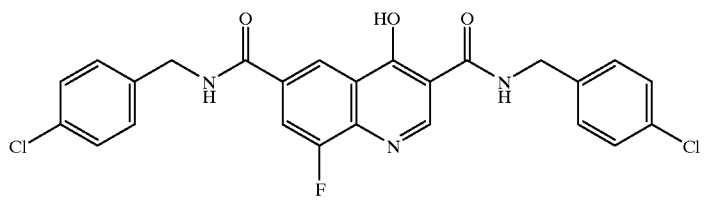

To a flask containing 3-{[(4-chlorobenzyl)amino]carbonyl}-8-fluoro-4-hydroxy-6-quinolinecarboxylic acid from Preparation No. 24 (0.11 g) and THF (3 mL) is added thionyl chloride (0.075 mL). The reaction mixture is stirred overnight then treated with one drop of DMF. After 4 hours, the reaction is concentrated under reduced pressure. The residue is triturated with toluene (2×) and dried in vacuo to afford a light yellow solid. The solid is dissolved in pyridine (2 mL), treated with p-chlorobenzylamine (0.04 mL), and a small amount of 4-dimethylaminopyridine is added. After stirring overinght, the reaction is concentrated under reduced pressure. The residue is triturated with toluene (3×) and dried in vacuo. The residue is adsorbed onto silica and chromatographed on silica eluting with 2% MeOH:CH$_2$Cl$_2$ to 6% MeOH:CH$_2$Cl$_2$. The product-containing fractions are evaporated to give a solid which is crystallized from methanol:toluene to afford 0.04 g of the title compound.

Physical characteristics are as follows:

¹H NMR (300 MHz, DMSO-$d_6$) 13.0, 10.2, 9.4, 8.6, 8.1, 7.4, 4.6, 4.5

HRMS (EI) found 497.0708.

PREPARATION 25
tert-Butyl-3-{[(4-chlorobenzyl)amino]carbonyl}-8-fluoro-4-hydroxy-6-quinolinylcarbamate

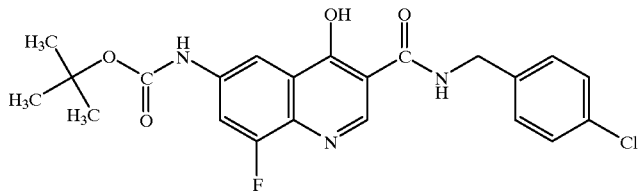

To a flask containing 3-{[(4-chlorobenzyl)amino]carbonyl}-8-fluoro-4-hydroxy-6-quinolinecarboxylic acid of Preparation No. 24 (1.33 g) and tert-butanol (20 mL) under an atmosphere of argon gas is added triethylamine (2.0 mL) and diphenyl-phosphoryl azide (1.0 mL). The reaction mixture is heated at reflux overnight. The reaction is cooled to room temperature and concentrated under reduced pressure. The residue is adsorbed onto silica and chromatographed on silica eluting with 2% MeOH:CH$_2$Cl$_2$ to 6% MeOH:CH$_2$Cl$_2$. The product-containing fractions are evaporated to give 0.93 g of the title compound as a tan solid.

Physical characteristics are as follows:

$^1$H NMR (300 MHz, DMSO-d$_6$) 12.8, 10.3, 9.9, 8.5, 8.1, 7.8, 7.4, 4.5, 1.48

MS (ESI) m/z 446 (M+H$^+$).

EXAMPLE 186

6-Amino-N-(4-chlorobenzyl)-8-fluoro-4-hydroxy-3-quinolinecarboxamide

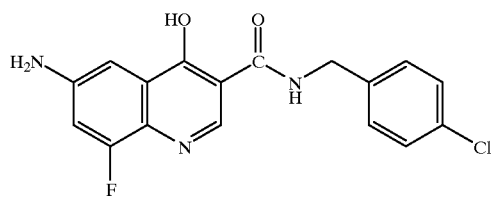

To a flask containing tert-butyl-3-{[(4-chlorobenzyl)amino]carbonyl}-8-fluoro-4-hydroxy-6-quinolinylcarbamate from Preparation No. 25 (0.06 g) and dichloromethane (2 mL) is added trifluoroacetic acid (2 mL). The reaction mixture is stirred 1 hour then concentrated under reduced pressure. The residue is triturated with toluene (3x) and dried in vacuo. The residue is adsorbed onto silica and chromatographed on silica eluting with 2% MeOH:CH$_2$Cl$_2$ to 6% MeOH:CH$_2$Cl$_2$. The product-containing fractions are evaporated to give 0.04 g of the title compound as a tan solid.

Physical characteristics are as follows:

$^1$H NMR (300 MHz, DMSO-d$_6$) 12.5, 10.5, 8.4, 7.4, 7.1, 7.0, 4.5

MS (FAB) m/z 346 (M+H$^+$)

HRMS (FAB) found 346.0761 (M+H$^+$).

EXAMPLE 187

N-(4-Chlorobenzyl)-8-fluoro-4-hydroxy-6-{[(4-methoxyphenyl)-sulfonyl]amino}-3-quinolinecarboxamide

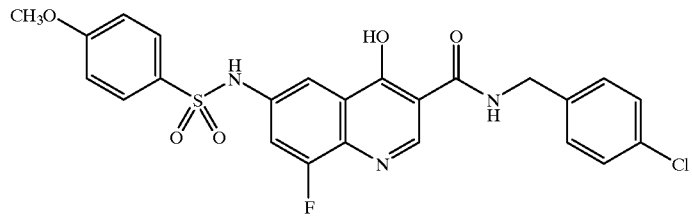

To a flask containing 6-amino-N-(4-chlorobenzyl)-8-fluoro-4-hydroxy-3-quinolinecarboxamide from Example No. 186 (0.06 g) and pyridine (1.5 mL) is added 4-methoxyphenylsulfonyl chloride (0.04 g). The reaction mixture is stirred for 2 hours then concentrated under reduced pressure. The residue is triturated with toluene (2x) and dried in vacuo. The residue is adsorbed onto silica and chromatographed on silica eluting with 2% MeOH:CH$_2$Cl$_2$ to 6% MeOH:CH$_2$Cl$_2$. The product-containing fractions are evaporated to give 0.04 g of the title compound as a white solid.

Physical characteristics are as follows:

$^1$H NMR (300 MHz, DMSO-d$_6$) 12.9, 10.7, 10.2, 8.5, 7.7, 7.4, 7.0, 4.5, 3.8

MS (ESI) m/z 516 (M+H$^+$)

Anal. found: C, 55.99; H, 3.81; N, 7.85.

EXAMPLE 188

N-(4-Chlorobenzyl)-4-hydroxy-6-[(2-hydroxyethyl)amino]-3-quinolinecarboxamide

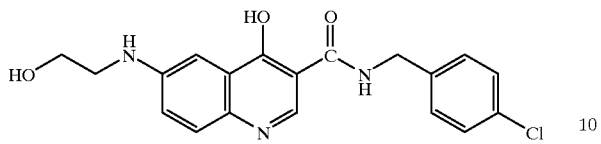

To a pressure tube containing 1-fluoro-4-nitrobenzene (10.6 mL) and absolute ethanol (20 mL) under an atmosphere of argon gas is added ethanolamine (7.2 mL). The reaction is tightly capped and heated to 90° C. After 1 hour, the reaction is cooled to room temperature and concentrated under reduced pressure. The residue is dried in vacuo. The solid is crystallized from 95% ethanol to give 4.1 g of 2-(4-nitroanilino)-1-ethanol as yellow crystals.

To a flask containing 2-(4-nitroanilino)-1-ethanol (0.91 g) in dichloromethane (25 mL) at 0° C. is added triethylamine (1.8 mL), acetyl chloride (0.85 mL) and 4-dimethylaminopyridine (0.06 g). The reaction mixture is allowed to warm to room temperature over 3 hours. The reaction mixture is diluted with diethyl ether, washed with saturated aqueous sodium bicarbonate, brine, dried over sodium sulfate and concentrated under reduced pressure. The residue is chromatographed on silica eluting with 50% ethyl acetate in heptane. The product-containing fractions are evaporated to give 0.61 g of 2-(4-Nitroanilino)ethyl acetate as a yellow solid To a Parr bottle containing 2-(4-nitroanilino)ethyl acetate (0.61 g) and ethyl acetate (10 mL) is added 10% palladium on carbon (0.05 g). The reaction mixture is shaken for 2 hours under 50 psi of hydrogen gas. The reaction mixture is filtered through Celite with ethyl acetate washes. The filtrate is concentrated under reduced pressure. The residue is treated with diethyl ethoxymethylenemalonate (0.60 mL) and heated to 135° C. under a flow of argon gas. After 1 hour the reaction is cooled to room temperature, adsorbed onto silica gel, and chromatographed on silica eluting with 60% to 80% ethyl acetate in heptane. The product-containing fractions are evaporated to give 0.45 g diethyl 2-[(4-{[2-(acetyloxy)ethyl]amino}-anilino)methylene]malonate as a yellow solid.

To a flask containing diethyl 2-[(4-{[2-(acetyloxy)ethyl]amino}anilino)-methylene]-malonate (0.18 g) is added diphenyl ether (2 mL). The reaction mixture is heated from room temperature to 250° C. over 30 minutes under a flow of argon gas. The reaction is cooled to room temperature and filtered. The collected precipitate is washed repeatedly with methanol:dichloromethane and the filtrate is concentrated under reduced pressure. The residue is adsorbed onto silica and chromatographed on silica eluting with 5% to 50% methanol in dichloromethane. The product-containing fractions are evaporated to give 0.04 g of ethyl 6-{[2-(acetyloxy)ethyl]amino}-4-hydroxy-3-quinolinecarboxylate.

To a flask containing ethyl 6-{[2-(acetyloxy)ethyl]amino)-4-hydroxy-3-quinolinecarboxylate (0.04 g) is added p-chlorobenzylamine (0.5 mL). The reaction is tightly capped and heated to 160° C. overnight. The reaction is cooled to room temperature, adsorbed onto silica and chromatographed on silica eluting with 3% to 10% methanol in dichloromethane. The product-containing fractions are evaporated to give 0.02 g of the title compound as a yellow solid.

Physical characteristics are as follows:
$^1$H NMR (300 MHz, DMSO-$d_6$) 10.7, 8.5, 7.4, 7.3, 7.2, 6.1, 4.7, 4.5, 3.6, 3.2

HRMS (FAB) found 372.1122 (M+H$^+$).

EXAMPLE 189

N-(4-Chlorobenzyl)-6-[ethyl(2-hydroxyethyl)amino]-4-hydroxy-3-quinolinecarboxamide

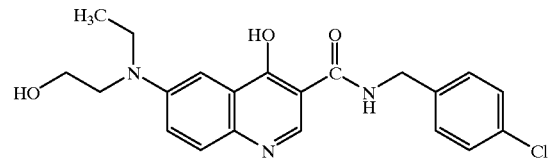

Following procedures analogous to those described in Example 188, the title compound is prepared from 2-(ethylamino)-1-ethanol.

Physical characteristics are as follows:
$^1$H NMR (300 MHz, DMSO-$d_6$) 12.5, 10.6, 8.5, 7.5,7.4, 7.34.7, 4.5, 3.5, 3.4, 1.1

HRMS (FAB) found 400.1429 (M+H$^+$).

EXAMPLE 190

N-(4-Chlorobenzyl)-4-hydroxy-6-(2-oxo-1,3-oxazolidin-3-yl)-3-quinolinecarboxamide

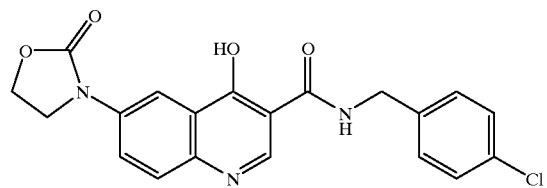

To a Parr bottle containing 2-(4-nitroanilino)-1-ethanol (1.1 g) and ethanol (25 mL) is added 10% palladium on carbon (0.06 g). The reaction mixture is shaken for 1 hour under 50 psi of hydrogen gas. The reaction mixture is filtered through Celite with ethanol washes. The filtrate is concentrated under reduced pressure. The residue is treated with diethyl ethoxymethylenemalonate (1.4 mL) and heated to 140 .C under a flow of argon gas. After 1 hour the reaction is cooled to room temperature, adsorbed onto silica gel, and chromatographed on silica eluting with 60% to 100% ethyl acetate in heptane. The product-containing fractions are evaporated to give 1.08 g of diethyl 2-((4-[(2-hydroxyethyl)amino]anilino}-methylene)malonate as a yellow solid.

To a flask containing diethyl 2-({4-[(2-hydroxyethyl)amino]anilino}methylene)-malonate (0.48 g) and 1,1'-carbonyldiimidazole (0.32 g) is added toluene (15 mL). The reaction mixture is heated to reflux under an argon atmosphere overnight. The reaction mixture is cooled to room temperatue and partioned between ethyl acetate and phosphate buffer (pH=7, 1M). The phases are separated and the aqueous layer is extracted with two additional portions of ethyl acetate. The combined organic layers are washed with buffer, brine, dried over sodium sulfate, filtered and concentrated under reduced pressure. The residue is chromatographed on silica eluting with ethyl acetate. The product-containing fractions are evaporated to give 0.46 g of diethyl 2-{[4-(2-oxo-1,3-oxazolidin-3-yl)anilino]methylene}malonate as a creme solid.

To a flask containing diethyl 2-{[4-(2-oxo-1,3-oxazolidin-3-yl)anilino]-methylene}-malonate (0.46 g) is added diphenyl ether (6 mL). The reaction mixture is heated from room temperature to 235° C. over 2 hours under a flow of argon gas. After 1 hour at 235° C. the reaction is cooled to room temperature, diluted with diethyl ether and filtered. The collected precipitate is washed repeatedly with diethyl ether then dried in vacuo to give 0.17 g of ethyl 4-hydroxy-6-(2-oxo-1,3-oxazolidin-3-yl)-3-quinolinecarboxylate as a tan solid.

To a flask containing ethyl 4-hydroxy-6-(2-oxo-1,3-oxazolidin-3-yl)-3-quinolinecarboxylate (0.17 g) is added p-chlorobenzylamine (1.0 mL). The reaction is tightly capped and heated to 185° C. over 1 hour. The reaction is cooled to room temperature and triturated with diethyl ether. The residue is adsorbed onto silica and chromatographed on silica eluting with 3% to 12% methanol in dichloromethane. The product-containing fractions are evaporated to give 0.12 g of the title compound as a off-white solid.

Physical characteristics are as follows:

$^1$H NMR (300 MHz, DMSO-$d_6$) 12.8, 10.4, 8.7, 8.2, 7.7, 7.4, 4.5, 4.4, 4.1

HRMS (FAB) found 398.0915 (M+H$^+$).

EXAMPLE 191

N-(4-Chlorobenzyl)-4-hydroxy-6-(4-morpholinylmethyl)-3-quinolinecarboxamide

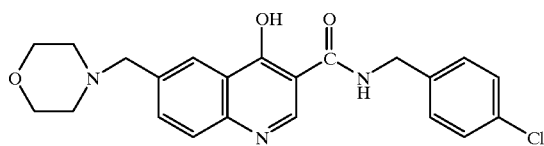

A solution of N-(4-chlorobenzyl)-4-hydroxy-6-(hydroxymethyl)-3-quinolinecarboxamide from Example No. 166 (1.0 g), collidine (0.45 mL), and DMAP (60.0 mg) in 50 mL anhydrous DMF is cooled to 0° C. Methanesulfonyl chloride (0.25 mL) is added dropwise. The reaction is stirred at room temperature for approx. 2–3 h. Morpholine (0.34 mL) is added. The product is precipitated by addition of H$_2$O. The crude product is adsorbed onto silica and chromatographed eluting with 2% MeOH in CH$_2$Cl$_2$. Fractions homogenous by TLC were combined and condensed to afford 352 mg of the title compound as a white solid.

Physical characteristics are as follows:

MP 219–220° C.;

$^1$H NMR (300 MHz, DMSO) 12.73, 10.46, 8.75, 8.16, 7.70, 7.38, 4.56, 3.58, 2.37;

IR (drift) 2977, 2929, 2901, 1660, 1620, 1536, 1490, 1362, 1295, 1113, 865, 844, 828, 799, 675 cm$^{-1}$.

HRMS (FAB) calcd for C$_{22}$H$_{22}$ClN$_3$O$_3$+H 412.1428, found 412.1440.

Anal. Found: C, 64.01; H, 5.34; N, 10.03.

PREPARATION 26

3-{[(4-Chlorobenzyl)amino]carbonyl}-8-fluoro-4-hydroxy-6-quinolinesulfonyl chloride

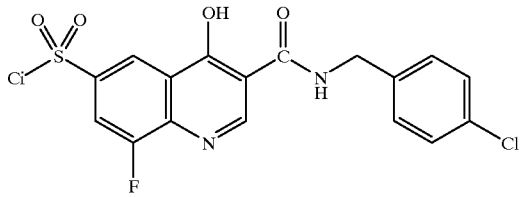

To a solution of 22.2 g of 2-fluoroaniline in 100 mL of acetic acid is added 32 g of ammonium thiocyanate. The flask is immersed in an ice bath and the mixture stirred during the dropwise addition of 32 g of bromine in 40 mL of acetic acid. After the addition, which takes ca 40 min., the mixture is stirred for 1 h at 0° C. and them dumped into 700 mL of rapidly stirred icewater. Conc. aqueous ammonia is added to neutralize HBr and bring the pH of the mixture to 4.0. The resulting yellow solid is filtered, washed well with water, and dried in vacuo to provide 27.72 g of 4-amino-3-fluorobenzenesulfenyl cyanide as a pale yellow solid.

A stirred biphasic mixture of 3.36 g of 4-Amino-3-fluorobenzenesulfenyl cyanide and 4.8 g of 50% aq. NaOH in 40 mL of THF and 20 mL of water is refluxed under argon for 1 h. Benzyl chloride (2.8 mL) is then added, and refluxing continued for 16 h. The mixture is then partitioned between water and ether, and the organic phase washed with water and brine, dried (Na$_2$SO$_4$), and concentrated under reduced pressure to give 5.8 g of yellow oil. Flash chromatography on silica using 20% EtOAc in heptane provides 3.59 g of 4-(benzylsulfanyl)-2-fluoroaniline as a yellow oil.

A neat mixture of 3.58 g of compound of 4-(benzylsulfanyl)-2-fluoroaniline and 3.48 g of diethyl ethoxymethylenemalonate is heated at 135° C. under a slow argon sweep for 1 h, then diluted with 25 mL of diphenyl ether and heated to 260° C., with maintenance of the argon sweep, and kept at that temperature for 90 min. The mixture is then cooled to ca 100° C. and added to 300 mL of stirred heptane. The precipitate is filtered, washed with heptane, and dried in vacuo to provide 4.01 g of ethyl 6-(benzylsulfanyl)-8-fluoro-4-hydroxy-3-quinolinecarboxylate as a yellow solid.

A solution of 3.93 g of of ethyl 6-(benzylsulfanyl)-8-fluoro-4-hydroxy-3 -quinolinecarboxylate in 8.8 g of 4-chlorobenzylamine is heated at 165° C. under argon for 16 h, then cooled and diluted with CHCl$_3$ and MeOH. The solution is washed with dil. HCl, dried (Na$_2$SO$_4$), and concentrated under reduced pressure to a yellow solid. Flash chromatography on silica using 3–6% MeOH in CH$_2$Cl$_2$ affords 4.73 g (95%) of 6-(benzylsulfanyl)-N-(4-chlorobenzyl)-8-fluoro-4-hydroxy-3-quinolinecarboxamide as a yellow solid.

Into 10.0 mL of glacial acetic acid, contained in a tared scintillation vial cooled in an ice bath, is bubbled chlorine gas. After ca 3-5 min., 1.32 g of Cl$_2$ has been absorbed, giving an approximate concentration of 1.8 M. A solution of 330 mg of 6-(benzylsulfanyl)-N-(4-chlorobenzyl)-8-fluoro-4-hydroxy-3-quinolinecarboxamide in mL of acetic acid and 1.0 mL of water is prepared with the aid of heat, and this solution is cooled to 0° C. for the addition of 1.4 mL of the freshly prepared chlorine solution. The solution is stirred for 15 min at 0° C., then added to 50 mL of ether. Volatiles are removed under reduced pressure, and toluene (50 mL) is added to the residue. Concentration of this solution under reduced pressure affords 337 mg of the sulfonyl chloride as a yellow solid of sufficient purity for sulfonylation of amines.

Physical properties as follows:
MS ES⁻ 426.8

EXAMPLE 192

N-(4-Chlorobenzyl)-8-fluoro-4-hydroxy-6-{[(1-naphthylmethyl)aminor]-sulfonyl}-3-quinolinecarboxamide

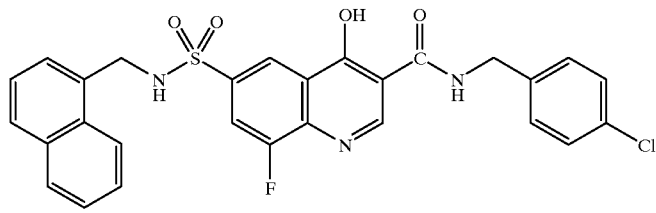

To a stirred solution of 73 μL of 1-naphthylmethylamine in 0.5 mL of pyridine is added 100 mg of sulfonyl chloride of Formula K-5 (wherein X=F). The solution is stirred for 1–18 h, then added dropwise to 3.5 mL of rapidly stirred 2 N aqueous HCl. The solid is filtered, washed well with water, and dried under vacuum. Flash chromatography of the solid on silica using 2-5% methanol in dichloromethane provides 57 mg of the title compound as a white solid.

Physical properties as follows:
$^1$H NMR (CDCl$_3$+CF$_3$CO$_2$D) δ 4.70, 4.74, 7.2–7.6, 7.82, 8.29, 9.35.
TLC R$_f$ 0.29 (4% MeOH in CH$_2$Cl$_2$).
HRMS (EI) 549.0922.

EXAMPLE 193
N-(4-Chlorobenzyl)-8-fluoro-4-hydroxy-6-({[2-(1H-indol-3-yl)ethyl]-amino)sulfonyl)-3-quinolinecarboxamide

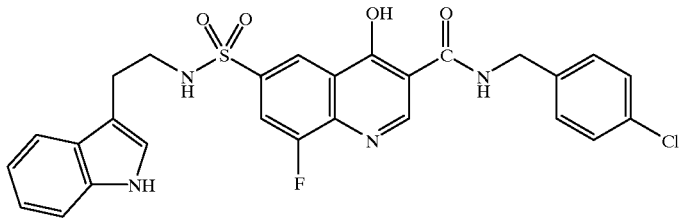

The title compound was prepared in analogy to that described in Example No. 192.

Physical properties as follows:

$^1$H NMR (CDCl$_3$+CD$_3$OD) δ 2.86, 3.31, 4.64, 6.82, 6.91, 7.11, 7.24, 7.31, 7.56, 8.37, 8.71, 10.36.

TLC R$_f$ 0.28 (4% MeOH in CH$_2$Cl$_2$).
HRMS (EI) 552.1033.

EXAMPLE 194

N-(4-Chlorobenzyl)-8-fluoro-6-{[(2-furylmethyl)amino]sulfonyl}-4-hydroxy-3-quinolinecarboxamide

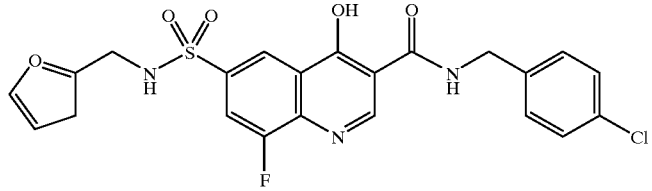

The title compound was prepared in analogy to that described in Example No. 192.
Physical properties as follows:
$^1$H NMR (CDCl$_3$+CD$_3$OD) δ 4.20, 4.64, 6.11, 7.13, 7.31, 7.79, 8.57, 8.75.
TLC R$_f$ 0.36 (6% MeOH in CH$_2$Cl$_2$).
HRMS (EI) 489.0556
Anal. Found: C, 53.76; H, 3.43; N, 8.54.

EXAMPLE 195

6-{[Bis(2-hydroxyethyl)amino]sulfonyl}-N-(4-chlorobenzyl)-8-fluoro-4-hydroxy-3-quinolinecarboxamide

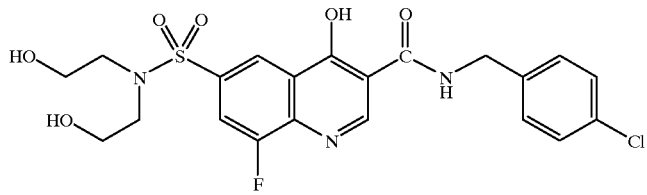

The title compound was prepared in analogy to that described in Example No. 192.

Physical properties as follows:

$^1$H NMR (CDCl$_3$+CD$_3$OD) δ 5.05, 3.8, 4.64, 7.32, 7.88, 8.61, 8.78.

TLC Rf 0.29 (8% MeOH in CH$_2$Cl$_2$).

HRMS (FAB) 498.0914.

EXAMPLE 196

Ethyl 2-{[(3-{[(4-chlorobenzyl)amino]carbonyl}-8-fluoro-4-hydroxy-6-quinolinyl)sulfonyl]amino)acetate

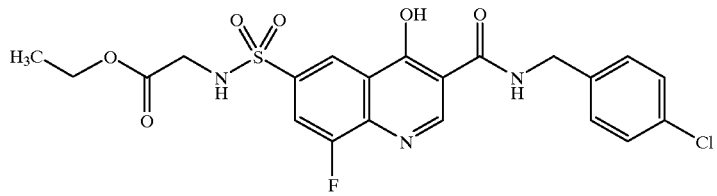

The title compound was prepared in analogy to that described in Example No.192.

Physical properties as follows:

$^1$H NMR (CDCl$_3$+CD$_3$OD) δ 1.18, 3.84, 4.06, 4.64, 7.31, 7.91, 8.65, 8.76.

TLC R$_f$ 0.47 (8% MeOH in CH$_2$Cl$_2$).

HRMS (FAB) 496.0763.

EXAMPLE 197

N-(4-Chlorobenzyl)-8-fluoro-4-hydroxy-6-{[(2-hydroxyethyl)amino]-sulfonyl}-3-quinolinecarboxamide

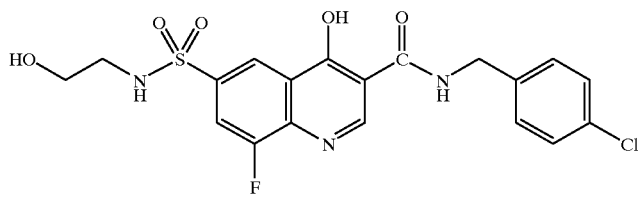

The title compound was prepared analogous to that described in Example No. 192.

Physical properties as follows:

$^1$H NMR (CDCl$_3$+CD$_3$OD) δ 3.07, 3.61, 4.64, 7.32, 7.91, 8.64, 8.78.

TLC $R_f$ 0.24 (8% MeOH in $CH_2Cl_2$).
HRMS (EI) 453.0558
Anal. Found: C, 50.20; H, 3.90; N, 9.00.

EXAMPLE 198

N-(4-Chlorobenzyl)-8-fluoro-4-hydroxy-6-(4-morpholinylsulfonyl)-3-quinolinecarboxamide

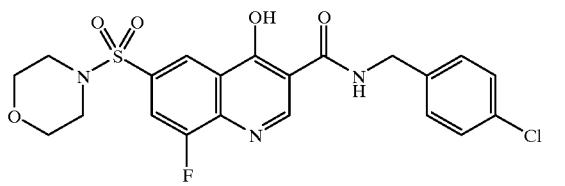

The title compound was prepared in analogy to that described in Example No. 192.

Physical properties as follows:

$^1$H NMR ($CDCl_3+CD_3OD$) δ 3.06, 3.76, 4.64, 7.31, 7.77, 8.56, 8.78.

TLC $R_f$ 0.50 (6% MeOH in $CH_2Cl_2$).
HRMS (EI) 479.0713.

EXAMPLE 199

N-(4-Chlorobenzyl)-8-fluoro-4-hydroxy-6-{[(2-pyridinylmethyl)amino]-sulfonyl}-3-quinolinecarboxamide

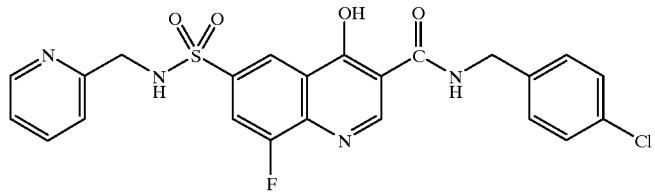

The title compound was prepared in analogy to that described in Example No. 192.

Physical properties as follows:

$^1$H NMR ($CDCl_3+CD_3OD$) δ 4.27, 4.64, 7.18, 7.3, 7.36, 7.67, 7.87, 8.39, 8.62, 9.74.

TLC $R_f$ 0.39 (8% MeOH in $CH_2Cl_2$).

HRMS (EI) 500.0709

Anal. Found: C, 54.38; H, 3.64; N, 10.89.

EXAMPLE 200

N-(4-Chlorobenzyl)-8-fluoro-4-hydroxy-6-[(2-pyridinylamino)-sulfonyl]-3-quinolinecarboxamide

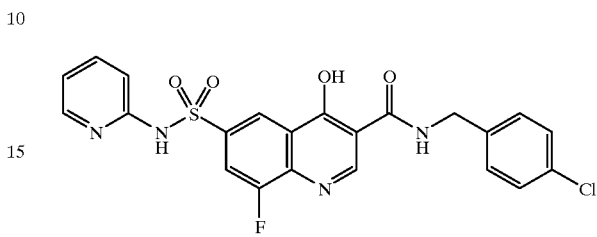

The title compound was prepared in analogy to that described in Example No. 192.

Physical properties as follows:

$^1$H NMR ($CDCl_3+CD_3OD$) δ 4.62, 6.81, 7.3–7.4, 7.72, 7.97, 8.75.

TLC $R_f$ 0.41 (8% MeOH in $CH_2Cl_2$).

HRMS (EI) 486.0563.

PREPARATION 27

Parallel Synthesis of Sulfonamides.

Amines (0.2 mmol each) are dissolved or suspended in 0.25 mL aliquots of pyridine in screw-capped vials. Liquid amines are dispensed by volume; solids by weight. In cases where amine salts are used, 34 μL of diisopropylethylamine per equivalent of acid is added. Into each vial is introduced 22±1 mg (50 μmol) of sulfonyl chloride of Formula K-5, and the vials are placed on a rocker for 4–20 h. At the end of the reaction time, each solution is added dropwise to 1.6 mL of rapidly stirred 2N HCl. The mixtures are stirred vigorously for 5 min, then filtered through plastic Burdick & Jackson fritted SPE reservoirs. The solids are washed well with water and dried under vacuum to provide the coupled products. The following examples were prepared according to this procedure.

| Example | Compound Name (Formula K-6) | MS(ES-) |
|---|---|---|
| 201 | N-(4-chlorobenzyl)-6-{[(cyclohexylmethyl)amino]sulfonyl}-8-fluoro-4-hydroxy-3-quinolinecarboxamide | 504 |
| 202 | N-(4-chlorobenzyl)-8-fluoro-4-hydroxy-6-({[2-(1-methyl-2-pyrrolidinyl)ethyl]amino}sulfonyl)-3-quinolinecarboxamide | 519 |
| 203 | N-(4-chlorobenzyl)-8-fluoro-4-hydroxy-6-({[2-(1-pyrrolidinyl)ethyl]amino}sulfonyl)-3-quinolinecarboxamide | 505 |
| 204 | N-(4-chlorobenzyl)-8-fluoro-6-{[(2-furylmethyl)amino]sulfonyl}-4-hydroxy-3-quinolinecarboxamide | 488 |
| 205 | N-(4-chlorobenzyl)-6-({[3-(cyclohexylamino)propyl]amino}sulfonyl)-8-fluoro-4-hydroxy-3-quinolinecarboxamide | 547 |
| 206 | N-(4-chlorobenzyl)-8-fluoro-4-hydroxy-6-{[(1-naphthylmethyl)amino]sulfonyl}-3-quinolinecarboxamide | 548 |
| 207 | N-(4-chlorobenzyl)-8-fluoro-4-hydroxy-6-({[2-(1H-imidazol-4-yl)ethyl]amino}sulfonyl)-3-quinolinecarboxamide | 502 |
| 208 | N-(4-chlorobenzyl)-8-fluoro-4-hydroxy-6-{[(tetrahydro-2-furanylmethyl)amino]sulfonyl}-3-quinolinecarboxamide | 492 |
| 209 | N-(4-chlorobenzyl)-8-fluoro-4-hydroxy-6-{[(2-thienylmethyl)amino]sulfonyl}-3-quinolinecarboxamide | 504 |
| 210 | N-(4-chlorobenzyl)-8-fluoro-4-hydroxy-6-({[2-(1H-indol-3-yl)ethyl]amino}sulfonyl)-3-quinolinecarboxamide | 551 |
| 211 | N-(4-chlorobenzyl)-8-fluoro-4-hydroxy-6-({[2-(5-methoxy-1H-indol-3-yl)ethyl]amino}sulfonyl)-3-quinolinecarboxamide | 581 |
| 212 | 6-{[(1,3-benzodioxol-5-ylmethyl)amino]sulfonyl}-N-(4-chlorobenzyl)-8-fluoro-4-hydroxy-3-quinolinecarboxamide | 542 |
| 213 | N-(4-chlorobenzyl)-8-fluoro-4-hydroxy-6-{[(2-morpholinoethyl)amino]sulfonyl}-3-quinolinecarboxamide | 521 |
| 214 | N-(4-chlorobenzyl)-8-fluoro-4-hydroxy-6-{[(3-morpholinopropyl)amino]sulfonyl}-3-quinolinecarboxamide | 535 |
| 215 | N-(4-chlorobenzyl)-8-fluoro-4-hydroxy-6-[({2-[(5-nitro-2-pyridinyl)amino]ethyl}amino)sulfonyl]-3-quinolinecarboxamide | 181 |
| 216 | N-(4-chlorobenzyl)-8-fluoro-4-hydroxy-6-{[(2-pyridinylmethyl)amino]sulfonyl}-3-quinolinecarboxamide | 499 |
| 217 | N-(4-chlorobenzyl)-8-fluoro-4-hydroxy-6-({[2-(2-pyridinyl)ethyl]amino}sulfonyl)-3-quinolinecarboxamide | 513 |
| 218 | N-(4-chlorobenzyl)-8-fluoro-4-hydroxy-6-{[(3-pyridinylmethyl)amino]sulfonyl}-3-quinolinecarboxamide | 499 |
| 219 | N-(4-chlorobenzyl)-8-fluoro-4-hydroxy-6-{[(4-pyridinylmethyl)amino]sulfonyl}-3-quinolinecarboxamide | 499 |
| 220 | N-(4-chlorobenzyl)-6-{[(4-chlorobenzyl)amino]sulfonyl}-8-fluoro-4-hydroxy-3-quinolinecarboxamide | 532 |
| 221 | N-(4-chlorobenzyl)-8-fluoro-4-hydroxy-6-{[(4-methoxybenzyl)amino]sulfonyl}-3-quinolinecarboxamide | 528 |
| 222 | N-(4-chlorobenzyl)-8-fluoro-4-hydroxy-6-[(neopentylamino)sulfonyl]-3-quinolinecarboxamide | 478 |
| 223 | N-(4-chlorobenzyl)-8-fluoro-4-hydroxy-6-{[(2-hydroxypropyl)amino]sulfonyl}-3-quinolinecarboxamide | 466 |
| 224 | N-(4-chlorobenzyl)-6-{[(2,3-dihydroxypropyl)amino]sulfonyl}-8-fluoro-4-hydroxy-3-quinolinecarboxamide | 482 |
| 225 | N-(4-chlorobenzyl)-6-{[(2,2-diphenylethyl)amino]sulfonyl}-8-fluoro-4-hydroxy-3-quinolinecarboxamide | 588 |
| 226 | 11-{[(3-{[(4-chlorobenzyl)amino]carbonyl}-8-fluoro-4-hydroxy-6-quinolinyl)sulfonyl]amino}undecanoic acid | 409 |
| 227 | 6-({[2-(acetylamino)ethyl]amino}sulfonyl)-N-(4-chlorobenzyl)-8-fluoro-4-hydroxy-3-quinolinecarboxamide | 493 |
| 228 | N-(4-chlorobenzyl)-8-fluoro-4-hydroxy-6-({[2-(2-hydroxyethoxy)ethyl]amino}sulfonyl)-3-quinolinecarboxamide | 496 |
| 229 | N-(4-chlorobenzyl)-8-fluoro-4-hydroxy-6-{[(2-hydroxyethyl)amino]sulfonyl}-3-quinolinecarboxamide | 452 |
| 230 | N-(4-chlorobenzyl)-8-fluoro-4-hydroxy-6-[(phenethylamino)sulfonyl]-3-quinolinecarboxamide | 512 |
| 231 | N-(4-chlorobenzyl)-6-{[(4-chlorophenethyl)amino]sulfonyl}-8-fluoro-4-hydroxy-3-quinolinecarboxamide | 546 |
| 232 | N-(4-chlorobenzyl)-8-fluoro-4-hydroxy-6-[(2-propynylamino)sulfonyl]-3-quinolinecarboxamide | 446 |
| 233 | N-(4-chlorobenzyl)-8-fluoro-4-hydroxy-6-[(isopentylamino)sulfonyl]-3-quinolinecarboxamide | 478 |
| 234 | N-(4-chlorobenzyl)-8-fluoro-4-hydroxy-6-{[(3-phenylpropyl)amino]sulfonyl}-3-quinolinecarboxamide | 526 |
| 235 | N-(4-chlorobenzyl)-8-fluoro-4-hydroxy-6-[(pentylamino)sulfonyl]-3-quinolinecarboxamide | 478 |
| 236 | 6-({[3,5-bis(trifluoromethyl)benzyl]amino}sulfonyl)-N-(4-chlorobenzyl)-8-fluoro-4-hydroxy-3-quinolinecarboxamide | 466 |
| 237 | N-(4-chlorobenzyl)-6-({[2-(1-cyclohexen-1-yl)ethyl]amino}-sulfonyl)-8-fluoro-4-hydroxy-3-quinolinecarboxamide | 516 |
| 238 | N-(4-chlorobenzyl)-8-fluoro-4-hydroxy-6-({[2-(1-naphthylamino)ethyl]amino}sulfonyl)-3-quinolinecarboxamide | 577 |

-continued

| Example | Compound Name (Formula K-6) | MS(ES-) |
|---|---|---|
| 239 | N-(4-chlorobenzyl)-8-fluoro-4-hydroxy-6-[(methylamino)sulfonyl]-3-quinolinecarboxamide | 422 |
| 240 | N-(4-chlorobenzyl)-6-{[(cyanomethyl)amino]sulfonyl}-8-fluoro-4-hydroxy-3-quinolinecarboxamide | 447 |
| 241 | N-(4-chlorobenzyl)-6-{[(2,4-dimethoxybenzyl)amino]sulfonyl}-8-fluoro-4-hydroxy-3-quinolinecarboxamide | 558 |
| 242 | N-(4-chlorobenzyl)-8-fluoro-4-hydroxy-6-{[(3-iodobenzyl)amino]sulfonyl}-3-quinolinecarboxamide | 624 |
| 243 | N-(4-chlorobenzyl)-8-fluoro-4-hydroxy-6-{[(2,2,2-trifluoroethyl)amino]sulfonyl}-3-quinolinecarboxamide | 490 |
| 244 | 6-{[(2-bromoethyl)amino]sulfonyl}-N-(4-chlorobenzyl)-8-fluoro-4-hydroxy-3-quinolinecarboxamide | 516 |
| 245 | N-(4-chlorobenzyl)-6-{[(2-chloroethyl)amino]sulfonyl}-8-fluoro-4-hydroxy-3-quinolinecarboxamide | 470 |
| 246 | N-(4-chlorobenzyl)-6-{[(3,4-dihydroxyphenethyl)amino]sulfonyl}-8-fluoro-4-hydroxy-3-quinolinecarboxamide | 544 |
| 247 | N-(4-chlorobenzyl)-6-({[2-ethylsulfanyl)ethyl]amino}sulfonyl)-8-fluoro-4-hydroxy-3-quinolinecarboxamide | 496 |
| 248 | 6-{[(3-bromopropyl)amino]sulfonyl}-N-(4-chlorobenzyl)-8-fluoro-4-hydroxy-3-quinolinecarboxamide | 530 |
| 249 | 6-({[4-(aminosulfonyl)benzyl]amino}sulfonyl)-N-(4-chlorobenzyl)-8-fluoro-4-hydroxy-3-quinolinecarboxamide | 409 |
| 250 | 6-[({2-[bis(2-hydroxyethyl)amino]ethyl}amino)sulfonyl]-N-(4-chlorobenzyl)-8-fluoro-4-hydroxy-3-quinolinecarboxamide | 539 |
| 251 | N-(4-chlorobenzyl)-6-({[2-(ethylsulfanyl)ethyl]amino}sulfonyl)-8-fluoro-4-hydroxy-3-quinolinecarboxamide | 496 |
| 252 | N-(4-chlorobenzyl)-6-{[(3,4-dimethylbenzyl)amino]sulfonyl}-8-fluoro-4-hydroxy-3-quinolinecarboxamide | 526 |
| 253 | N-(4-chlorobenzyl)-6-{[(cyclopropylmethyl)amino]sulfonyl}-8-fluoro-4-hydroxy-3-quinolinecarboxamide | 462 |
| 254 | 6-{[(4-bromobenzyl)amino]sulfonyl}-N-(4-chlorobenzyl)-8-fluoro-4-hydroxy-3-quinolinecarboxamide | 578 |
| 255 | N-(4-chlorobenzyl)-8-fluoro-4-hydroxy-6-({[2-(2-thienyl)ethyl]amino}sulfonyl)-3-quinolinecarboxamide | 518 |
| 256 | N-(4-chlorobenzyl)-8-fluoro-4-hydroxy-6-{[(2-phenoxyethyl)amino]sulfonyl}-3-quinolinecarboxamide | 528 |
| 257 | tert-butyl 2-{[(3-{[(4-chlorobenzyl)amino]carbonyl}-8-fluoro-4-hydroxy-6-quinolinyl)sulfonyl]amino}acetate | 522 |
| 258 | tert-butyl 3-{[(3-{[(4-chlorobenzyl)amino]carbonyl}-8-fluoro-4-hydroxy-6-quinolinyl)sulfonyl]amino}propanoate | 536 |
| 259 | N-(4-chlorobenzyl)-8-fluoro-4-hydroxy-6-({[3-(trifluoromethoxy)benzyl]amino}sulfonyl)-3-quinolinecarboxamide | 378 |
| 260 | N-(4-chlorobenzyl)-8-fluoro-4-hydroxy-6-{[(2-{[2-(hydroxymethyl)phenyl]sulfanyl}benzyl)amino]sulfonyl}-3-quinolinecarboxamide | 636 |
| 261 | N-(4-chlorobenzyl)-8-fluoro-4-hydroxy-6-({[4-(1,2,3-thiadiazol-4-yl)benzyl]amino}sulfonyl)-3-quinolinecarboxamide | 582 |
| 262 | N-(4-chlorobenzyl)-6-{[(4-chloro-2-fluorobenzyl)amino]sulfonyl}-8-fluoro-4-hydroxy-3-quinolinecarboxamide | 550 |
| 263 | N-(4-chlorobenzyl)-8-fluoro-4-hydroxy-6-[({2-[(2-hydroxyethyl)sulfanyl]ethyl}amino)sulfonyl]-3-quinolinecarboxamide | 512 |
| 264 | 6-{[(2-amino-2-methylpropyl)amino]sulfonyl}-N-(4-chlorobenzyl)-8-fluoro-4-hydroxy-3-quinolinecarboxamide | 479 |
| 265 | 6-{[(2-amino-2-oxoethyl)amino]sulfonyl}-N-(4-chlorobenzyl)-8-fluoro-4-hydroxy-3-quinolinecarboxamide | 465 |
| 266 | 6-{[(4-aminobenzyl)amino]sulfonyl}-N-(4-chlorobenzyl)-8-fluoro-4-hydroxy-3-quinolinecarboxamide | 513 |

EXAMPLE 267

Di(tert-butyl) 3-(3-{[(4-chlorobenzyl)amino]carbonyl}-8-fluoro-4-hydroxy-6-quinolinyl)propyl phosphate

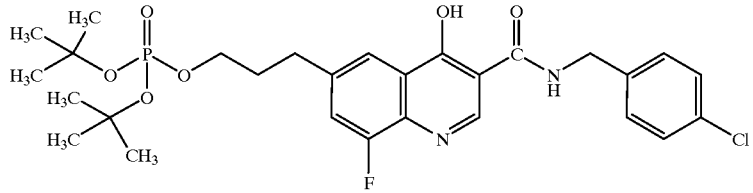

To a stirred solution of 78 mg of from N-(4-chlorobenzyl)-8-fluoro-4-hydroxy-6-(3-hydroxypropyl)-3-quinolinecarboxamide from Example No. 110 and 17 mg of 1H-tetrazole in 1 mL of 1:1 chloroform-methanol, under argon, is added 77 μL of di-tert-butyl diethyl phosphoramidite. After 4 h, the solution is cooled to 0° C., and a slight excess (ca 80 mg) of m-CPBA is added. The solution is stirred for 20 min, then quenched with aqueous NaHSO$_3$. The organic phase is washed with dilute aqueous HCl and NaHCO$_3$, dried (Na$_2$SO$_4$), and concentrated under reduced pressure. Flash chromatography of the residue on silica using 2–4% methanol in dichloromethane provides 118 mg of the title compound as a white solid.

Physical properties as follows:

$^1$H NMR (CDCl$_3$) δ 1.50, 2.0, 2.9, 4.0, 4.6, 7.2–7.3, 7.9–8.1, 8.9, 10.6 ppm.

HRMS 580.1478.

EXAMPLE 268

3-(3-{[(4-Chlorobenzyl)amino]carbonyl}-8-fluoro-4-hydroxy-6-quinolinyl)propyl dihydrogen phosphate

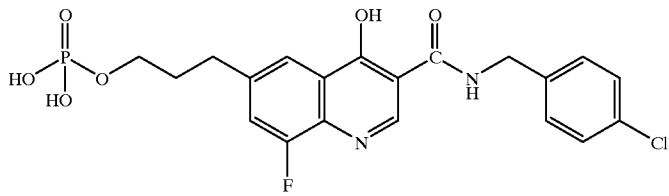

A solution of 95 mg of compound of Example 267 (F-2 wherein X=CH$_2$ and Y=F) in 1 mL of 1:1 TFA-dichloromethane is stirred for 30 min, then added dropwise to 50 mL of rapidly stirred 2:1 ether-hexane. The solid is filtered off, washed with hexane, and dried under vacuum to provide 65 mg of the title compound as a white solid.

Physical properties as follows:

$^1$H NMR (CDCl$_3$) δ 2.1, 2.9, 4.0, 4.65, 7.3, 7.4, 8.0, 8.9 ppm.

HRMS 469.0742.

EXAMPLE 269

3-(3-{[(4-Chlorobenzyl)amino]carbonyl-4-hydroxy-6-quinolinyl)propyl dihydrogen phosphate

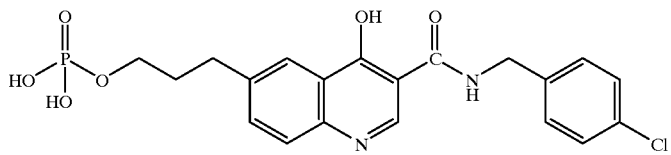

Prepared from N-(4-chlorobenzyl)-4-hydroxy-6-(3-hydroxypropyl)-3-quinolinecarboxamide (Example No. 144), according to the procedures described in Examples 267 and 268.

Physical properties as follows:

$^1$H NMR (CDCl$_3$) δ 2.1, 3.0, 3.4, 4.0, 4.66, 7.3, 7.8, 8.2 ppm.

HRMS 451.0831.

EXAMPLE 270 tert-Butyl 3-(3-{[(4-chlorobenzyl)amino]carbonyl}-4-hydroxy-6-quinolinyl)propyl phosphonate

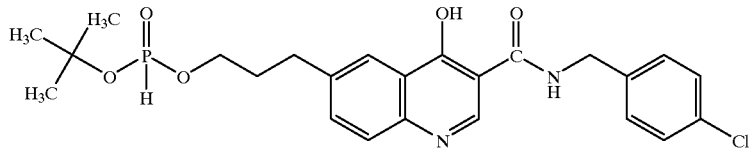

To a suspension of 75 mg of compound N-(4-chlorobenzyl)-4-hydroxy-6-(3-hydroxypropyl)-3-quinolinecarboxamide from Example No. 144, and 30 mg of 1H-tetrazole in 2 mL of 1:1 chloroform-THF, stirred under argon, is added 130 µL of di-tert-butyl diethyl phosphoramidite. After 18 h the solution washed with dilute HCl, the aqueous phase being extracted with two portions of chloroform. The organic phase is dried ($Na_2SO_4$) and concentrated under reduced pressure, and the residue flash chromatographed on silica using 2–4% methanol in dichloromethane to provide 90 mg of the title compound as a white solid.

Physical properties as follows:

$^1$H NMR (CDCl$_3$) δ 1.53, 2.1, 2.9, 4.0, 4.6, 5.75, 7.2, 7.4, 8.06, 8.2, 8.8 ppm.

IR 2979, 1662, 1527, 1490, 1260, 973 cm$^{-1}$.

HRMS 491.1494

EXAMPLE 271 tert-Butyl 3-(3-{[(4-chlorobenzyl)amino]carbonyl}-8-fluoro-4-hydroxy-6-quinolinyl)propyl phosphonate

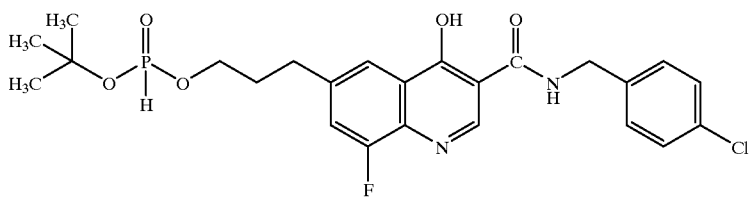

Prepared from N-(4-chlorobenzyl)-8-fluoro-4-hydroxy-6-(3-hydroxypropyl)-3-quinolinecarboxamide (Example No. 110), according to the procedure described in Example No. 270.

Physical properties as follows:

$^1$H NMR (CDCl$_3$) δ 1.53, 2.1, 2.9, 4.1, 4.6, 5.75, 7.2, 8.0, 8.07, 8.9, 10.6 ppm.

HRMS 509.1424.

EXAMPLE 272

3-(3-{[(4-Chlorobenzyl)amino]carbonyl}-4-hydroxy-6-quinolinyl)propyl hydrogen phosphonate

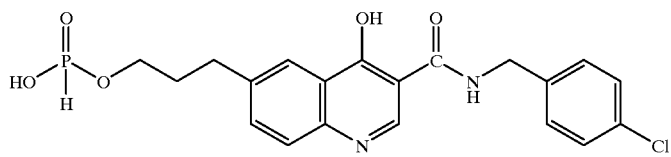

A solution of 50.0 mg of tert-butyl 3-(3-{[(4-chlorobenzyl)amino]carbonyl}-4-hydroxy-6-quinolinyl)propyl phosphonate from Example No. 270 in 0.5 mL of 1:1 TFA-dichloromethane is stirred for 2 h, then added slowly to 20 mL of rapidly stirred hexane. The resulting solution was concentrated under reduced pressure to provide 45.6 mg of the title compound as a white crystalline solid.

Physical properties as follows:

$^1$H NMR (CDCl$_3$) δ 2.0, 2.9, 4.0, 4.6, 5.8, 7.3, 7.7, 7.9, 8.0, 8.1 ppm.

HRMS 435.0871

EXAMPLE 273

Sodium 2-[{8-[3-(3-{[(4-chlorobenzyl)amino]carbonyl}-8-fluoro-4-hydroxy-6-quinolinyl)propoxy]-8-oxooctanoyl}(methyl)amino]-1-ethanesulfonate

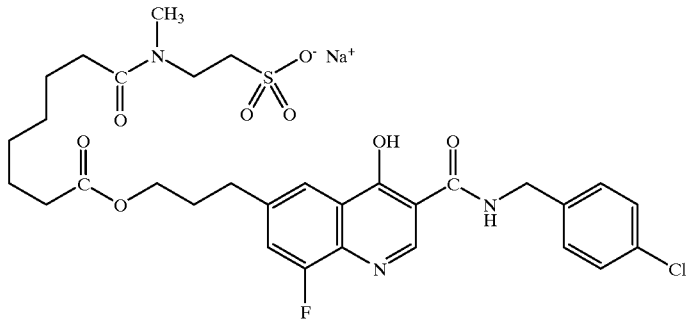

To a stirred mixture of 78 mg of N-(4-chlorobenzyl)-8-fluoro-4-hydroxy-6-(3-hydroxypropyl)-3-quinolinecarboxamide from Example No. 110, 27 mg of DMAP, and 0.46 mL of a 0.65 M solution of suleptanic acid triethylammonium salt in acetonitrile, in 1 mL of 1:1 THF-chloroform, was added 38 µL of diisopropylcarbodiimide. The solution was stirred for 18 h, then concentrated under reduced pressure. Flash chromatography of the residue on silica using 5–15% methanol in dichloromethane provided a solid. This was dissolved in chloroform-butanol-methanol, and the solution stirred with saturated aqueous sodium sulfate. The organic phase was filtered through anhydrous sodium sulfate and concentrated under reduced pressure to afford 121 mg of the title compound as a white solid.

Physical properties as follows:

$^1$H NMR (CDCl$_3$) δ 1.1–1.6, 2.0–2.4, 2.8–3.3, 3.7–4.1, 4.7, 6.8, 7.3, 8.0, 8.1, 8.8 ppm.

HRMS 688.1858.

EXAMPLE 274

Sodium 2-[(8-{[3-(3-{[(4-chlorobenzyl)amino]carbonyl}-4-hydroxy-6-quinolinyl)-2-propynyl]oxy}-8-oxooctanoyl)(methyl)amino]-1-ethanesulfonate

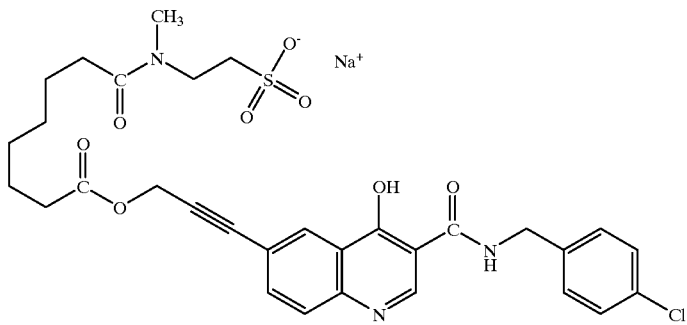

Prepared from N-(4-chlorobenzyl)-4-hydroxy-6-(3-hydroxy-1-propynyl)-3-quinolinecarboxamide (Example No. 134) according to the procedure described in Example 273.

Physical properties as follows:

$^1$H NMR (CDCl$_3$) δ 1.2–1.7, 2.2–2.5, 2.9–3.2, 3.4, 3.8, 4.6, 4.9, 6.7, 7.3, 7.5–7.7, 8.1, 8.4, 8.8 ppm.

HRMS 643.1749.

EXAMPLE 275

Sodium 2-[(8-{[3-(3-{[(4-chlorobenzyl)amino]carbonyl-8-fluoro-4-hydroxy-6-quinolinyl)-2-propynyl]oxy}-8-oxooctanoyl)(methyl)amino]-1-ethanesulfonate

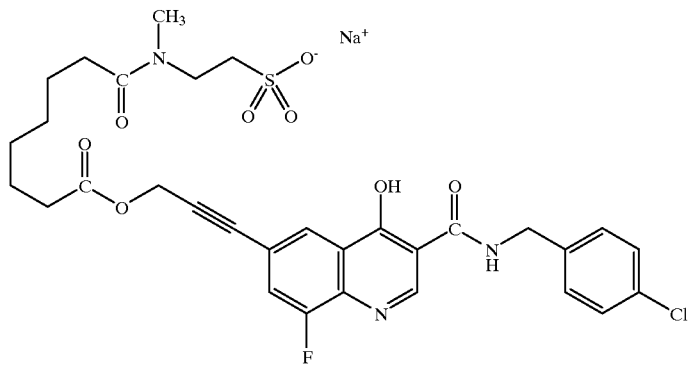

Prepared from N-(4-Chlorobenzyl)-8-fluoro-4-hydroxy-6-(3-hydroxy-1-propynyl)-3-quinolinecarboxamide, according to the procedure described in Example 273.

Physical properties as follows:

$^1$H NMR (CDCl$_3$) δ 1.2–1.7, 2.2–2.4, 3.0–3.2, 3.7, 4.6, 4.9, 7.3, 7.4, 8.2, 8.8 ppm.

HRMS 684.1561

EXAMPLE 276

Sodium 2-[18-[3-(3-{[(4-chlorobenzyl)amino]carbonyl}-4-hydroxy-6-quinolinyl)propoxy]-8-oxooctanoyl}(methyl)amino]-1-ethanesulfonate

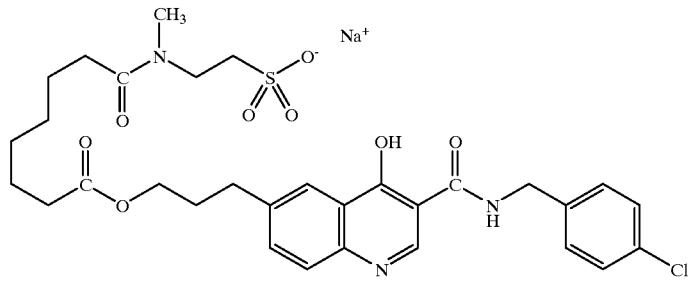

Prepared from N-(4-chlorobenzyl)-4-hydroxy-6-(3-hydroxypropyl)-3-quinolinecarboxamide (Example No. 144), according to the procedure described in Example 273.

Physical properties as follows:

$^1$H NMR (CDCl$_3$) δ 1.3, 1.5–1.7, 2.0, 2.2–2.5, 2.8–3.3, 3.8, 4.1, 4.6, 6.8, 7.1–7.4, 7.5, 8.1, 8.2, 8.8 ppm.

HRMS 647.2073

PREPARATION 28
3-(Benzylsulfanyl)aniline

To a cold (0° C.), stirred slurry of 1.7 g of sodium hydride oil dispersion (60%) in 100 mL of dry THF, under argon, is added via cannula 4.95 g of 3-aminothiophenol in 5 mL of THF. After 5 min, 4.6 mL of benzyl chloride is added. The mixture is allowed to warm to room temperature and stirred for 18 h, then cooled to 0° C. and partitioned between water and diethyl ether. The organic phase is washed with water and brine, dried (Na$_2$SO$_4$), and concentrated under reduced pressure. Flash chromatography of the residual oil on silica using 30% ethyl acetate in heptane provides 7.57 g of the title compound as a beige crystalline solid, which may be recrystallized from ether-hexane.

Physical properties as follows:

$^1$H NMR (CDCl$_3$) δ 3.7, 4.10, 6.5, 6.6, 6.7, 7.0, 7.2–7.3 ppm.

HRMS 216.0837

Anal. Found: C, 72.54; H, 6.13; N, 6.55; S, 14.84.

PREPARATION 29
Ethyl 7-(benzylsulfanyl)-4-hydroxy-3-quinolinecarboxylate

A mixture of 7.40 g of 3-(benzylsulfanyl)aniline from Preparation No. 28 and 7.70 g of diethyl ethoxymethylene malonate is heated at 135° C. under a gentle flow of argon for 2 h, then diluted with 30 mL of diphenyl ether and heated to 260–270° C. After 45 min, the solution was added to 500 mL of stirred heptane. The resulting solid was filtered, washed well with hexane, and dried under vacuum to afford 8.32 g of the title compound.

Physical properties as follows:

$^1$H NMR (CDCl$_3$) δ 1.5, 4.4, 4.6, 7.2–7.5, 7.7, 7.8, 8.3, 9.2 ppm.

MS ES+ 340

PREPARATION 30
7-(Benzylsulfanyl)-N-(4-chlorobenzyl)-4-hydroxy-3-quinolinecarboxamide A mixture of 4.07 g of ethyl 7-(benzylsulfanyl)-4-hydroxy-3-quinolinecarboxylate from Preparation No. 29 and 8.5 g of 4-chlorobenzylamine is heated at 165° C. for 18 h, then cooled and partitioned between 1 N HCl and chloroform-methanol. The organic phase is dried (MgSO$_4$) and concentrated under reduced pressure, and the residue flash chromatographed on silica using 2–5% methanol in dichloromethane to provide 4.82 g of the title compound.

Physical properties as follows:

$^1$H NMR (CDCl$_3$) δ 4.13, 4.6, 7.1–7.4, 8.2, 8.6 ppm.

MS ES+ 435

PREPARATION 31

3-{[(4-Chlorobenzyl)amino]carbonyl}-4-hydroxy-7-quinolinesulfonyl chloride

Into 10.0 mL of glacial acetic acid, contained in a tared scintillation vial cooled in an ice bath, is bubbled chlorine gas. After ca 3-5 min., 1.29 g of Cl$_2$ has been absorbed, giving an approximate concentration of 1.8 M. A solution of 306 mg of 7-(benzylsulfanyl)-N-(4-chlorobenzyl)-4-hydroxy-3-quinolinecarboxamide from Preparation No. 30 in 10 mL of acetic acid and 1.0 mL of water is prepared with the aid of heat, and this solution is cooled to 0° C. for the addition of 1.8 mL of the freshly prepared chlorine solution. The solution is stirred for 15 min at 0° C., then added to 50 mL of ether. Volatiles are removed under reduced pressure, and toluene (50 mL) is added to the residue. Concentration of this solution under reduced pressure affords 344 mg of the sulfonyl chloride as a yellow solid of sufficient purity for sulfonylation of amines.

Physical properties as follows:

MS (ES−) 409, 411

EXAMPLE 277

N-(4-Chlorobenzyl)-4-hydroxy-7-{[(1-naphthylmethyl)amino]-sulfonyl}-3-quinolinecarboxamide

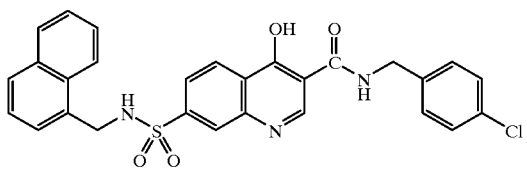

To a stirred solution of 44 μL of 1-naphthylmethylamine and 51 μL of diisopropylethylamine in 0.5 mL of pyridine is added 100 mg of 3-{[(4-chlorobenzyl)amino]carbonyl}-4-hydroxy-7-quinolinesulfonyl chloride from Preparation No. 31. After 18 h, the solution is added to 3.5 mL of rapidly stirred 2 N HCl, and the resulting solid is filtered, washed well with water, and dried under vacuum. Flash chromatography of the solid on silica gel using 2–5% methanol in dichloromethane provides 48 mg of the title compound as a white solid.

Physical properties as follows:

$^1$H NMR (CDCl$_3$) δ 4.70, 4.79, 7.2–7.5, 7.6, 7.8, 8.2, 9.5 ppm.

HRMS 531.1010

EXAMPLE 278

N-(4-Chlorobenzyl)-4-hydroxy-7-(methylsulfanyl)-3-quinolinecarboxamide

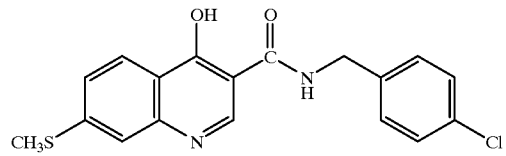

A neat mixture of 2.8 g of compound of 3-methylthioaniline and 4.0 g of diethyl ethoxymethylenemalonate is heated at 135° C. under a slow argon sweep for 1 h, then diluted with 25 mL of diphenyl ether and heated to 260° C., with maintenance of the argon sweep, and kept at that temperature for 90 min. The mixture is then cooled to ca 100° C. and added to 300 mL of stirred 1:1 ether-hexane. The precipitate is filtered, washed with hexane, and dried in vacuo to provide 1.35 g of crude material as a tan solid, which is recrystallized from acetic acid-water to afford 1.06 g of ethyl 4-hydroxy-7-(methylsulfanyl)-3-quinolinecarboxylate.

A solution of 50 mg of ethyl 4-hydroxy-7-(methylsulfanyl)-3-quinolinecarboxylate in 200 μL of 4-chlorobenzylamine is heated at 190° C. under argon for 16 h, then cooled and diluted with CHCl$_3$ and MeOH. The solution is washed with dil. HCl, dried (Na$_2$SO$_4$), and concentrated under reduced pressure to a yellow solid. Flash chromatography on silica using 2–4% MeOH in CH$_2$Cl$_2$ affords 62.4 mg (92%) of N-(4-chlorobenzyl)-4-hydroxy-7-(methylsulfanyl)-3-quinolinecarboxamide.

Physical properties as follows:

$^1$H NMR (CDCl$_3$) δ 2.54, 2.6, 4.63, 7.3, 8.2, 8.6 ppm.

HRMS 358.0561

Anal. Found C, 60.11; H, 4.28; N, 7.82

EXAMPLE 279

N-(4-Chlorobenzyl)-8-hydroxy[1,3]dioxolo [4,5-g]quinoline-7-carboxamide

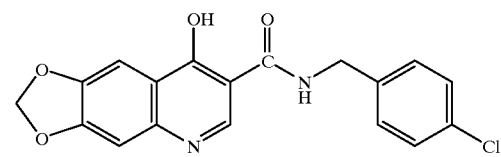

Prepared from ethyl 8-hydroxy[1,3]dioxolo [4,5-g]quinoline-7-carboxylate, using the aminolysis conditions described for Example 278.

Physical properties as follows:

$^1$H NMR (CDCl$_3$+CD$_3$OD) δ 4.63, 6.12, 6.90, 7.3, 7.67, 8.60 ppm.

HRMS (FAB) 357.0638.

EXAMPLE 280
6-Benzoyl-N-(4-chlorobenzyl)-4-hydroxy-3-quinolinecarboxamide
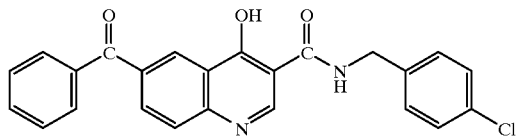
Prepared from 4-aminobenzophenone, using conditions described in Example 278.
Physical properties as follows:
$^1$H NMR (CDCl$_3$+CD$_3$OD) δ 4.62, 7.3, 7.5, 7.6, 7.8, 8.2, 8.7 ppm.
HRMS (FAB) 417.1001
Anal. Found: C, 68.84; H, 4.25; N, 6.71.
CHART A
A-1
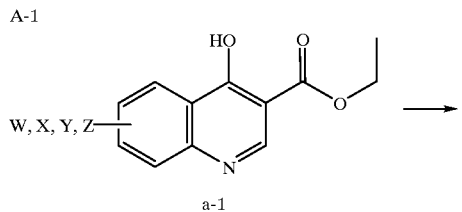
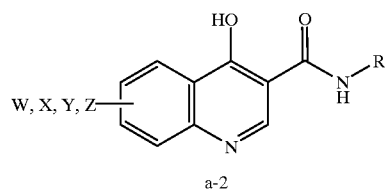
A-2
a-1 ⟶ a-2
A-3
a-1 ⟶ 
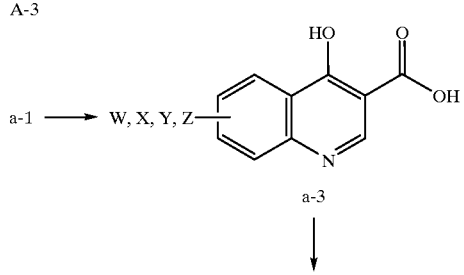
A-4
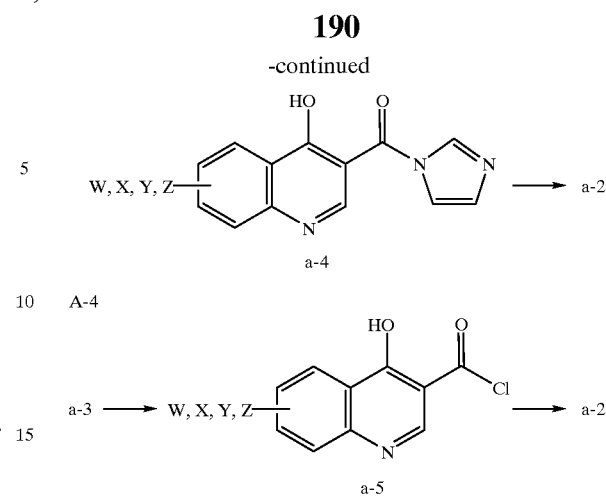
CHART B
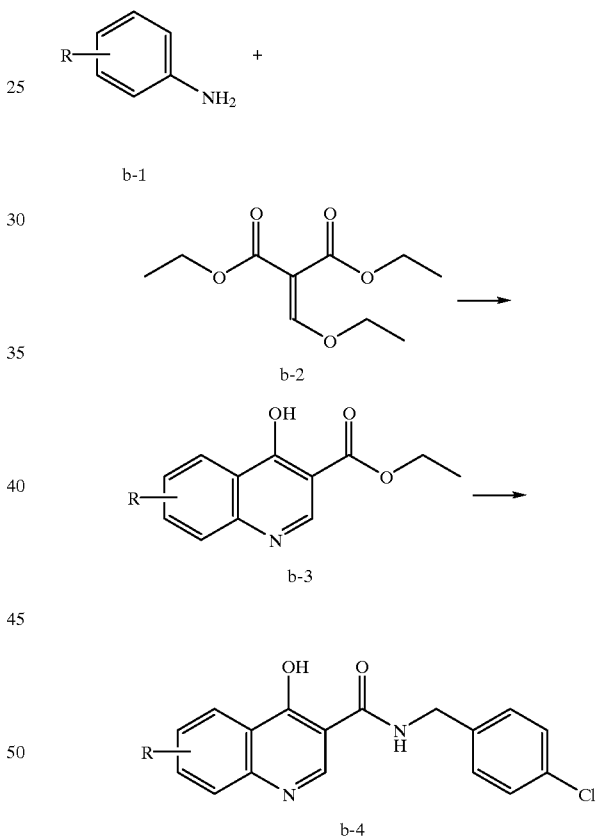

CHART C
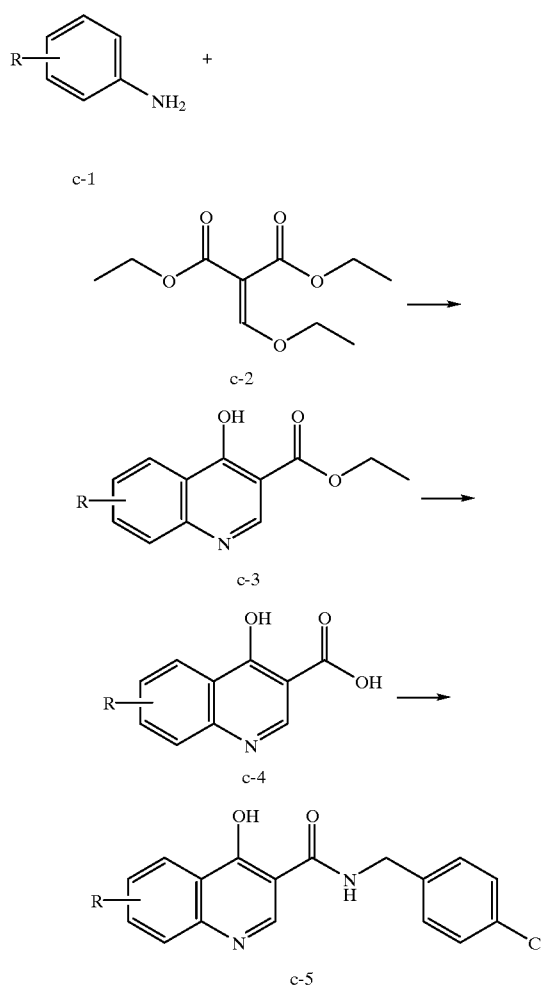
CHART D
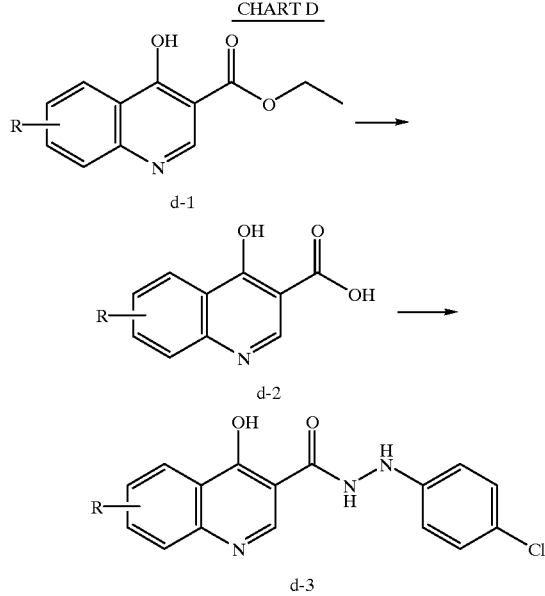
CHART E
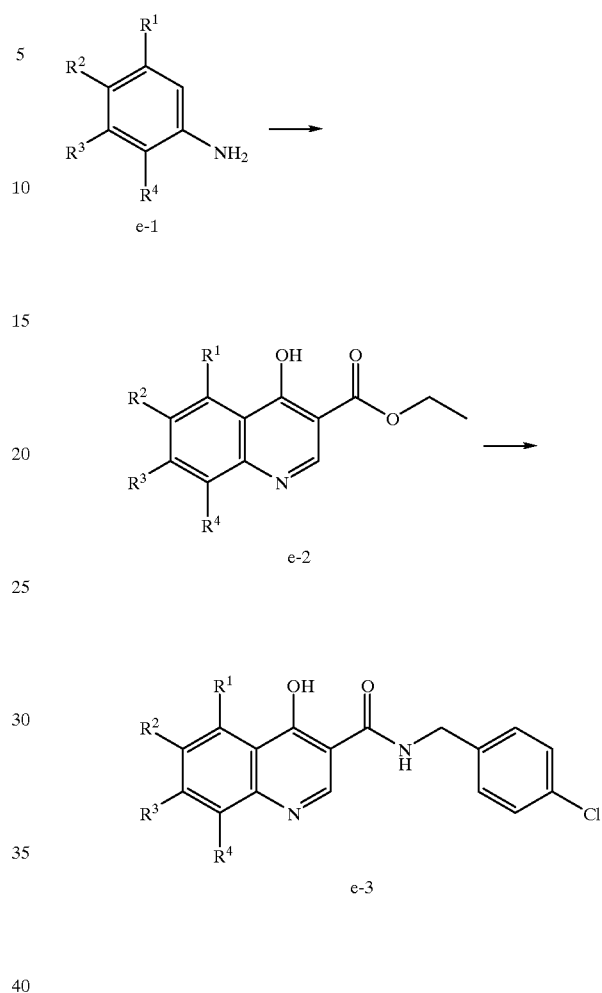
CHART F
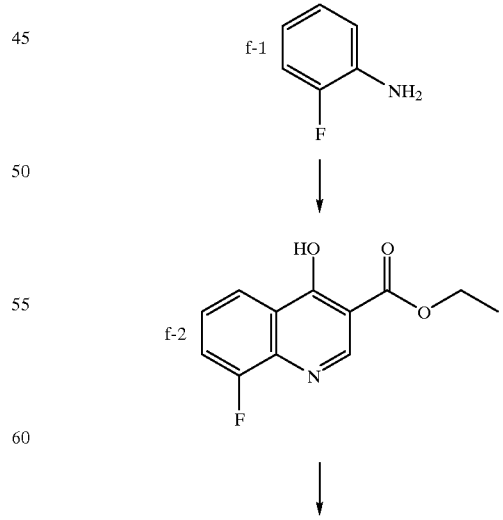

193
-continued
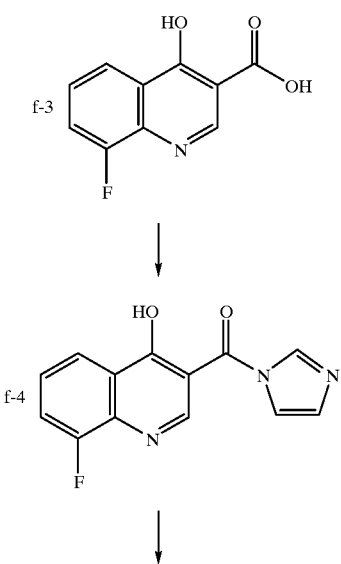
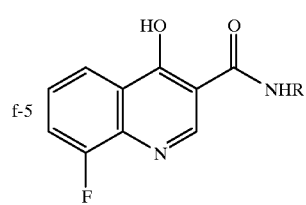
194
CHART G
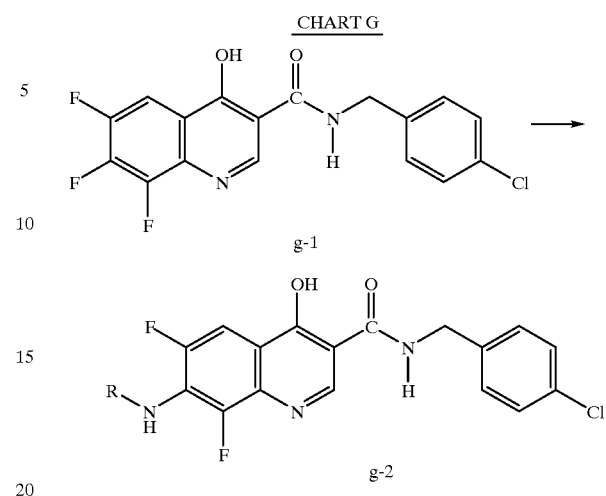
CHART H
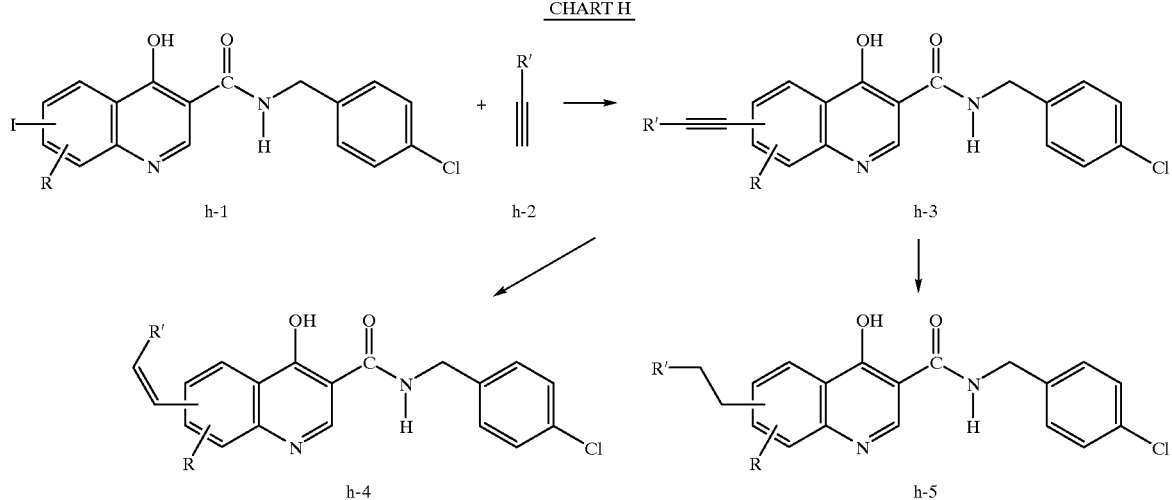
CHART I
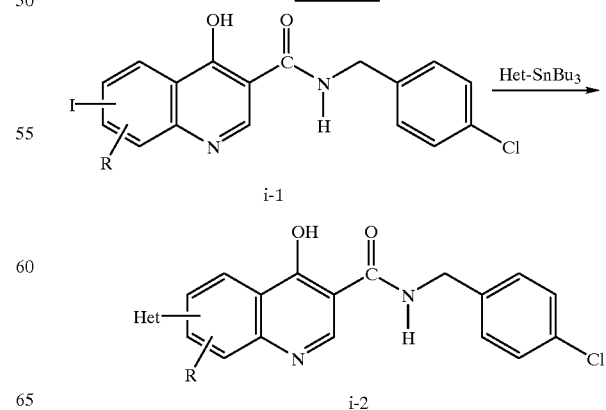

CHART J
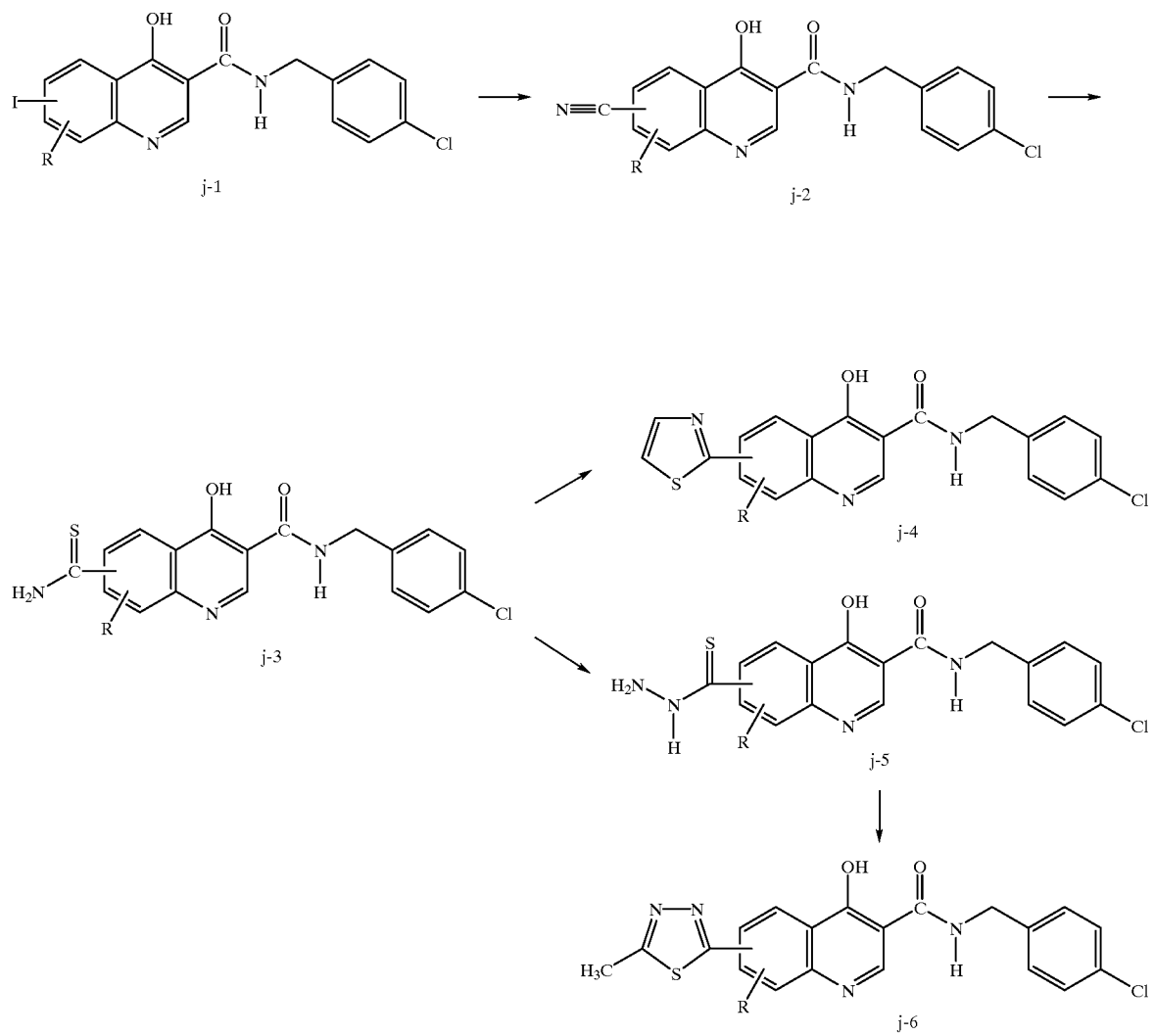
CHART K
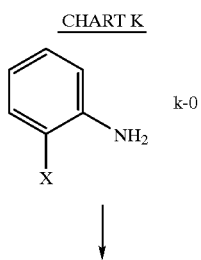

197
-continued
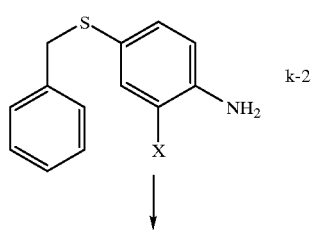
k-2
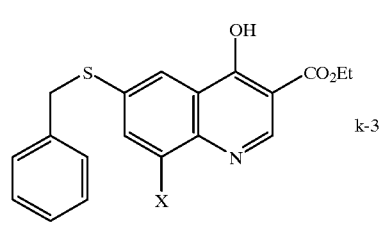
k-3
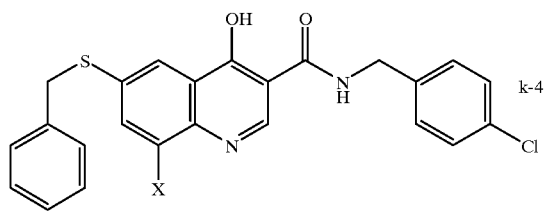
k-4
198
-continued
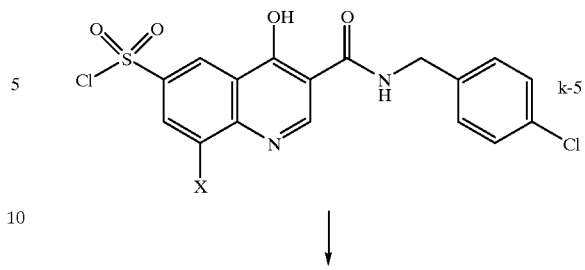
k-5
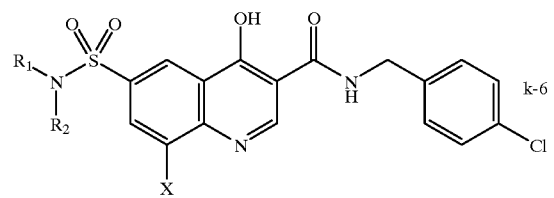
k-6

CHART L
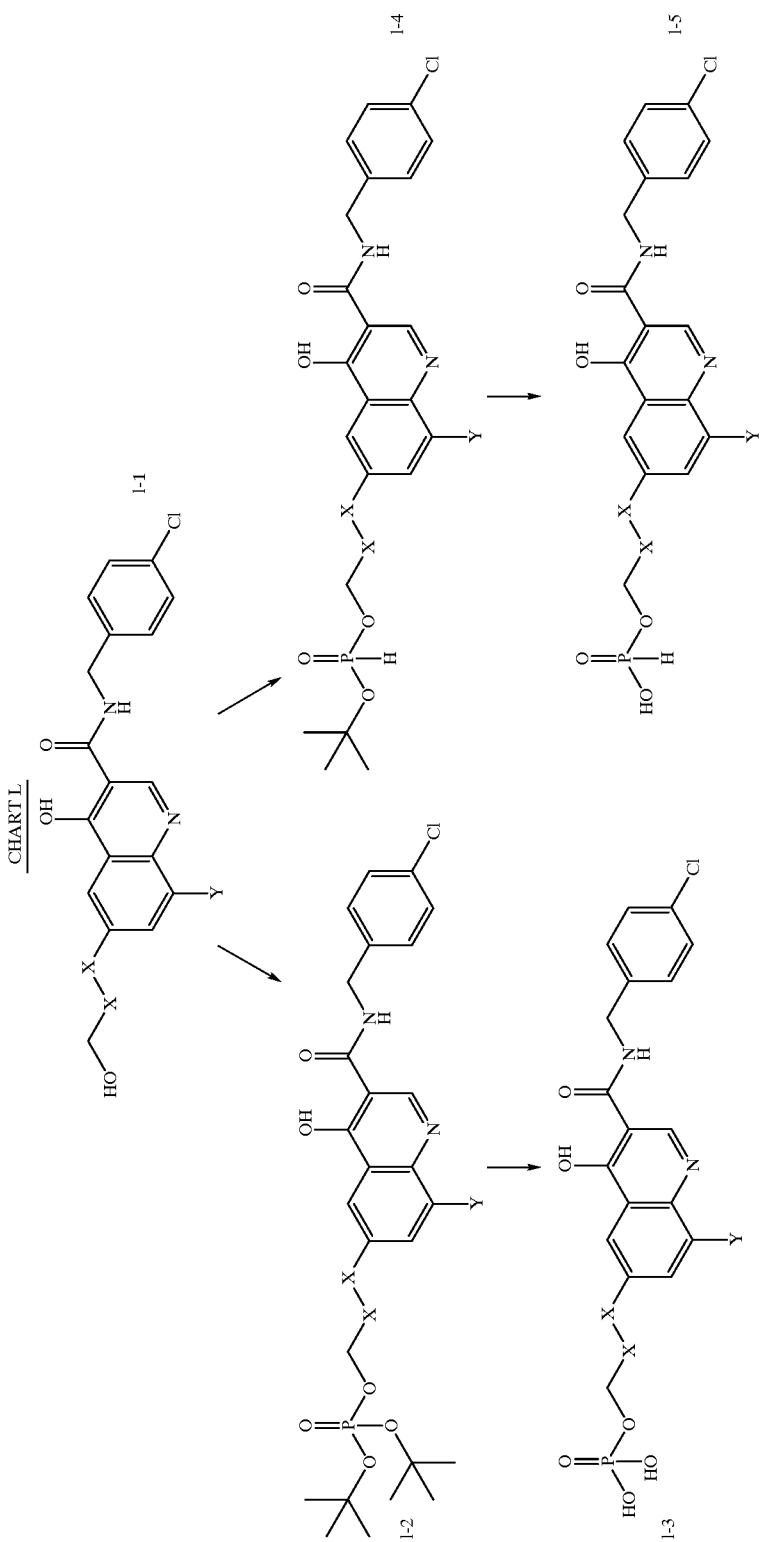

201 202
CHART M
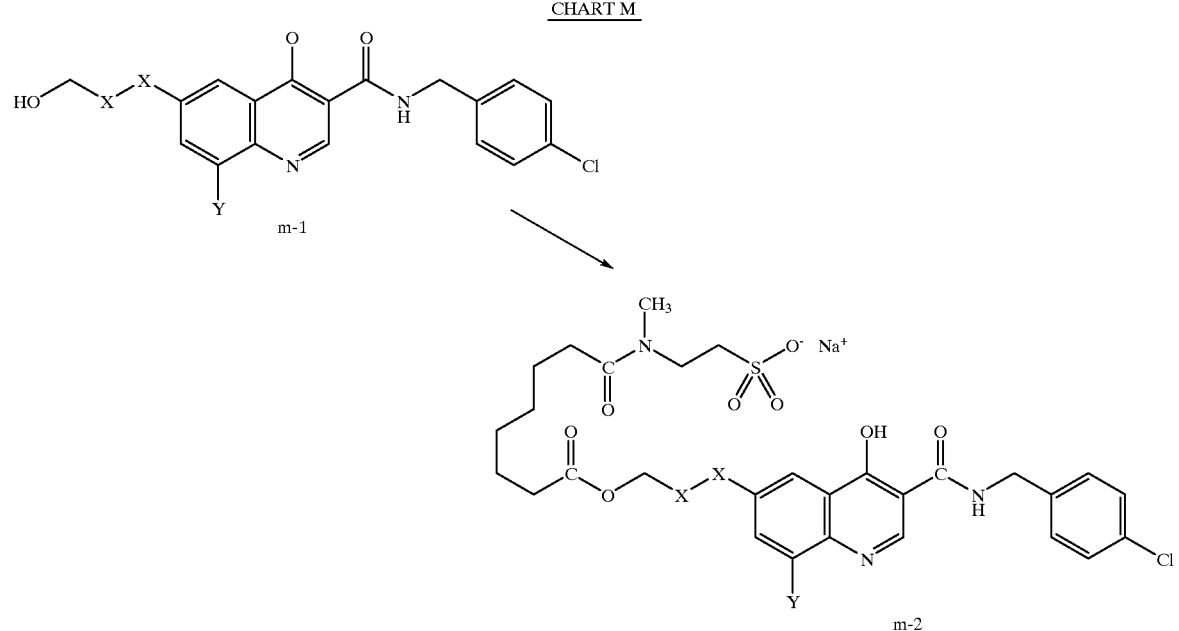
CHART N
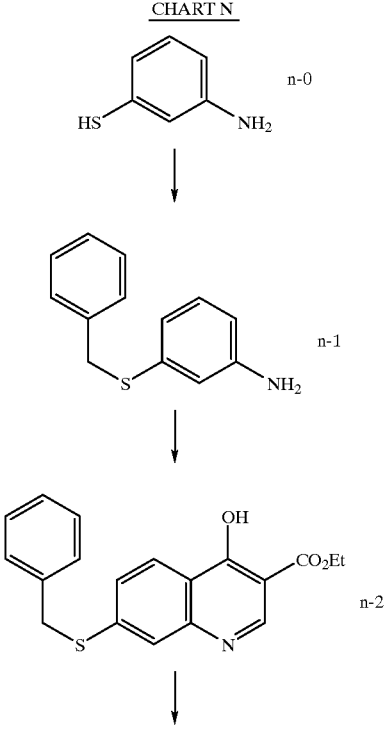

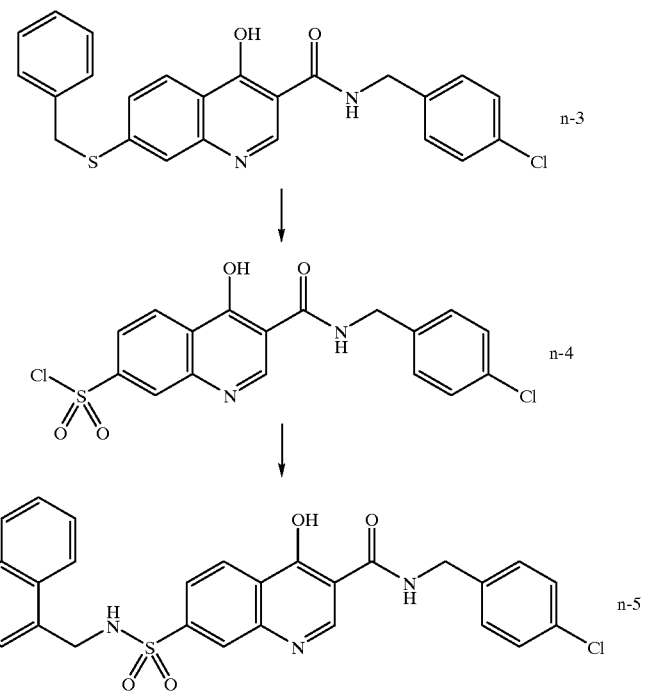
CHART O
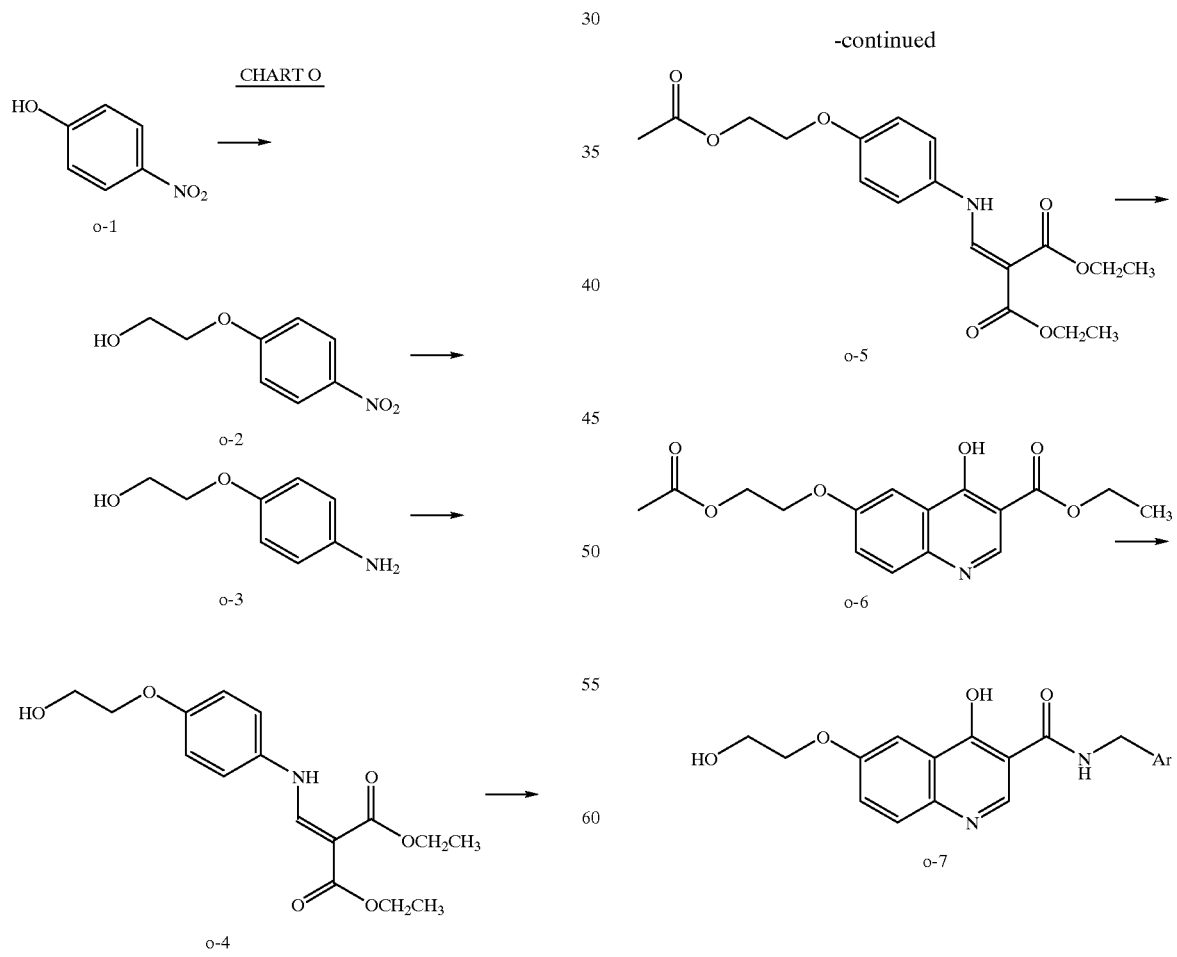

CHART P
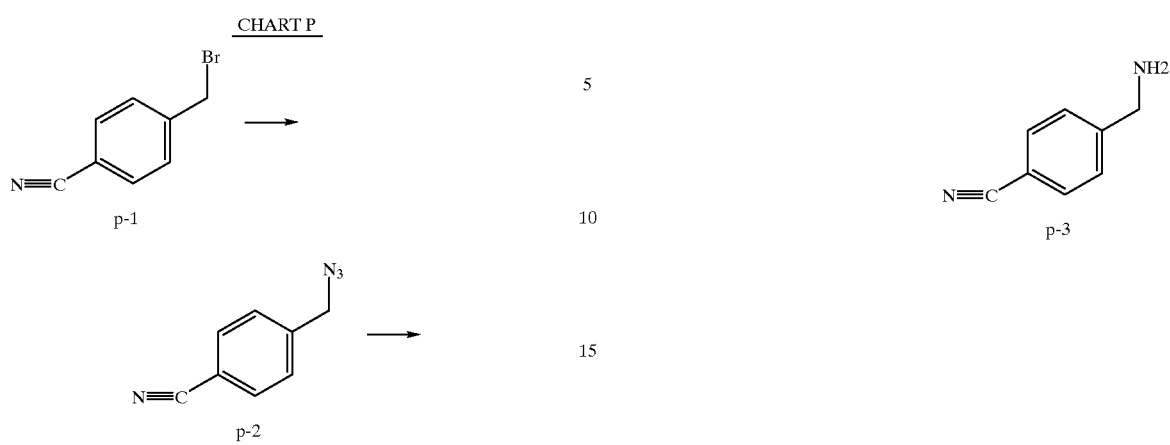
CHART Q
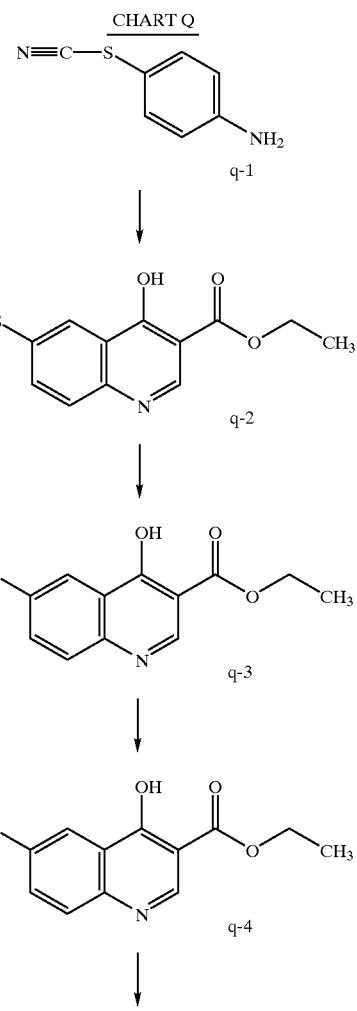

-continued
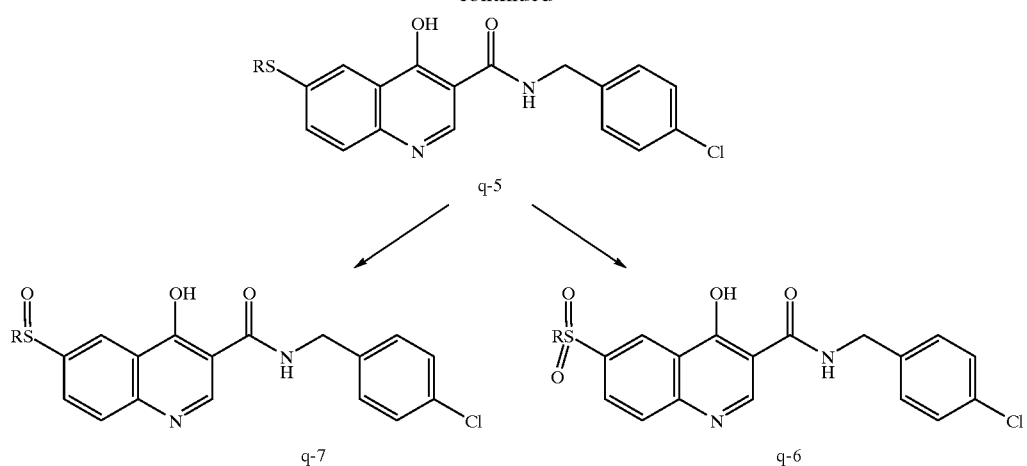
q-5
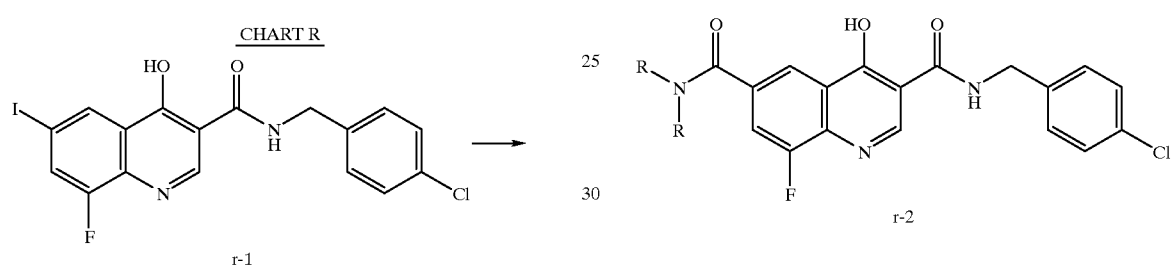
q-7          q-6
CHART R
-continued
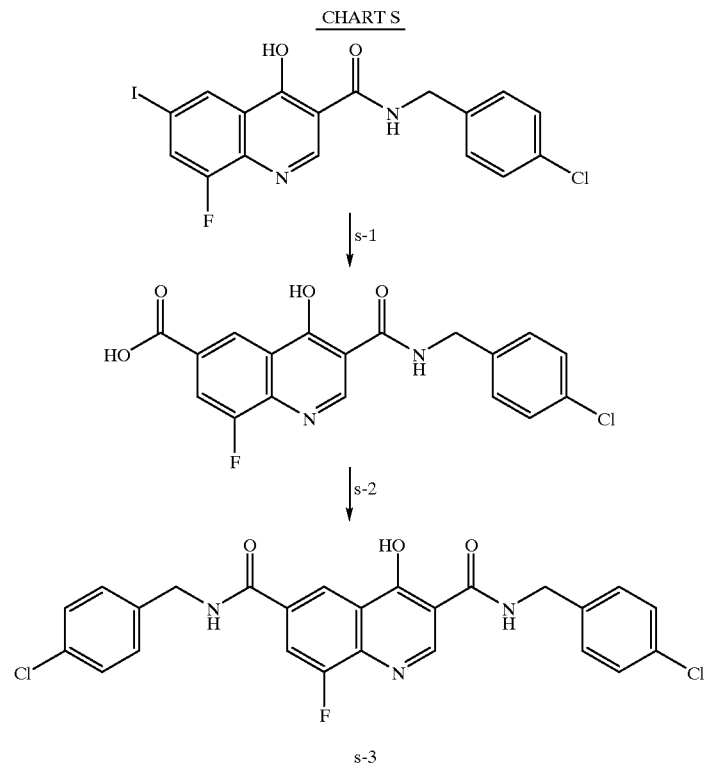

CHART T
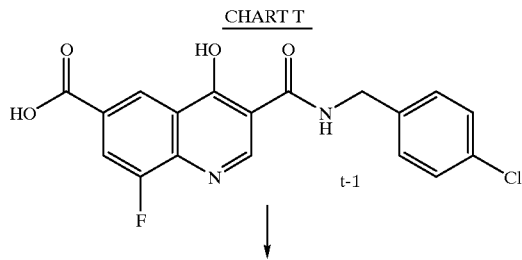
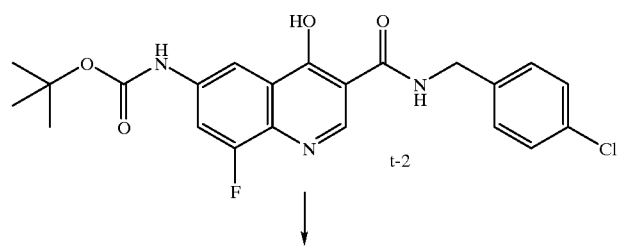
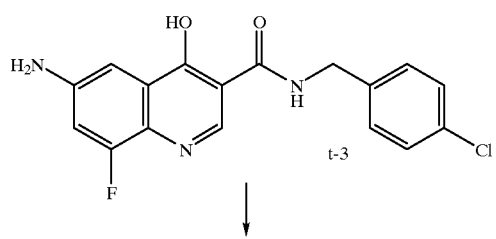
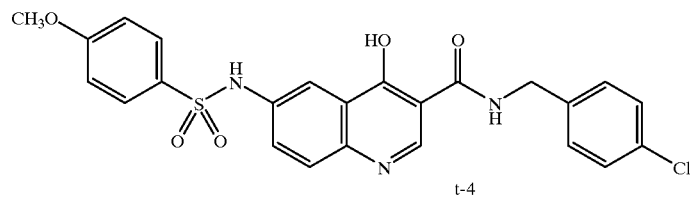
CHART U
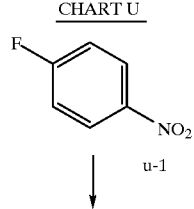

211
-continued
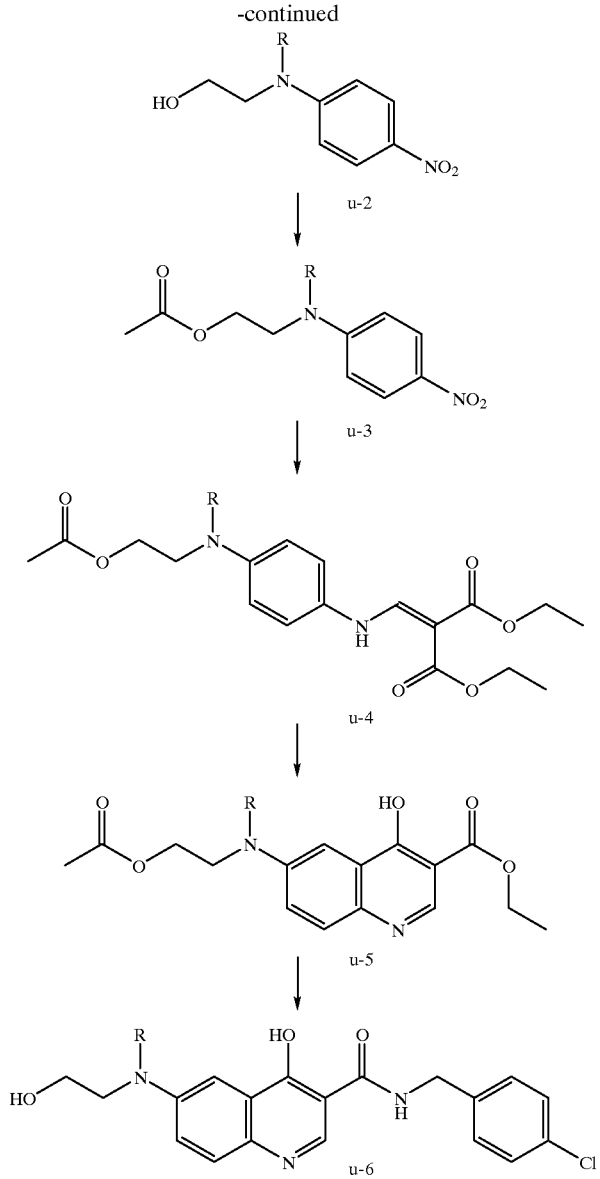
CHART V
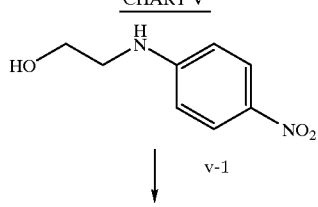
-continued
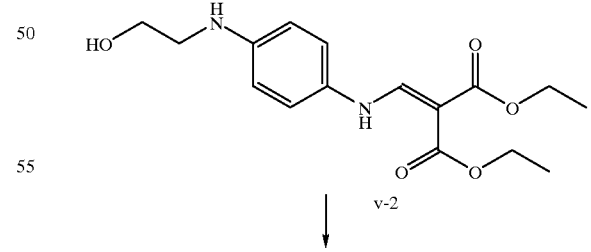

-continued

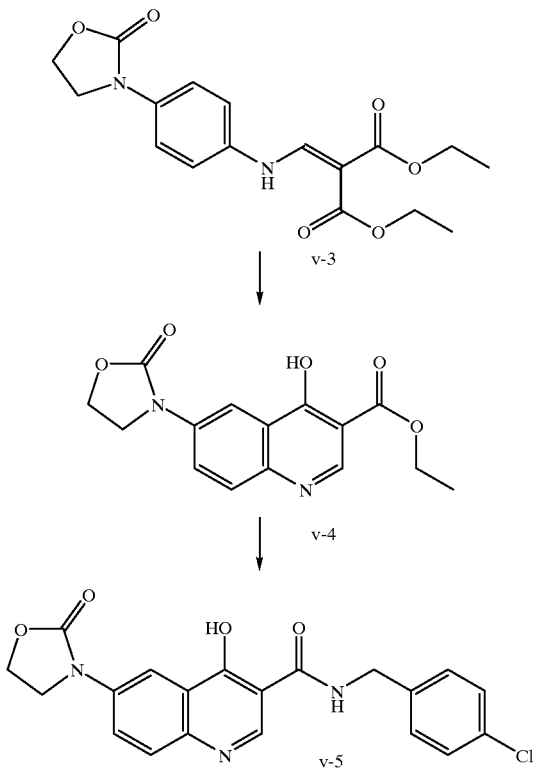

We claim:
1. A compound of formula I

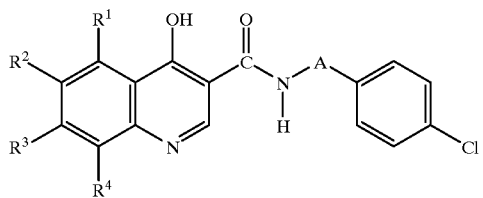

or a pharmaceutically acceptable salt thereof wherein
A is:
a) —CH$_2$—, or
b) —NH—;
R$^1$, R$^2$, R$^3$ and R$^4$ are independently
a) —H,
b) halo,
c) —CN,
d) —NO$_2$,
e) aryl,
f) het,
g) —OR$^5$,
h) C$_{1-12}$ alkyl,
i) C$_{1-2}$ alkyl substituted with one to three —CN, halo, —NO$_2$, OR$^5$, —C(=O)R$^5$, —COOR$^5$, het, aryl, —SR$^5$, —OR$^6$, —NR$^7$R$^8$, —OP(=O)(R$^9$)$_2$, —OPH (=O)R$^9$, —OC(=O)R$^{10}$, —O-glycyl, —O-valyl or —O-lysyl,
j) —Cr≡CR$^{11}$,
k) —CH=CH—R$^{12}$,
l) —(CH$_2$)$_m$—C(=O)R$^{13}$,
m) —SR$^{14}$,
n) —C(=S)R$^{15}$,
o) —(CH$_2$)$_m$—SO$_i$R$^{13}$,
p) —NR$^7$R$^8$,
q) —NHSO$_i$R$^{13}$,
r) R$^1$ and R$^2$ taken together are het or C$_{4-6}$ cycloalkyl, or
s) R$^2$ and R$^3$ taken together are het or C$_{4-6}$ cycloalkyl;
R$^5$ is
a) H,
b) C$_{1-8}$ alkyl, optionally substituted with one to three —OH, CN, C$_{1-4}$ alkoxy, halo, —NO$_2$, het or aryl,
c) aryl, or
d) het;
R$^6$ is
a) —SO$_2$C$_{1-6}$ alkyl,
b) —SO$_2$—(CH$_2$)$_m$-aryl, or
c) —SO$_2$—(CH$_2$)$_m$-het;
R$^7$ and R$^8$ are independently
a) H,
b) C$_{1-8}$ alkyl, optionally substituted with one to three —NO$_2$, halo, —CN, OR$^5$, aryl, het, C$_{3-6}$ cycloalkyl, C$_{1-6}$ alkynyl, C$_{1-6}$ alkenyl, —SR$^{14}$, or NR$^{16}$R$^{17}$,
c) aryl,
d) het,
e) —(CH$_2$)$_m$—C(=O)OR$^5$,
f) —(CH$_2$)$_m$—C(=O)R$^5$, or
g) R$^7$ and R$^8$ taken together to form het;
R$^9$ is
a) —OH, or
b) —OC$_{1-8}$ alkyl;
R$^{10}$ is
a) H,
b) C$_{1-8}$ alkyl,
c) —NR$^7$R$^8$,
d) C$_{1-8}$ alkyl substituted with one to two halo, het, —NR$^7$R$^8$, —COOH —O(CH$_2$)$_m$COOH or —C(=O)N(C$_{1-4}$ alkyl)(CH$_2$)$_n$S(=O)$_2$O$^-$M$^+$;
R$^{11}$ is
a) C$_{1-8}$ alkyl,
b) C$_{1-8}$ alkyl substituted with one to three —CN, halo, —NO$_2$, —COOR$^5$, —C(=O)R$^5$, —SR$^5$, aryl, —OR$^5$, —NR$^7$R$^8$, —OP(=O)(R$^9$)$_2$, —OPH(=O)R$^9$ —OC (=O)R$^{10}$, —O-glycyl, —O-valyl or —O-lysyl or
c) —(CH$_2$)$_m$-het;
R$^{12}$ is
a) H,
b) —CN,
c) C$_{1-8}$ alkyl,
d) C$_{1-8}$ alkyl substituted with one to three —CN, halo, —NO$_2$, —C(=O)R$^5$, —COOR$^5$, aryl, het, —SR$^5$, —OR$^5$, —NR$^7$R$^8$, —OP(=O)(R$^9$)$_2$ or —OPH(=O) R$^9$,
e) —C(=O)R$^5$, or
f) —COOR$^5$;
R$^{13}$ is
a) C$_{1-8}$ alkyl,
b) C$_{1-8}$ alkyl substituted one to three —CN, halo, —NO$_2$, —C(=O)R$^5$, het, aryl, —COOR$^5$, —SR$^5$, —OR$^5$ or —NR$^7$R$^8$, c) het,
d) aryl,
e) —NR$^7$R$^8$,
f) OR$^5$,
g) halo;

R$^{14}$ is
a) C$_{1-8}$ alkyl, or
b) C$_{1-8}$ alkyl substituted with one to three —CN, halo, —NO$_2$, —C(=O)R$^5$, —COOR$^5$, het, aryl, —OR$^5$, or —NR$^7$R$^8$;

R$^{15}$ is
a) —NH$_2$, or
b) —NHNH$_2$;

R$^{16}$ and R$^{17}$ is independently
a) H,
b) C$_{1-4}$ alkyl,
c) —C(=O)C$_{1-4}$ alkyl, or
d) —C(=O)—(CH)$_m$-aryl;

aryl is phenyl or naphthyl, optionally substituted with R$^{18}$;
het is a 5-, 6- or 7-membered saturated or unsaturated heterocyclic ring having 1–3 heteroatoms selected from the group consisting of nitrogen, oxygen and sulfur, wherein the heteroclyclic ring is optionally fused to a benzene ring, wherein aryl, het and benzene ring are optionally substituted with R$^{18}$;

R$^{18}$ is
a) halo,
b) —NO$_2$,
c) phenyl, optionally substituted with one to five —OH, —CN, halo, —NO$_2$, C$_{1-6}$ alkyl, het, or OC$_{1-4}$ alkyl,
d) C$_{1-8}$ alkyl, optionally substituted with one to three halo, —CN, —NO$_2$, aryl, —SR$^5$, —OR$^5$ or —NR$^7$R$^8$,
e) OR$^5$, or
f) —SO$_2$NH$_2$;

M is sodium, potassium or lithium atom;
i is 1 or 2;
m is 0, 1, 2, or 4;
n is 1,2, 3 or 4;
and with the following provisos:

(a) where R$^2$, R$^3$ and R$^4$ are each hydrogen, then R$^1$ is other than methoxy,
(b) where R$^4$ is Cl, and R$^2$ and R$^3$ are each hydrogen, then R$^1$ is other than methyl,
(c) where R$^1$ is hydrogen, R$^2$ and R$^4$ are each fluoro, R$^3$ is het, then het is other than substituted piperazinyl,
(d) where R$^1$ and R$^3$ are each hydrogen, R$^2$ is fluoro, then R$^4$ is other than fluoro,
(e) where R$^2$ and R$^4$ are each hydrogen, R$^1$ is fluoro, then R$^3$ is other than fluoro,
(f) where R$^1$ and R$^3$ are each hydrogen, R$^2$ is chloro, then R$^4$ is other than chloro,
(g) where R$^1$, R$^2$ and R$^3$ are each hydrogen, then R$^4$ is not bromo,
(h) where R$^1$, R$^3$ and R$^4$ are each hydrogen, then R$^2$ is not trifluoromethoxy,
(i) where R$^1$, R$^2$ and R$^4$ are each hydrogen, then R$^3$ is not trifluoromethoxy, and
(j) where R$^1$, R$^2$ and R$^3$ are each hydrogen, then R$^4$ is not morpholinyl.

2. A compound of claim 1 wherein A is —CH$_2$—.
3. A compound of claim 1 wherein R$^1$, R$^2$, R$^3$ and R$^4$ are independently a) halo,
b) —CN,
c) —NO$_2$,
d) phenyl,
e) het,
f) —OR$^5$,
g) C$_{1-6}$ alkyl,
h) C$_{1-6}$ alkyl substituted with one to three —CN, halo, OR$^5$, —C(=O)R$^5$, het, —COOR$^5$, phenyl, —OP(=O)(R$^9$)$_2$, —OPH(=O)R$^9$ or —OC(=O)R$^{10}$,
i) —C≡CR$^{11}$,
j) —CH=CH—R$^{12}$,
k) —C(=O)R$^{13}$,
l) —SR$^{14}$,
m) —SO$_i$R$^{13}$,
n) —NR$^7$R$^8$,
o) —NHSO$_i$R$^{13}$, or
p) R$^1$ and R$^2$ taken together are het;

R$^5$ is
a) H,
b) C$_{1-4}$ alkyl, optionally substituted with one to three —OH, halo, —CN, C$_{1-4}$ alkoxy or phenyl, or
c) phenyl;

R$^7$ and R$^8$ are independently
a) H,
b) C$_{1-4}$ alkyl, optionally substituted with one to three —NO$_2$, halo, —CN, OR$^5$ or phenyl,
c) aryl,
d) —(CH$_2$)$_m$—C(=O)OR$^5$, or
e) —(CH$_2$)$_m$—C(=O)R$^5$;

R$^9$ is
a) —OH, or
b) —OC$_{1-8}$ alkyl;

R$^{10}$ is
a) H,
b) —NR$^7$R$^8$, or
c) C$_{1-8}$ alkyl substituted with one to two halo, het, —NR$^7$R$^8$ or —C(=O)N(C$_{1-4}$ alkyl)(CH$_2$)$_n$S(=O)$_2$O$^-$M$^+$;

R$^{11}$ is
a) C$_{1-8}$ alkyl substituted with one to three halo, —CN, —C(=O)R$^5$, phenyl, —OR$^5$, —NR$^7$R$^8$ or —OC(=O)R$^{10}$;

R$^{12}$ is
a) —CN,
b) —C(=O)R$^5$, or
c) C$_{1-4}$ alkyl substituted with one to three —CN, halo or —OR$^5$, R$^{13}$ is
a) C$_{1-4}$ alkyl,
b) C$_{1-4}$ alkyl substituted with one to three -phenyl, —OR$^5$ or —NR$^7$R$^8$,
c) phenyl,
e) —NR$^7$R$^8$, or
f) OR$^5$;

R$^{14}$ is
a) C$_{1-4}$ alkyl, optionally substituted with phenyl;

aryl is phenyl or naphthyl, in each occurrence phenyl is optionally substituted with R$^{18}$;
het is pyrrolyl, morpholinyl, thiophenyl, thiazolyl, pyridinyl, thiadiazolyl or 2-oxo-oxazolyl, wherein het is optionally substituted with R$^{18}$, $R^{18}$ is
  a) halo,
  b) phenyl,
  c) $C_{1-4}$ alkyl, optionally substituted with one to three halo or $OR^5$; or
  d) $OR^5$;
M is sodium, potassium or lithium atom;
i is 2;
m is 0, 1, 2, or 4; and
n is 1, 2, 3 or 4.

4. A compound of claim 1 wherein
$R^1$ is H;
$R^2$, $R^3$ and $R^4$ are independently
  a) fluoro,
  b) het,
  c) —$oR^5$,
  d) $C_{1-6}$ alkyl substituted with halo, $OR^5$, —$C(=O)R^5$, —$OP(=O)(R^9)_2$, het, —$OPH(=O)R^9$ or —$OC(=O)R^{10}$,
  e) —$C\equiv CR^{11}$,
  f) —$CH=CH—R^{12}$,
  g) —$C(=O)R^{13}$, or
  h) —$NR^7R^8$;
$R^5$ is
  a) H, or
  b) $C_{1-4}$ alkyl, optionally substituted with —OH, halo or $C_{1-4}$ alkoxy;
$R^7$ and $R^8$ are independently
  a) H,
  b) $C_{1-4}$ alkyl, optionally substituted with one to two halo, —$OR^5$ or phenyl, or
  c) —$C(=O)OR^5$;
$R^9$ is
  a) —OH, or
  b) —$OC_{1-4}$ alkyl;
$R^{10}$ is $C_{1-8}$ alkyl substituted with one or two of the following
  a) —$C(=O)N(C_{1-4}$ alkyl$)(CH_2)_nS(=O)_2O^-M^+$,
  b) halo, or
  c) —$NR^7R^8$;
$R^{11}$ is $C_{1-4}$ alkyl substituted with —$OR^5$, —$NR^7R^8$ or —$OC(=O)R^{10}$;
$R^{12}$ is $C_{1-4}$ alkyl substituted with —$OR^5$;
$R^{13}$ is $C_{1-4}$ alkyl substituted with —$OR^5$;
het is morpholinyl or thiophenyl;
M is sodium, potassium or lithium atom; and
n is 1 or 2.

5. A compound of claim 1 wherein
$R^1$ and $R^3$ are independently H,
$R^4$ is
  a) H,
  b) fluoro, or
  c) —$OR^5$;
$R^2$ is
  a) thiophenyl,
  b) $C_{1-6}$ alkyl substituted with —$OR^5$, —$OP(=O)(OH)_2$, —$OPH(=O)(OH)$ or —$OC(=O)R^{10}$,
  c) —$C\equiv CR^{11}$, or
  d) —$CH=CH—R^{12}$;

$R^5$ is
  a) H, or
  b) $C_{1-4}$ alkyl, optionally substituted with —OH or $C_{1-4}$ alkoxy;
$R^{10}$ is $C_{1-8}$ alkyl substituted with one or two of the followings
  a) —$C(=O)N(C_{1-4}$ alkyl$)(CH_2)_2S(=O)_2O^-M^+$, or
  b) —$NH_2$;
$R^{11}$ is $C_{1-4}$ alkyl substituted with —$OR^5$ or —$OC(=O)R^{10}$;
$R^{12}$ is $C_{1-4}$ alkyl substituted with —$OR^5$; and
M is sodium atom.

6. A compound of formula I

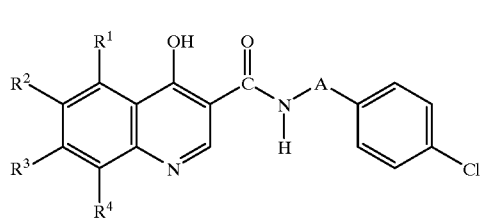

or a pharmaceutically acceptable salt thereof wherein
A is —$CH_2$—:
$R^1$, $R^2$, $R^3$ and $R^4$ are independently
  a) het,
  b) $C_{1-2}$ alkyl substituted with one to three —$C(=O)R^5$, het, aryl, —$NR^7R^8$, —$OP(=O)(R^9)_2$, —$OPH(=O)R^9$ or —$OC(=O)R^{10}$,
  c) —$C\equiv CR^{11}$,
  d) —$CH=CH—R^{12}$,
  e) —$C(=S)R^{15}$,
  f) —$NR^7R^8$,
  g) —$NHSO_iR^{13}$,
  h) $R^1$ and $R^2$ taken together are het or $C_{4-6}$ cycloalkyl, or
  i) $R^2$ and $R^3$ taken together are het or $C_{4-6}$cycloalkyl;
$R^5$ is
  a) H,
  b) $C_{1-8}$ alkyl, optionally substituted with one to three —OH, CN, $C_{1-4}$ alkoxy, halo, —$NO_2$, het or aryl,
  c) aryl, or
  d) het;
$R^7$ and $R^8$ are independently
  a) H,
  b) $C_{1-8}$ alkyl, optionally substituted with one to three —$NO_2$, halo, —CN, $OR^5$, aryl or het,
  c) aryl,
  d) het,
  e) —$(CH_2)_m—C(=O)OR^5$,
  f) —$(CH_2)_m—C(=O)R^5$, or
  g) $R^7$ and $R^8$ taken together to form het;
$R^9$ is
  a) —OH, or
  b) —$OC_{1-8}$ alkyl;
$R^{10}$ is
  a) H,
  b) $C_{1-8}$ alkyl,
  c) —$NR^7R^8$,
  d) $C_{1-8}$ alkyl substituted with one to two halo, het, —$NR^7R^8$ or —$C(=O)N(C_{1-4}$ alkyl$)(CH_2)_nS(=O)_2O^-M^+$;

R¹¹ is
a) $C_{1-8}$ alkyl,
b) $C_{1-8}$ alkyl substituted with one to three —CN, halo, —NO₂, —COOR⁵, —C(=O)R⁵, —SR⁵, aryl, —OR⁵, —NR⁷R⁸, —OP(=O)(R⁹)₂, —OPH(=O)R⁹ or —OC(=O)R¹⁰, or
c) —(CH₂)$_m$-het;

R¹² is
a) H,
b) —CN,
c) $C_{1-8}$ alkyl,
d) $C_{1-8}$ alkyl substituted with one to three —CN, halo, —NO₂, —C(=O)R⁵, —COOR⁵, aryl, het, —SR⁵, —OR⁵, —NR⁷R⁸, —OP(=O)(R⁹)₂ or —OPH(=O)R⁹,
e) —C(=O)R⁵, or
f) —COOR⁵;

R¹³ is
a) $C_{1-8}$ alkyl,
b) —(CH₂)$_m$-alkyl substituted one to three —CN, halo, —NO₂, —C(=O)R⁵, het, aryl, —COOR⁵, —SR⁵, —OR⁵ or —NR⁷R⁸,
c) het,
d) aryl,
e) —NR⁷R⁸, or
f) OR⁵;

R¹⁵ is
a) —NH₂, or
b) —NHNH₂;

aryl is phenyl or naphthyl, optionally substituted with R¹⁶;
het is a 5-, 6- or 7-membered saturated or unsaturated heterocyclic ring having 1–3 heteroatoms selected from the group consisting of nitrogen, oxygen and sulfur, wherein the heteroclyclic ring is optionally fused to a benzene ring, and optionally substituted with R¹⁸;

R¹⁸ is
a) halo,
b) —NO₂,
c) phenyl, optionally substituted with one to five —OH, —CN, halo, —NO₂, $C_{1-6}$ alkyl, or $OC_{1-4}$ alkyl,
c) $C_{1-8}$ alkyl, optionally substituted with one to three halo, —CN, —NO₂, aryl, —SR⁵, OR⁵ or —NR⁷R⁸, or
e) OR⁵;

M is sodium, potassium or lithium atom;
i is 1 or 2;
m is 0, 1, 2, or 4;
n is 1, 2, 3 or 4;
and with the following provisos:
(a) where R¹ is hydrogen, R² and R⁴ are each fluoro, R³ is het, then het is other than substituted piperazinyl,
(b) where R¹, R² and R³ are each hydrogen, then R⁴ is not morpholinyl,
(c) where R¹, R², R³ and R⁴ are independently —NR⁷R⁸, then R⁷ and R⁸ are not hydrogen or alkyl,
(d) het is other than cyclic amino.

7. A method of treating infections from herpesviruses which comprises administering to a patient in need thereof an effective amount of a compound of formula I as shown in claim 1.

8. The method of claim 7 wherein said herpesviruses is herpes simplex virus types 1, herpes simplex virus types 2, varicella zoster virus, cytomegalovirus, Epstein-Barr virus, human herpes viruses 6, human herpes viruses 7 or human herpes viruses 8.

9. The method of claim 7 wherein said herpesviruses is human cytomegalovirus.

10. The method of claim 7 wherein the effective amount of a compound administered orally, parenterally or topically.

11. The method of claim 7 wherein the effective amount of a compound is in an amount of from about 0.1 to about 300 mg/kg of body weight.

12. The method of claim 7 wherein the effective amount of a compound is in an amount of from about 1 to about 30 mg/kg of body weight.

13. A pharmaceutical composition which comprises an effective amount of a compound of claim 1 and a pharmaceutically acceptable carrier.

14. A compound of claim 1 which is
(1) N-[(4-chlorophenyl)methyl]-4-hydroxy-7-(trifluoromethyl)-3-quinolinecarboxamide;
(2) 7-amino-N-[(4-chlorophenyl)methyl]-4-hydroxy-3-quinolinecarboxamide;
(3) N-[(4-chlorophenyl)methyl]-8-fluoro-4,6-dihydroxy-3-quinolinecarboxamide;
(4) 6-bromo-N-[(4-chlorophenyl)methyl]-8-fluoro-3-quinolinecarboxamide;
(5) N-[(4-chlorophenyl)methyl]-8-fluoro-4-hydroxy-6-iodo-3-quinolinecarboxamide;
(6) N-[(4-chlorophenyl)methyl]-4-hydroxy-3-quinolinecarboxamide;
(7) N-[(4-chlorophenyl)methyl]-4-hydroxy-7-methoxy-3-quinolinecarboxamide;
(8) N-[(4-chlorophenyl)methyl]-4-hydroxy-5,7-bis(trifluoromethyl)-3-quinolinecarboxamide;
(9) N-[(4-chlorophenyl)methyl]-7-fluoro-4-hydroxy-3-quinolinecarboxamide;
(10) N-[(4-chlorophenyl)methyl]-6-fluoro-4-hydroxy-3-quinolinecarboxamide;
(11) N-[(4-chlorophenyl)methyl]-4-hydroxy-7-methyl-3-quinolinecarboxamide;
(12) N-[(4-chlorophenyl)methyl]-8-fluoro-4-hydroxy-3-quinolinecarboxamide;
(13) N-[(4-chlorophenyl)methyl]-4-hydroxy-6-nitro-3-quinolinecarboxamide;
(14) N-[(4-chlorophenyl)methyl]-5,6,7,8-tetrafluoro-4-hydroxy-3-quinolinecarboxamide;
(15) N-[(4-chlorophenyl)methyl]-6,7,8-trifluoro-4-hydroxy-3-quinolinecarboxamide;
(16) 6,7,8-trifluoro-4-hydroxy-3-quinolinecarboxylic acid 2-(4-chlorophenyl)hydrazide;
(17) N-[(4-chlorophenyl)methyl]-5,8-difluoro-4-hydroxy-3-quinolinecarboxamide;
(18) N-[(4-chlorophenyl)methyl]-7,8-difluoro-4-hydroxy-3 -quinolinecarboxamide;
(19) 6-benzoyl-N-(4-chlorobenzyl)-4-hydroxy-3-quinolinecarboxamide;
(20) N-[(4-chlorophenyl)methyl]-4-hydroxy-8-methoxy-3-quinolinecarboxamide;
(21) 6-chloro-N-[(4-chlorophenyl)methyl]-4-hydroxy-3-quinolinecarboxamide;
(22) N-[(4-chlorophenyl)methyl]-4-hydroxy-6-methyl-3-quinolinecarboxamide;
(23) N-[(4-chlorophenyl)methyl]-4-hydroxy-6-methoxy-3-quinolinecarboxamide;

(24) N-[(4-chlorophenyl)methyl]-6-cyano-4-hydroxy-3-quinolinecarboxamide;

(25) 7-(acetylamino)-N-[(4-chlorophenyl)methyl]-4-hydroxy-3-quinolinecarboxamide;

(26) N-[(4-chlorophenyl)methyl]-4-hydroxy-7-[(methylsulfonyl)amino]-3-quinolinecarboxamide;

(27) N-[(4-chlorophenyl)methyl]-7-(dimethylamino)-4-hydroxy-3-quinolinecarboxamide;

(28) 6-amino-N-[(4-chlorophenyl)methyl]-4-hydroxy-3-quinolinecarboxamide;

(29) N-[(4-chlorophenyl)methyl]-4-hydroxy-6-[(methylsulfonyl)amino]-3-quinolinecarboxamide;

(30) N-[(4-chlorophenyl)methyl]-6-(dimethylamino)-4-hydroxy-3-quinolinecarboxamide;

(31) 6-(acetylamino)-N-[(4-chlorophenyl)methyl]-4-hydroxy-3-quinolinecarboxamide;

(32) N-[(4-chlorophenyl)methyl]-4-hydroxy-7-(1-pyrrolyl)-3-quinolinecarboxamide;

(33) N-[(4-chlorophenyl)methyl]-4-hydroxy-7-[(phenylsulfonyl)amino]-3-quinolinecarboxamide;

(34) N-[(4-chlorophenyl)methyl]-4-hydroxy-7-[[(phenylmethyl)sulfonyl]amino]-3-quinolinecarboxamide;

(35) N-[(4-chlorophenyl)methyl]-7-[[(4-chlorophenyl)sulfonyl]amino]-4-hydroxy-3-quinolinecarboxamide;

(36) 8-fluoro-4-hydroxy-3-quinolinecarboxylic acid 2-(4-chlorophenyl)hydrazide;

(37) N-[(4-chlorophenyl)methyl]-8-fluoro-4-hydroxy-6-methyl-3-quinolinecarboxamide;

(38) N-(4-chlorobenzyl)-8-hydroxy[1,3]dioxolo[4,5-g]quinoline-7-carboxamide;

(39) N-[(4-chlorophenyl)methyl]-4-hydroxy-6-iodo-3-quinolinecarboxamide;

(40) N-[(4-chlorophenyl)methyl]-6-(cyanomethyl)-4-hydroxy-3-quinolinecarboxamide;

(41) N-[(4-chlorophenyl)methyl]-4,5-dihydroxy-3-quinolinecarboxamide;

(42) 7,8-dichloro-N-[(4-chlorophenyl)methyl]-4-hydroxy-3-quinolinecarboxamide;

(43) N-[(4-chlorophenyl)methyl]-4,6-dihydroxy-3-quinolinecarboxamide;

(44) N-[(4-chlorophenyl)methyl]-4,8-dihydroxy-3-quinolinecarboxamide;

(45) 8-chloro-N-[(4-chlorophenyl)methyl]-4-hydroxy-3-quinolinecarboxamide;

(46) N-[(4-chlorophenyl)methyl]-4-hydroxy-6-[[(1-phenyl-1H-pyrazol-5-yl)amino]sulfonyl]-3-quinolinecarboxamide;

(47) N-[(4-chlorophenyl)methyl]-8-cyano-4-hydroxy-3-quinolinecarboxamide;

(48) N-[(4-chlorophenyl)methyl]-4-hydroxy-8-nitro-3-quinolinecarboxamide;

(49) 7-amino-N-[(4-chlorophenyl)methyl]-4-hydroxy-8-methyl-3-quinolinecarboxamide;

(50) N-[(4-chlorophenyl)methyl]-6-cyano-8-fluoro-4-hydroxy-3-quinolinecarboxamide;

(51) 6-(aminothioxomethyl)-N-[(4-chlorophenyl)methyl]-8-fluoro-4-hydroxy-3-quinolinecarboxamide;

(52) N-[(4-chlorophenyl)methyl]-8-fluoro-4-hydroxy-6-(3-hydroxy-1-propynyl)-3-quinolinecarboxamide;

(53) 8-fluoro-4-hydroxy-6-iodo-3-quinolinecarboxylic acid 2-(4-chlorophenyl)-hydrazide;

(54) 8-fluoro-4-hydroxy-6-methyl-3-quinolinecarboxylic acid 2-(4-chlorophenyl)hydrazide;

(55) N-((4-chlorophenyl)methyl)-7-chloro-4-hydroxy-3-quinolinecarboxamide;

(56) N-((4-chlorophenyl)methyl)-6-bromo-4-hydroxy-3-quinolinecarboxamide;

(57) N-((4-chlorophenyl)methyl)-4-hydroxy-6-phenyl-3-quinolinecarboxamide;

(58) N-((4-chlorophenyl)methyl)-8-chloro-4-hydroxy-5-trifluoromethyl-3-quinolinecarboxamide;

(59) N-((4-chlorophenyl)methyl)-6,8-dimethoxy-4-hydroxy-3-quinolinecarboxamide;

(60) N-((4-chlorophenyl)methyl)-6,7-dimethoxy-4-hydroxy-3-quinolinecarboxamide;

(61) N-((4-chlorophenyl)methyl)-4-hydroxy-5-methyl-3-quinolinecarboxamide;

(62) N-[(4-chlorophenyl)methyl]-6-(1,1-dimethylethyl)-4-hydroxy-3-quinolinecarboxamide;

(63) N-[(4-chlorophenyl)methyl]-7,8-dihydro-4-hydroxy-6H-cyclopenta[g]quinoline-3-carboxamide;

(64) N-[(4-chlorophenyl)methyl]-1,4-dihydro-8-(methylthio)-4-oxo-3-quinolinecarboxamide;

(65) N-[(4-chlorophenyl)methyl]-9-hydroxythiazolo[5,4-f]quinoline-8-carboxamide;

(66) sodium 2-[(8-{[3-(3-{[(4-chlorobenzyl)amino]carbonyl}-4-hydroxy-6-quinolinyl)-2-propynyl]oxy}-8-oxooctanoyl)(methyl)amino]-1-ethanesulfonate;

(67) sodium 2-[(8-{[3-(3-{[(4-chlorobenzyl)amino]carbonyl}-8-fluoro-4-hydroxy-6-quinolinyl)-2-propynyl]oxy}-8-oxooctanoyl)(methyl)amino]-1-ethanesulfonate;

(68) sodium 2-[{8-[3-(3-{[(4-chlorobenzyl)amino]carbonyl}-4-hydroxy-6-quinolinyl)propoxy]-8-oxooctanoyl)}(methyl)amino]-1-ethanesulfonate;

(69) N-(4-chlorobenzyl)-4-hydroxy-7-{[(1-naphthylmethyl)amino]sulfonyl}-3-quinolinecarboxamide;

(70) N-(4-chlorobenzyl)-4-hydroxy-7-(methylsulfanyl)-3-quinolinecarboxamide;

(71) N-[(4-chlorophenyl)methyl]-4-hydroxy-6-[(phenylmethyl)thio]-7-(trifluoromethyl)-3-quinolinecarboxamide;

(72) 3-(3-{[(4-chlorobenzyl)amino]carbonyl}-4-hydroxy-6-quinolinyl)propyl hydrogen phosphonate;

(73) N-[(4-chlorophenyl)methyl]-8-fluoro-4-hydroxy-6-(2-thiazolyl)-3-quinolinecarboxamide;

(74) N-[(4-chlorophenyl)methyl]-8-fluoro-4-hydroxy-6-(2-thiophenyl)-3-quinolinecarboxamide;

(75) N-((4-chlorophenyl)methyl)-4-hydroxy-5-trifluoromethyl-3-quinolinecarboxamide;

(76) N-((4-chlorophenyl)methyl)-8-fluoro-4-hydroxy-6-(2-methylphenyl)-3-quinolinecarboxamide;

(77) N-((4-chlorophenyl)methyl)-6,7-difluoro-4-hydroxy-8-(tetrahydro-2H-pyran-4-oxy)-3-quinolinecarboxamide;

(78) N-((4-chlorophenyl)methyl)-6,7-difluoro-4-hydroxy-8-methoxy-3-quinolinecarboxamide;

(79) N-((4-chlorophenyl)methyl)-7,8-dimethoxy-6-fluoro-4-hydroxy-3-quinolinecarboxamide;

(80) N-((4-chlorophenyl)methyl)-6,8-difluoro-4-hydroxy-7-(4-(hydroxymethyl)-phenoxy)-3-quinolinecarboxamide;

(81) N-((4-chlorophenyl)methyl)-6,8-difluoro-4-hydroxy-7-methoxy-3-quinolinecarboxamide;

(82) N-((4-chlorophenyl)methyl)-6,8-difluoro-4-hydroxy-7-(2-(methoxy)ethoxy)-3-quinolinecarboxamide;

(83) N-((4-chlorophenyl)methyl)-6,7-difluoro-4-hydroxy-8-(2-(methoxy)ethoxy)-3-quinolinecarboxamide;

(84) N-((4-chlorophenyl)methyl)-7,8-di(2-(methoxy)ethoxy)-6-fluoro-4-hydroxy-3-quinolinecarboxamide;

(85) N-((4-chlorophenyl)methyl)-6,8-difluoro-4-hydroxy-7-(1-methylethoxy)-3-quinolinecarboxamide;

(86) N-(4-chlorobenzyl)-8-fluoro-4-hydroxy-6-(1,3-thiazol-2-yl)-3-quinolinecarboxamide;

(87) N-(4-chlorobenzyl)-6,8-difluoro-4-hydroxy-7-[(2-methoxyethyl)amino]-3-quinolinecarboxamide;

(88) N-(4-chlorobenzyl)-6-(5-cyano-1-pentynyl)-8-fluoro-4-hydroxy-3-quinolinecarboxamide;

(89) N-(4-chlorobenzyl)-8-fluoro-4-hydroxy-6-(2-pyridinyl)-3-quinolinecarboxamide;

(90) N'-(4-chlorophenyl)-4-hydroxy-6-iodo-3-quinolinecarbohydrazide;

(91) N-(4-chlorobenzyl)-8-fluoro-4-hydroxy-6-[2-(2-pyridinyl)ethynyl]-3-quinolinecarboxamide;

(92) N-(4-chlorobenzyl)-6,8-difluoro-4-hydroxy-7-[(2-hydroxyethyl)amino]-3-quinolinecarboxamide;

(93) N-(4-chlorobenzyl)-8-fluoro-4-hydroxy-6-(4-hydroxy-1-butynyl)-3-quinolinecarboxamide;

(94) N-(4-chlorobenzyl)-8-fluoro-4-hydroxy-6-(3-methoxy-1-propynyl)-3-quinolinecarboxamide;

(95) N-(4-chlorobenzyl)-8-fluoro-4-hydroxy-6-(3-hydroxy-1-butynyl)-3-quinolinecarboxamide;

(96) 6-(4-bromo-2-thienyl)-N-(4-chlorobenzyl)-8-fluoro-4-hydroxy-3-quinolinecarboxamide;

(97) N-(4-chlorobenzyl)-8-fluoro-6-(hydrazinocarbothioyl)-4-hydroxy-3-quinolinecarboxamide;

(98) N-(4-chlorobenzyl)-8-fluoro-4-hydroxy-6-(4-hydroxybutyl)-3-quinolinecarboxamide;

(99) N-(4-chlorobenzyl)-8-fluoro-4-hydroxy-6-(5-methyl-1,3,4-thiadiazol-2-yl)-3-quinolinecarboxamide;

(100) N-(4-chlorobenzyl)-4-hydroxy-7-(3-hydroxy-1-propynyl)-3-quinolinecarboxamide;

(101) 7-(aminocarbothioyl)-N-(4-chlorobenzyl)-4-hydroxy-3-quinolinecarboxamide;

(102) N-(4-chlorobenzyl)-8-fluoro-4-hydroxy-6-(3-methoxypropyl)-3-quinolinecarboxamide;

(103) N-(4-chlorobenzyl)-8-fluoro-4-hydroxy-6-[(Z)-4-hydroxy-1-butenyl]-3-quinolinecarboxamide;

(104) N-(4-chlorobenzyl)-6-(5-cyanopentyl)-8-fluoro-4-hydroxy-3-quinolinecarboxamide;

(105) N-(4-chlorobenzyl)-8-fluoro-4-hydroxy-6-(3-hydroxy-3-methylbutyl)-3-quinolinecarboxamide;

(106) N-(4-chlorobenzyl)-8-fluoro-4-hydroxy-6-(5-hydroxy-1-pentynyl)-3-quinolinecarboxamide;

(107) 6-{3-[benzyl(methyl)amino]propyl}-N-(4-chlorobenzyl)-8-fluoro-4-hydroxy-3-quinolinecarboxamide;

(108) methyl 3-{[(4-chlorobenzyl)amino]carbonyl}-8-fluoro-4-hydroxy-6-quinolinecarboxylate;

(109) N-(4-chlorobenzyl)-8-fluoro-4-hydroxy-6-(3-hydroxypropyl)-3-quinolinecarboxamide;

(110) N-(4-chlorobenzyl)-4-hydroxy-7-(3-hydroxypropyl)-3-quinolinecarboxamide;

(111) ethyl (E)-3-(3-{[(4-chlorobenzyl)amino]carbonyl}-8-fluoro-4-hydroxy-6-quinolinyl)-2-propenoate;

(112) sodium 2-[18-[3-(3-{[(4-chlorobenzyl)amino]carbonyl}-8-fluoro-4-hydroxy-6-quinolinyl)propoxy]-8-oxooctanoyl}(methyl)amino]-1-ethanesulfonate;

(113) 3-(3-{[(4-chlorobenzyl)amino]carbonyl}-8-fluoro-4-hydroxy-6-quinolinyl)-propanoic acid;

(114) 5-(3-{[(4-chlorobenzyl)amino]carbonyl}-8-fluoro-4-hydroxy-6-quinolinyl)-4-pentynoic acid;

(115) N-[(4-chlorophenyl)methyl]-9]hydroxy-3H-pyrazolo[4,3-fl quinoline-8-carboxamide;

(116) N-(4-chlorobenzyl)-4-hydroxy-6-iodo-8-methoxy-3-quinolinecarboxamide;

(117) N-(4-chlorobenzyl)-4-hydroxy-6-(3-hydroxy-1-propynyl)-8-methoxy-3-quinolinecarboxamide;

(118) N-(4-chlorobenzyl)-4-hydroxy-8-methoxy-6-(3-methoxy-1-propynyl)-3-quinolinecarboxamide;

(119) N-(4-chlorobenzyl)-4-hydroxy-6-(3-hydroxypropyl)-8-methoxy-3-quinolinecarboxamide;

(120) N-(4-chlorobenzyl)-4-hydroxy-6-(3-hydroxy-1-propynyl)-8-(trifluoromethyl)-3-quinolinecarboxamide;

(121) N-(4-chlorobenzyl)-4-hydroxy-6-(3-hydroxy-1-propynyl)-8-(trifluoromethoxy)-3-quinolinecarboxamide;

(122) N-(4-chlorobenzyl)-4-hydroxy-6-(3-hydroxypropyl)-8-(trifluoromethyl)-3-quinolinecarboxamide;

(123) N-(4-chlorobenzyl)-4-hydroxy-8-(2-hydroxyethoxy)-6-(3-hydroxypropyl)-3-quinolinecarboxamide;

(124) N-(4-chlorobenzyl)-4-hydroxy-6-(3-hydroxy-1,1-dimethylpropyl)-3-quinolinecarboxamide;

(125) N-(4-chlorobenzyl)-8-fluoro-4-hydroxy-6-[3-(methylsulfanyl)-1-propynyl]-3-quinolinecarboxamide;

(126) N-(4-chlorobenzyl)-6-[3-(ethylsulfanyl)-1-propynyl]-8-fluoro-4-hydroxy-3-quinolinecarboxamide;

(127) N-(4-chlorobenzyl)-8-fluoro-4-hydroxy-6-[(Z)-3-(methylsulfanyl)-1-propenyl]-3-quinolinecarboxamide;

(128) N-(4-chlorobenzyl)-6-[(Z)-3-(ethylsulfanyl)-1-propenyl]-8-fluoro-4-hydroxy-3-quinolinecarboxamide;

(129) N-(4-chlorobenzyl)-8-fluoro-4-hydroxy-6-[3-(methylsulfanyl)propyl]-3-quinolinecarboxamide;

(130) 3-(3-{[(4-chlorobenzyl)amino]carbonyl}-8-fluoro-4-hydroxy-6-quinolinyl)-2-propynyl formate;

(131) N-(4-chlorobenzyl)-8-fluoro-4-hydroxy-6-(3-hydroxybutyl)-3-quinolinecarboxamide;

(132) N-(4-chlorobenzyl)-6-[(E)-2-cyanoethenyl]-8-fluoro-4-hydroxy-3-quinolinecarboxamide;

(133) N-(4-chlorobenzyl)-4-hydroxy-6-(3-hydroxy-1-propynyl)-3-quinolinecarboxamide;

(134) N-(4-chlorobenzyl)-6-[(Z)-3-hydroxy-1-propenyl]-4-oxo-1,4-dihydro-3-quinolinecarboxamide;

(135) N-(4-chlorobenzyl)-6-[(E)-3-hydroxy-1-propenyl]-4-oxo-1,4-dihydro-3-quinolinecarboxamide;

(136) N-(4-chlorobenzyl)-8-fluoro-4-hydroxy-6-[(Z)-3-hydroxy-1-propenyl]-3-quinolinecarboxamide;

(137) N-(4-chlorobenzyl)-6-(2-cyanoethyl)-8-fluoro-4-hydroxy-3-quinolinecarboxamide;

(138) N-(4-chlorobenzyl)-8-fluoro-4-hydroxy-6-(3-oxopropyl)-3-quinolinecarboxamide;

(139) N-(4-chlorobenzyl)-4-hydroxy-7-(4-hydroxybutyl)-3-quinolinecarboxamide;

(140) N-(4-chlorobenzyl)-8-fluoro-4-hydroxy-6-(hydroxymethyl)-3-quinolinecarboxamide;

(141) 3-(3-{[(4-chlorobenzyl)amino]carbonyl}-8-fluoro-4-hydroxy-6-quinolinyl)propyl methanesulfonate;

(142) N-(4-chlorobenzyl)-8-fluoro-6-(3-fluoro-1-propynyl)-4-hydroxy-3-quinolinecarboxamide;

(143) N-(4-chlorobenzyl)-4-hydroxy-6-(3-hydroxypropyl)-3-quinolinecarboxamide;

(144) 3-(3-{[(4-chlorobenzyl)amino]carbonyl}-8-fluoro-4-hydroxy-6-quinolinyl)propyl 2-bromoacetate;

(145) 3-(3-{[(4-chlorobenzyl)amino]carbonyl}-8-fluoro-4-hydroxy-6-quinolinyl)propyl 2-[(tert-butoxycarbonyl)amino]-3-methylbutanoate;

(146) 3-(3-{[(4-chlorobenzyl)amino]carbonyl}-8-fluoro-4-hydroxy-6-quinolinyl)propyl 2-(4-morpholinyl)acetate;

(147) 3-(3-{[(4-chlorobenzyl)amino]carbonyl}-8-fluoro-4-hydroxy-6-quinolinyl)propyl 2-(dimethylamino)acetate;

(148) 3-(3-{[(4-chlorobenzyl)amino]carbonyl}-8-fluoro-4-hydroxy-6-quinolinyl)propyl 2-amino-3-methylbutanoate;

(149) 3-(3-{[(4-chlorobenzyl)amino]carbonyl}-8-fluoro-4-hydroxy-6-quinolinyl)-2-propynyl phenylcarbamate;

(150) N-(4-chlorobenzyl)-4-hydroxy-6-propyl-3-quinolinecarboxamide;

(151) N-(4-chlorobenzyl)-4-hydroxy-6-(3-hydroxy-1-butynyl)-3-quinolinecarboxamide;

(152) N-(4-chlorobenzyl)-8-fluoro-4-hydroxy-6-[(E)-3-oxo-1-butenyl]-3-quinolinecarboxamide;

(153) N-(4-chlorobenzyl)-8-fluoro-4-hydroxy-6-(5-hydroxypentyl)-3-quinolinecarboxamide;

(154) 3-(3-{[(4-chlorobenzyl)amino]carbonyl}-8-fluoro-4-hydroxy-6-quinolinyl)propyl 2,6-bis [(tert-butoxycarbonyl)amino]hexanoate;

(155) 3-(3-{[(4-chlorobenzyl)amino]carbonyl}-8-fluoro-4-hydroxy-6-quinolinyl)propyl 2,6-diaminohexanoate, trifluoroacetic acid salt;

(156) N-(4-chlorobenzyl)-4-hydroxy-6-(3-hydroxybutyl)-3-quinolinecarboxamide;

(157) N-(4-chlorobenzyl)-8-fluoro-4-hydroxy-6-(4-morpholinylmethyl)-3-quinolinecarboxamide;

(158) 3-(3-{[(4-chlorobenzyl)amino]carbonyl}-8-fluoro-4-hydroxy-6-quinolinyl)propyl phenylcarbamate;

(159) N-(4-chlorobenzyl)-8-fluoro-4-hydroxy-6-(3-oxobutyl)-3-quinolinecarboxamide;

(160) 3-(3-{[(4-chlorobenzyl)amino]carbonyl}-4-hydroxy-6-quinolinyl)-2-propynyl 2,6-bis[(tert-butoxycarbonyl)amino]hexanoate;

(161) 3-(3-{[(4-chlorobenzyl)amino]carbonyl}-4-hydroxy-6-quinolinyl)-2-propynyl 2,6-diaminohexanoate, trifluoroacetic acid salt;

(162) N-(4-chlorobenzyl)-4-hydroxy-6-[(2-hydroxyethoxy)methyl]-3-quinolinecarboxamide;

(163) N-(4-chlorobenzyl)-4-hydroxy-6-{[2-hydroxy-1-(hydroxymethyl)ethoxy]methyl}-3-quinolinecarboxamide;

(164) Methyl 3-{[(4-chlorobenzyl)amino]carbonyl}-4-hydroxy-6-quinolinecarboxylate;

(165) N-(4-chlorobenzyl)-4-hydroxy-6-(hydroxymethyl)-3-quinolinecarboxamide;

(166) 6-chloro-N-(4-chlorobenzyl)-4-hydroxy-8-methyl-3-quinolinecarboxamide;

(167) N-(4-chlorobenzyl)-5,6,8-trifluoro-4-hydroxy-3-quinolinecarboxamide;

(168) N-(4-chlorobenzyl)-6,7-difluoro-4-hydroxy-3-quinolinecarboxamide;

(169) N-(4-chlorobenzyl)-8-fluoro-4-hydroxy-6-(methylsulfanyl)-3-quinolinecarboxamide;

(170) N-(4-chlorobenzyl)-8-fluoro-4-hydroxy-6-[(2-hydroxyethyl)sulfanyl]-3-quinolinecarboxamide;

(171) 6-[(2-aminoethyl)sulfanyl]-N-(4-chlorobenzyl)-8-fluoro-4-hydroxy-3-quinolinecarboxamide hydrobromide;

(172) N-(4-chlorobenzyl)-8-fluoro-4-hydroxy-6-({[(2-methoxyethoxy)methyl]sulfanyl}-3-quinolinecarboxamide;

(173) N-(4-chlorobenzyl)-8-fluoro-4-hydroxy-6-{[2-(4-morpholinyl)ethyl]sulfanyl}-3-quinolinecarboxamide;

(174) N-(4-chlorobenzyl)-8-fluoro-4-hydroxy-6-(methylsulfinyl)-3-quinolinecarboxamide;

(175) N-(4-chlorobenzyl)-8-fluoro-4-hydroxy-6-(methylsulfonyl)-3-quinolinecarboxamide;

(176) N-(4-chlorobenzyl)-8-fluoro-4-hydroxy-6-[(2-hydroxyethyl)sulfinyl]-3-quinolinecarboxamide;

(177) N-(4-chlorobenzyl)-4-hydroxy-6-(2-thienyl)-3-quinolinecarboxamide;

(178) N-(4-chlorobenzyl)-4-hydroxy-6-(2-hydroxyethoxy)-3-quinolinecarboxamide;

(179) N-(4-chlorobenzyl)-8-fluoro-4-hydroxy-6-(4-morpholinylcarbonyl)-3-quinolinecarboxamide;

(180) $N^3$-(4-chlorobenzyl)-8-fluoro-4-hydroxy-$N^6$-(2-hydroxyethyl)-3,6-quinolinedicarboxamide;

(181) $N^3$-(4-chlorobenzyl)-8-fluoro-4-hydroxy-$N^6,N$~6~-dimethyl-3,6-quinolinedicarboxamide;

(182) $N^3$-(4-chlorobenzyl)-8-fluoro-4-hydroxy-$N^6$-(4-hydroxyphenethyl)-3,6-quinolinedicarboxamide;

(183) N3-(4-chlorobenzyl)-8-fluoro-4-hydroxy-3,6-quinolinedicarboxamide;

(184) $N^3,N^6$-bis(4-chlorobenzyl)-8-fluoro-4-hydroxy-3,6-quinolinedicarboxamide;

(185) 6-amino-N-(4-chlorobenzyl)-8-fluoro-4-hydroxy-3-quinolinecarboxamide;

(186) N-(4-chlorobenzyl)-8-fluoro-4-hydroxy-6-{[(4-methoxyphenyl)sulfonyl]amino}-3-quinolinecarboxamide;

(187) N-(4-chlorobenzyl)-4-hydroxy-6-[(2-hydroxyethyl)amino]-3-quinolinecarboxamide;

(188) N-(4-chlorobenzyl)-6-[ethyl(2-hydroxyethyl)amino]-4-hydroxy-3-quinolinecarboxamide;

(189) N-(4-chlorobenzyl)-4-hydroxy-6-(2-oxo-1,3-oxazolidin-3-yl)-3-quinolinecarboxamide;

(190) N-(4-chlorobenzyl)-4-hydroxy-6-(4-morpholinylmethyl)-3-quinolinecarboxamide;

(191) N-(4-chlorobenzyl)-8-fluoro-4-hydroxy-6-{[(1-naphthylmethyl)amino]sulfonyl}-3-quinolinecarboxamide;

(192) N-(4-chlorobenzyl)-8-fluoro-4-hydroxy-6-({[2-(1H-indol-3-yl)ethyl]amino}sulfonyl)-3-quinolinecarboxamide;

(193) N-(4-chlorobenzyl)-8-fluoro-6-{[(2-furylmethyl)amino]sulfonyl}-4-hydroxy-3-quinolinecarboxamide;

(194) 6-{[bis(2-hydroxyethyl)amino]sulfonyl}-N-(4-chlorobenzyl)-8-fluoro-4-hydroxy-3-quinolinecarboxamide;

(195) ethyl 2-{[(3-{[(4-chlorobenzyl)amino]carbonyl}-8-fluoro-4-hydroxy-6-quinolinyl)sulfonyl]amino}acetate;

(196) N-(4-chlorobenzyl)-8-fluoro-4-hydroxy-6-{[(2-hydroxyethyl)amino]sulfonyl}-3-quinolinecarboxamide;

(197) N-(4-chlorobenzyl)-8-fluoro-4-hydroxy-6-(4-morpholinylsulfonyl)-3-quinolinecarboxamide;

(198) N-(4-chlorobenzyl)-8-fluoro-4-hydroxy-6-{[(2-pyridinylmethyl)amino]sulfonyl}-3-quinolinecarboxamide;

(199) N-(4-chlorobenzyl)-8-fluoro-4-hydroxy-6-[(2-pyridinylamino)sulfonyl]-3-quinolinecarboxamide;

(200) N-(4-chlorobenzyl)-6-{[(cyclohexylmethyl)amino]sulfonyl}-8-fluoro-4-hydroxy-3-quinolinecarboxamide;

(201) N-(4-chlorobenzyl)-8-fluoro-4-hydroxy-6-(rI[2-(1-methyl-2-pyrrolidinyl)ethyl]amino}sulfonyl)-3-quinolinecarboxamide;

(202) N-(4-chlorobenzyl)-8-fluoro-4-hydroxy-6-({[2-(1-pyrrolidinyl)ethyl]amino}sulfonyl)-3-quinolinecarboxamide;

(203) N-(4-chlorobenzyl)-8-fluoro-6-{[(2-furylmethyl)amino]sulfonyl}-4-hydroxy-3-quinolinecarboxamide;

(204) N-(4-chlorobenzyl)-6-({[3-(cyclohexylamino)propyl]amino}sulfonyl)-8-fluoro-4-hydroxy-3-quinolinecarboxamide;

(205) N-(4-chlorobenzyl)-8-fluoro-4-hydroxy-6-{[(1-naphthylmethyl)amino]sulfonyl}-3-quinolinecarboxamide;

(206) N-(4-chlorobenzyl)-8-fluoro-4-hydroxy-6-({[2-(1H-imidazol-4-yl)ethyl]amino}-sulfonyl)-3-quinolinecarboxamide;

(207) N-(4-chlorobenzyl)-8-fluoro-4-hydroxy-6-{[(tetrahydro-2-furanylmethyl)amino]-sulfonyl}-3-quinolinecarboxamide;

(208) N-(4-chlorobenzyl)-8-fluoro-4-hydroxy-6-{[(2-thienylmethyl)amino]sulfonyl}-3-quinolinecarboxamide;

(209) N-(4-chlorobenzyl)-8-fluoro-4-hydroxy-6-({[2-(1H-indol-3-yl)ethyl]amino}sulfonyl)-3-quinolinecarboxamide;

(210) N-(4-chlorobenzyl)-8-fluoro-4-hydroxy-6-({[2-(5-methoxy-1H-indol-3-yl)ethyl]amino}sulfonyl)-3-quinolinecarboxamide;

(211) 6-{[(1,3-benzodioxol-5-ylmethyl)amino]sulfonyl}-N-(4-chlorobenzyl)-8-fluoro-4-hydroxy-3-quinolinecarboxamide;

(212) N-(4-chlorobenzyl)-8-fluoro-4-hydroxy-6-({[2-(4-morpholinyl)ethyl]amino}-sulfonyl)-3-quinolinecarboxamide;

(213) N-(4-chlorobenzyl)-8-fluoro-4-hydroxy-6-({[3-(4-morpholinyl)propyl]amino}-sulfonyl)-3-quinolinecarboxamide;

(214) N-(4-chlorobenzyl)-8-fluoro-4-hydroxy-6-[({2-[(5-nitro-2-pyridinyl)amino]ethyl}-amino)sulfonyl]-3-quinolinecarboxamide;

(215) N-(4-chlorobenzyl)-8-fluoro-4-hydroxy-6-{[(2-pyridinylmethyl)amino]sulfonyl}-3-quinolinecarboxamide;

(216) N-(4-chlorobenzyl)-8-fluoro-4-hydroxy-6-({[2-(2-pyridinyl)ethyl]amino}sulfonyl)-3-quinolinecarboxamide;

(217) N-(4-chlorobenzyl)-8-fluoro-4-hydroxy-6-{[(3-pyridinylmethyl)amino]sulfonyl}-3-quinolinecarboxamide;

(218) N-(4-chlorobenzyl)-8-fluoro-4-hydroxy-6-{[(4-pyridinylmethyl)amino]sulfonyl}-3-quinolinecarboxamide;

(219) N-(4-chlorobenzyl)-6-{[(4-chlorobenzyl)amino]sulfonyl}-8-fluoro-4-hydroxy-3-quinolinecarboxamide;

(220) N-(4-chlorobenzyl)-8-fluoro-4-hydroxy-6-{[(4-methoxybenzyl)amino]sulfonyl}-3-quinolinecarboxamide;

(221) N-(4-chlorobenzyl)-8-fluoro-4-hydroxy-6-[(neopentylamino)sulfonyl]-3-quinolinecarboxamide;

(222) N-(4-chlorobenzyl)-8-fluoro-4-hydroxy-6-{[(2-hydroxypropyl)amino]sulfonyl}-3-quinolinecarboxamide;

(223) N-(4-chlorobenzyl)-6-{[(2,3-dihydroxypropyl)amino]sulfonyl}-8-fluoro-4-hydroxy-3-quinolinecarboxamide;

(224) N-(4-chlorobenzyl)-6-{[(2,2-diphenylethyl)amino]sulfonyl]-8-fluoro-4-hydroxy-3-quinolinecarboxamide;

(225) 11-{[(3-{[(4-chlorobenzyl)amino]carbonyl}-8-fluoro-4-hydroxy-6-quinolinyl)sulfonyl]amino}undecanoic acid;

(226) 6-({[2-(acetylamino)ethyl]amino}sulfonyl)-N-(4-chlorobenzyl)-8-fluoro-4-hydroxy-3-quinolinecarboxamide;

(227) N-(4-chlorobenzyl)-8-fluoro-4-hydroxy-6-({[2-(2-hydroxyethoxy)ethyl]amino}-sulfonyl)-3-quinolinecarboxamide;

(228) N-(4-chlorobenzyl)-8-fluoro-4-hydroxy-6-{[(2-hydroxyethyl)amino]sulfonyl}-3-quinolinecarboxamide;

(229) N-(4-chlorobenzyl)-8-fluoro-4-hydroxy-6-[(phenethylamino)sulfonyl]-3-quinolinecarboxamide;

(230) N-(4-chlorobenzyl)-6-{[(4-chlorophenethyl)amino]sulfonyl}-8-fluoro-4-hydroxy-3-quinolinecarboxamide;

(231) N-(4-chlorobenzyl)-8-fluoro-4-hydroxy-6-[(2-propynylamino)sulfonyl]-3-quinolinecarboxamide;

(232) N-(4-chlorobenzyl)-8-fluoro-4-hydroxy-6-[(isopentylamino)sulfonyl]-3-quinolinecarboxamide;

(233) N-(4-chlorobenzyl)-8-fluoro-4-hydroxy-6-{[(3-phenylpropyl)amino]sulfonyl}-3-quinolinecarboxamide;

(234) N-(4-chlorobenzyl)-8-fluoro-4-hydroxy-6-[(pentylamino)sulfonyl]-3-quinolinecarboxamide;

(235) 6-({[3,5-bis(trifluoromethyl)benzyl]amino}sulfonyl)-N-(4-chlorobenzyl)-8-fluoro-4-hydroxy-3-quinolinecarboxamide;

(236) N-(4-chlorobenzyl)-6-({[2-(1-cyclohexen-1-yl)ethyl]amino}sulfonyl)-8-fluoro-4-hydroxy-3-quinolinecarboxamide;

(237) N-(4-chlorobenzyl)-8-fluoro-4-hydroxy-6-(({2-(1-naphthylamino)ethyl]amino}-sulfonyl)-3-quinolinecarboxamide;

(238) N-(4-chlorobenzyl)-8-fluoro-4-hydroxy-6-[(methylamino)sulfonyl]-3-quinolinecarboxamide;

(239) N-(4-chlorobenzyl)-6-{[(cyanomethyl)amino]sulfonyl}-8-fluoro-4-hydroxy-3-quinolinecarboxamide;
(240) N-(4-chlorobenzyl)-6-{[(2,4-dimethoxybenzyl)amino]sulfonyl}-8-fluoro-4-hydroxy-3-quinolinecarboxamide;
(241) N-(4-chlorobenzyl)-8-fluoro-4-hydroxy-6-{[(3-iodobenzyl)amino]sulfonyl}-3-quinolinecarboxamide;
(242) N-(4-chlorobenzyl)-8-fluoro-4-hydroxy-6-{[(2,2,2-trifluoroethyl)amino]sulfonyl}-3-quinolinecarboxamide;
(243) 6-{[(2-bromoethyl)amino]sulfonyl}-N-(4-chlorobenzyl)-8-fluoro-4-hydroxy-3-quinolinecarboxamide;
(244) N-(4-chlorobenzyl)-6-{[(2-chloroethyl)amino]sulfonyl}-8-fluoro-4-hydroxy-3-quinolinecarboxamide;
(245) N-(4-chlorobenzyl)-6-{[(3,4-dihydroxyphenethyl)amino]sulfonyl}-8-fluoro-4-hydroxy-3-quinolinecarboxamide;
(246) N-(4-chlorobenzyl)-6-({[2-(ethylsulfanyl)ethyl]amino}sulfonyl)-8-fluoro-4-hydroxy-3-quinolinecarboxamide;
(247) 6-{[(3-bromopropyl)amino]sulfonyl}-N-(4-chlorobenzyl)-8-fluoro-4 -hydroxy-3-quinolinecarboxamide;
(248) 6-({[4-(aminosulfonyl)benzyl]amino}sulfonyl)-N-(4-chlorobenzyl)-8-fluoro-4-hydroxy-3-quinolinecarboxamide;
(249) 6-[({2-[bis(2-hydroxyethyl)amino]ethyl}amino)sulfonyl]-N-(4-chlorobenzyl)-8-fluoro-4-hydroxy-3-quinolinecarboxamide;
(250) N-(4-chlorobenzyl)-6-{[2-(ethylsulfanyl)ethyl]amino}sulfonyl)-8-fluoro-4-hydroxy-3-quinolinecarboxamide;
(251) N-(4-chlorobenzyl)-6-{[(3,4-dimethylbenzyl)amino]sulfonyl}-8-fluoro-4-hydroxy-3-quinolinecarboxamide;
(252) N-(4-chlorobenzyl)-6-{[(cyclopropylmethyl)amino]sulfonyl}-8-fluoro-4-hydroxy-3-quinolinecarboxamide;
(253) 6-{[(4-bromobenzyl)amino]sulfonyl}-N-(4-chlorobenzyl)-8-fluoro-4-hydroxy-3-quinolinecarboxamide;
(254) N-(4-chlorobenzyl)-8-fluoro-4-hydroxy-6-({[2-(2-thienyl)ethyl]amino}sulfonyl)-3-quinolinecarboxamide;
(255) N-(4-chlorobenzyl)-8-fluoro-4-hydroxy-6-([(2-phenoxyethyl)amino]sulfonyl}-3-quinolinecarboxamide;
(256) tert-butyl 2-{[(3-{[(4-chlorobenzyl)amino]carbonyl}-8-fluoro-4-hydroxy-6-quinolinyl)sulfonyl]amino}acetate;
(257) tert-butyl 3-{[(3-{[(4-chlorobenzyl)amino]carbonyl}-8-fluoro-4-hydroxy-6-quinolinyl)sulfonyl]amino}propanoate;
(258) N-(4-chlorobenzyl)-8-fluoro-4-hydroxy-6-({[3-(trifluoromethoxy)benzyl]amino}sulfonyl)-3-quinolinecarboxamide;
(259) N-(4-chlorobenzyl)-8-fluoro-4-hydroxy-6-{[(2-{[2-(hydroxymethyl)phenyl]sulfanyl}-benzyl)amino]sulfonyl}-3-quinolinecarboxamide;
(260) N-(4-chlorobenzyl)-8-fluoro-4-hydroxy-6-({[4-(1,2,3-thiadiazol-4-yl)benzyl]amino}sulfonyl)-3-quinolinecarboxamide;
(261) N-(4-chlorobenzyl)-6-{[(4-chloro-2-fluorobenzyl)amino]sulfonyl}-8-fluoro-4-hydroxy-3-quinolinecarboxamide;
(262) N-(4-chlorobenzyl)-8-fluoro-4-hydroxy-6-[({2-[(2-hydroxyethyl)sulfanyl]ethyl}-amino)sulfonyl]-3-quinolinecarboxamide
(263) 6-{[(2-amino-2-methylpropyl)amino]sulfonyl}-N-(4-chlorobenzyl)-8-fluoro-4-hydroxy-3-quinolinecarboxamide;
(264) 6-{[(2-amino-2-oxoethyl)amino]sulfonyl}-N-(4-chlorobenzyl)-8-fluoro-4-hydroxy-3-quinolinecarboxamide;
(265) 6-{[(4-aminobenzyl)amino]sulfonyl}-N-(4-chlorobenzyl)-8-fluoro-4 -hydroxy-3-quinolinecarboxamide;
(266) di(tert-butyl) 3-(3-{[(4-chlorobenzyl)amino]carbonyl}-8-fluoro-4-hydroxy-6-quinolinyl)propyl phosphate;
(267) 3-(3-{[(4-chlorobenzyl)amino]carbonyl}-8-fluoro-4-hydroxy-6-quinolinyl)propyl dihydrogen phosphate;
(268) 3-(3-{[(4-chlorobenzyl)amino]carbonyl}-4-hydroxy-6-quinolinyl)propyl dihydrogen phosphate;
(269) tert-butyl 3-(3-{[(4-chlorobenzyl)aminor]carbonyl}-4-hydroxy-6-quinolinyl)propyl phosphonate;
(270) tert-butyl 3-(3-{[(4-chlorobenzyl)amino]carbonyl}-8-fluoro-4-hydroxy-6-quinolinyl)propyl phosphonate;
(271) (E)-3-(3-{[(4-chlorobenzyl)amino]carbonyl}-8-fluoro-4-hydroxy-6-quinolinyl)-2-propenoic acid; or
(272) N-[(4-chlorophenyl)methyl]-4-hydroxy-7-iodo-3-quinolinecarboamide.

15. A compound of claim 1 which is:
(1) 7-amino-N-(4-chlorobenzyl)-4-hydroxy-3-quinolinecarboxamide;
(2) N-(4-chlorobenzyl)-4-hydroxy-7-methoxy-3-quinolinecarboxamide;
(3) N-(4-chlorobenzyl)-7-fluoro-4-hydroxy-3-quinolinecarboxamide;
(4) N-(4-chlorobenzyl)-8-fluoro-4-hydroxy-3-quinolinecarboxamide;
(5) 6-chloro-N-(4-chlorobenzyl)-4-hydroxy-3-quinolinecarboxamide;
(6) N-(4-chlorobenzyl)-4-hydroxy-6-methyl-3-quinolinecarboxamide;
(7) N-(4-chlorobenzyl)-4-hydroxy-6-methoxy-3-quinolinecarboxamide;
(9) N-(4-chlorobenzyl)-4-hydroxy-6-iodo-3-quinolinecarboxamide;
(10) N-(4-chlorobenzyl)-4-hydroxy-6-phenyl-3-quinolinecarboxamide;
(11) N-(4-chlorobenzyl)-4-hydroxy-6,8-dimethoxy-3-quinolinecarboxamide;
(12) 6-(tert-butyl)-N-(4-chlorobenzyl)-4-hydroxy-3-quinolinecarboxamide;
(13) N-(4-chlorobenzyl)-6-(cyanomethyl)-4-hydroxy-3-quinolinecarboxamide;
(14) N-(4-chlorobenzyl)-9-hydroxy[1,3]thiazolo[5,4-f]quinoline-8-carboxamide;
(15) N-(4-chlorobenzyl)-8-fluoro -4-hydroxy-6-(3-hydroxy-1-propynyl)-3-quinolinecarboxamide;
(16) N-(4-chlorobenzyl)-8-fluoro-4-hydroxy-6-(1,3-thiazol-2-yl)-3-quinolinecarboxamide;

(17) N-(4-chlorobenzyl)-8-fluoro-4-hydroxy-6-(2-thienyl)-3-quinolinecarboxamide;

(18) N-(4-chlorobenzyl)-8-fluoro-4-hydroxy-6-(3-methoxy-1-propynyl)-3-quinolinecarboxamide;

(19) 6-(4-bromo-2-thienyl)-N-(4-chlorobenzyl)-8-fluoro-4-hydroxy-3-quinolinecarboxamide;

(20) N-(4-chlorobenzyl)-8-fluoro-4-hydroxy-6-(4-hydroxybutyl)-3-quinolinecarboxamide;

(21) N-(4-chlorobenzyl)-8-fluoro-4-hydroxy-6-[(Z)-4-hydroxy-1-butenyl]-3-quinolinecarboxamide;

(22) N-((4-chlorobenzyl)-6,8-difluoro-4-hydroxy-7-[4-(hydroxymethyl)phenoxy]-3-quinolinecarboxamide;

(23) N-((4-chlorobenzyl)-6,8-difluoro-4-hydroxy-7-methoxy-3-quinolinecarboxamide;

(24) N-(4-chlorobenzyl)-8-fluoro-4-hydroxy-6-(5-hydroxy-1-pentynyl)-3-quinolinecarboxamide;

(25) 3-(3-{[(4-chlorobenzyl)amino]carbonyl}-8-fluoro-4-hydroxy-6-quinolinyl)-2-propynyl formate;

(26) N-(4-chlorobenzyl)-8-fluoro-4-hydroxy-6-(3-hydroxypropyl)-3-quinolinecarboxamide;

(27) N-(4-chlorobenzyl)-4-hydroxy-7-(3-hydroxypropyl)-3-quinolinecarboxamide;

(28) N-((4-chlorobenzyl)-8-fluoro-4-hydroxy-6-(3-hydroxybutyl)-3-quinolinecarboxamide;

(29) N-((4-chlorobenzyl)-6-[(E)-2-cyanoethenyl]-8-fluoro-4-hydroxy-3-quinolinecarboxamide;

(30) N-((4-chlorobenzyl)-4-hydroxy-6-(3-hydroxy-1-propynyl)-8-methoxy-3-quinolinecarboxamide;

(31) N-(4-chlorobenzyl)-4-hydroxy-6-(3-hydroxy-1-propynyl)-3-quinolinecarboxamide;

(32) N-(4-chlorobenzyl)-4-hydroxy-8-methoxy-6-(3-methoxy-1-propynyl)-3-quinolinecarboxamide;

(33) N-(4-chlorobenzyl)-8-fluoro-4-hydroxy-6-[(Z)-3-hydroxy-1-propenyl]-3-quinolinecarboxamide;

(34) N-(4-chlorobenzyl)-8-fluoro-4-hydroxy-6-(3-oxopropyl)-3-quinolinecarboxamide;

(35) N-(4-chlorobenzyl)-4-hydroxy-7-(4-hydroxybutyl)-3-quinolinecarboxamide;

(36) N-(4-chlorobenzyl)-4-hydroxy-6-iodo-8-methoxy-3-quinolinecarboxamide;

(37) N-(4-chlorobenzyl)-8-fluoro-6-(3-fluoro-1-propynyl)-4-hydroxy-3-quinolinecarboxamide;

(38) N-(4-chlorobenzyl)-4-hydroxy-6-(3-hydroxypropyl)-3-quinolinecarboxamide;

(39) 3-(3-{[(4-chlorobenzyl)amino]carbonyl}-8-fluoro-4-hydroxy-6-quinolinyl)propyl 2-bromoacetate;

(40) 3-(3-{[(4-chlorobenzyl)amino]carbonyl}-8-fluoro-4-hydroxy-6-quinolinyl)propyl 2-[(tert-butoxycarbonyl)amino]-3-methylbutanoate;

(41) 3-(3-{[(4-chlorobenzyl)amino]carbonyl}-8-fluoro-4-hydroxy-6-quinolinyl)propyl 2-amino-3-methylbutanoate;

(42) 3-(3-{[(4-chlorobenzyl)amino]carbonyl}-8-fluoro-4-hydroxy-6-quinolinyl)-2-propynyl phenylcarbamate;

(43) N-((4-chlorobenzyl)-4-hydroxy-6-propyl-3-quinolinecarboxamide

(44) N-((4-chlorobenzyl)-4-hydroxy-6-(3-hydroxypropyl)-8-methoxy-3-quinolinecarboxamide;

(45) N-(4-chlorobenzyl)-8-fluoro-4-hydroxy-6-(methylsulfanyl)-3-quinolinecarboxamide;

(46) N-(4-chlorobenzyl)-4-hydroxy-7-{[(1-naphthylmethyl)amino]sulfonyl}-3-quinolinecarboxamide;

(47) N-(4-chlorobenzyl)-8-fluoro-4-hydroxy-6-[(E)-3-oxo-1-butenyl]-3-quinolinecarboxamide;

(48) N-(4-chlorobenzyl)-4-hydroxy-6-(3-hydroxy-1-propynyl)-8-(trifluoromethoxy)-3-quinolinecarboxamide;

(49) sodium 2-[{8-[3-(3-{[(4-chlorobenzyl)amino]carbonyl}-8-fluoro-4-hydroxy-6-quinolinyl)propoxy]-8-oxooctanoyl}(methyl)amino]-1-ethanesulfonate;

(50) 3-(3-{[(4-chlorobenzyl)amino]carbonyl}-8-fluoro-4-hydroxy-6-quinolinyl)propyl dihydrogen phosphate;

(51) 3-(3-{[(4-chlorobenzyl)amino]carbonyl}-8-fluoro-4-hydroxy-6-quinolinyl)propyl 2,6-bis [(tert-butoxycarbonyl)amino]hexanoate;

(52) tert-butyl 3-(3-{[(4-chlorobenzyl)amino]carbonyl}-8-fluoro-4-hydroxy-6-quinolinyl)propyl phosphonate;

(53) sodium 2-[(8-{[3-(3-{[(4-chlorobenzyl)amino]carbonyl}-8-fluoro-4-hydroxy-6-quinolinyl)-2-propynyl]oxy}-8-oxooctanoyl)(methyl)amino]-1-ethanesulfonate;

(54) N-(4-chlorobenzyl)-4-hydroxy-6-(2-hydroxyethoxy)-3-quinolinecarboxamide;

(55) 3-(3-{[(4-chlorobenzyl)amino]carbonyl}-8-fluoro-4-hydroxy-6-quinolinyl)propyl 2,6-diaminohexanoate trifluoroacetic acid salt;

(56) N-(4-chlorobenzyl)-4-hydroxy-6-[(2-hydroxyethyl)amino]-3-quinolinecarboxamide;

(57) N-(4-chlorobenzyl)-4-hydroxy-6-(3-hydroxybutyl)-3-quinolinecarboxamide;

(58) sodium 2-[(8-1[3-(3-{[(4-chlorobenzyl)amino]carbonyl}-4-hydroxy-6-quinolinyl)-2-propynyl]oxy}-8-oxooctanoyl)(methyl)amino]-1-ethanesulfonate;

(59) sodium 2-[{8-[3-(3-{[(4-chlorobenzyl)amino]carbonyl}-4-hydroxy-6-quinolinyl)propoxy]-8-oxooctanoyl}(methyl)amino]-1-ethanesulfonate;

(60) tert-butyl 3-(3-{[(4-chlorobenzyl)amino]carbonyl}-4-hydroxy-6-quinolinyl)propyl phosphonate;

(61) 3-(3-{[(4-chlorobenzyl)amino]carbonyl}-4-hydroxy-6-quinolinyl)propyl dihydrogen phosphate;

(62) N-(4-chlorobenzyl)-4-hydroxy-8-(2-hydroxyethoxy)-6-(3-hydroxypropyl)-3-quinolinecarboxamide;

(63) N-(4-chlorobenzyl)-8-fluoro-4-hydroxy-6-(4-morpholinylmethyl)-3-quinolinecarboxamide;

(64) N-(4-chlorobenzyl)-8-fluoro-4-hydroxy-6-(3-oxobutyl)-3-quinolinecarboxamide;

(65) N-(4-chlorobenzyl)-4-hydroxy-6-(2-oxo-1,3-oxazolidin-3-yl)-3-quinolinecarboxamide;

(66) 3-(3-{[(4-chlorobenzyl)amino]carbonyl}-4-hydroxy-6-quinolinyl)-2-propynyl 2,6-bis [(tert-butoxycarbonyl)amino]hexanoate;

(67) N-(4-chlorobenzyl)-6-[(Z)-3-hydroxy-1-propenyl]-4-oxo-1,4-dihydro-3-quinolinecarboxamide;

(68) N-(4-chlorobenzyl)-6-[(E)-3-hydroxy-1-propenyl]-4-oxo-1,4-dihydro-3-quinolinecarboxamide;

(69) 3-(3-{[(4-chlorobenzyl)amino]carbonyl}-4-hydroxy-6-quinolinyl)-2-propynyl 2,6-diaminohexanoate trifluoroacetic acid salt;

(70) 3-(3-{[(4-chlorobenzyl)amino]carbonyl}-4-hydroxy-6-quinolinyl)propyl hydrogen phosphonate;

(71) N-(4-chlorobenzyl)-4-hydroxy-6-(2-thienyl)-3-quinolinecarboxamide;

(72) N-((4-chlorobenzyl)-4-hydroxy-6-[(2-hydroxyethoxy)methyl]-3-quinolinecarboxamide;

(73) N-(4-chlorobenzyl)-4-hydroxy-6-(3-hydroxy-1,1-dimethylpropyl)-3-quinolinecarboxamide;

(74) N-(4-chlorobenzyl)-4-hydroxy-6-{[2-hydroxy-1-(hydroxymethyl)ethoxy]methyl}-3-quinolinecarboxamide;

(75) N-((4-chlorobenzyl)-4-hydroxy-6-(hydroxymethyl)-3-quinolinecarboxamide;

(76) Methyl 3-{[(4-chlorobenzyl)amino]carbonyl}-4-hydroxy-6-quinolinecarboxylate; or

(77) N-(4-chlorobenzyl)-4-hydroxy-6-(4-morpholinylmethyl)-3-quinolinecarboxamide.

16. A compound of claim 1 which is:

(1) N-(4-chlorobenzyl)-4-hydroxy-7-methoxy-3-quinolinecarboxamide;

(2) N-(4-chlorobenzyl)-7-fluoro-4-hydroxy-3-quinolinecarboxamide;

(3) N-(4-chlorobenzyl)-8-fluoro-4-hydroxy-3-quinolinecarboxamide;

(4) N-(4-chlorobenzyl)-4-hydroxy-6-methoxy-3-quinolinecarboxamide;

(5) N-(4-chlorobenzyl)-8-fluoro-4-hydroxy-6-(2-thienyl)-3-quinolinecarboxamide;

(6) N-(4-chlorobenzyl)-8-fluoro-4-hydroxy-6-(4-hydroxybutyl)-3-quinolinecarboxamide;

(7) N-(4-chlorobenzyl)-8-fluoro-4-hydroxy-6-[(Z)-4-hydroxy-1-butenyl]-3-quinolinecarboxamide;

(8) N-(4-chlorobenzyl)-8-fluoro-4-hydroxy-6-(3-hydroxypropyl)-3-quinolinecarboxamide;

(9) N-(4-chlorobenzyl)-4-hydroxy-7-(3-hydroxypropyl)-3-quinolinecarboxamide;

(10) N-(4-chlorobenzyl)-4-hydroxy-6-(3-hydroxy-1-propynyl)-8-methoxy-3-quinolinecarboxamide;

(11) N-(4-chlorobenzyl)-4-hydroxy-6-(3-hydroxy-1-propynyl)-3-quinolinecarboxamide;

(12) N-(4-chlorobenzyl)-4-hydroxy-8-methoxy-6-(3-methoxy-1-propynyl)-3-quinolinecarboxamide;

(13) N-(4-chlorobenzyl)-4-hydroxy-7-(4-hydroxybutyl)-3-quinolinecarboxamide;

(14) N-(4-chlorobenzyl)-4-hydroxy-6-(3-hydroxypropyl)-3-quinolinecarboxamide;

(15) 3-(3-{[(4-chlorobenzyl)amino]carbonyl}-8-fluoro-4-hydroxy-6-quinolinyl)propyl 2-bromoacetate;

(16) 3-(3-{[(4-chlorobenzyl)amino]carbonyl}-8-fluoro-4-hydroxy-6-quinolinyl)propyl 2-amino-3-methylbutanoate;

(17) N-(4-chlorobenzyl)-4-hydroxy-6-(3-hydroxypropyl)-8-methoxy-3-quinolinecarboxamide;

(18) sodium 2-[{8-[3-(3-{[(4-chlorobenzyl)amino]carbonyl}-8-fluoro-4-hydroxy-6-quinolinyl)propoxy]-8-oxooctanoyl}(methyl)amino]-1-ethanesulfonate;

(19) 3-(3-{[(4-chlorobenzyl)amino]carbonyl}-8-fluoro-4-hydroxy-6-quinolinyl)propyl dihydrogen phosphate;

(20) 3-(3-{[(4-chlorobenzyl)amino]carbonyl}-8-fluoro-4-hydroxy-6-quinolinyl)propyl 2,6-bis[(tert-butoxycarbonyl)amino]hexanoate;

(21) tert-butyl 3-(3-{[(4-chlorobenzyl)amino]carbonyl}-8-fluoro-4-hydroxy-6-quinolinyl)propyl phosphonate;

(22) 3-(3-([(4-chlorobenzyl)amino]carbonyl}-8-fluoro-4-hydroxy-6-quinolinyl)propyl 2,6-diaminohexanoate trifluoroacetic acid salt;

(23) N-(4-chlorobenzyl)-4-hydroxy-6-[(2-hydroxyethyl)amino]-3-quinolinecarboxamide;

(24) N-(4-chlorobenzyl)-4-hydroxy-6-(3-hydroxybutyl)-3-quinolinecarboxamide;

(25) sodium 2-[(8-{[3-(3-([(4-chlorobenzyl)amino]carbonyl}-4-hydroxy-6-quinolinyl)-2-propynyl]oxy}-8-oxooctanoyl)(methyl)amino]-1-ethanesulfonate;

(26) sodium 2-[{8-[3-(3-{[(4-chlorobenzyl)amino]carbonyl}-4-hydroxy-6-quinolinyl)propoxy]-8-oxooctanoyl}(methyl)amino]-1-ethanesulfonate;

(27) tert-butyl 3-(3-{[(4-chlorobenzyl)amino]carbonyl}-4-hydroxy-6-quinolinyl)propyl phosphonate;

(28) 3-(3-{[(4-chlorobenzyl)amino]carbonyl}-4-hydroxy-6-quinolinyl)propyl dihydrogen phosphate;

(29) N-(4-chlorobenzyl)-4-hydroxy-8-(2-hydroxyethoxy)-6-(3-hydroxypropyl)-3-quinolinecarboxamide;

(30) N-(4-chlorobenzyl)-8-fluoro-4-hydroxy-6-(4-morpholinylmethyl)-3-quinolinecarboxamide;

(31) 3-(3-{[(4-chlorobenzyl)amino]carbonyl}-4-hydroxy-6-quinolinyl)-2-propynyl 2,6-bis[(tert-butoxycarbonyl)amino]hexanoate;

(32) N-(4-chlorobenzyl)-6-[(Z)-3-hydroxy-1-propenyl]-4-oxo-1,4-dihydro-3-quinolinecarboxamide;

(33) N-(4-chlorobenzyl)-6-[(E)-3-hydroxy-1-propenyl]-4-oxo-1,4-dihydro-3-quinolinecarboxamide;

(34) 3-(3-{[(4-chlorobenzyl)amino]carbonyl}-4-hydroxy-6-quinolinyl)-2-propynyl 2,6-diaminohexanoate trifluoroacetic acid salt;

(35) 3-(3-{[(4-chlorobenzyl)amino]carbonyl}-4-hydroxy-6-quinolinyl)propyl hydrogen phosphonate;

(36) N-(4-chlorobenzyl)-4-hydroxy-6-(2-thienyl)-3-quinolinecarboxamide

(37) N-(4-chlorobenzyl)-4-hydroxy-6-[(2-hydroxyethoxy)methyl]-3-quinolinecarboxamide;

(38) N-(4-chlorobenzyl)-4-hydroxy-6-(3-hydroxy-1,1-dimethylpropyl)-3-quinolinecarboxamide;

(39) methyl 3-{[(4-chlorobenzyl)amino]carbonyl}-4-hydroxy-6-quinolinecarboxylate; or

(40) N-(4-chlorobenzyl)-4-hydroxy-6-(4-morpholinylmethyl)-3-quinolinecarboxamide.

17. A compound of claim 1 which is:

(1) N-(4-chlorobenzyl)-8-fluoro-4-hydroxy-6-(3-hydroxypropyl)-3-quinolinecarboxamide;

(2) N-(4-chlorobenzyl)-4-hydroxy-6-(3-hydroxy-1-propynyl)-8-methoxy-3-quinolinecarboxamide;

(3) N-(4-chlorobenzyl)-4-hydroxy-8-methoxy-6-(3-methoxy-1-propynyl)-3-quinolinecarboxamide;

(4) N-(4-chlorobenzyl)-4-hydroxy-6-(3-hydroxypropyl)-3-quinolinecarboxamide;

(5) N-(4-chlorobenzyl)-4-hydroxy-6-(3-hydroxypropyl)-8-methoxy-3-quinolinecarboxamide;

(6) sodium 2-[(8-{[3-(3-{[(4-chlorobenzyl)amino]carbonyl}-4-hydroxy-6-quinolinyl)-2-propynyl]oxy}-8-oxooctanoyl)(methyl)amino]-1-ethanesulfonate;

(7) sodium 2-[{8-[3-(3-{[(4-chlorobenzyl)amino]carbonyl}-4-hydroxy-6-quinolinyl)propoxy]-8-oxooctanoyl}(methyl)amino]-1-ethanesulfonate;

(8) 3-(3-{[(4-chlorobenzyl)amino]carbonyl}-4-hydroxy-6-quinolinyl)propyl dihydrogen phosphate;

(9) N-(4-chlorobenzyl)-6-[(Z)-3-hydroxy-1-propenyl]-4-oxo-1,4-dihydro-3-quinolinecarboxamide;

(10) N-(4-chlorobenzyl)-6-[(E)-3-hydroxy-1-propenyl]-4-oxo-1,4-dihydro-3-quinolinecarboxamide;

(11) 3-(3-{[(4-chlorobenzyl)amino]carbonyl}-4-hydroxy-6-quinolinyl)-2-propynyl 2,6-diaminohexanoate trifluoroacetic acid salt;

(12) 3-(3-{[(4-chlorobenzyl)amino]carbonyl}-4-hydroxy-6-quinolinyl)propyl hydrogen phosphonate;

(13) N-(4-chlorobenzyl)-4-hydroxy-6-(2-thienyl)-3-quinolinecarboxamide;

(14) N-((4-chlorobenzyl)-4-hydroxy-6-[(2-hydroxyethoxy)methyl]-3-quinolinecarboxamide; or

(15) N-(4-chlorobenzyl)-4-hydroxy-6-(4-morpholinylmethyl)-3-quinolinecarboxamide.

\* \* \* \* \*

UNITED STATES PATENT AND TRADEMARK OFFICE
CERTIFICATE OF CORRECTION

PATENT NO.    : 6,093,732
DATED         : July 25, 2000
INVENTOR(S)   : JA Tucker et al.

It is certified that error appears in the above-identified patent and that said Letters Patent is hereby corrected as shown below:

Column 213,
Line 66, change "j) —Cr≡CR$^{11}$," to -- j)  -C≡CR$^{11}$, --

Column 217,
Line 18, change "c) —oR$^5$," to -- c) -OR$^5$, --

Signed and Sealed this

Tenth Day of May, 2005

JON W. DUDAS
*Director of the United States Patent and Trademark Office*